US009487764B2

(12) United States Patent
Falb et al.

(10) Patent No.: US 9,487,764 B2

(45) Date of Patent: Nov. 8, 2016

(54) BACTERIA ENGINEERED TO TREAT DISEASES ASSOCIATED WITH HYPERAMMONEMIA

(71) Applicant: Synlogic, Inc., Cambridge, MA (US)

(72) Inventors: Dean Falb, Sherborn, MA (US); Vincent M. Isabella, Cambridge, MA (US); Jonathan W. Kotula, Somerville, MA (US); Paul F. Miller, Salem, CT (US)

(73) Assignee: Synlogic, Inc., Cambridge, MA (US)

( * ) Notice: Subject to any disclaimer, the term of this patent is extended or adjusted under 35 U.S.C. 154(b) by 0 days.

(21) Appl. No.: 14/960,333

(22) Filed: Dec. 4, 2015

(65) Prior Publication Data

US 2016/0177274 A1 Jun. 23, 2016

Related U.S. Application Data

(60) Provisional application No. 62/087,854, filed on Dec. 5, 2014, provisional application No. 62/173,706, filed on Jun. 10, 2015, provisional application No. 62/256,041, filed on Nov. 16, 2015, provisional application No. 62/103,513, filed on Jan. 14, 2015, provisional application No. 62/150,508, filed on Apr. 21, 2015, provisional application No. 62/173,710, filed on Jun. 10, 2015, provisional application No. 62/256,039, filed on Nov. 16, 2015, provisional application No. 62/184,811, filed on Jun. 25, 2015, provisional application No. 62/183,935, filed on Jun. 24, 2015, provisional application No. 62/263,329, filed on Dec. 4, 2015.

(51) Int. Cl.

| | |
|---|---|
| ***A01N 63/00*** | (2006.01) |
| ***C12N 1/20*** | (2006.01) |
| ***C12N 9/10*** | (2006.01) |
| ***C12R 1/19*** | (2006.01) |
| ***C12N 15/52*** | (2006.01) |
| ***C12N 15/70*** | (2006.01) |
| ***C12P 13/10*** | (2006.01) |
| ***C12R 1/01*** | (2006.01) |
| ***A61K 35/741*** | (2015.01) |

(52) U.S. Cl.

CPC ........... *C12N 9/1029* (2013.01); *A61K 35/741* (2013.01); *C12N 9/1025* (2013.01); *C12N 15/52* (2013.01); *C12N 15/70* (2013.01); *C12P 13/10* (2013.01); *C12R 1/01* (2013.01); *C12R 1/19* (2013.01); *C12Y 203/01001* (2013.01)

(58) Field of Classification Search

None

See application file for complete search history.

(56) References Cited

U.S. PATENT DOCUMENTS

| | | | | |
|---|---|---|---|---|
| 5,589,168 | A | 12/1996 | Allen et al. | |
| 5,989,463 | A | 11/1999 | Tracy et al. | |
| 6,203,797 | B1 | 3/2001 | Perry | |
| 6,835,376 | B1 | 12/2004 | Neeser et al. | |
| 7,731,976 | B2 | 6/2010 | Cobb et al. | |
| 2003/0166191 | A1 | 9/2003 | Gardner et al. | |
| 2016/0177274 | A1* | 6/2016 | Falb | C12R 1/19 424/93.2 |

OTHER PUBLICATIONS

Alifano et al. Histidine biosynthetic pathway and genes: structure, regulation, and evolution. *Microbiol Rev.* Mar. 1996;60(1):44-69.

Altenhoefer et al. The probiotic *Escherichia coli* strain Nissle 1917 interferes with invasion of human intestinal epithelial cells by different enteroinvasive bacterial pathogens. *FEMS Immunol Med Microbiol.* Apr. 9, 2004;40(3):223-9.

Andersen et al. Uracil uptake in *Escherichia coli* K-12: isolation of *uraA* mutants and cloning of the gene. *J Bacteriol.* Apr. 1995;177(8):2008-13.

Arthur et al. Intestinal inflammation targets cancer-inducing activity of the microbiota. *Science.* Oct. 5, 2012;338(6103):120-3. NIH Public Access Author Manuscript; available in PMC May 6, 2013 (11 pages).

Aoyagi et al. Gastrointestinal urease in man. Activity of mucosal urease. *Gut.* Dec. 1966;7(6):631-5.

Arai et al. Expression of the nir and nor genes for denitrification of Pseudomonas aeruginosa requires a novel CRP/FNR-related transcriptional regulator, DNR, in addition to ANR. *FEBS Lett.* Aug. 28, 1995;371(1):73-6.

Caldara et al. The arginine regulon of *Escherichia coli*: whole-system transcriptome analysis discovers new genes and provides an integrated view of arginine regulation. *Microbiology.* Nov. 2006;152(Pt 11):3343-54.

Caldara et al. Arginine biosynthesis in *Escherichia coli*: experimental perturbation and mathematical modeling. *J Biol Chem.* Mar. 7, 2008;283(10):6347-58.

Caldovic et al. N-acetylglutamate synthase: structure, function and defects. *Mol Genet Metab.* 2010;100 Suppl 1:S13-9. NIH Public Access Author Manuscript; available in PMC Feb. 26, 2011 (16 pages).

Callura et al. Tracking, tuning, and terminating microbial physiology using synthetic riboregulators. *Proc Natl Acad Sci U S A.* Sep. 7, 2010;107(36):15898-903.

Castiglione et al. The transcription factor DNR from *Pseudomonas aeruginosa* specifically requires nitric oxide and haem for the activation of a target promoter in *Escherichia coli. Microbiology.* Sep. 2009;155(Pt 9):2838-44.

(Continued)

*Primary Examiner* — Michael Burkhart

(74) *Attorney, Agent, or Firm* — Finnegan, Henderson, Farabow, Garrett & Dunner, LLP

(57) ABSTRACT

Genetically engineered bacteria, pharmaceutical compositions thereof, and methods of modulating and treating disorders associated with hyperammonemia are disclosed.

18 Claims, 75 Drawing Sheets

(56) References Cited

OTHER PUBLICATIONS

Charlier et al. Arginine regulon of *Escherichia coli* K-12. A study of repressor-operator interactions and of in vitro binding affinities versus in vivo repression. *J Mol Biol*. Jul. 20, 1992;226(2):367-86.
Clarkson et al. Diaminopimelic Acid and Lysine Auxotrophs of *Pseudomonas aeruginosa* 8602. *J. Gen. Microbiol*. 1971;66:161-9.
Crabeel et al. Characterization of the *Saccharomyces cerevisiae* ARG7 gene encoding ornithine acetyltransferase, an enzyme also endowed with acetylglutamate synthase activity. *Eur J Biochem*. Dec. 1, 1997;250(2):232-41.
Cuevas-Ramos et al. *Escherichia coli* induces DNA damage in vivo and triggers genomic instability in mammalian cells. *Proc Natl Acad Sci U S A*. Jun. 22, 2010;107(25):11537-42.
Cunin et al. Molecular basis for modulated regulation of gene expression in the arginine regulon of *Escherichia coli* K-12. *Nucleic Acids Res*. Aug. 11, 1983;11(15):5007-19.
Cunin et al. Biosynthesis and metabolism of arginine in bacteria. *Microbiol Rev*. Sep. 1986;50(3):314-52. Erratum in: *Microbiol Rev*. Mar. 1987;51(1):178.
Deignan et al. Contrasting features of urea cycle disorders in human patients. *Mol Genet Metab*. Jan. 2008;93(1);7-14. NIH Public Access Author Manuscript; available in PMC Jun. 8, 2009 (13 pages).
Deutscher. The mechanisms of carbon catabolite repression in bacteria. *Curr Opin Microbiol*. Apr. 2008;11(2):87-93.
Diaz et al. Ammonia control and neurocognitive outcome among urea cycle disorder patients treated with glycerol phenylbutyrate. *Hepatology*. Jun. 2013;57(6):2171-9.
Dinleyici et al. *Saccharomyces boulardii* CNCM 1-745 in different clinical conditions. *Expert Opin Biol Ther*. Nov. 2014;14(11):1593-609.
Dogovski et al. Enzymology of Bacterial Lysine Biosynthesis. Chapter 9 in *Biochemistry*. Prof. Deniz Ekinci (Ed.), InTech, Mar. 2012; pp. 225-262. ISBN: 978-953-51-0076-8. [online] Retrieved from: http://www.intechopen.com/books/biochemistry/enzymology-of-bacterial-lysine-biosynthesis (39 pages).
Doolittle et al. A new allele of the sparse fur gene in the mouse. *J Hered*. May-Jun. 1974;65(3):194-5.
Eckhardt and Leisinger. Isolation and characterization of mutants with a feedback resistant N-acetylglutamate synthase in *Escherichia coli* K 12. *Mol Gen Genet*. Jun. 19, 1975;138(3):225-32.
Eiglmeier et al. Molecular genetic analysis of FNR-dependent promoters. *Mol Microbiol*. Jul. 1989;3(7):869-78.
Feng et al. Role of phosphorylated metabolic intermediates in the regulation of glutamine synthetase synthesis in *Escherichia coli*. *J Bacteriol*. Oct. 1992;174(19):6061-70.
Fraga et al. Real-Time PCR. *Current Protocols Essential Laboratory Techniques*. John Wiley & Sons, Inc., 2008; Unit 10.3, pp. 1-33.
Galimand et al. Positive FNR-like control of anaerobic arginine degradation and nitrate respiration in *Pseudomonas aeruginosa*. *J Bacteriol*. Mar. 1991;173(5):1598-606.
Gamper et al. Anaerobic regulation of transcription initiation in the arcDABC operon of Pseudomonas aeruginosa. *J Bacteriol*. Aug. 1991;173(15):4742-50.
Gardner et al. Construction of a genetic toggle switch in *Escherichia coli*. *Nature*. 2000;403:339-42.
Gerdes et al. Essential genes on metabolic maps. *Curr. Opin. Biotechnol.*, Oct. 2006;17(5):448-56.
Görke and Stülke. Carbon catabolite repression in bacteria: many ways to make the most out of nutrients. *Nat Rev Microbiol*. Aug. 2008;6(8):613-24.
Häberle et al. Suggested guidelines for the diagnosis and management of urea cycle disorders. *Orphanet J Rare Dis*. May 29, 2012;7:32 (30 pages).
Häberle, J. Clinical and biochemical aspects of primary and secondary hyperammonemic disorders. *Arch Biochem Biophys*. Aug. 15, 2013;536(2):101-8.
Hasegawa et al. Activation of a consensus FNR-dependent promoter by DNR of *Pseudomonas aeruginosa* in response to nitrite. *FEMS Microbiol Lett*. Sep. 15, 1998;166(2):213-7.
Hodges et al. The *spf*$^{ash}$ mouse: A missense mutation in the ornithine transcarbamylase gene also causes aberrant mRNA splicing. *Proc Natl Acad Sci U S A*. Jun. 1989;86(11):4142-6.
Hoeren et al. Sequence and expression of the gene encoding the respiratory nitrous-oxide reductase from *Paracoccus denitrificans*. *Eur J Biochem*. Nov. 15, 1993;218(1):49-57.
Hoffmann and Kölker. Defects in amino acid catabolism and the urea cycle. *Handbk Clin Neurol*. 2013;113:1755-73.
Hosseini et al. Propionate as a health-promoting microbial metabolite in the human gut. *Nutr Rev*. May 2011;69(5):245-58.
Isabella et al. Deep sequencing-based analysis of the anaerobic stimulon in *Neisseria gonorrhoeae*. *BMC Genomics*. Jan. 20, 2011;12:51 (24 pages).
Konieczna et al. Bacterial urease and its role in long-lasting human diseases. *Curr Protein Pept Sci*. Dec. 2012;13(8):789-806.
Lazier et al. Hyperammonemic encephalopathy in an adenocarcinoma patient managed with carglumic acid. *Curr Oncol*. Oct. 2014;21(5):e736-9.
Leonard. Disorders of the urea cycle and related enzymes. *Inborn Metabolic Diseases*, 4th ed Heidelberg: Springer Medizin Verlag, 2006; pp. 263-72.
Lim et al. Nucleotide sequence of the *argR* gene of *Escherichia coli* K-12 and isolation of its product, the arginine repressor. *Proc Natl Acad Sci U S A*. Oct. 1987;84(19):6697-701.
Liu et al. Methanococci use the diaminopimelate aminotransferase (DapL) pathway for lysine biosynthesis. *J Bacteriol*. Jul. 2010;192(13):3304-10.
Lodeiro et al. Robustness in *Escherichia coli* glutamate and glutamine synthesis studied by a kinetic model. *J Biol Phys*. Apr. 2008; 34(1-2):91-106.
Lopez and Anderson. Synthetic Auxotrophs with Ligand-Dependent Essential Genes for a BL21(DE3) Biosafety Strain. *ACS Synthetic Biology*. Dec. 2015;4(12):1279-86.
Makarova et al. Conservation of the binding site for the arginine repressor in all bacterial lineages. *Genome Biol*. 2001;2(4):research0013.1-0013.8.
Maas et al. Studies on the mechanism of repression of arginine biosynthesis in *Escherichia coli*. II. Dominance of repressibility in diploids. *J Mol Biol*. Mar. 1964;8:365-70.
Maas, W.K. The arginine repressor of *Escherichia coli*. *Microbiol Rev*. Dec. 1994;58(4):631-40.
Meadow et al. Interrelationships between lysine and alpha epsilon-diaminopimelic acid and their derivatives and analogues in mutants of *Escherichia coli*. *Biochem J*. Jun. 1957;66(2):270-82.
Meng et al. Nucleotide sequence of the *Escherichia coli* cad operon: a system for neutralization of low extracellular pH. *J Bacteriol*. Apr. 1992;174(8):2659-69.
Moore et al. Regulation of FNR dimerization by subunit charge repulsion. *J Biol Chem*. Nov. 3, 2006;281(44):33268-75.
Mountain et al. Cloning of a *Bacillus subtilis* restriction fragment complementing auxotrophic mutants of eight *Escherichia coli* genes of arginine biosynthesis. *Mol Gen Genet*. 1984;197(1):82-9.
Nagamani et al. Optimizing therapy for argininosuccinic aciduria. *Mol Genet Metab*. Sep. 2012;107(1-2):10-14. NIH Public Access Author Manuscript; available in PMC Sep. 1, 2013 (12 pages).
Nicaise et al. Control of acute, chronic, and constitutive hyperammonemia by wild-type and genetically engineered *Lactobacillus plantarum* in rodents. *Hepatology*. Oct. 2008;48(4):1184-92.
Nicoloff et al. Two arginine repressors regulate arginine biosynthesis in *Lactobacillus plantarum*. *J Bacteriol*. Sep. 2004;186(18):6059-69.
Nougayrede et al. *Escherichia coli* induces DNA double-strand breaks in eukaryotic cells. *Science*. Aug. 11, 2006;313(5788):848-51.
Olier et al. Genotoxicity of *Escherichia coli* Nissle 1917 strain cannot be dissociated from its probiotic activity. *Gut Microbes*. Nov.-Dec. 2012;3(6):501-9.
Pham et al. Multiple myeloma-induced hyperammonemic encephalopathy: An entity associated with high in-patient mortality. *Leuk Res*. Oct. 2013;37(10):1229-32.

(56) References Cited

OTHER PUBLICATIONS

Purcell et al. Rule-Based Design of Synthetic Transcription Factors in Eukaryotes. *ACS Synthetic Biology*. 2014;3(10):737-744; online publication date Dec. 12, 2013.
Rajagopal et al. Use of inducible feedback-resistant *N*-acetylglutamate synthetase (*argA*) genes for enhanced arginine biosynthesis by genetically engineered *Escherichia coli* K-12 strains. *Appl Environ Microbiol*. May 1998;64(5):1805-11.
Ray et al. The effects of mutation of the *anr* gene on the aerobic respiratory chain of *Pseudomonas aeruginosa*. *FEMS Microbiol Lett*. Nov. 15, 1997;156(2):227-32.
Reboul et al. Structural and dynamic requirements for optimal activity of the essential bacterial enzyme dihydrodipicolinate synthase. *PLoS Comput Biol*. 2012;8(6):e1002537 [online] DOI: 10.1371/journal.pcbi.1002537 (11 pages).
Reister et al. Complete genome sequence of the Gram-negative probiotic *Escherichia coli* strain Nissle 1917. *J Biotechnol*. Oct. 10, 2014;187:106-7.
Rembacken et al. Non-pathogenic *Escherichia coli* versus mesalazine for the treatment of ulcerative colitis: a randomised trial. *Lancet*. Aug. 21, 1999;354(9179):635-9.
Saint-Girons et al. Structure and autoregulation of the *metJ* regulatory gene in *Escherichia coli*. *J Biol Chem*. Nov. 25, 1984;259(22):14282-5.
Salmon et al. Global gene expression profiling in *Escherichia coli* K12. The effects of oxygen availability and FNR. *J Biol Chem*. Aug. 8, 2003;278(32):29837-55.
Sat et al. The *Escherichia coli mazEF* suicide module mediates thymineless death. *J Bacteriol*. Mar. 2003;185(6):1803-7.
Sawers. Identification and molecular characterization of a transcriptional regulator from *Pseudomonas aeruginosa* PAO1 exhibiting structural and functional similarity to the FNR protein of *Escherichia coli*. *Mol Microbiol*. Jun. 1991;5(6):1469-81.
Schneider et al. Arginine catabolism and the arginine succinyltransferase pathway in *Escherichia coli*. *J Bacteriol*. Aug. 1998; 180(16): 4278-86.
Schultz. Clinical use of *E. coli* Nissle 1917 in inflammatory bowel disease. *Inflamm Bowel Dis*. Jul. 2008;14(7):1012-8.
Shoeman et al. Regulation of methionine synthesis in *Escherichia coli*: Effect of *metJ* gene product and S-adenosylmethionine on the expression of the *metF* gene. *Proc Natl Acad Sci U S A*. Jun. 1985;82(11):3601-5.
Sonnenborn and Schulze. The non-pathogenic *Escherichia coli* strain Nissle 1917—features of a versatile probiotic. *Microbial Ecology in Health and Disease*. 2009;21:122-58.
Suiter et al. Fitness consequences of a regulatory polymorphism in a seasonal environment. *Proc Natl Acad Sci U S A*. Oct. 28, 2003;100(22):12782-6.
Summerskill. On the origin and transfer of ammonia in the human gastrointestinal tract. *Medicine*. Nov. 1996;45(6):491-6.
Szwajkajzer et al. Quantitative analysis of DNA binding by the *Escherichia coli* arginine repressor. *J Mol Biol*. Oct. 5, 2001;312(5):949-62.
Tian et al. Binding of the arginine repressor of *Escherichia coli* K12 to its operator sites. *J Mol Biol*. Jul. 20, 1992;226(2):387-97.
Tian et al. Explanation for different types of regulation of arginine biosynthesis in *Escherichia coli* B and *Escherichia coli* K12 caused by a difference between their arginine repressors. *J Mol Biol*. Jan. 7, 1994;235(1):221-30.
Torres-Vega et al. Delivery of glutamine synthetase gene by baculovirus vectors: a proof of concept for the treatment of acute hyperammonemia. *Gene Ther*. Oct. 23, 2014;22(1):58-64.
Trunk et al. Anaerobic adaptation in *Pseudomonas aeruginosa*: definition of the Anr and Dnr regulons. *Environ Microbiol*. Jun. 2010;12(6):1719-33.
Tuchman et al. Enhanced production of arginine and urea by genetically engineered *Escherichia coli* K-12 strains. *Appl Environ Microbiol*. Jan. 1997;63(1):33-8.
Ukena et al. Probiotic *Escherichia coli* Nissle 1917 inhibits leaky gut by enhancing mucosal integrity. *PLoS One*. Dec. 12, 2007;2(12):e1308. [online] DOI: 10.1371/journal.pone.0001308 (11 pages).
Unden et al. Alternative respiratory pathways of *Escherichia coli*: energetics and transcriptional regulation in response to electron acceptors. *Biochim Biophys Acta*. Jul. 4, 1997;1320(3):217-34.
Van Heeswijk et al. Nitrogen assimilation in *Escherichia coli*: putting molecular data into a systems perspective. *Microbiol Mol Biol Rev*. Dec. 2013;77(4):628-95.
Vander Wauven et al. *Pseudomonas aeruginosa* mutants affected in anaerobic growth on arginine: evidence for a four-gene cluster encoding the arginine deiminase pathway. *J Bacteriol*. Dec. 1984;160(3):928-34.
Walker. Severe hyperammonaemia in adults not explained by liver disease. *Ann Clin Biochem*. May 2012;49(Pt 3):214-28.
Winteler et al. The homologous regulators ANR of *Pseudomonas aeruginosa* and FNR of *Escherichia coli* have overlapping but distinct specificities for anaerobically inducible promoters. *Microbiology*. Mar. 1996;142 (Pt 3):685-93.
Wright et al. GeneGuard: A modular plasmid system designed for biosafety. *ACS Synth Biol*. Mar. 20, 2015;4(3):307-16.
Wu et al. Direct regulation of the natural competence regulator gene *tfoX* by cyclic AMP (cAMP) and cAMP receptor protein in *Vibrios*. *Sci Rep*. Oct. 7, 2015;5:14921 (15 pages).
Zhang and Lin. DEG 5.0, a database of essential genes in both prokaryotes and eukaryotes. *Nucl. Acids Res*. 2009;37(suppl. 1):D455-8.
Zimmermann et al. Anaerobic growth and cyanide synthesis of *Pseudomonas aeruginosa* depend on *anr*, a regulatory gene homologous with *fnr* of *Escherichia coli*. *Mol Microbiol*. Jun. 1991;5(6):1483-90.

* cited by examiner

FIG. 2A
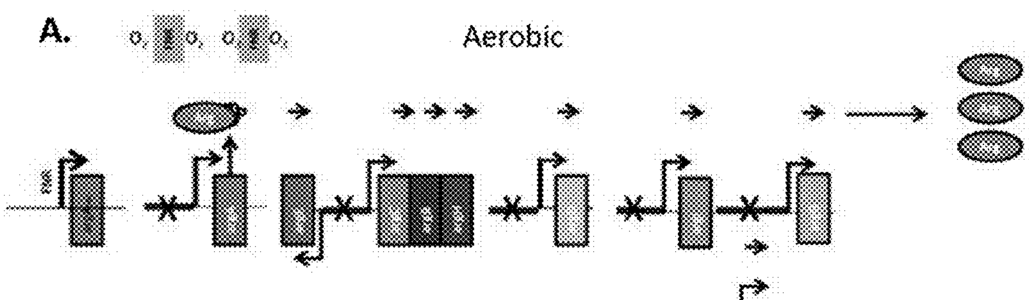
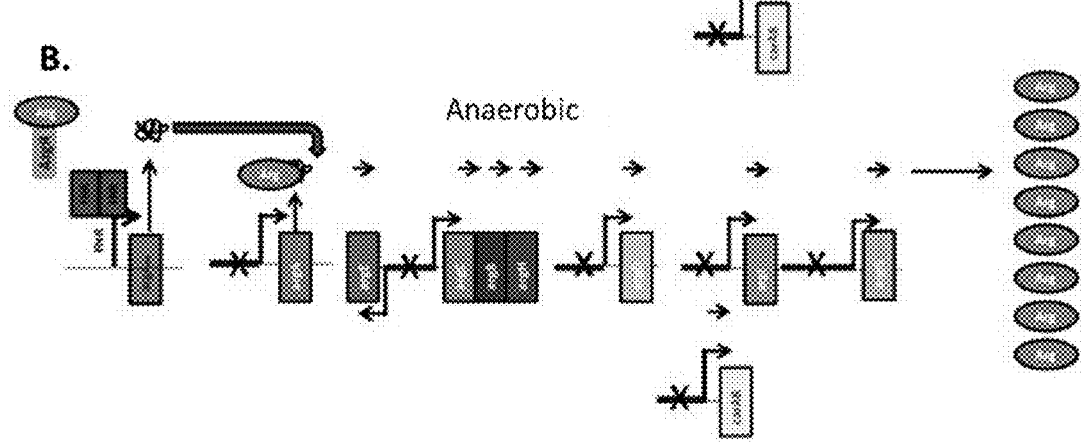
FIG. 2B

FIG. 3
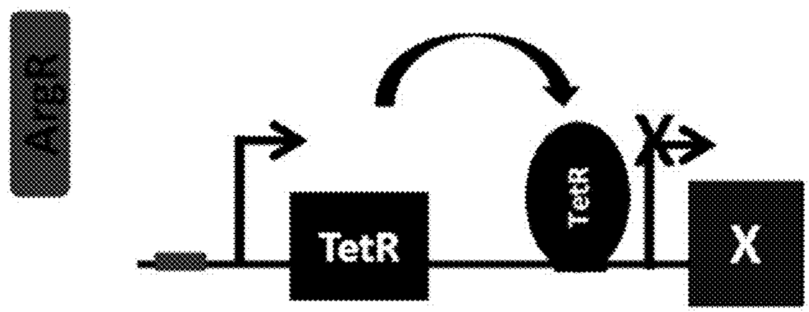
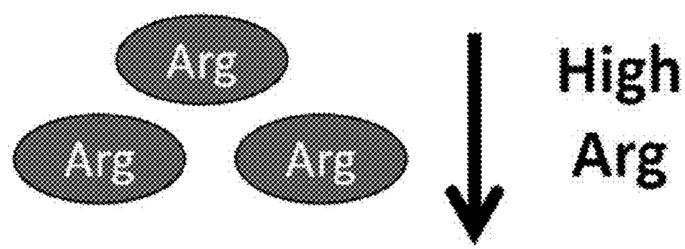
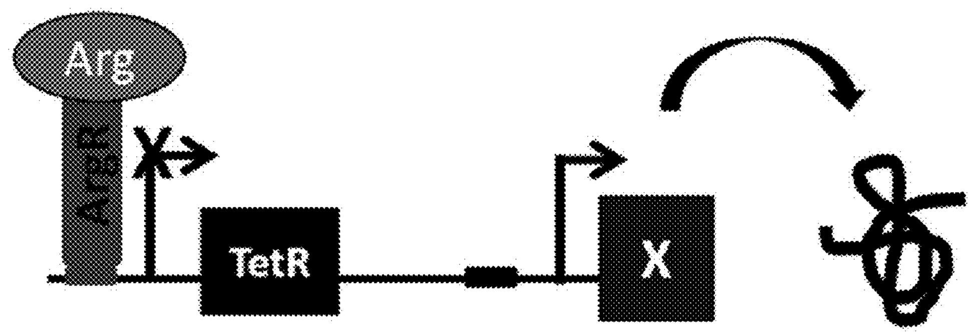

FIG. 6

| Regulatory region | 123456789012345678901234567890 |
| --- | --- |
| argA WT (SEQ ID NO: 1) | GCAAAAAAACAGAATAAAAATACAATAATT TCGAATAATCATGCAAAGAGGTGTACCGTG |
| argA mutant (SEQ ID NO: 2) | gcaaaaaaacactttaaaaacttaataatt tcctttaatcacttaaagaggtgtaccgtg |
| argI WT (SEQ ID NO: 3) | AGACTTGCAAATGAATAATCATCCATATAG ATTGAATTTTAATTCATTAAGGCGTTAGCC ACAGGAGGGATCTATG |
| argI mutant (SEQ ID NO: 4) | agacttgcaaacttatacttatccatatag attttgttttaatttgttaaggcgttagcc acaggagggatctatg |
| argCBH WT (SEQ ID NO: 5) | TCATTGTTGACACACCTCTGGTCATGATAG TATCAATATTCATGCAGTATTTATGAATAA AAATACACTAACGTTGAGCGTAATAAAACC CACCAGCCGTAAGGTGAATGTTTTACGTTT AACCTGGCAACCAGACATAAGAAGGTGAAT AGCCCCGATG |
| argCBH mutant (SEQ ID NO: 6) | tcattgttgacacacctctggtcatgatag tatcaaacttcatgggatatttatctttaa aaatacttgaacgttgagcgtaataaaacc caccagccgtaaggtgaatgttttacgttt aacctggcaaccagacataagaaggtgaat agccccgatg |

| Regulatory region | 123456789012345678901234567890 |
|---|---|
| argE WT (SEQ ID NO: 7) | CATCGGGGCTATTCACCTTCTTATGTCTGG TTGCCAGGTTAAACGTAAAACATTCACCTT ACGGCTGGTGGGTTTTATTACGCTCAACGT TAGTGTATTTTTATTCATAAATACTGCCATG AATATTGATACTATCATGACCAGAGGTGTG TCAACAATGA |
| argE mutant (SEQ ID NO: 8) | catcggggctattcaccttcttatgtctgg ttgccaggttaaacgtaaaacattcacctt acggctggtgggttttattacgctcaacgt tcaagtatttttaaagataaatatcccatg aagtttgatactatcatgaccagaggtgtg tcaacaatga |
| carAB WT (SEQ ID NO: 9) | AGCAGATTTGCATTGATTTACGTCATCATT GTGAATTAATATGCAAATAAAGTGAGTGAA TATTCTCTGGAGGGTGTTTTG |
| carAB mutant (SEQ ID NO: 10) | agcagatttgcattgatttacgtcatcatt gtcttttaatatcttaataactggagtgac gtttctctggagggtgttttg |
| argD WT (SEQ ID NO: 11) | TTTCTGATTGCCATTCAGTGATTTTTTATG CATATTTTGTGATTATAATTTCATATTTAT TTATGCGTAACAGGGTGATCATGAGATG |
| argD mutant (SEQ ID NO: 12) | tttctgattgccattcagtctttttttact tatattttgtctttataatcttatatttat ttatgcgtaacagggtgatcatgagatg |

FIG. 6 (Continued)

| Regulatory region | 123456789012345678901234567890 |
|---|---|
| argG WT (SEQ ID NO: 13) | CTAATCA***CG****TG*AATGA**ATA***TCCAGT*TCACT TTCATTTGTTGAATACTTTTACCTTCTCCT GCTTTCCCTTAAGCGCATTATTTTACAAAA AACACACTAAACTCTTCCTGTCTCCGATAA AAGATG*ATTAAATGAAAACTCATT*TAT*TTT* *GCATAAAAATTCAGT*GAAAGCAGAAATCCA GGCTCATCATCAGTTAATTAAGCAGGGTGT TATTTTATG |
| argG mutant (SEQ ID NO: 14) | ctaatcaccttaatgaatcttcagttcact ttcatttgttgaatacttttaccttctcct gctttcccttaagcgcattattttacaaaa aacacactaaactcttcctgtctccgataa aagatgatcttatgaaaaccttttttatttc ttataaaaatcttgtgaaagcagaaatcca ggctcatcatcagttaattaagcagggtgt tattttatg |
| argG mutant (SEQ ID NO: 15) | cctgaaacgtggcaaattctactcgttttg ggtaaaaaatgcaaatactgctgggatttg gtgtaccgagacgggacgtaaaatctgcag gcattatagtgatccacgccacattttgtc aacgtttattgctaatcattgacggctagc tcagtcctaggtacagtgctagcACCCGTT TTTTTGGGCTAGAAATAATTTTGTTTAACT TTAAGAAGGAGATATACATACCC |

| **FNR-responsive regulatory region** | **12345678901234567890123456789012345678901234567890** |
|---|---|
| SEQ ID NO: 16 | ATCCCCATCACTCTTGATGGAGATCAATTCCCCAAGCTGCTAGAGCGTTA<br>CCTTGCCCTTAAACATTAGCAATGTCGATTTATCAGAGGGCCGACAGGCT<br>CCCACAGGAGAAAACCG |
| SEQ ID NO: 17 | CTCTTGATCGTTATCAATTCCCACGCTGTTTCAGAGCGTTACCTTGCCCT<br>TAAACATTAGCAATGTCGATTTATCAGAGGGCCGACAGGCTCCCACAGGA<br>GAAAACCG |
| *nirB1*<br>SEQ ID NO: 18 | GTCAGCATAACACCCTGACCTCTCATTAATTGTTCATGCCGGGCGGCACT<br>ATCGTCGTCCGGCCTTTTCCTCTCTTACTCTGCTACGTACATCTATTTCT<br>ATAAATCCGTTCAATTTGTCTGTTTTTTGCACAAACATGAAATATCAGAC<br>AATTCCGTGACTTAAGAAAATTTATACAAATCAGCAATATACCCCTTAAG<br>GAGTATATAAAGGTGAATTTGATTTACATCAATAAGCGGGGTTGCTGAAT<br>CGTTAAGGTAGGCGGTAATAGAAAAGAAATCGAGGCAAAA |
| *nirB2*<br>SEQ ID NO: 19 | CGGCCCGATCGTTGAACATAGCGGTCCGCAGGCGGCACTGCTTACAGCAA<br>ACGGTCTGTACGCTGTCGTCTTTGTGATGTGCTTCCTGTTAGGTTTCGTC<br>AGCCGTCACCGTCAGCATAACACCCTGACCTCTCATTAATTGCTCATGCC<br>GGACGGCACTATCGTCGTCCGGCCTTTTCCTCTCTTCCCCCGCTACGTGC<br>ATCTATTTCTATAAACCCGCTCATTTTGTCTATTTTTTGCACAAACATGA<br>AATATCAGACAATTCCGTGACTTAAGAAAATTTATACAAATCAGCAATAT<br>ACCCATTAAGGAGTATATAAAGGTGAATTTGATTTACATCAATAAGCGGG<br>GTTGCTGAATCGTTAAGGTAGGCGGTAATAGAAAAGAAATCGAGGCAAAA<br>atgtttgtttaactttaagaaggagatatacat |
| *nirB3*<br>SEQ ID NO: 20 | GTCAGCATAACACCCTGACCTCTCATTAATTGCTCATGCCGGACGGCACT<br>ATCGTCGTCCGGCCTTTTCCTCTCTTCCCCCGCTACGTGCATCTATTTCT<br>ATAAACCCGCTCATTTTGTCTATTTTTTGCACAAACATGAAATATCAGAC<br>AATTCCGTGACTTAAGAAAATTTATACAAATCAGCAATATACCCATTAAG<br>GAGTATATAAAGGTGAATTTGATTTACATCAATAAGCGGGGTTGCTGAAT<br>CGTTAAGGTAGGCGGTAATAGAAAAGAAATCGAGGCAAAA |
| *ydfZ*<br>SEQ ID NO: 21 | ATTTCCTCTCATCCCATCCGGGGTGAGAGTCTTTTCCCCCGACTTATGGC<br>TCATGCATGCATCAAAAAAGATGTGAGCTTGATCAAAAACAAAAAATATT<br>TCACTCGACAGGAGTATTTATATTGCGCCCGTTACGTGGGCTTCGACTGT<br>AAATCAGAAAGGAGAAAACACCT |

| | |
|---|---|
| *nirB+RBS* SEQ ID NO: 22 | GTCAGCATAACACCCTGACCTCTCATTAATTGTTCATGCCGGGCGGCACTATCGTCGTCCGGCCTTTTCCTCTCTTACTCTGCTACGTACATCTATTTCTATAAATCCGTTCAATTTGTCTGTTTTTTGCACAAACATGAAATATCAGACAATTCCGTGACTTAAGAAAATTTATACAAATCAGCAATATACCCCTTAAGGAGTATATAAAGGTGAATTTGATTTACATCAATAAGCGGGGTTGCTGAATCGTTAA**GGATCC**CTCTAGAAATAATTTTGTTTAACTTTAAGAAGGAGATATACAT |
| *ydfZ+RBS* SEQ ID NO: 23 | CATTTCCTCTCATCCCATCCGGGGTGAGAGTCTTTTCCCCCGACTTATGGCTCATGCATGCATCAAAAAAGATGTGAGCTTGATCAAAAACAAAAAATATTTCACTCGACAGGAGTATTTATATTGCGCCC**GGATCC**CTCTAGAAATAATTTTGTTTAACTTTAAGAAGGAGATATACAT |
| *fnrS1* SEQ ID NO: 24 | AGTTGTTCTTATTGGTGGTGTTGCTTTATGGTTGCATCGTAGTAAATGGTTGTAACAAAAGCAATTTTTCCGGCTGTCTGTATACAAAAACGCCGTAAAGTTTGAGCGAAGTCAATAAACTCTCTACCCATTCAGGGCAATATCTCTCTT**GGATCC**CTCTAGAAATAATTTTGTTTAACTTTAAGAAGGAGATATACAT |
| *fnrS2* SEQ ID NO: 25 | AGTTGTTCTTATTGGTGGTGTTGCTTTATGGTTGCATCGTAGTAAATGGTTGTAACAAAAGCAATTTTTCCGGCTGTCTGTATACAAAAACGCCGCAAAGTTTGAGCGAAGTCAATAAACTCTCTACCCATTCAGGGCAATATCTCTCTTGGATCCAAAGTGAACTCTAGAAATAATTTTGTTTAACTTTAAGAAGGAGATATACAT |
| *nirB+crp* SEQ ID NO: 26 | TCGTCTTTGTGATGTGCTTCCTGTTAGGTTTCGTCAGCCGTCACCGTCAGCATAACACCCTGACCTCTCATTAATTGCTCATGCCGGACGGCACTATCGTCGTCCGGCCTTTTCCTCTCTTCCCCCGCTACGTGCATCTATTTCTATAAACCCGCTCATTTTGTCTATTTTTTGCACAAACATGAAATATCAGACAATTCCGTGACTTAAGAAAATTTATACAAATCAGCAATATACCCATTAAGGAGTATATAAAGGTGAATTTGATTTACATCAATAAGCGGGGTTGCTGAATCGTTAAGGTAGaaatgtgatctagttcacatttGCGGTAATAGAAAAGAAATCGAGGCAAAA*atgtttgtttaactttaagaaggagatatacat* |
| *fnrS+crp* SEQ ID NO: 27 | AGTTGTTCTTATTGGTGGTGTTGCTTTATGGTTGCATCGTAGTAAATGGTTGTAACAAAAGCAATTTTTCCGGCTGTCTGTATACAAAAACGCCGCAAAGTTTGAGCGAAGTCAATAAACTCTCTACCCATTCAGGGCAATATCTCTCaaatgtgatctagttcacattt*tttgtttaactttaagaaggagatatacat* |

**Nucleotide sequence of exemplary *argA*$^{fbr}$ sequence**

(SEQ ID NO: 28)

ATGGTAAAGGAACGTAAAACCGAGTTGGTCGAGGGATTCCGCCATTCGGTTCCCTGTA
TCAATACCCACCGGGGAAAAACGTTTGTCATCATGCTCGGCGGTGAAGCCATTGAGCA
TGAGAATTTCTCCAGTATCGTTAATGATATCGGGTTGTTGCACAGCCTCGGCATCCGT
CTGGTGGTGGTCTATGGCGCACGTCCGCAGATCGACGCAAATCTGGCTGCGCATCACC
ACGAACCGCTGTATCACAAGAATATACGTGTGACCGACGCCAAAACACTGGAACTGGT
GAAGCAGGCTGCGGGAACATTGCAACTGGATATTACTGCTCGCCTGTCGATGAGTCTC
AATAACACGCCGCTGCAGGGCGCGCATATCAACGTCGTCAGTGGCAATTTTATTATTG
CCCAGCCGCTGGGCGTCGATGACGGCGTGGATTACTGCCATAGCGGGCGTATCCGGCG
GATTGATGAAGACGCGATCCATCGTCAACTGGACAGCGGTGCAATAGTGCTAATGGGG
CCGGTCGCTGTTTCAGTCACTGGCGAGAGCTTTAACCTGACCTCGGAAGAGATTGCCA
CTCAACTGGCCATCAAACTGAAAGCTGAAAAGATGATTGGTTTTTGCTCTTCCCAGGG
CGTCACTAATGACGACGGTGATATTGTCTCCGAACTTTTCCCTAACGAAGCGCAAGCG
CGGGTAGAAGCCCAGGAAGAGAAAGGCGATTACAACTCCGGTACGGTGCGCTTTTTGC
GTGGCGCAGTGAAAGCCTGCCGCAGCGGCGTGCGTCGCTGTCATTTAATCAGTTATCA
GGAAGATGGCGCGCTGTTGCAAGAGTTGTTCTCACGCGACGGTATCGGTACGCAGATT
GTGATGGAAAGCGCCGAGCAGATTCGTCGCGCAACAATCAACGATATTGGCGGTATTC
TGGAGTTGATTCGCCCACTGGAGCAGCAAGGTATTCTGGTACGCCGTTCTCGCGAGCA
GCTGGAGATGGAAATCGACAAATTCACCATTATTCAGCGCGATAACACGACTATTGCC
TGCGCCGCGCTCTATCCGTTCCCGGAAGAGAAGATTGGGGAAATGGCCTGTGTGGCAG
TTCACCCGGATTACCGCAGTTCATCAAGGGGTGAAGTTCTGCTGGAACGCATTGCCGC
TCAGGCTAAGCAGAGCGGCTTAAGCAAATTGTTTGTGCTGACCACGCGCAGTATTCAC
TGGTTCCAGGAACGTGGATTTACCCCAGTGGATATTGATTTACTGCCCGAGAGCAAAA
AGCAGTTGTACAACTACCAGCGTAAATCCAAAGTGTTGATGGCGGATTTAGGGTAA

FIG. 8B

**Nucleotide sequence of exemplary FNR promoter-driven *argA^fbr* plasmid**

(SEQ ID NO: 29)

GTAAAACGACGGCCAGTGAATTCGAGCTCGGTACCATCCCCATCACTCTTGATGGAGATCAA
TTCCCCAAGCTGCTAGAGCGTTACCTTGCCCTTAAACATTAGCAATGTCGATTTATCAGAGG
GCCGACAGGCTCCCACAGGAGAAAACCGATGGTAAAGGAACGTAAAACCGAGTTGGTCGAGG
GATTCCGCCATTCGGTTCCCTGTATCAATACCCACCGGGAAAAACGTTTGTCATCATGCTC
GGCGGTGAAGCCATTGAGCATGAGAATTTCTCCAGTATCGTTAATGATATCGGGTTGTTGCA
CAGCCTCGGCATCCGTCTGGTGGTGGTCTATGGCGCACGTCCGCAGATCGACGCAAATCTGG
CTGCGCATCACCACGAACCGCTGTATCACAAGAATATACGTGTGACCGACGCCAAAACACTG
GAACTGGTGAAGCAGGCTGCGGGAACATTGCAACTGGATATTACTGCTCGCCTGTCGATGAG
TCTCAATAACACGCCGCTGCAGGGCGCGCATATCAACGTCGTCAGTGGCAATTTTATTATTG
CCCAGCCGCTGGGCGTCGATGACGGCGTGGATTACTGCCATAGCGGGCGTATCCGGCGGATT
GATGAAGACGCGATCCATCGTCAACTGGACAGCGGTGCAATAGTGCTAATGGGGCCGGTCGC
TGTTTCAGTCACTGGCGAGAGCTTTAACCTGACCTCGGAAGAGATTGCCACTCAACTGGCCA
TCAAACTGAAAGCTGAAAAGATGATTGGTTTTTGCTCTTCCCAGGGCGTCACTAATGACGAC
GGTGATATTGTCTCCGAACTTTTCCCTAACGAAGCGCAAGCGCGGGTAGAAGCCCAGGAAGA
GAAAGGCGATTACAACTCCGGTACGGTGCGCTTTTTGCGTGGCGCAGTGAAAGCCTGCCGCA
GCGGCGTGCGTCGCTGTCATTTAATCAGTTATCAGGAAGATGGCGCGCTGTTGCAAGAGTTG
TTCTCACGCGACGGTATCGGTACGCAGATTGTGATGGAAAGCGCCGAGCAGATTCGTCGCGC
AACAATCAACGATATTGGCGGTATTCTGGAGTTGATTCGCCCACTGGAGCAGCAAGGTATTC
TGGTACGCCGTTCTCGCGAGCAGCTGGAGATGGAAATCGACAAATTCACCATTATTCAGCGC
GATAACACGACTATTGCCTGCGCCGCGCTCTATCCGTTCCCGGAAGAGAAGATTGGGGAAAT
GGCCTGTGTGGCAGTTCACCCGGATTACCGCAGTTCATCAAGGGGTGAAGTTCTGCTGGAAC
GCATTGCCGCTCAGGCTAAGCAGAGCGGCTTAAGCAAATTGTTTGTGCTGACCACGCGCAGT
ATTCACTGGTTCCAGGAACGTGGATTTACCCCAGTGGATATTGATTTACTGCCCGAGAGCAA
AAAGCAGTTGTACAACTACCAGCGTAAATCCAAAGTGTTGATGGCGGATTTAGGGTAAACAG
AATAAAAATACAATAATTTCGAATAATCATGCAAAGCTTGGCGTAATCATGGTCATAGCTGT
TTCCTGTGTGAAATTGTTATCCGCTCACAATTCCACACAACATACGAGCCGGAAGCATGTAC
GGGTTTTGCTGCCCGCAAACGGGCTGTTCTGGTGTTGCTAGTTTGTTATCAGAATCGCAGAT
CCGGCTTCAGGTTTGCCGGCTGAAAGCGCTATTTCTTCCAGAATTGCCATGATTTTTTCCCC
ACGGGAGGCGTCACTGGCTCCCGTGTTGTCGGCAGCTTTGATTCGATAAGCAGCATCGCCTG
TTTCAGGCTGTCTATGTGTGACTGTTGAGCTGTAACAAGTTGTCTCAGGTGTTCAATTTCAT
GTTCTAGTTGCTTTGTTTTACTGGTTTCACCTGTTCTATTAGGTGTTACATGCTGTTCATCT
GTTACATTGTCGATCTGTTCATGGTGAACAGCTTTAAATGCACCAAAAACTCGTAAAAGCTC
TGATGTATCTATCTTTTTTACACCGTTTTCATCTGTGCATATGGACAGTTTTCCCTTTGATA
TCTAACGGTGAACAGTTGTTCTACTTTTGTTTGTTAGTCTTGATGCTTCACTGATAGATACA
AGAGCCATAAGAACCTCAGATCCTTCCGTATTTAGCCAGTATGTTCTCTAGTGTGGTTCGTT
GTTTTTGCGTGAGCCATGAGAACGAACCATTGAGATCATGCTTACTTTGCATGTCACTCAAA
AATTTTGCCTCAAAACTGGTGAGCTGAATTTTTGCAGTTAAAGCATCGTGTAGTGTTTTTCT
TAGTCCGTTACGTAGGTAGGAATCTGATGTAATGGTTGTTGGTATTTTGTCACCATTCATTT
TTATCTGGTTGTTCTCAAGTTCGGTTACGAGATCCATTTGTCTATCTAGTTCAACTTGGAAA
ATCAACGTATCAGTCGGGCGGCCTCGCTTATCAACCACCAATTTCATATTGCTGTAAGTGTT
TAAATCTTTACTTATTGGTTTCAAAACCCATTGGTTAAGCCTTTTAAACTCATGGTAGTTAT
TTTCAAGCATTAACATGAACTTAAATTCATCAAGGCTAATCTCTATATTTGCCTTGTGAGTT
TTCTTTTGTGTTAGTTCTTTTAATAACCACTCATAAATCCTCATAGAGTATTTGTTTTCAAA

```
AGACTTAACATGTTCCAGATTATATTTTATGAATTTTTTTAACTGGAAAAGATAAGGCAATA
TCTCTTCACTAAAAACTAATTCTAATTTTTCGCTTGAGAACTTGGCATAGTTTGTCCACTGG
AAAATCTCAAAGCCTTTAACCAAAGGATTCCTGATTTCCACAGTTCTCGTCATCAGCTCTCT
GGTTGCTTTAGCTAATACACCATAAGCATTTTCCCTACTGATGTTCATCATCTGAGCGTATT
GGTTATAAGTGAACGATACCGTCCGTTCTTTCCTTGTAGGGTTTTCAATCGTGGGGTTGAGT
AGTGCCACACAGCATAAAATTAGCTTGGTTTCATGCTCCGTTAAGTCATAGCGACTAATCGC
TAGTTCATTTGCTTTGAAAACAACTAATTCAGACATACATCTCAATTGGTCTAGGTGATTTT
AATCACTATACCAATTGAGATGGGCTAGTCAATGATAATTACTAGTCCTTTTCCTTTGAGTT
GTGGGTATCTGTAAATTCTGCTAGACCTTTGCTGGAAAACTTGTAAATTCTGCTAGACCCTC
TGTAAATTCCGCTAGACCTTTGTGTGTTTTTTTTGTTTATATTCAAGTGGTTATAATTTATA
GAATAAAGAAAGAATAAAAAAAGATAAAAAGAATAGATCCCAGCCCTGTGTATAACTCACTA
CTTTAGTCAGTTCCGCAGTATTACAAAAGGATGTCGCAAACGCTGTTTGCTCCTCTACAAAA
CAGACCTTAAAACCCTAAAGGCTTAAGTAGCACCCTCGCAAGCTCGGGCAAATCGCTGAATA
TTCCTTTTGTCTCCGACCATCAGGCACCTGAGTCGCTGTCTTTTTCGTGACATTCAGTTCGC
TGCGCTCACGGCTCTGGCAGTGAATGGGGGTAAATGGCACTACAGGCGCCTTTTATGGATTC
ATGCAAGGAAACTACCCATAATACAAGAAAAGCCCGTCACGGGCTTCTCAGGGCGTTTTATG
GCGGGTCTGCTATGTGGTGCTATCTGACTTTTTGCTGTTCAGCAGTTCCTGCCCTCTGATTT
TCCAGTCTGACCACTTCGGATTATCCCGTGACAGGTCATTCAGACTGGCTAATGCACCCAGT
AAGGCAGCGGTATCATCAACAGGCTTACCCGTCTTACTGTCTTTTCTACGGGGTCTGACGCT
CAGTGGAACGAAAACTCACGTTAAGGGATTTTGGTCATGAGATTATCAAAAAGGATCTTCAC
CTAGATCCTTTTAAATTAAAAATGAAGTTTTAAATCAATCTAAAGTATATATGAGTAAACTT
GGTCTGACAGTTACCAATGCTTAATCAGTGAGGCACCTATCTCAGCGATCTGTCTATTTCGT
TCATCCATAGTTGCCTGACTCCCCGTCGTGTAGATAACTACGATACGGGAGGGCTTACCATC
TGGCCCCAGTGCTGCAATGATACCGCGAGACCCACGCTCACCGGCTCCAGATTTATCAGCAA
TAAACCAGCCAGCCGGAAGGGCCGAGCGCAGAAGTGGTCCTGCAACTTTATCCGCCTCCATC
CAGTCTATTAATTGTTGCCGGGAAGCTAGAGTAAGTAGTTCGCCAGTTAATAGTTTGCGCAA
CGTTGTTGCCATTGCTACAGGCATCGTGGTGTCACGCTCGTCGTTTGGTATGGCTTCATTCA
GCTCCGGTTCCCAACGATCAAGGCGAGTTACATGATCCCCCATGTTGTGCAAAAAAGCGGTT
AGCTCCTTCGGTCCTCCGATCGTTGTCAGAAGTAAGTTGGCCGCAGTGTTATCACTCATGGT
TATGGCAGCACTGCATAATTCTCTTACTGTCATGCCATCCGTAAGATGCTTTTCTGTGACTG
GTGAGTACTCAACCAAGTCATTCTGAGAATAGTGTATGCGGCGACCGAGTTGCTCTTGCCCG
GCGTCAATACGGGATAATACCGCGCCACATAGCAGAACTTTAAAAGTGCTCATCATTGGAAA
ACGTTCTTCGGGGCGAAAACTCTCAAGGATCTTACCGCTGTTGAGATCCAGTTCGATGTAAC
CCACTCGTGCACCCAACTGATCTTCAGCATCTTTTACTTTCACCAGCGTTTCTGGGTGAGCA
AAAACAGGAAGGCAAAATGCCGCAAAAAAGGGAATAAGGGCGACACGGAAATGTTGAATACT
CATACTCTTCCTTTTTCAATATTATTGAAGCATTTATCAGGGTTATTGTCTCATGAGCGGAT
ACATATTTGAATGTATTTAGAAAAATAAACAAATAGGGGTTCCGCGCACATTTCCCCGAAAA
GTGCCACCTGACGTCTAAGAAACCATTATTATCATGACATTAACCTATAAAAATAGGCGTAT
CACGAGGCCCTTTCGTCTCGCGCGTTTCGGTGATGACGGTGAAAACCTCTGACACATGCAGC
TCCCGGAGACGGTCACAGCTTGTCTGTAAGCGGATGCCGGGAGCAGACAAGCCCGTCAGGGC
GCGTCAGCGGGTGTTGGCGGGTGTCGGGGCTGGCTTAACTATGCGGCATCAGAGCAGATTGT
ACTGAGAGTGCACCATATGCGGTGTGAAATACCGCACAGATGCGTAAGGAGAAAATACCGCA
TCAGGCGCCATTCGCCATTCAGGCTGCGCAACTGTTGGGAAGGGCGATCGGTGCGGGCCTCT
TCGCTATTACGCCAGCTGGCGAAAGGGGGATGTGCTGCAAGGCGATTAAGTTGGGTAACGCC
AGGGTTTTCCCAGTCACGACGTT
```

**Nucleotide sequence of exemplary FNR promoter-driven *argA*$^{fbr}$ sequence**

(SEQ ID NO: 30)

AGTTGTTCTTATTGGTGGTGTTGCTTTATGGTTGCATCGTAGTAAATGGTTGTAACAA
AAGCAATTTTTCCGGCTGTCTGTATACAAAAACGCCGCAAAGTTTGAGCGAAGTCAAT
AAACTCTCTACCCATTCAGGGCAATATCTCTCTTggatccaaagtgaactctagaaat
aattttgtttaactttaagaaggagatatacatATGGTAAAGGAACGTAAAACCGAG
TTGGTCGAGGGATTCCGCCATTCGGTTCCCTGTATCAATACCCACCGGGGAAAAACG
TTTGTCATCATGCTCGGCGGTGAAGCCATTGAGCATGAGAATTTCTCCAGTATCGTT
AATGATATCGGGTTGTTGCACAGCCTCGGCATCCGTCTGGTGGTGGTCTATGGCGCA
CGTCCGCAGATCGACGCAAATCTGGCTGCGCATCACCACGAACCGCTGTATCACAAG
AATATACGTGTGACCGACGCCAAAACACTGGAACTGGTGAAGCAGGCTGCGGGAACA
TTGCAACTGGATATTACTGCTCGCCTGTCGATGAGTCTCAATAACACGCCGCTGCAG
GGCGCGCATATCAACGTCGTCAGTGGCAATTTTATTATTGCCCAGCCGCTGGGCGTC
GATGACGGCGTGGATTACTGCCATAGCGGGCGTATCCGGCGGATTGATGAAGACGCG
ATCCATCGTCAACTGGACAGCGGTGCAATAGTGCTAATGGGGCCGGTCGCTGTTTCA
GTCACTGGCGAGAGCTTTAACCTGACCTCGGAAGAGATTGCCACTCAACTGGCCATC
AAACTGAAAGCTGAAAAGATGATTGGTTTTTGCTCTTCCCAGGGCGTCACTAATGAC
GACGGTGATATTGTCTCCGAACTTTTCCCTAACGAAGCGCAAGCGCGGGTAGAAGCC
CAGGAAGAGAAAGGCGATTACAACTCCGGTACGGTGCGCTTTTTGCGTGGCGCAGTG
AAAGCCTGCCGCAGCGGCGTGCGTCGCTGTCATTTAATCAGTTATCAGGAAGATGGC
GCGCTGTTGCAAGAGTTGTTCTCACGCGACGGTATCGGTACGCAGATTGTGATGGAA
AGCGCCGAGCAGATTCGTCGCGCAACAATCAACGATATTGGCGGTATTCTGGAGTTG
ATTCGCCCACTGGAGCAGCAAGGTATTCTGGTACGCCGTTCTCGCGAGCAGCTGGAG
ATGGAAATCGACAAATTCACCATTATTCAGCGCGATAACACGACTATTGCCTGCGCC
GCGCTCTATCCGTTCCCGGAAGAGAAGATTGGGGAAATGGCCTGTGTGGCAGTTCAC
CCGGATTACCGCAGTTCATCAAGGGGTGAAGTTCTGCTGGAACGCATTGCCGCTCAG
GCTAAGCAGAGCGGCTTAAGCAAATTGTTTGTGCTGACCACGCGCAGTATTCACTGG
TTCCAGGAACGTGGATTTACCCCAGTGGATATTGATTTACTGCCCGAGAGCAAAAAG
CAGTTGTACAACTACCAGCGTAAATCCAAAGTGTTGATGGCGGATTTAGGGTAA FIG. 13A
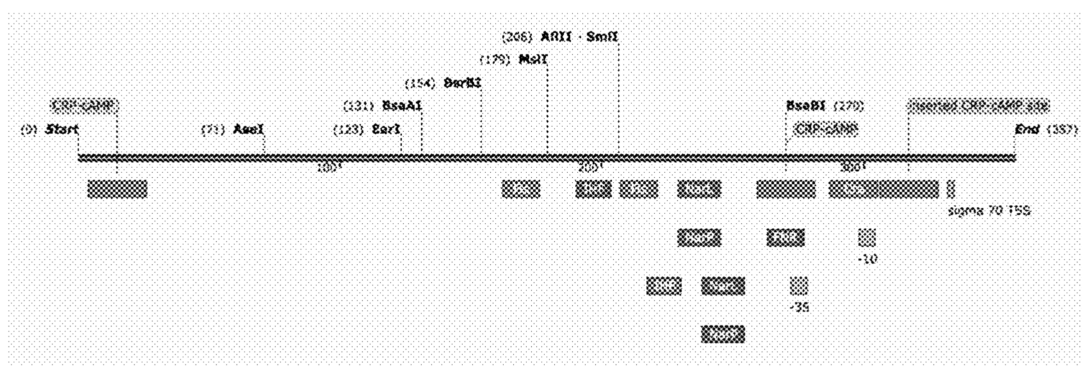
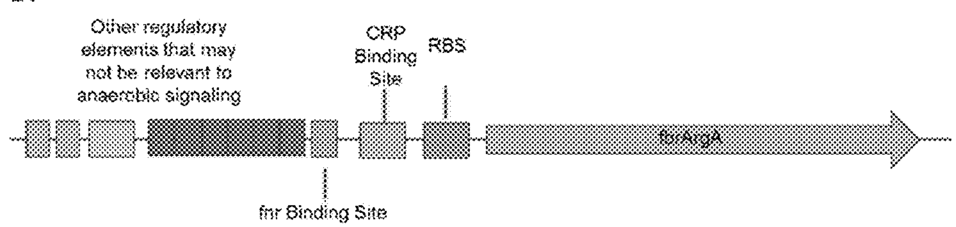
FIG. 13B FIG. 14A
A.
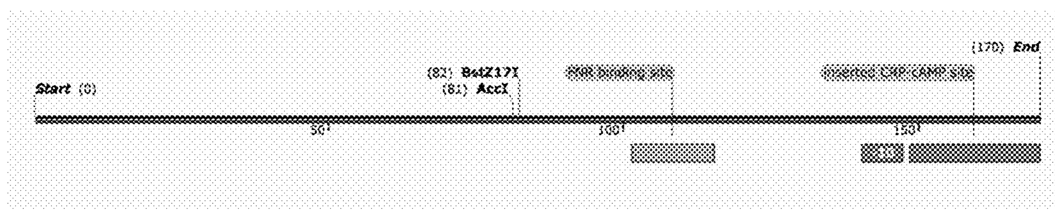
B.
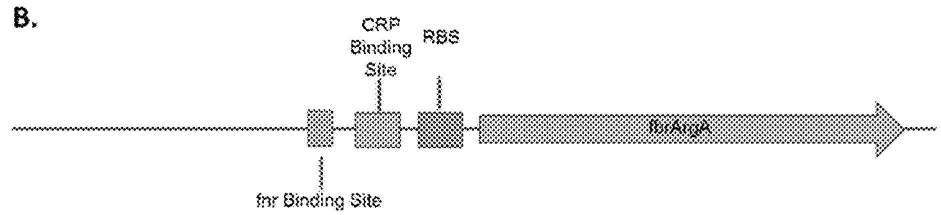
FIG. 14B

FIG. 15

| | |
|---|---|
| **Wild-type argG (SEQ ID NO: 31)** | gtgatccacgccacattttgtcaacgtttattgctaatcaCGTG AATGAATATCCAGTtcactttcatttgttgaatacttttacctt ctcctgctttcccttaagcgcattattttacaaaaaacacacta aactcttcctgtctccgataaaagatgATTAAATGAAAACTCAT TtatTTTGCATAAAAATTCAGTgaaagcagaaatccaggctcat catcagttaattaagcagggtgttattttatgacgacgattct caagcatctcccggtaggtcaacgtattggtatcgctttttcc ggcggtctggacaccagtgccgcactgctgtggatgcgacaaa agggagcggttccttatgcatatactgcaaacctgggccagcc agacgaagaggattatgatgcgatccctcgtcgtgccatggaa tacggcgcggagaacgcacgtctgatcgactgccgcaaacaac tggtggccgaaggtattgccgctattcagtgtggcgcatttca taacaccactggtggactgacctatttcaacacgacgccgctg ggccgcgccgtgaccggcaccatgctggttgctgctatgaaag aagatggcgtgaatatctggggtgacggcagcacctataaagg aaacgatatcgaacgtttctaccgttacggtctgctgaccaat gctgaactgcagatttacaaaccgtggcttgatactgacttta ttgatgaactgggtggccgtcatgagatgtctgaatttatgat tgcctgcggtttcgactacaaaatgtctgtcgaaaaagcttac tccacggactccaacatgcttggtgcaacgcatgaagcgaagg atctggaatacctcaactccagcgtcaaaatcgtcaacccaat tatgggcgtgaagttttgggatgagagcgtgaaaatcccggca gaagaagtcacagtacgctttgagcaaggtcatccggtggcgc tgaacggtaaaacctttagcgacgacgtagaaatgatgctgga agctaaccgcatcggc |
| **Constitutive argG (SEQ ID NO: 31)** | ttgacggctagctcagtcctaggtacagtgctagcACCCGTTTT TTTGGGCTAGAAATAATTTTGTTTAACTTTAAGAAGGAGATATA CATACCCatgacgacgattctcaagcatctcccggtaggtcaa |

| | |
|---|---|
| | cgtattggtatcgctttttccggcggtctggacaccagtgccg<br>cactgctgtggatgcgacaaaagggagcggttccttatgcata<br>tactgcaaacctgggccagccagacgaagaggattatgatgcg<br>atccctcgtcgtgccatggaatacggcgcggagaacgcacgtc<br>tgatcgactgccgcaaacaactggtggccgaaggtattgccgc<br>tattcagtgtggcgcatttcataacaccactggtggactgacc<br>tatttcaacacgacgccgctgggccgcgccgtgaccggcacca<br>tgctggttgctgctatgaaagaagatggcgtgaatatctgggg<br>tgacggcagcacctataaaggaaacgatatcgaacgtttctac<br>cgttacggtctgctgaccaatgctgaactgcagatttacaaac<br>cgtggcttgatactgactttattgatgaactgggtggccgtca<br>tgagatgtctgaatttatgattgcctgcggtttcgactacaaa<br>atgtctgtcgaaaaagcttactccacggactccaacatgcttg<br>gtgcaacgcatgaagcgaaggatctggaatacctcaactccag<br>c |

**Nucleotide sequence of exemplary BAD promoter-driven *argA*$^{fbr}$ (SEQ ID NO: 33)**

cgacggtggcgataggcatccgggtggtgctcaaaagcagcttcgcctgactgatgcgc
tggtcctcgcgccagcttaatacgctaatccctaactgctggcggaacaaatgcgacag
acgcgacggcgacaggcagacatgctgtgcgacgctggcgatatcaaaattactgtctg
ccaggtgatcgctgatgtactgacaagcctcgcgtacccgattatccatcggtggatgg
agcgactcgttaatcgcttccatgcgccgcagtaacaattgctcaagcagatttatcgc
cagcaattccgaatagcgcccttccccttgtccggcattaatgatttgcccaaacaggt
cgctgaaatgcggctggtgcgcttcatccgggcgaaagaaaccggtattggcaaatatc
gacggccagttaagccattcatgccagtaggcgcgcggacgaaagtaaacccactggtg
ataccattcgtgagcctccggatgacgaccgtagtgatgaatctctccaggcgggaaca
gcaaaatatcacccggtcggcagacaaattctcgtccctgatttttcaccacccctga
ccgcgaatggtgagattgagaatataacctttcattcccagcggtcggtcgataaaaaa
atcgagataaccgttggcctcaatcggcgttaaacccgccaccagatgggcgttaaacg
agtatcccggcagcaggggatcattttgcgcttcagccatacttttcatactcccgcca
ttcagagaagaaaccaattgtccatattgcatcagacattgccgtcactgcgtcttta
ctggctcttctcgctaacccaaccggtaaccccgcttattaaaagcattctgtaacaaa
gcgggaccaaagccatgacaaaaacgcgtaacaaaagtgtctataatcacggcagaaaa
gtccacattgattatttgcacggcgtcacactttgctatgccatagcatttttatccat
aagattagcggatccagcctgacgctttttttcgcaactctctactgtttctccata*cc*
*cgtttttttggatggagtgaaacg*ATGGTAAAGGAACGTAAAACCGAGTTGGTCGAGGG
ATTCCGCCATTCGGTTCCCTGTATCAATACCCACCGGGGAAAAACGTTTGTCATCATGC
TCGGCGGTGAAGCCATTGAGCATGAGAATTTCTCCAGTATCGTTAATGATATCGGGTTG
TTGCACAGCCTCGGCATCCGTCTGGTGGTGGTCTATGGCGCACGTCCGCAGATCGACGC
AAATCTGGCTGCGCATCACCACGAACCGCTGTATCACAAGAATATACGTGTGACCGACG
CCAAAACACTGGAACTGGTGAAGCAGGCTGCGGGAACATTGCAACTGGATATTACTGCT
CGCCTGTCGATGAGTCTCAATAACACGCCGCTGCAGGGCGCGCATATCAACGTCGTCAG
TGGCAATTTTATTATTGCCCAGCCGCTGGGCGTCGATGACGGCGTGGATTACTGCCATA
GCGGGCGTATCCGGCGGATTGATGAAGACGCGATCCATCGTCAACTGGACAGCGGTGCA
ATAGTGCTAATGGGGCCGGTCGCTGTTTCAGTCACTGGCGAGAGCTTTAACCTGACCTC GGAAGAGATTGCCACTCAACTGGCCATCAAACTGAAAGCTGAAAAGATGATTGGTTTTT
GCTCTTCCCAGGGCGTCACTAATGACGACGGTGATATTGTCTCCGAACTTTTCCCTAAC
GAAGCGCAAGCGCGGGTAGAAGCCCAGGAAGAGAAAGGCGATTACAACTCCGGTACGGT
GCGCTTTTTGCGTGGCGCAGTGAAAGCCTGCCGCAGCGGCGTGCGTCGCTGTCATTTAA
TCAGTTATCAGGAAGATGGCGCGCTGTTGCAAGAGTTGTTCTCACGCGACGGTATCGGT
ACGCAGATTGTGATGGAAAGCGCCGAGCAGATTCGTCGCGCAACAATCAACGATATTGG
CGGTATTCTGGAGTTGATTCGCCCACTGGAGCAGCAAGGTATTCTGGTACGCCGTTCTC
GCGAGCAGCTGGAGATGGAAATCGACAAATTCACCATTATTCAGCGCGATAACACGACT
ATTGCCTGCGCCGCGCTCTATCCGTTCCCGGAAGAGAAGATTGGGGAAATGGCCTGTGT
GGCAGTTCACCCGGATTACCGCAGTTCATCAAGGGGTGAAGTTCTGCTGGAACGCATTG
CCGCTCAGGCTAAGCAGAGCGGCTTAAGCAAATTGTTTGTGCTGACCACGCGCAGTATT
CACTGGTTCCAGGAACGTGGATTTACCCCAGTGGATATTGATTTACTGCCCGAGAGCAA
AAAGCAGTTGTACAACTACCAGCGTAAATCCAAAGTGTTGATGGCGGATTTAGGGTAAT
GGGAATTAGCCATGGTCCATATGAATATCCTCCTTAGTTCCTATTCC gaagttcctatt
ccgaagttcctattctctagaaagtataggaacttc GAAGCAGCTCCAGCCTACACAAT
CGCTCAAGACGTGTAATGCTGCAATCTGCATGCAAGCTTGGCACTGGCCACGCAAAAAG
GCCATCCGTCAGGATGGCCTTCTGCTTAATTTGATGCCTGGCAGTTTATGGCGGGCGTC
CTGCCCGCCACCCTCCGGGCCGTTGCTTCGCAACGTTCAAATCCGCTCCCGGCGGATTT
GTCCTACTCAGGAGAGCGTTCACCGACAAACAACAGATAAAACGAAAGGCCCAGTCTTT
CGACTGAGCCTTTCGTTTTATTTGATGCCTGGCAGTTCCCTACTCTCGCATGctcgagc
catgggacgtccaggtattagaagccaacctggcgctgccaaaacacaacctggtcacg
ctcacctggggcaatgtcagcgccgttgatcgcgggcgcggcgtcctggtgatcaaacc
ttccggcgtcgactacagcatcatgaccgctgacgatatggtcgtggtcagcatcgaaa
ccggtgaagtggttgaaggtacgaaaaagccctcctccgacacgccaactcaccggctg
ctctatcaggcattcccgtctattggcggcattgtgcacacacactcgcgccacgccac
catctgggcgcaggcgggccagtcgattccagcagccggcaccacccacgccgactatt
tctacggcaccattccctgcacccgcaaaatgaccgacgcagaaatcaacggtgaatat
gagtgggaaaccggtaacgtcatcgtagaaaccttcgaaaaacagggtatcaatgcagc
gcaaatgcccggcgtgctggtccattctcacggcccatttgcatggggaaaaaacgccg

FIG. 18 (Continued)

aagatgcggtgcataacgccatcgtgctggaagaagtcgcttatatggggatattctgc
cgtcagttagcgccgcagttaccggatatgcagcaaacgctgctggataaacactatct
gcgtaagcatggcgcgaaggcatattacgggcagtaa FIG. 18 (Continued)

FIG. 21A

| pSC101 plasmid (SEQ ID NO: 34) |
|---|
| ATTAAGTTGGGTAACGCCAGGGTTTTCCCAGTCACGACGTTATTGCGTTGCGCTCACTGCCCGC<br>TTTCCAGTCGGGAAACCTGTCGTGCCAGCTGCATTAATGAATCGGCCAACGCGCGGGGAGAGGC<br>GGTTTGCGTATTGGGCGCTCTTCCGCTTCCTCGCTCACTGACTCGCTGCGCTCGGTCGTTCGGC<br>TGCGGCGAGCGGTATCAGCTCACTCAAAGGCGGTAGTACGGGTTTTGCTGCCCGCAAACGGGCT<br>GTTCTGGTGTTGCTAGTTTGTTATCAGAATCGCAGATCCGGCTTCAGGTTTGCCGGCTGAAAGC<br>GCTATTTCTTCCAGAATTGCCATGATTTTTTCCCCACGGGAGGCGTCACTGGCTCCCGTGTTGT<br>CGGCAGCTTTGATTCGATAAGCAGCATCGCCTGTTTCAGGCTGTCTATGTGTGACTGTTGAGCT<br>GTAACAAGTTGTCTCAGGTGTTCAATTTCATGTTCTAGTTGCTTTGTTTTACTGGTTTCACCTG<br>TTCTATTAGGTGTTACATGCTGTTCATCTGTTACATTGTCGATCTGTTCATGGTGAACAGCTTT<br>AAATGCACCAAAAACTCGTAAAAGCTCTGATGTATCTATCTTTTTTACACCGTTTTCATCTGTG<br>CATATGGACAGTTTTCCCTTTGATATCTAACGGTGAACAGTTGTTCTACTTTTGTTTGTTAGTC<br>TTGATGCTTCACTGATAGATACAAGAGCCATAAGAACCTCAGATCCTTCCGTATTTAGCCAGTA<br>TGTTCTCTAGTGTGGTTCGTTGTTTTTGCGTGAGCCATGAGAACGAACCATTGAGATCATGCTT<br>ACTTTGCATGTCACTCAAAAATTTTGCCTCAAAACTGGTGAGCTGAATTTTTGCAGTTAAAGCA<br>TCGTGTAGTGTTTTTCTTAGTCCGTTACGTAGGTAGGAATCTGATGTAATGGTTGTTGGTATTT<br>TGTCACCATTCATTTTTATCTGGTTGTTCTCAAGTTCGGTTACGAGATCCATTTGTCTATCTAG<br>TTCAACTTGGAAAATCAACGTATCAGTCGGGCGGCCTCGCTTATCAACCACCAATTTCATATTG<br>CTGTAAGTGTTTAAATCTTTACTTATTGGTTTCAAAACCCATTGGTTAAGCCTTTTAAACTCAT<br>GGTAGTTATTTTCAAGCATTAACATGAACTTAAATTCATCAAGGCTAATCTCTATATTTGCCTT<br>GTGAGTTTTCTTTTGTGTTAGTTCTTTTAATAACCACTCATAAATCCTCATAGAGTATTTGTTT<br>TCAAAAGACTTAACATGTTCCAGATTATATTTTATGAATTTTTTTAACTGGAAAAGATAAGGCA<br>ATATCTCTTCACTAAAAACTAATTCTAATTTTTCGCTTGAGAACTTGGCATAGTTTGTCCACTG<br>GAAAATCTCAAAGCCTTTAACCAAAGGATTCCTGATTTCCACAGTTCTCGTCATCAGCTCTCTG<br>GTTGCTTTAGCTAATACACCATAAGCATTTTCCCTACTGATGTTCATCATCTGAGCGTATTGGT<br>TATAAGTGAACGATACCGTCCGTTCTTTCCTTGTAGGGTTTTCAATCGTGGGGTTGAGTAGTGC<br>CACACAGCATAAAATTAGCTTGGTTTCATGCTCCGTTAAGTCATAGCGACTAATCGCTAGTTCA<br>TTTGCTTTGAAAACAACTAATTCAGACATACATCTCAATTGGTCTAGGTGATTTTAATCACTAT<br>ACCAATTGAGATGGGCTAGTCAATGATAATTACTAGTCCTTTTCCTTTGAGTTGTGGGTATCTG<br>TAAATTCTGCTAGACCTTTGCTGGAAAACTTGTAAATTCTGCTAGACCCTCTGTAAATTCCGCT<br>AGACCTTTGTGTGTTTTTTTTGTTTATATTCAAGTGGTTATAATTTATAGAATAAAGAAAGAAT<br>AAAAAAAGATAAAAAGAATAGATCCCAGCCCTGTGTATAACTCACTACTTTAGTCAGTTCCGCA<br>GTATTACAAAAGGATGTCGCAAACGCTGTTTGCTCCTCTACAAAACAGACCTTAAAACCCTAAA<br>GGCTTAAGTAGCACCCTCGCAAGCTCGGGCAAATCGCTGAATATTCCTTTTGTCTCCGACCATC<br>AGGCACCTGAGTCGCTGTCTTTTTCGTGACATTCAGTTCGCTGCGCTCACGGCTCTGGCAGTGA<br>ATGGGGGTAAATGGCACTACAGGCGCCTTTTATGGATTCATGCAAGGAAACTACCCATAATACA<br>AGAAAAGCCCGTCACGGGCTTCTCAGGGCGTTTTATGGCGGGTCTGCTATGTGGTGCTATCTGA<br>CTTTTTGCTGTTCAGCAGTTCCTGCCCTCTGATTTTCCAGTCTGACCACTTCGGATTATCCCGT<br>GACAGGTCATTCAGACTGGCTAATGCACCCAGTAAGGCAGCGGTATCATCAACAGGCTTACCCG<br>TCTTACTGTCTTTTCTACGGGGTCTGACGCTCAGTGGAACGAAAACTCACGTTAAGGGATTTTG<br>GTCATGAGATTATCAAAAAGGATCTTCACCTAGATCCTTTTAAATTAAAAATGAAGTTTTAAAT<br>CAATCTAAAGTATATATGAGTAAACTTGGTCTGACAGTTACCAATGCTTAATCAGTGAGGCACC<br>TATCTCAGCGATCTGTCTATTTCGTTCATCCATAGTTGCCTGACTCCCCGTCGTGTAGATAACT<br>ACGATACGGGAGGGCTTACCATCTGGCCCCAGTGCTGCAATGATACCGCGAGACCCACGCTCAC |

CGGCTCCAGATTTATCAGCAATAAACCAGCCAGCCGGAAGGGCCGAGCGCAGAAGTGGTCCTGC
AACTTTATCCGCCTCCATCCAGTCTATTAATTGTTGCCGGGAAGCTAGAGTAAGTAGTTCGCCA
GTTAATAGTTTGCGCAACGTTGTTGCCATTGCTACAGGCATCGTGGTGTCACGCTCGTCGTTTG
GTATGGCTTCATTCAGCTCCGGTTCCCAACGATCAAGGCGAGTTACATGATCCCCCATGTTGTG
CAAAAAAGCGGTTAGCTCCTTCGGTCCTCCGATCGTTGTCAGAAGTAAGTTGGCCGCAGTGTTA
TCACTCATGGTTATGGCAGCACTGCATAATTCTCTTACTGTCATGCCATCCGTAAGATGCTTTT
CTGTGACTGGTGAGTACTCAACCAAGTCATTCTGAGAATAGTGTATGCGGCGACCGAGTTGCTC
TTGCCCGGCGTCAATACGGGATAATACCGCGCCACATAGCAGAACTTTAAAAGTGCTCATCATT
GGAAAACGTTCTTCGGGGCGAAAACTCTCAAGGATCTTACCGCTGTTGAGATCCAGTTCGATGT
AACCCACTCGTGCACCCAACTGATCTTCAGCATCTTTTACTTTCACCAGCGTTTCTGGGTGAGC
AAAAACAGGAAGGCAAAATGCCGCAAAAAAGGGAATAAGGGCGACACGGAAATGTTGAATACTC
ATACTCTTCCTTTTTCAATATTATTGAAGCATTTATCAGGGTTATTGTCTCATGAGCGGATACA
TATTTGAATGTATTTAGAAAAATAAACAAATAGGGGTTCCGCGCACATTTCCCCGAAAAGTGCC
ACCTGACGTCTAAGAAACCATTATTATCATGACATTAACCTATAAAAATAGGCGTATCACGAGG
CCCTTTCGTCTCGCGCGTTTCGGTGATGACGGTGAAAACCTCTGACACATGCAGCTCCCGGAGA
CGGTCACAGCTTGTCTGTAAGCGGATGCCGGGAGCAGACAAGCCCGTCAGGGCGCGTCAGCGGG
TGTTGGCGGGTGTCGGGGCTGGCTTAACTATGCGGCATCAGAGCAGATTGTACTGAGAGTGCAC
CATATGCGGTGTGAAATACCGCACAGATGCGTAAGGAGAAAATACCGCATCAGGCGCCATTCGC
CATTCAGGCTGCGCAACTGTTGGGAAGGGCGATCGGTGCGGGCCTCTTCGCTATTACGCCAGCT
GGCGAAAGGGGGATGTGCTGCAAGGCG

**Nucleotide sequence of exemplary *fnrS* promoter-driven *argA*$^{fbr}$ pSC101 plasmid (SEQ ID NO: 35)**

ggtacc*AGTTGTTCTTATTGGTGGTGTTGCTTTATGGTTGCATCGTAGTAAATGGTTGTAACAA*
*AAGCAATTTTTCCGGCTGTCTGTATACAAAAACGCCGCAAAGTTTGAGCGAAGTCAATAAACTC*
*TCTACCCATTCAGGGCAATATCTCTCTT*ggatccaaagtgaactctagaaataattttgtttaa
ctttaagaaggagatatacatATGGTAAAGGAACGTAAAACCGAGTTGGTCGAGGGATTCCGCC
ATTCGGTTCCCTGTATCAATACCCACCGGGGAAAAACGTTTGTCATCATGCTCGGCGGTGAAGC
CATTGAGCATGAGAATTTCTCCAGTATCGTTAATGATATCGGGTTGTTGCACAGCCTCGGCATC
CGTCTGGTGGTGGTCTATGGCGCACGTCCGCAGATCGACGCAAATCTGGCTGCGCATCACCACG
AACCGCTGTATCACAAGAATATACGTGTGACCGACGCCAAAACACTGGAACTGGTGAAGCAGGC
TGCGGGAACATTGCAACTGGATATTACTGCTCGCCTGTCGATGAGTCTCAATAACACGCCGCTG
CAGGGCGCGCATATCAACGTCGTCAGTGGCAATTTTATTATTGCCCAGCCGCTGGGCGTCGATG
ACGGCGTGGATTACTGCCATAGCGGGCGTATCCGGCGGATTGATGAAGACGCGATCCATCGTCA
ACTGGACAGCGGTGCAATAGTGCTAATGGGGCCGGTCGCTGTTTCAGTCACTGGCGAGAGCTTT
AACCTGACCTCGGAAGAGATTGCCACTCAACTGGCCATCAAACTGAAAGCTGAAAAGATGATTG
GTTTTTGCTCTTCCCAGGGCGTCACTAATGACGACGGTGATATTGTCTCCGAACTTTTCCCTAA
CGAAGCGCAAGCGCGGGTAGAAGCCCAGGAAGAGAAAGGCGATTACAACTCCGGTACGGTGCGC
TTTTTGCGTGGCGCAGTGAAAGCCTGCCGCAGCGGCGTGCGTCGCTGTCATTTAATCAGTTATC
AGGAAGATGGCGCGCTGTTGCAAGAGTTGTTCTCACGCGACGGTATCGGTACGCAGATTGTGAT
GGAAAGCGCCGAGCAGATTCGTCGCGCAACAATCAACGATATTGGCGGTATTCTGGAGTTGATT
CGCCCACTGGAGCAGCAAGGTATTCTGGTACGCCGTTCTCGCGAGCAGCTGGAGATGGAAATCG
ACAAATTCACCATTATTCAGCGCGATAACACGACTATTGCCTGCGCCGCGCTCTATCCGTTCCC
GGAAGAGAAGATTGGGGAAATGGCCTGTGTGGCAGTTCACCCGGATTACCGCAGTTCATCAAGG
GGTGAAGTTCTGCTGGAACGCATTGCCGCTCAGGCTAAGCAGAGCGGCTTAAGCAAATTGTTTG
TGCTGACCACGCGCAGTATTCACTGGTTCCAGGAACGTGGATTTACCCCAGTGGATATTGATTT
ACTGCCCGAGAGCAAAAAGCAGTTGTACAACTACCAGCGTAAATCCAAAGTGTTGATGGCGGAT
TTAGGGTAAGGAAGTTTGTCTAGATCTCAGGCGTGGATGGCTTGGCGTAATCATGGTCATAGCT
GTTTCCTGTGTGAAATTGTTATCCGCTCACAATTCCACACAACATACGAGCCGGAAGCATAAAG
TGTAAAGCCTGGGGTGCCTAATGAGTGAGCTAACTCACATTAATTGCGTTGCGCTCACTGCCCG
CTTTCCAGTCGGGAAACCTGTCGTGCCAGCTGCATTAATGAATCGGCCAACGCGCGGGGAGAGG
CGGTTTGCGTATTGGGCGCTCTTCCGCTTCCTCGCTCACTGACTCGCTGCGCTCGGTCGTTCGG
CTGCGGCGAGCGGTATCAGCTCACTCAAAGGCGGTAGTACGGGTTTTGCTGCCCGCAAACGGGC
TGTTCTGGTGTTGCTAGTTTGTTATCAGAATCGCAGATCCGGCTTCAGGTTTGCCGGCTGAAAG
CGCTATTTCTTCCAGAATTGCCATGATTTTTTCCCCACGGGAGGCGTCACTGGCTCCCGTGTTG
TCGGCAGCTTTGATTCGATAAGCAGCATCGCCTGTTTCAGGCTGTCTATGTGTGACTGTTGAGC
TGTAACAAGTTGTCTCAGGTGTTCAATTTCATGTTCTAGTTGCTTTGTTTTACTGGTTTCACCT
GTTCTATTAGGTGTTACATGCTGTTCATCTGTTACATTGTCGATCTGTTCATGGTGAACAGCTT
TAAATGCACCAAAAACTCGTAAAAGCTCTGATGTATCTATCTTTTTTACACCGTTTTCATCTGT
GCATATGGACAGTTTTCCCTTTGATATCTAACGGTGAACAGTTGTTCTACTTTTGTTTGTTAGT
CTTGATGCTTCACTGATAGATACAAGAGCCATAAGAACCTCAGATCCTTCCGTATTTAGCCAGT
ATGTTCTCTAGTGTGGTTCGTTGTTTTTGCGTGAGCCATGAGAACGAACCATTGAGATCATGCT
TACTTTGCATGTCACTCAAAAATTTTGCCTCAAAACTGGTGAGCTGAATTTTTGCAGTTAAAGC
ATCGTGTAGTGTTTTTCTTAGTCCGTTACGTAGGTAGGAATCTGATGTAATGGTTGTTGGTATT
TTGTCACCATTCATTTTTATCTGGTTGTTCTCAAGTTCGGTTACGAGATCCATTTGTCTATCTA

```
GTTCAACTTGGAAAATCAACGTATCAGTCGGGCGGCCTCGCTTATCAACCACCAATTTCATATT
GCTGTAAGTGTTTAAATCTTTACTTATTGGTTTCAAAACCCATTGGTTAAGCCTTTTAAACTCA
TGGTAGTTATTTTCAAGCATTAACATGAACTTAAATTCATCAAGGCTAATCTCTATATTTGCCT
TGTGAGTTTTCTTTTGTGTTAGTTCTTTTAATAACCACTCATAAATCCTCATAGAGTATTTGTT
TTCAAAAGACTTAACATGTTCCAGATTATATTTTATGAATTTTTTTAACTGGAAAAGATAAGGC
AATATCTCTTCACTAAAAACTAATTCTAATTTTTCGCTTGAGAACTTGGCATAGTTTGTCCACT
GGAAAATCTCAAAGCCTTTAACCAAAGGATTCCTGATTTCCACAGTTCTCGTCATCAGCTCTCT
GGTTGCTTTAGCTAATACACCATAAGCATTTTCCCTACTGATGTTCATCATCTGAGCGTATTGG
TTATAAGTGAACGATACCGTCCGTTCTTTCCTTGTAGGGTTTTCAATCGTGGGGTTGAGTAGTG
CCACACAGCATAAAATTAGCTTGGTTTCATGCTCCGTTAAGTCATAGCGACTAATCGCTAGTTC
ATTTGCTTTGAAAACAACTAATTCAGACATACATCTCAATTGGTCTAGGTGATTTTAATCACTA
TACCAATTGAGATGGGCTAGTCAATGATAATTACTAGTCCTTTTCCTTTGAGTTGTGGGTATCT
GTAAATTCTGCTAGACCTTTGCTGGAAAACTTGTAAATTCTGCTAGACCCTCTGTAAATTCCGC
TAGACCTTTGTGTGTTTTTTTTGTTTATATTCAAGTGGTTATAATTTATAGAATAAAGAAAGAA
TAAAAAAAGATAAAAAGAATAGATCCCAGCCCTGTGTATAACTCACTACTTTAGTCAGTTCCGC
AGTATTACAAAAGGATGTCGCAAACGCTGTTTGCTCCTCTACAAAACAGACCTTAAAACCCTAA
AGGCTTAAGTAGCACCCTCGCAAGCTCGGGCAAATCGCTGAATATTCCTTTTGTCTCCGACCAT
CAGGCACCTGAGTCGCTGTCTTTTTCGTGACATTCAGTTCGCTGCGCTCACGGCTCTGGCAGTG
AATGGGGGTAAATGGCACTACAGGCGCCTTTTATGGATTCATGCAAGGAAACTACCCATAATAC
AAGAAAAGCCCGTCACGGGCTTCTCAGGGCGTTTTATGGCGGGTCTGCTATGTGGTGCTATCTG
ACTTTTTGCTGTTCAGCAGTTCCTGCCCTCTGATTTTCCAGTCTGACCACTTCGGATTATCCCG
TGACAGGTCATTCAGACTGGCTAATGCACCCAGTAAGGCAGCGGTATCATCAACAGGCTTACCC
GTCTTACTGTCTTTTCTACGGGGTCTGACGCTCAGTGGAACGAAAACTCACGTTAAGGGATTTT
GGTCATGAGATTATCAAAAAGGATCTTCACCTAGATCCTTTTAAATTAAAAATGAAGTTTTAAA
TCAATCTAAAGTATATATGAGTAAACTTGGTCTGACAGTTACCAATGCTTAATCAGTGAGGCAC
CTATCTCAGCGATCTGTCTATTTCGTTCATCCATAGTTGCCTGACTCCCCGTCGTGTAGATAAC
TACGATACGGGAGGGCTTACCATCTGGCCCCAGTGCTGCAATGATACCGCGAGACCCACGCTCA
CCGGCTCCAGATTTATCAGCAATAAACCAGCCAGCCGGAAGGGCCGAGCGCAGAAGTGGTCCTG
CAACTTTATCCGCCTCCATCCAGTCTATTAATTGTTGCCGGGAAGCTAGAGTAAGTAGTTCGCC
AGTTAATAGTTTGCGCAACGTTGTTGCCATTGCTACAGGCATCGTGGTGTCACGCTCGTCGTTT
GGTATGGCTTCATTCAGCTCCGGTTCCCAACGATCAAGGCGAGTTACATGATCCCCCATGTTGT
GCAAAAAAGCGGTTAGCTCCTTCGGTCCTCCGATCGTTGTCAGAAGTAAGTTGGCCGCAGTGTT
ATCACTCATGGTTATGGCAGCACTGCATAATTCTCTTACTGTCATGCCATCCGTAAGATGCTTT
TCTGTGACTGGTGAGTACTCAACCAAGTCATTCTGAGAATAGTGTATGCGGCGACCGAGTTGCT
CTTGCCCGGCGTCAATACGGGATAATACCGCGCCACATAGCAGAACTTTAAAAGTGCTCATCAT
TGGAAAACGTTCTTCGGGGCGAAAACTCTCAAGGATCTTACCGCTGTTGAGATCCAGTTCGATG
TAACCCACTCGTGCACCCAACTGATCTTCAGCATCTTTTACTTTCACCAGCGTTTCTGGGTGAG
CAAAAACAGGAAGGCAAAATGCCGCAAAAAAGGGAATAAGGGCGACACGGAAATGTTGAATACT
CATACTCTTCCTTTTTCAATATTATTGAAGCATTTATCAGGGTTATTGTCTCATGAGCGGATAC
ATATTTGAATGTATTTAGAAAAATAAACAAATAGGGGTTCCGCGCACATTTCCCCGAAAAGTGC
CACCTGACGTCTAAGAAACCATTATTATCATGACATTAACCTATAAAAATAGGCGTATCACGAG
GCCCTTTCGTCTCGCGCGTTTCGGTGATGACGGTGAAAACCTCTGACACATGCAGCTCCCGGAG
ACGGTCACAGCTTGTCTGTAAGCGGATGCCGGGAGCAGACAAGCCCGTCAGGGCGCGTCAGCGG
GTGTTGGCGGGTGTCGGGGCTGGCTTAACTATGCGGCATCAGAGCAGATTGTACTGAGAGTGCA
CCATATGCGGTGTGAAATACCGCACAGATGCGTAAGGAGAAAATACCGCATCAGGCGCCATTCG
CCATTCAGGCTGCGCAACTGTTGGGAAGGGCGATCGGTGCGGGCCTCTTCGCTATTACGCCAGC
TGGCGAAAGGGGGATGTGCTGCAAGGCG
```

FIG. 21B (Continued)

Brightness of constitutive RFP integrated in three locations:

1. AraB/C
2. MalE/K
3. MetY/ArgG
4. Nissle (non-fluorescent)

Day 5 blood ammonia (BA) comparisons

- Nissle - 220 mM BA
- Syn016 - 105 mM BA
- Difference = 115 mM
- Average mouse blood volume ~1.5 mL
- SYN016 prevented absorption of 172.5 μmoles

FIG. 28A
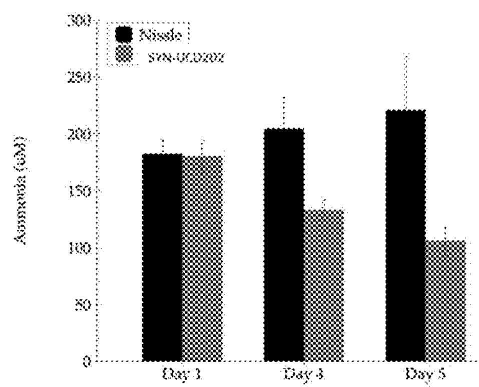
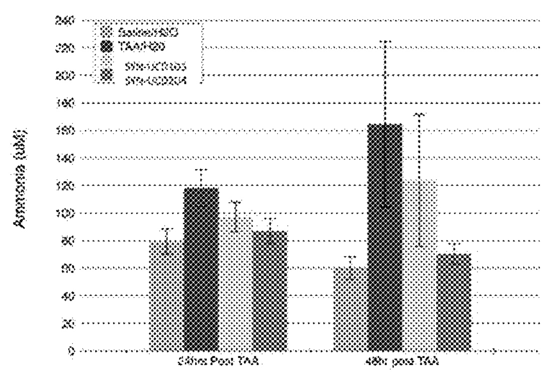
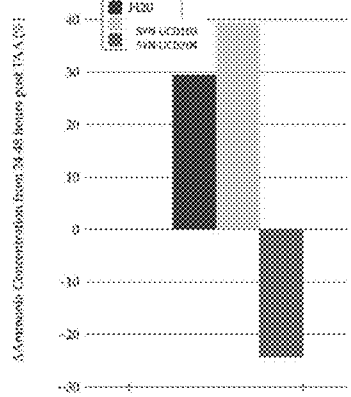
FIG. 28B
FIG. 28C

FIG. 30

| Parameter | Value |
|---|---|
| Maximum burden of $NH_4^+$ (in blood) in hyperammonemic patients (UCD<HE) | 800 μmols total excess $NH_4^+$ Total blood ammonia levels: ~1000 μmols |
| Arginine production target: $NH_4^+$ burden | 267 μmol/day (1 Arg = 3 $NH_4^+$) |
| Target arginine production rate: $NH_4^+$ burden | 267 μmol/day/$10^{11}$ bacteria |
| Lab assay target: $NH_4^+$ burden | 0.11 μmol/hr/$10^9$ bacteria |
| Current arginine production rate | 1.25 μmol/hr/$10^9$ bacteria |
| | |
| Maximum flux of $NH_4^+$ (in blood from colon); in healthy individuals>UCD | 800 μmols/hr |
| Arginine production target: $NH_4^+$ flux | 267 μmols/hr |
| Target arginine production rate: $NH_4^+$ flux | 267 μmols/hr/$10^{11}$ bacteria |
| Lab assay target: $NH_4^+$ flux | 2.67 μmol/hr/$10^9$ bacteria |

Total arginine production: 0.11 g/day if based on flux rate (267 μmol/day/$10^{11}$ bacteria), or 0.26 g/day if based on the maximum production rate of the strain 1.25 μmol/hr/$10^9$ bacteria

FIG. 31

Synthetic Biotic Targeting UCD

- Engineered probiotic bacterial therapeutic to consume excess ammonia and produce beneficial byproducts to improve patient outcomes
  - Many UCD patients are also administered arginine or citrulline as adjunctive co-therapy with ammonia scavenging treatment
  - Eliminates protein restriction
- Highly controllable kill switch and genomic auxotrophy to ensure safety

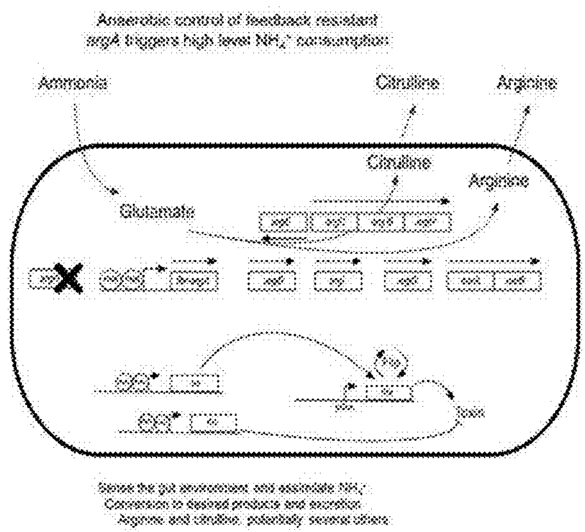

FIG. 33

| Amino Acid | Oligonucleotide | Cell wall |
|---|---|---|
| cysE | thyA | dapA |
| glnA | uraA | dapB |
| ilvD | | dapD |
| leuB | | dapE |
| lysA | | dapF |
| serA | | |
| metA | | |
| glyA | | |
| hisB | | |
| ilvA | | |
| pheA | | |
| proA | | |
| thrC | | |
| trpC | | |
| tyrA | | |

FIG. 34

| Gene | argA | cysE | glnA | glyA | hisB | ilvA | leuB | lysA | metA |
| --- | --- | --- | --- | --- | --- | --- | --- | --- | --- |
| AA Auxotroph | Arginine | Cysteine | Glutamine | Glycine | Histidine | Isoleucine | Leucine | Lysine | Methionine |
| Pre-Gavage | | | | | | | | | |
| 24 hours | | | | | | | | | |
| 48 hours | | | | | | | | | |

| Gene | pheA | proA | serA | thrC | trpC | tyrA | ilvD | thyA | uraA | flhD |
| --- | --- | --- | --- | --- | --- | --- | --- | --- | --- | --- |
| AA Auxotroph | Phenylalanine | Proline | Serine | Threonine | Tryptophan | Tyrosine | Valine/Isoleucine/Leucine | Thiamine | Uracil | FlhD |
| Pre-Gavage | | | | | | | | | | |
| 24 hours | | | | | | | | | | |
| 48 hours | | | | | | | | | | |

Present

Absent

FIG.49

| Wild-type clbA (SEQ ID NO: 36) |
| --- |
| caaatatcacataatcttaacatatcaataaacacagtaaagtttcatgtgaaaaacatcaaacataaaatacaagctcggaatacgaa<br>tcacgctatacacattgctaacaggaatgagattatctaaatgaggattgatatattaattggacatactagtttttttcatcaaacca<br>gtagagataacttccttcactatctcaatgaggaagaaataaaacgctatgatcagtttcatttgtgagtgataaagaactctatatt<br>ttaagccgtatcctgctcaaaacagcactaaaagatatcaacctgatgtctcattacaatcatggcaatttagtacgtgcaaatatgg<br>caaaccatttatagtttttcctcagttggcaaaaagatttttttaacctttcccatactatagatacagtagccgttgctattagtt<br>ctcactgcgagcttggtgtcgatattgaacaaataagagatttagacaactcttatctgaatatcagtcagcatttttttactccacag<br>gaagctactaacatagtttcacttcctcgttatgaaggtcaattactttttggaaaatgtggacgctcaaagaagcttacatcaaata<br>tcgaggtaaaggcctatctttaggactggattgtattgaatttcatttaacaaataaaaaactaacttcaaaatatagaggttcacctg<br>tttatttctctcaatggaaaatatgtaactcatttctcgcattagcctctccactcatcaccctaaaataactattgagctatttcct<br>atgcagtcccaactttatcaccacgactatcagctaattcattcgtcaaatgggcagaattgaatcgccacggataatctagacacttc<br>tgagccgtcgataatattgattttcatattccgtcggtggtgtaagtatcccgcataatcgtgccattcacatttag |
| **clbA knockout (SEQ ID NO: 37)** |
| ggatgggggaaacatggataagttcaaagaaaaaacccgttatctctgcgtgaaagacaagtattgcgcatgctggcacaaggtgat<br>gagtactctcaaatatcacataatcttaacatatcaataaacacagtaaagtttcatgtgaaaaacatcaaacataaaatacaagctcg<br>gaatacgaatcacgctatacacattgctaacaggaatgagattatctaaatgaggattgaTGTGTAGGCTGGAGCTGCTTCGAAGTTCC<br>TATACTTTCTAGAGAATAGGAACTTCGGAATAGGAACTTCGGAATAGGAACTAAGGAGGATATTCATATGtcgtcaaatgggcagaatt<br>gaatcgccacggataatctagacacttctgagccgtcgataatattgattttcatattccgtcggtgg |

FIG. 57
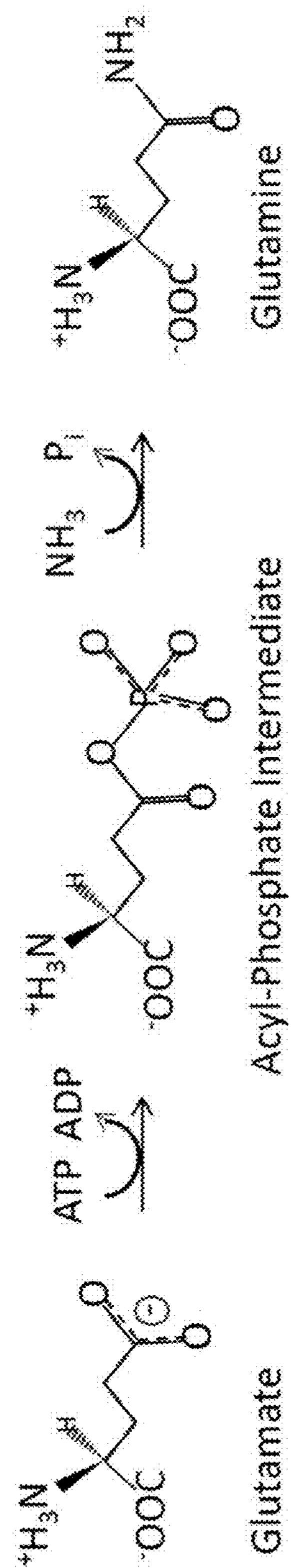
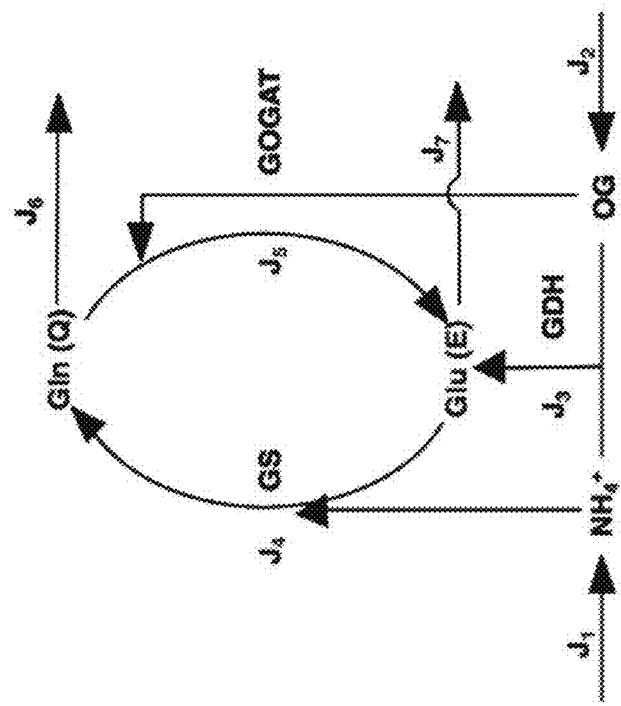

FIG. 58
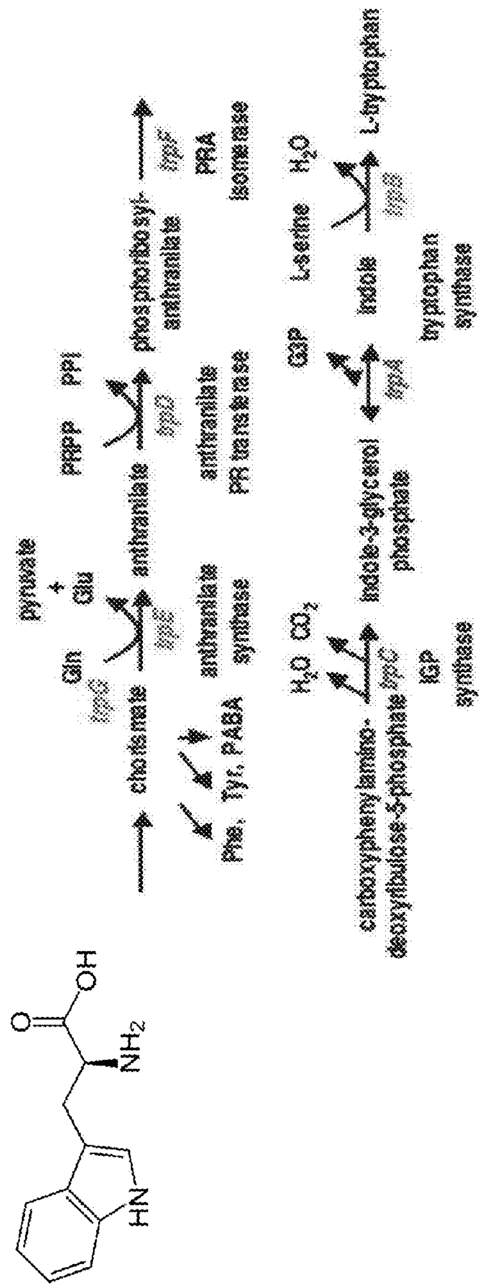
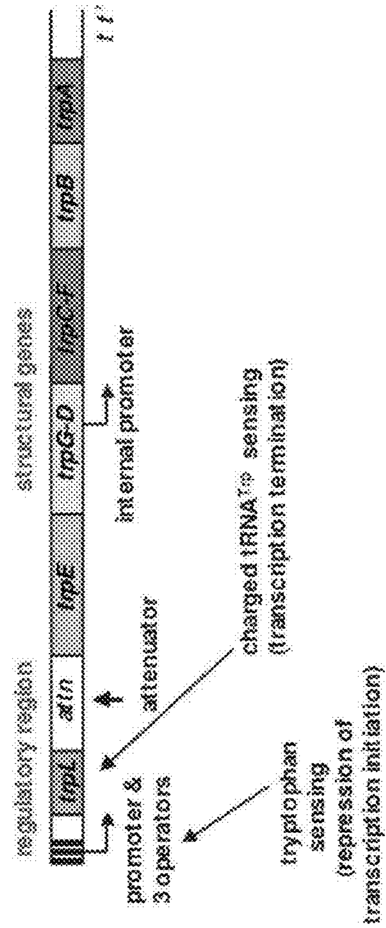

"Dead Man" Kill Switch: Cells viable only in the presence of arabinose (or other sugar)

FIG. 63

I. Inherent Safety

- Nissle -background chassis is a naturally occurring probiotic widely used
  - Isolated from human microbiome
  - Extensive human safety profile
- Genes being refactored are derived from human genome or commensal microorganism
  - Transient: non-colonizing probiotic well characterized

II. Engineered Safety- Waste Management

Auxotrophy

- thyA (DNA synthesis)
- dapA (cell wall synthesis)
- serA and metA (amino acid auxotrophs)

Kill Switch

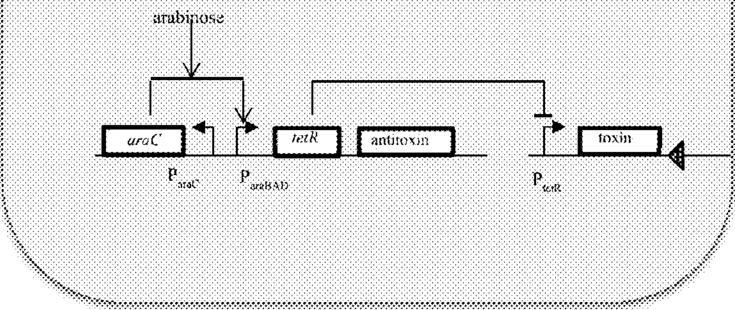

BACTERIA ENGINEERED TO TREAT DISEASES ASSOCIATED WITH HYPERAMMONEMIA

This application claims the benefit of U.S. Provisional Application No. 62/087,854, filed Dec. 5, 2014; U.S. Provisional Application No. 62/173,706, filed Jun. 10, 2015; U.S. Provisional Application No. 62/256,041, filed Nov. 16, 2015; U.S. Provisional Application No. 62/103,513, filed Jan. 14, 2015; U.S. Provisional Application No. 62/150,508, filed Apr. 21, 2015; U.S. Provisional Application No. 62/173,710, filed Jun. 10, 2015; U.S. Provisional Application No. 62/256,039, filed Nov. 16, 2015; U.S. Provisional Application No. 62/184,811, filed Jun. 25, 2015; U.S. Provisional Application No. 62/183,935, filed Jun. 24, 2015; and U.S. Provisional Application No. 62/263,329, filed Dec. 4, 2015, which are incorporated herein by reference in their entirety to provide continuity of disclosure.

SEQUENCE LISTING

The instant application contains a Sequence Listing which has been submitted electronically in ASCII format and is hereby incorporated by reference in its entirety. Said ASCII copy, created on Mar. 9, 2016, is named 12671.0006-00000_SL.txt and is 46,692 bytes in size.

This disclosure relates to compositions and therapeutic methods for reducing excess ammonia and converting ammonia and/or nitrogen into alternate byproducts. In certain aspects, the disclosure relates to genetically engineered bacteria that are capable of reducing excess ammonia, particularly in low-oxygen conditions, such as in the mammalian gut. In certain aspects, the compositions and methods disclosed herein may be used for modulating or treating disorders associated with hyperammonemia, e.g., urea cycle disorders and hepatic encephalopathy.

Ammonia is highly toxic and generated during metabolism in all organs (Walker, 2012). Hyperammonemia is caused by the decreased detoxification and/or increased production of ammonia. In mammals, the urea cycle detoxifies ammonia by enzymatically converting ammonia into urea, which is then removed in the urine. Decreased ammonia detoxification may be caused by urea cycle disorders (UCDs) in which urea cycle enzymes are defective, such as argininosuccinic aciduria, arginase deficiency, carbamoylphosphate synthetase deficiency, citrullinemia, N-acetylglutamate synthetase deficiency, and ornithine transcarbamylase deficiency (Häberle et al., 2012). The National Urea Cycle Disorders Foundation estimates that the prevalence of UCDs is 1 in 8,500 births. In addition, several non-UCD disorders, such as hepatic encephalopathy, portosystemic shunting, and organic acid disorders, can also cause hyperammonemia. Hyperammonemia can produce neurological manifestations, e.g., seizures, ataxia, stroke-like lesions, coma, psychosis, vision loss, acute encephalopathy, cerebral edema, as well as vomiting, respiratory alkalosis, hypothermia, or death (Häberle et al., 2012; Häberle et al., 2013).

Ammonia is also a source of nitrogen for amino acids, which are synthesized by various biosynthesis pathways. For example, arginine biosynthesis converts glutamate, which comprises one nitrogen atom, to arginine, which comprises four nitrogen atoms. Intermediate metabolites formed in the arginine biosynthesis pathway, such as citrulline, also incorporate nitrogen. Thus, enhancement of arginine biosynthesis may be used to incorporate excess nitrogen in the body into non-toxic molecules in order to modulate or treat conditions associated with hyperammonemia. Likewise, histidine biosynthesis, methionine biosynthesis, lysine biosynthesis, asparagine biosynthesis, glutamine biosynthesis, and tryptophan biosynthesis are also capable of incorporating excess nitrogen, and enhancement of those pathways may be used to modulate or treat conditions associated with hyperammonemia.

Current therapies for hyperammonemia and UCDs aim to reduce ammonia excess, but are widely regarded as suboptimal (Nagamani et al., 2012; Hoffmann et al., 2013; Torres-Vega et al., 2014). Most UCD patients require substantially modified diets consisting of protein restriction. However, a low-protein diet must be carefully monitored; when protein intake is too restrictive, the body breaks down muscle and consequently produces ammonia. In addition, many patients require supplementation with ammonia scavenging drugs, such as sodium phenylbutyrate, sodium benzoate, and glycerol phenylbutyrate, and one or more of these drugs must be administered three to four times per day (Leonard, 2006; Diaz et al., 2013). Side effects of these drugs include nausea, vomiting, irritability, anorexia, and menstrual disturbance in females (Leonard, 2006). In children, the delivery of food and medication may require a gastrostomy tube surgically implanted in the stomach or a nasogastric tube manually inserted through the nose into the stomach. When these treatment options fail, a liver transplant may be required (National Urea Cycle Disorders Foundation). Thus, there is significant unmet need for effective, reliable, and/or long-term treatment for disorders associated with hyperammonemia, including urea cycle disorders.

The invention provides genetically engineered bacteria that are capable of reducing excess ammonia and converting ammonia and/or nitrogen into alternate byproducts. In certain embodiments, the genetically engineered bacteria reduce excess ammonia and convert ammonia and/or nitrogen into alternate byproducts selectively in low-oxygen environments, e.g., the gut. In certain embodiments, the genetically engineered bacteria are non-pathogenic and may be introduced into the gut in order to reduce toxic ammonia. As much as 70% of excess ammonia in a hyperammonemic patient accumulates in the gastrointestinal tract. Another aspect of the invention provides methods for selecting or targeting genetically engineered bacteria based on increased levels of ammonia and/or nitrogen consumption, or production of a non-toxic byproduct, e.g., arginine or citrulline. The invention also provides pharmaceutical compositions comprising the genetically engineered bacteria, and methods of modulating and treating disorders associated with hyperammonemia, e.g., urea cycle disorders and hepatic encephalopathy.

BRIEF DESCRIPTION OF THE FIGURES

FIG. 1A depicts relatively low arginine production under aerobic conditions due to arginine ("Arg" in oval) interacting with ArgA (squiggle ✾) to inhibit (indicated by "X") ArgA activity, while oxygen ($O_2$) prevents (indicated by "X") FNR (dotted boxed FNR) from dimerizing and activating the FNR promoter (grey FNR box) and the $argA^{fbr}$ gene under its control. FIG. 1B depicts up-regulated arginine production under anaerobic conditions due to FNR dimerizing (two dotted boxed FNRs) and inducing FNR promoter (grey FNR box)-mediated expression of $ArgA^{fbr}$ (squiggle ✾ above $argA^{fbr}$), which is resistant to inhibition by arginine. This overcomes (curved arrow) the inhibition of the wild-type ArgA caused by arginine ("Arg" in oval) interacting with ArgA (squiggle above box depicting argA). Each gene in the arginine regulon is depicted by a rectangle containing the name of the gene. Each arrow adjacent to one or a cluster of rectangles depict the promoter responsible for driving transcription, in the direction of the arrow, of such gene(s). Heavier lines adjacent one or a series of rectangles depict ArgR binding sites, which are not utilized because of the ArgR deletion in this bacterium. Arrows above each rectangle depict the expression product of each gene.

FIGS. 2A and 2B depict an alternate exemplary embodiment of the present invention. FIG. 2A depicts the embodiment under aerobic conditions where, in the presence of oxygen, the FNR proteins (FNR boxes) remain as monomers and are unable to bind to and activate the FNR promoter ("FNR") which drives expression of the arginine feedback resistant argA$^{fbr}$ gene. The wild-type ArgA protein is functional, but is susceptible to negative feedback inhibition by binding to arginine, thus keeping arginine levels at or below normal. All of the arginine repressor (ArgR) binding sites in the promoter regions of each arginine biosynthesis gene (argA, argE, argC, argB, argH, argD, argl, argG, carA, and carB) have been mutated (black bars; black "X") to reduce or eliminate binding to ArgR. FIG. 2B depicts the same embodiment under anaerobic conditions where, in the absence of oxygen the FNR protein (FNR boxes) dimerizes and binds to and activates the FNR promoter ("FNR"). This drives expression of the arginine feedback resistant argA$^{fbr}$ gene (black squiggle ( )=argA$^{fbr}$ gene expression product), which is resistant to feedback inhibition by arginine ("Arg" in ovals). All of the arginine repressor (ArgR) binding sites in the promoter regions of each arginine biosynthetic gene (argA, argE, argC, argB, argH, argD, argl, argG, carA, and carB) have been mutated (black bars) to reduce or eliminate binding to ArgR (black "X"), thus preventing inhibition by an arginine-ArgR complex. This allows high level production of arginine. The organization of the arginine biosynthetic genes in FIGS. 1A and 1B is representative of that found in *E. coli* strain Nissle.

FIG. 3 depicts another embodiment of the invention. In this embodiment, a construct comprising an ArgR binding site (black bar) in a promoter driving expression of the Tet repressor (TetR) from the tetR gene is linked to a second promoter comprising a TetR binding site (black bar between TetR and X) that drives expression of gene X. Under low arginine concentrations, TetR is expressed and inhibits the expression of gene X. At high arginine concentrations, ArgR associates with arginine and binds to the ArgR binding site, thereby inhibiting expression of TetR from the tetR gene. This, in turn, removes the inhibition by TetR allowing gene X expression (black squiggle ( )).

FIG. 6 depicts the wild-type genomic sequences comprising ArgR binding sites and mutants thereof for each arginine biosynthesis operon in *E. coli* Nissle. For each wild-type sequence, the ARG boxes are indicated in italics, and the start codon of each gene is boxed. The RNA polymerase binding sites are underlined (Cunin, 1983; Maas, 1994). Bases that are protected from DNA methylation during ArgR binding are highlighted, and bases that are protected from hydroxyl radical attack during ArgR binding are bolded (Charlier et al., 1992). The highlighted and bolded bases are the primary targets for mutations to disrupt ArgR binding.

FIG. 7 depicts the nucleic acid sequences of exemplary regulatory region sequences comprising a FNR-responsive promoter sequence. Underlined sequences are predicted ribosome binding sites, and bolded sequences are restriction sites used for cloning. Exemplary sequences comprising a FNR promoter include, but are not limited to, SEQ ID NO: 16, SEQ ID NO: 17, nirB1 promoter (SEQ ID NO: 18), nirB2 promoter (SEQ ID NO: 19), nirB3 promoter (SEQ ID NO: 20), ydfZ promoter(SEQ ID NO: 21) nirB promoter fused to a strong ribosome binding site (SEQ ID NO: 22), ydfZ promoter fused to a strong ribosome binding site (SEQ ID NO: 23), an anaerobically induced small RNA gene fnrS promoter selected from fnrS1 (SEQ ID NO: 24) and fnrS2 (SEQ ID NO: 25), nirB promoter fused to a CRP binding site (SEQ ID NO: 26), and fnrS promoter fused to a CRP binding site (SEQ ID NO: 27).

FIG. 8A depicts the nucleic acid sequence of an exemplary argA$^{fbr}$ sequence. FIG. 8B depicts the nucleic acid sequence of an exemplary FNR promoter-driven argA$^{fbr}$ plasmid. The FNR promoter sequence is bolded and the argA$^{fbr}$ sequence is boxed FIG. 9 depicts the nucleic acid sequence of an exemplary FNR promoter-driven argA$^{fbr}$ sequence. The FNR promoter sequence is bolded, the ribosome binding site is highlighted, and the argA$^{fbr}$ sequence is boxed.

FIGS. 13A and 13B depict exemplary embodiments of a FNR-responsive promoter fused to a CRP binding site. FIG. 13A depicts a map of the FNR-CRP promoter region, with restriction sites shown in bold. FIG. 13B depicts a schematic diagram of the argA$^{fbr}$ gene under the control of an exemplary FNR promoter (nirB promoter), fused to both a CRP binding site and a ribosome binding site. Other regulatory elements may also be present.

FIGS. 14A and 14B depict alternate exemplary embodiments of a FNR-responsive promoter fused to a CRP binding site. FIG. 14A depicts a map of the FNR-CRP promoter region, with restriction shown in bold. FIG. 14B depicts a schematic diagram of the argA$^{fbr}$ gene under the control of an exemplary FNR promoter (fnrS promoter), fused to both a CRP binding site and a ribosome binding site.

FIG. 15 depicts the wild-type genomic sequence of the regulatory region and 5' portion of the argG gene in *E. coli* Nissle, and a constitutive mutant thereof. The promoter region of each sequence is underlined, and a 5' portion of the argG gene is boxed . In the wild-type sequence, ArgR binding sites are in uppercase and underlined. In the mutant sequence, the 5' untranslated region is in uppercase and underlined. Bacteria expressing argG under the control of the constitutive promoter are capable of producing arginine. Bacteria expressing argG under the control of the wild-type, ArgR-repressible promoter are capable of producing citrulline.

FIG. 18 depicts the nucleic acid sequence of an exemplary BAD promoter-driven argA$^{fbr}$ construct. All bolded sequences are Nissle genomic DNA. A portion of the araC gene is bolded and underlined, the argA$^{fbr}$ gene is boxed, and the bolded sequence in between is the promoter that is activated by the presence of arabinose. The ribosome binding site is in italics, the terminator sequences are highlighted, and the FRT site is boxed . A portion of the araD gene is boxed in dashes.

FIG. 21A depicts the nucleic acid sequence of a pSC101 plasmid. FIG. 21B depicts the nucleotide sequence of a fnrS promoter-driven argA$^{fbr}$ pSC101 plasmid. The argA$^{fbr}$ sequence is boxed, the ribosome binding site is highlighted, and the fnrS promoter is capitalized and bolded.

FIGS. 28A, 28B, and 28C depict bar graphs of ammonia levels in hyperammonemic TAA mice. FIG. 28A depicts a bar graph of ammonia levels in hyperammonemic mice treated with unmodified control Nissle or SYN-UCD202, a genetically engineered strain in which the Arg repressor gene is deleted and the argA$^{fbr}$ gene is under the control of a tetracycline-inducible promoter on a high-copy plasmid. A total of 96 mice were tested, and the error bars represent standard error. Ammonia levels in mice treated with SYN-UCD202 are lower than ammonia levels in mice treated with unmodified control Nissle at day 4 and day 5. FIG. 28B depicts a bar graph showing in vivo efficacy (ammonia consumption) of SYN-UCD204 in the TAA mouse model of hepatic encephalopathy, relative to streptomycin-resistant control Nissle (SYN-UCD103) and vehicle-only controls. FIG. 28C depicts a bar graph of the percent change in blood ammonia concentration between 24-48 hours post-TAA treatment.

FIG. 30 depicts a chart of ammonia consumption kinetics and dosing. This information may be used to determine the amount of arginine that needs to be produced in order to absorb a therapeutically relevant amount of ammonia in UCD patients. Similar calculations may be performed for citrulline production.

FIG. 31 depicts an exemplary schematic of synthetic genetic circuits for treating UCDs and disorders characterized by hyperammonemia, via the conversion of ammonia to desired products, such as citrulline or arginine.

FIG. 32A depicts a map of the astC promoter driving expression of thyA. FIG. 32B depicts a schematic diagram of the thyA gene under the control of an astC promoter. The regulatory region comprises binding sites for CRP, ArgR, and RNA polymerase (RNAP), and may also comprise additional regulatory elements.

FIG. 33 depicts a table of exemplary bacterial genes which may be disrupted or deleted to produce an auxotrophic strain. These include, but are not limited to, genes required for oligonucleotide synthesis, amino acid synthesis, and cell wall synthesis.

FIG. 34 depicts a table illustrating the survival of various amino acid auxotrophs in the mouse gut, as detected 24 hours and 48 hours post-gavage. These auxotrophs were generated using BW25113, a non-Nissle strain of *E. coli.*

FIG. 49 depicts exemplary sequences of a wild-type clbA construct and a clbA knockout construct.

FIG. 57 depicts an exemplary glutamine biosynthesis pathway.

FIG. 58 depicts an exemplary tryptophan biosynthesis pathway.

FIG. 61 also depicts another non-limiting embodiment of the disclosure, wherein the expression of an essential gene not found in the recombinant bacteria is activated by an exogenous environmental signal. In the absence of arabinose, the AraC transcription factor adopts a conformation that represses transcription of the essential gene under the control of the araBAD promoter and the bacterial cell cannot survive. In the presence of arabinose, the AraC transcription factor undergoes a conformational change that allows it to bind to and activate the AraBAD promoter, which induces expression of the essential gene and maintains viability of the bacterial cell.

FIG. 63 depicts a summary of the safety design of the recombinant bacteria of the disclosure, including the inherent safety of the recombinant bacteria, as well as the engineered safety-waste management (including kill switches and/or auxotrophy).

DESCRIPTION OF EMBODIMENTS

Figure 1A:
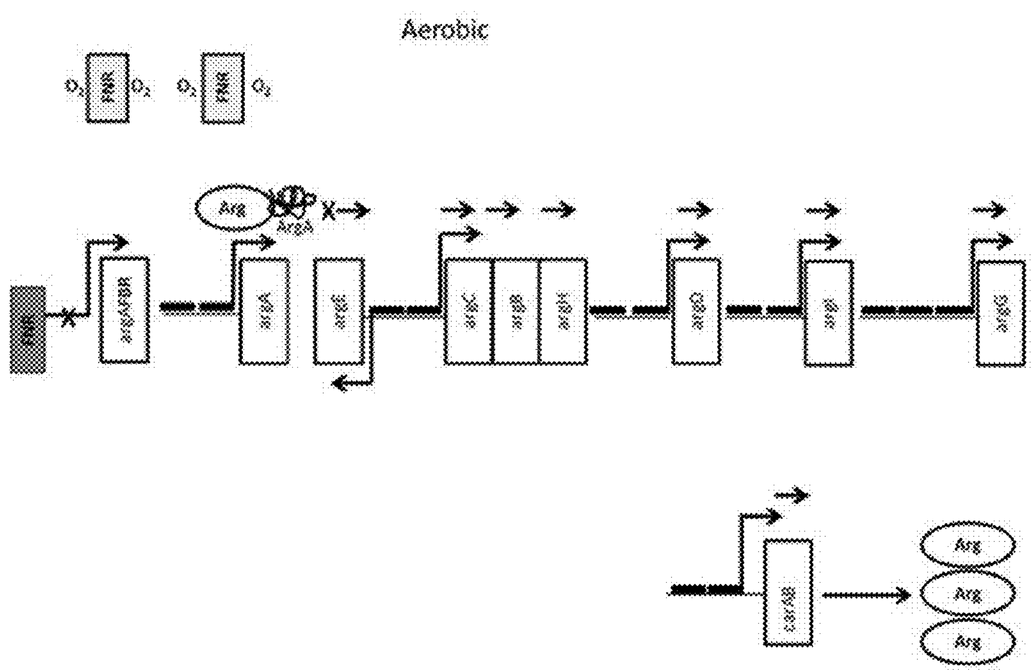
FIGS. 1A and 1B depict the state of the arginine regulon in one embodiment of an ArgR deletion bacterium of the invention under non-inducing (FIG. 1A) and inducing (FIG. 1B) conditions.
Figure 1B:
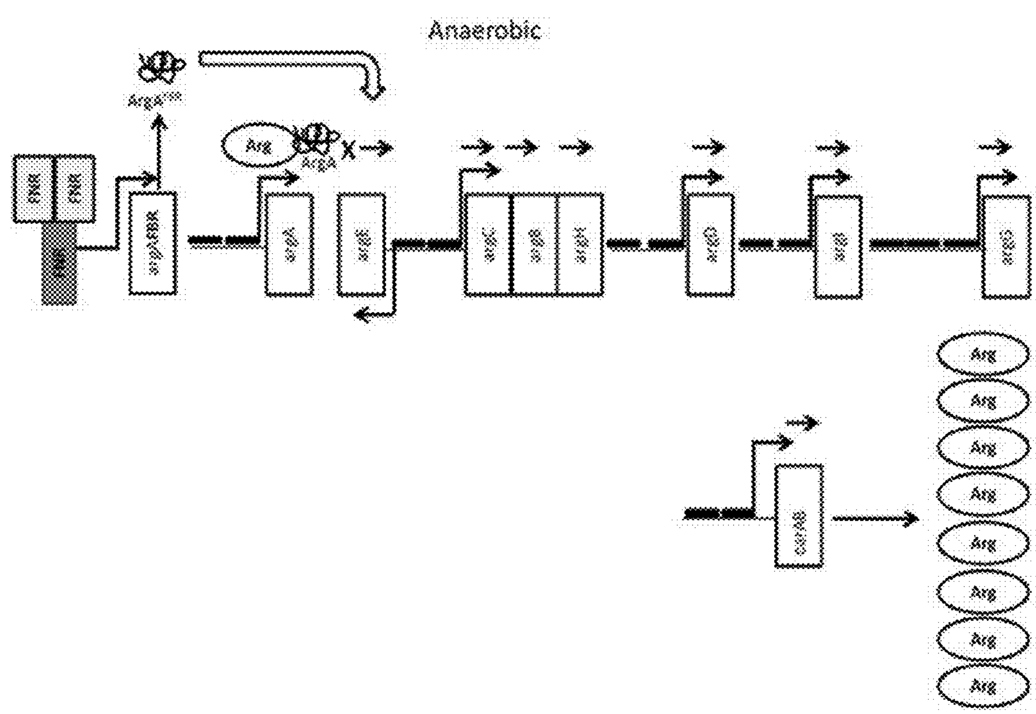
Figure 4:
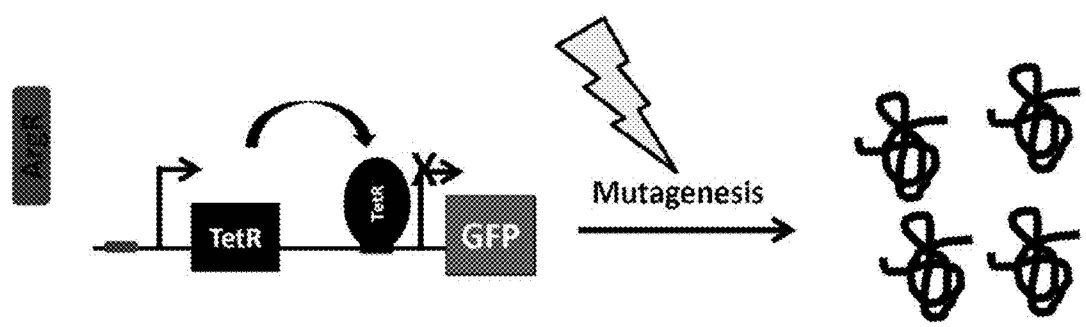
FIG. 4 depicts another embodiment of the invention. In this embodiment, a construct comprising an ArgR binding site (black bar) in a promoter driving expression of the Tet repressor (TetR) from the tetR gene is linked to a second promoter comprising a TetR binding site (black bar bound to TetR oval) that drives expression of green fluorescent protein ("GFP"). Under low arginine concentrations, TetR is expressed and inhibits the expression of GFP. At high arginine concentrations, ArgR associates with arginine and binds to the ArgR binding site, thereby inhibiting expression of TetR from the tetR gene. This, in turn, removes the inhibition by TetR allowing GFP expression. By mutating a host containing this construct, high arginine producers can be selected on the basis of GFP expression using fluorescence-activated cell sorting ("FACS").
Figure 5:
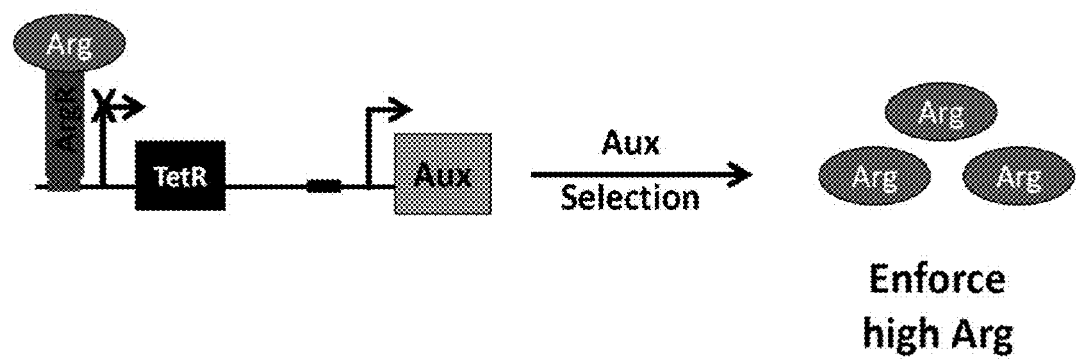
FIG. 5 depicts another embodiment of the invention. In this embodiment, a construct comprising an ArgR binding site (black bar bound by the ArgR-Arg complex) in a promoter driving expression of the Tet repressor (not shown) from the tetR gene is linked to a second promoter comprising a TetR binding site (black bar) that drives expression of an auxotrophic protein necessary for host survival ("AUX"). Under high arginine concentrations, the ArgR-arginine complex binds to the ArgR binding site, thereby inhibiting expression of TetR from the tetR gene. This, in turn, allows expression of AUX, allowing the host to survive. Under low arginine concentrations, TetR is expressed from the tetR gene and inhibits the expression of AUX, thus killing the host. The construct in FIG. 5 enforces high arginine ("Arg") production by making it necessary for host cell survival through its control of AUX expression.
Figure 10:
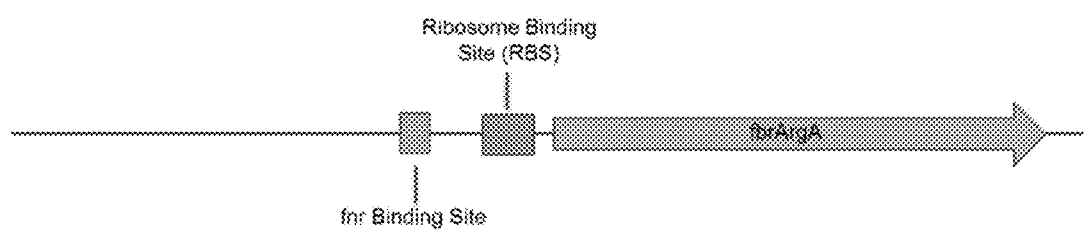
FIG. 10 depicts a schematic diagram of the argA$^{fbr}$ gene under the control of an exemplary FNR promoter (fnrS) fused to a strong ribosome binding site.
Figure 11:
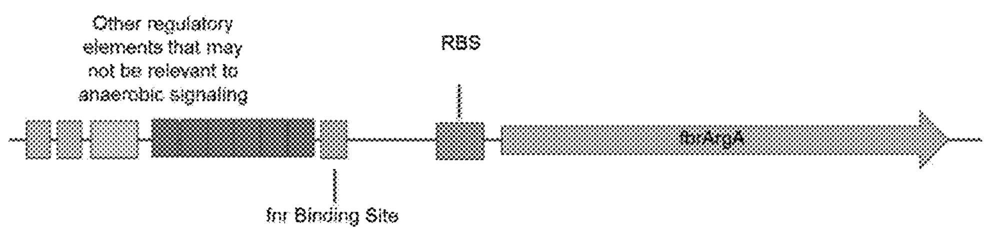
FIG. 11 depicts another schematic diagram of the argA$^{fbr}$ gene under the control of an exemplary FNR promoter (nirB) fused to a strong ribosome binding site. Other regulatory elements may also be present.
Figure 12:
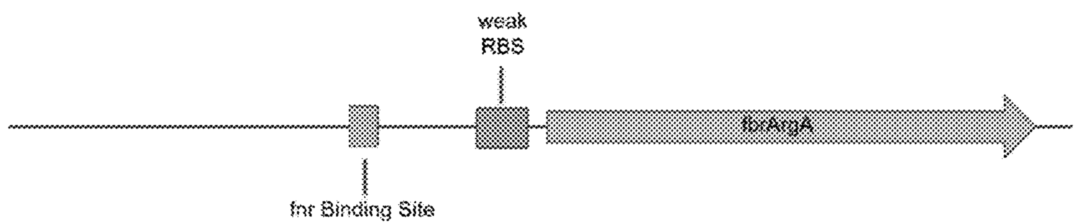
FIG. 12 depicts a schematic diagram of the argA$^{fbr}$ gene under the control of an exemplary FNR promoter (nirB) fused to a weak ribosome binding site.
Figure 16:
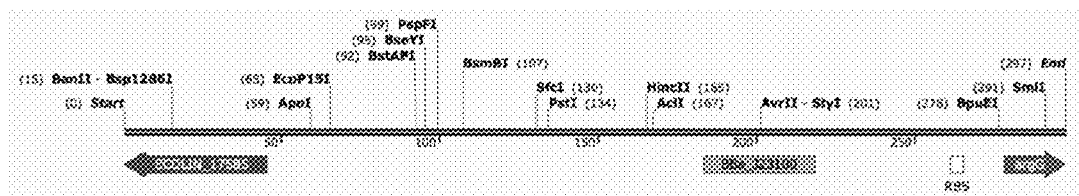
FIG. 16 depicts an exemplary embodiment of a constitutively expressed argG construct in *E. coli* Nissle. The constitutive promoter is BBa_J23100, boxed in gray. Restriction sites for use in cloning are in bold.
Figure 17:
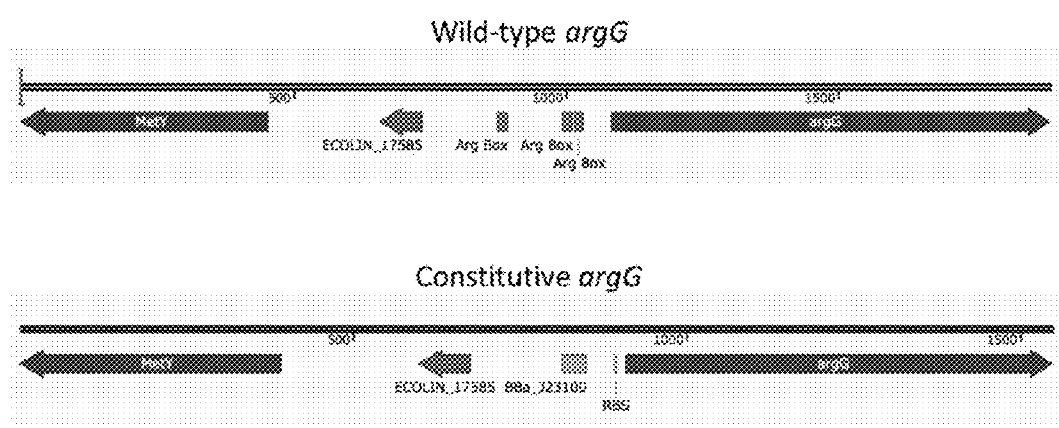
FIG. 17 depicts a map of the wild-type argG operon *E. coli* Nissle, and a constitutively expressing mutant thereof. ARG boxes are present in the wild-type operon, but absent from the mutant. ArgG is constitutively expressed under the control of the BBa_J23100 promoter.
Figure 19:
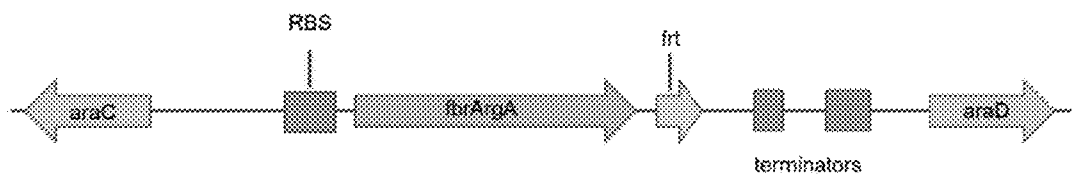
FIG. 19 depicts a schematic diagram of an exemplary BAD promoter-driven argA$^{fbr}$ construct. In this embodiment, the argA$^{fbr}$ gene is inserted between the araC and araD genes. ArgA$^{fbr}$ is flanked by a ribosome binding site, a FRT site, and one or more transcription terminator sequences.
Figure 20:
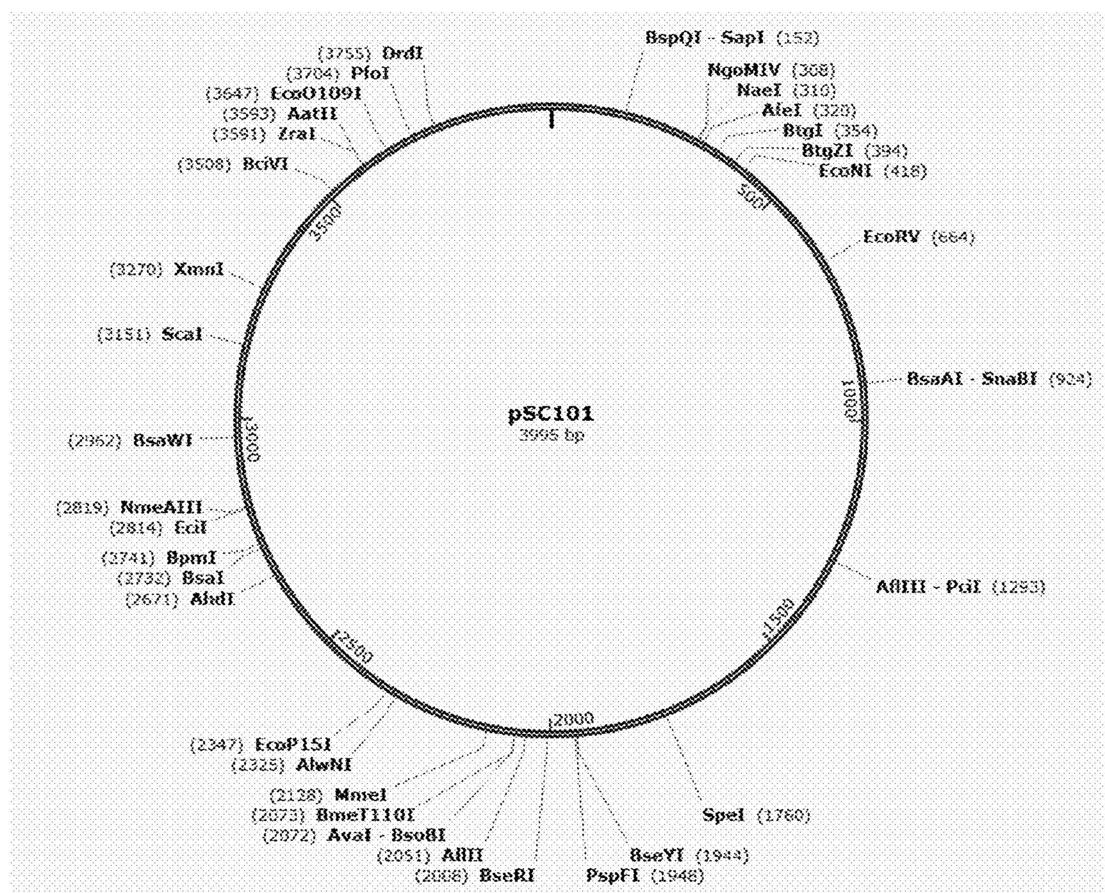
FIG. 20 depicts a map of the pSC101 plasmid. Restriction sites are shown in bold.

The invention includes genetically engineered bacteria, pharmaceutical compositions thereof, and methods of modulating or treating disorders associated with hyperammonemia, e.g., urea cycle disorders and hepatic encephalopathy. The genetically engineered bacteria are capable of reducing excess ammonia, particularly in low-oxygen conditions, such as in the mammalian gut. In certain embodiments, the genetically engineered bacteria reduce excess ammonia by incorporating excess nitrogen in the body into non-toxic molecules, e.g., arginine, citrulline, methionine, histidine, lysine, asparagine, glutamine, or tryptophan.

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

"Hyperammonemia," "hyperammonemic," or "excess ammonia" is used to refer to increased concentrations of ammonia in the body. Hyperammonemia is caused by decreased detoxification and/or increased production of ammonia. Decreased detoxification may result from urea cycle disorders (UCDs), such as argininosuccinic aciduria, arginase deficiency, carbamoylphosphate synthetase deficiency, citrullinemia, N-acetylglutamate synthetase deficiency, and ornithine transcarbamylase deficiency; or from bypass of the liver, e.g., open ductus hepaticus; and/or deficiencies in glutamine synthetase (Hoffman et al., 2013; Häberle et al., 2013). Increased production of ammonia may result from infections, drugs, neurogenic bladder, and intestinal bacterial overgrowth (Häberle et al., 2013). Other disorders and conditions associated with hyperammonemia include, but are not limited to, liver disorders such as hepatic encephalopathy, acute liver failure, or chronic liver failure; organic acid disorders; isovaleric aciduria; 3-methylcrotonylglycinuria; methylmalonic acidemia; propionic aciduria; fatty acid oxidation defects; carnitine cycle defects; carnitine deficiency; β-oxidation deficiency; lysinuric protein intolerance; pyrroline-5-carboxylate synthetase deficiency; pyruvate carboxylase deficiency; ornithine aminotransferase deficiency; carbonic anhydrase deficiency; hyperinsulinism-hyperammonemia syndrome; mitochondrial disorders; valproate therapy; asparaginase therapy; total parenteral nutrition; cystoscopy with glycine-containing solutions; post-lung/bone marrow transplantation; portosystemic shunting; urinary tract infections; ureter dilation; multiple myeloma; and chemotherapy (Hoffman et al., 2013; Häberle et al., 2013; Pham et al., 2013; Lazier et al., 2014). In healthy subjects, plasma ammonia concentrations are typically less than about 50 μmol/L (Leonard, 2006). In some embodiments, a diagnostic signal of hyperammonemia is a plasma ammonia concentration of at least about 50 μmol/L, at least about 80 μmol/L, at least about 150 μmol/L, at least about 180 μmol/L, or at least about 200 μmol/L (Leonard, 2006; Hoffman et al., 2013; Haberle et al., 2013).

"Ammonia" is used to refer to gaseous ammonia ($NH_3$), ionic ammonia ($NH_4^+$), or a mixture thereof. In bodily fluids, gaseous ammonia and ionic ammonium exist in equilibrium:

$$NH_3+H^+ \leftrightarrow NH_4^+$$

Some clinical laboratory tests analyze total ammonia ($NH_3+NH_4^+$) (Walker, 2012). In any embodiment of the invention, unless otherwise indicated, "ammonia" may refer to gaseous ammonia, ionic ammonia, and/or total ammonia.

"Detoxification" of ammonia is used to refer to the process or processes, natural or synthetic, by which toxic ammonia is removed and/or converted into one or more non-toxic molecules, including but not limited to: arginine, citrulline, methionine, histidine, lysine, asparagine, glutamine, tryptophan, or urea. The urea cycle, for example, enzymatically converts ammonia into urea for removal from the body in the urine. Because ammonia is a source of nitrogen for many amino acids, which are synthesized via numerous biochemical pathways, enhancement of one or more of those amino acid biosynthesis pathways may be used to incorporate excess nitrogen into non-toxic molecules. For example, arginine biosynthesis converts glutamate, which comprises one nitrogen atom, to arginine, which comprises four nitrogen atoms, thereby incorporating excess nitrogen into non-toxic molecules. In humans, arginine is not reabsorbed from the large intestine, and as a result, excess arginine in the large intestine is not considered to be harmful. Likewise, citrulline is not reabsorbed from the large intestine, and as a result, excess citrulline in the large intestine is not considered to be harmful. Arginine biosynthesis may also be modified to produce citrulline as an end product; citrulline comprises three nitrogen atoms and thus the modified pathway is also capable of incorporating excess nitrogen into non-toxic molecules.

"Arginine regulon," "arginine biosynthesis regulon," and "arg regulon" are used interchangeably to refer to the collection of operons in a given bacterial species that comprise the genes encoding the enzymes responsible for converting glutamate to arginine and/or intermediate metabolites, e.g., citrulline, in the arginine biosynthesis pathway. The arginine regulon also comprises operators, promoters, ARG boxes, and/or regulatory regions associated with those operons. The arginine regulon includes, but is not limited to, the operons encoding the arginine biosynthesis enzymes N-acetylglutamate synthetase, N-acetylglutamate kinase, N-acetylglutamylphosphate reductase, acetylornithine am inotransferase, N-acetylornithinase, ornithine transcarbamylase, argininosuccinate synthase, argininosuccinate lyase, carbamoylphosphate synthase, operators thereof, promoters thereof, ARG boxes thereof, and/or regulatory regions thereof. In some embodiments, the arginine regulon comprises an operon encoding ornithine acetyltransferase and associated operators, promoters, ARG boxes, and/or regulatory regions, either in addition to or in lieu of N-acetylglutamate synthetase and/or N-acetylornithinase. In some embodiments, one or more operons or genes of the arginine regulon may be present on a plasmid in the bacterium. In some embodiments, a bacterium may comprise multiple copies of any gene or operon in the arginine regulon, wherein one or more copies may be mutated or otherwise altered as described herein.

One gene may encode one enzyme, e.g., N-acetylglutamate synthetase (argA). Two or more genes may encode distinct subunits of one enzyme, e.g., subunit A and subunit B of carbamoylphosphate synthase (carA and carB). In some bacteria, two or more genes may each independently encode the same enzyme, e.g., ornithine transcarbamylase (argF and argI). In some bacteria, the arginine regulon includes, but is not limited to, argA, encoding N-acetylglutamate synthetase; argB, encoding N-acetylglutamate kinase; argC, encoding N-acetylglutamylphosphate reductase; argD, encoding acetylornithine aminotransferase; argE, encoding N-acetylornithinase; argG, encoding argininosuccinate synthase; argH, encoding argininosuccinate lyase; one or both of argF and argI, each of which independently encodes ornithine transcarbamylase; carA, encoding the small subunit of carbamoylphosphate synthase; carB, encoding the large subunit of carbamoylphosphate synthase; operons thereof; operators thereof; promoters thereof; ARG boxes thereof; and/or regulatory regions thereof. In some embodiments, the arginine regulon comprises argJ, encoding ornithine acetyltransferase (either in addition to or in lieu of N-acetylglutamate synthetase and/or N-acetylornithinase), operons thereof, operators thereof, promoters thereof, ARG boxes thereof, and/or regulatory regions thereof.

"Arginine operon," "arginine biosynthesis operon," and "arg operon" are used interchangeably to refer to a cluster of one or more of the genes encoding arginine biosynthesis enzymes under the control of a shared regulatory region comprising at least one promoter and at least one ARG box. In some embodiments, the one or more genes are co-transcribed and/or co-translated. Any combination of the genes encoding the enzymes responsible for arginine biosynthesis may be organized, naturally or synthetically, into an operon. For example, in *B. subtilis*, the genes encoding N-acetylglutamylphosphate reductase, N-acetylglutamate kinase, N-acetylornithinase, N-acetylglutamate kinase, acetylornithine am inotransferase, carbamoylphosphate synthase, and ornithine transcarbamylase are organized in a single operon, argCAEBD-carAB-argF (see, e.g., Table 2), under the control of a shared regulatory region comprising a promoter and ARG boxes. In *E. coli* K12 and Nissle, the genes encoding N-acetylornithinase, N-acetylglutamylphosphate reductase, N-acetylglutamate kinase, and argininosuccinate lyase are organized in two bipolar operons, argECBH. The operons encoding the enzymes responsible for arginine biosynthesis may be distributed at different loci across the chromosome. In unmodified bacteria, each operon may be repressed by arginine via ArgR. In some embodiments, arginine and/or intermediate byproduct production may be altered in the genetically engineered bacteria of the invention by modifying the expression of the enzymes encoded by the arginine biosynthesis operons as provided herein. Each arginine operon may be present on a plasmid or bacterial chromosome. In addition, multiple copies of any arginine operon, or a gene or regulatory region within an arginine operon, may be present in the bacterium, wherein one or more copies of the operon or gene or regulatory region may be mutated or otherwise altered as described herein. In some embodiments, the genetically engineered bacteria are engineered to comprise multiple copies of the same product (e.g., operon or gene or regulatory region) to enhance copy number or to comprise multiple different components of an operon performing multiple different functions.

"ARG box consensus sequence" refers to an ARG box nucleic acid sequence, the nucleic acids of which are known to occur with high frequency in one or more of the regulatory regions of argR, argA, argB, argC, argD, argE, argF, argG, argH, argI, argJ, carA, and/or carB. As described above, each arg operon comprises a regulatory region comprising at least one 18-nucleotide imperfect palindromic sequence, called an ARG box, that overlaps with the promoter and to which the repressor protein binds (Tian et al., 1992). The nucleotide sequences of the ARG boxes may vary for each operon, and the consensus ARG box sequence is A/T nTGAAT A/T A/T T/A T/A ATTCAn T/A (Maas, 1994). The arginine repressor binds to one or more ARG boxes to actively inhibit the transcription of the arginine biosynthesis enzyme(s) that are operably linked to that one or more ARG boxes.

"Mutant arginine regulon" or "mutated arginine regulon" is used to refer to an arginine regulon comprising one or more nucleic acid mutations that reduce or eliminate arginine-mediated repression of each of the operons that encode the enzymes responsible for converting glutamate to arginine and/or an intermediate byproduct, e.g., citrulline, in the arginine biosynthesis pathway, such that the mutant arginine regulon produces more arginine and/or intermediate byproduct than an unmodified regulon from the same bacterial subtype under the same conditions. In some embodiments, the genetically engineered bacteria comprise an arginine feedback resistant N-acetylglutamate synthase mutant, e.g., $argA^{fbr}$, and a mutant arginine regulon comprising one or more nucleic acid mutations in at least one ARG box for one or more of the operons that encode the arginine biosynthesis enzymes N-acetylglutamate kinase, N-acetylglutamylphosphate reductase, acetylornithine aminotransferase, N-acetylornithinase, ornithine transcarbamylase, argininosuccinate synthase, argininosuccinate lyase, and carbamoylphosphate synthase, thereby derepressing the regulon and enhancing arginine and/or intermediate byproduct biosynthesis. In some embodiments, the genetically engineered bacteria comprise a mutant arginine repressor comprising one or more nucleic acid mutations such that arginine repressor function is decreased or inactive, or the genetically engineered bacteria do not have an arginine repressor (e.g., the arginine repressor gene has been deleted), resulting in derepression of the regulon and enhancement of arginine and/or intermediate byproduct biosynthesis. In some embodiments, the genetically engineered bacteria comprise an arginine feedback resistant N-acetylglutamate synthase mutant, e.g., $argA^{fbr}$, a mutant arginine regulon comprising one or more nucleic acid mutations in at least one ARG box for each of the operons that encode the arginine biosynthesis enzymes, and/or a mutant or deleted arginine repressor. In some embodiments, the genetically engineered bacteria comprise an arginine feedback resistant N-acetylglutamate synthase mutant, e.g., $argA^{fbr}$ and a mutant arginine regulon comprising one or more nucleic acid mutations in at least one ARG box for each of the operons that encode the arginine biosynthesis enzymes. In some embodiments, the genetically engineered bacteria comprise an arginine feedback resistant N-acetylglutamate synthase mutant, e.g., $argA^{fbr}$ and a mutant or deleted arginine repressor. In some embodiments, the mutant arginine regulon comprises an operon encoding wild-type N-acetylglutamate synthetase and one or more nucleic acid mutations in at least one ARG box for said operon. In some embodiments, the mutant arginine regulon comprises an operon encoding wild-type N-acetylglutamate synthetase and mutant or deleted arginine repressor. In some embodiments, the mutant arginine regulon comprises an operon encoding ornithine acetyltransferase (either in addition to or in lieu of N-acetylglutamate synthetase and/or N-acetylornithinase) and one or more nucleic acid mutations in at least one ARG box for said operon.

The ARG boxes overlap with the promoter in the regulatory region of each arginine biosynthesis operon. In the mutant arginine regulon, the regulatory region of one or more arginine biosynthesis operons is sufficiently mutated to disrupt the palindromic ARG box sequence and reduce ArgR binding, but still comprises sufficiently high homology to the promoter of the non-mutant regulatory region to be recognized as the native operon-specific promoter. The operon comprises at least one nucleic acid mutation in at least one ARG box such that ArgR binding to the ARG box and to the regulatory region of the operon is reduced or eliminated. In some embodiments, bases that are protected from DNA methylation and bases that are protected from hydroxyl radical attack during ArgR binding are the primary targets for mutations to disrupt ArgR binding (see, e.g., FIG. 6). The promoter of the mutated regulatory region retains sufficiently high homology to the promoter of the non-mutant regulatory region such that RNA polymerase binds to it with sufficient affinity to promote transcription of the operably linked arginine biosynthesis enzyme(s). In some embodiments, the G/C:A/T ratio of the promoter of the mutant differs by no more than 10% from the G/C:A/T ratio of the wild-type promoter.

In some embodiments, more than one ARG box may be present in a single operon. In one aspect of these embodiments, at least one of the ARG boxes in an operon is altered to produce the requisite reduced ArgR binding to the regulatory region of the operon. In an alternate aspect of these embodiments, each of the ARG boxes in an operon is altered to produce the requisite reduced ArgR binding to the regulatory region of the operon.

"Reduced" ArgR binding is used to refer to a reduction in repressor binding to an ARG box in an operon or a reduction in the total repressor binding to the regulatory region of said operon, as compared to repressor binding to an unmodified ARG box and regulatory region in bacteria of the same subtype under the same conditions. In some embodiments, ArgR binding to a mutant ARG box and regulatory region of an operon is at least about 50% lower, at least about 60% lower, at least about 70% lower, at least about 80% lower, at least about 90% lower, or at least about 95% lower than ArgR binding to an unmodified ARG box and regulatory region in bacteria of the same subtype under the same conditions. In some embodiments, reduced ArgR binding to a mutant ARG box and regulatory region results in at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold increased mRNA expression of the one or more genes in the operon.

"ArgR" or "arginine repressor" is used to refer to a protein that is capable of suppressing arginine biosynthesis by regulating the transcription of arginine biosynthesis genes in the arginine regulon. When expression of the gene that encodes for the arginine repressor protein ("argR") is increased in a wild-type bacterium, arginine biosynthesis is decreased. When expression of argR is decreased in a wild-type bacterium, or if argR is deleted or mutated to inactivate arginine repressor function, arginine biosynthesis is increased.

Bacteria that "lack any functional ArgR" and "ArgR deletion bacteria" are used to refer to bacteria in which each arginine repressor has significantly reduced or eliminated activity as compared to unmodified arginine repressor from bacteria of the same subtype under the same conditions. Reduced or eliminated arginine repressor activity can result in, for example, increased transcription of the arginine biosynthesis genes and/or increased concentrations of arginine and/or intermediate byproducts, e.g., citrulline. Bacteria in which arginine repressor activity is reduced or eliminated can be generated by modifying the bacterial argR gene or by modifying the transcription of the argR gene. For example, the chromosomal argR gene can be deleted, can be mutated, or the argR gene can be replaced with an argR gene that does not exhibit wild-type repressor activity.

"Operably linked" refers a nucleic acid sequence, e.g., a gene encoding feedback resistant ArgA, that is joined to a regulatory region sequence in a manner which allows expression of the nucleic acid sequence, e.g., acts in cis.

An "inducible promoter" refers to a regulatory region that is operably linked to one or more genes, wherein expression of the gene(s) is increased in the presence of an inducer of said regulatory region.

"Exogenous environmental condition(s)" refer to setting(s) or circumstance(s) under which the promoter described above is induced. In some embodiments, the exogenous environmental conditions are specific to the gut of a mammal. In some embodiments, the exogenous environmental conditions are specific to the upper gastrointestinal tract of a mammal. In some embodiments, the exogenous environmental conditions are specific to the lower gastrointestinal tract of a mammal. In some embodiments, the exogenous environmental conditions are specific to the small intestine of a mammal. In some embodiments, the exogenous environmental conditions are low-oxygen, microaerobic, or anaerobic conditions, such as the environment of the mammalian gut. In some embodiments, exogenous environmental conditions are molecules or metabolites that are specific to the mammalian gut, e.g., propionate. In some embodiments, the genetically engineered bacteria of the invention comprise an oxygen level-dependent promoter. Bacteria have evolved transcription factors that are capable of sensing oxygen levels. Different signaling pathways may be triggered by different oxygen levels and occur with different kinetics. An "oxygen level-dependent promoter" or "oxygen level-dependent regulatory region" refers to a nucleic acid sequence to which one or more oxygen level-sensing transcription factors is capable of binding, wherein the binding and/or activation of the corresponding transcription factor activates downstream gene expression.

Examples of oxygen level-dependent transcription factors include, but are not limited to, FNR, ANR, and DNR. Corresponding FNR-responsive promoters, ANR-responsive promoters, and DNR-responsive promoters are known in the art (see, e.g., Castiglione et al., 2009; Eiglmeier et al., 1989; Galimand et al., 1991; Hasegawa et al., 1998; Hoeren et al., 1993; Salmon et al., 2003), and non-limiting examples are shown in Table 1.

TABLE 1

Examples of transcription factors and responsive genes and regulatory regions

| Transcription Factor | Examples of responsive genes, promoters, and/or regulatory regions: |
|---|---|
| FNR | nirB, ydfZ, pdhR, focA, ndH, hlyE, narK, narX, narG, yfiD, tdcD |
| ANR | arcDABC |
| DNR | norb, norC |

As used herein, a "non-native" nucleic acid sequence refers to a nucleic acid sequence not normally present in a bacterium, e.g., an extra copy of an endogenous sequence, or a heterologous sequence such as a sequence from a different species, strain, or substrain of bacteria, or a sequence that is modified and/or mutated as compared to the unmodified sequence from bacteria of the same subtype. In some embodiments, the non-native nucleic acid sequence is a synthetic, non-naturally occurring sequence (see, e.g., Purcell et al., 2013). The non-native nucleic acid sequence may be a regulatory region, a promoter, a gene, and/or one or more genes in gene cassette. In some embodiments, "non-native" refers to two or more nucleic acid sequences that are not found in the same relationship to each other in nature. The non-native nucleic acid sequence may be present on a plasmid or chromosome. In some embodiments, the genetically engineered bacteria of the invention comprise a gene cassette that is operably linked to a directly or indirectly inducible promoter that is not associated with said gene cassette in nature, e.g., a FNR-responsive promoter operably linked to a butyrogenic gene cassette.

"Constitutive promoter" refers to a promoter that is capable of facilitating continuous transcription of a coding sequence or gene under its control and/or to which it is operably linked. Constitutive promoters and variants are well known in the art and include, but are not limited to, BBa_J23100, a constitutive *Escherichia coli* $\sigma^S$ promoter (e.g., an osmY promoter (International Genetically Engineered Machine (iGEM) Registry of Standard Biological Parts Name BBa_J45992; BBa_J45993)), a constitutive *Escherichia coli* $\sigma^{32}$ promoter (e.g., htpG heat shock promoter (BBa_J45504)), a constitutive *Escherichia coli* $\sigma^{70}$ promoter (e.g., lacq promoter (BBa_J54200; BBa_J56015), *E. coli* CreABCD phosphate sensing operon promoter (BBa_J64951), GlnRS promoter (BBa_K088007), lacZ promoter (BBa_K119000; BBa_K119001); M13K07 gene I promoter (BBa_M13101); M13K07 gene II promoter (BBa_M13102), M13K07 gene III promoter (BBa_M13103), M13K07 gene IV promoter (BBa_M13104), M13K07 gene V promoter (BBa_M13105), M13K07 gene VI promoter (BBa_M13106), M13K07 gene VIII promoter (BBa_M13108), M13110 (BBa_M13110)), a constitutive *Bacillus subtilis* $\sigma^A$ promoter (e.g., promoter veg (BBa_K143013), promoter 43 (BBa_K143013), $P_{liaG}$ (BBa_K823000), $P_{lepA}$ (BBa_K823002), $P_{veg}$ (BBa_K823003)), a constitutive *Bacillus subtilis* $\sigma^B$ promoter (e.g., promoter ctc (BBa_K143010), promoter gsiB (BBa_K143011)), a *Salmonella* promoter (e.g., Pspv2 from *Salmonella* (BBa_K112706), Pspv from *Salmonella* (BBa_K112707)), a bacteriophage T7 promoter (e.g., T7 promoter (BBa_$_I$712074; BBa_$_I$719005; BBa_J34814; BBa_J64997; BBa_K113010; BBa_K113011; BBa_K113012; BBa_R0085; BBa_R0180; BBa_R0181; BBa_R0182; BBa_R0183; BBa_Z0251; BBa_Z0252; BBa_Z0253)), and a bacteriophage SP6 promoter (e.g., SP6 promoter (BBa_J64998)).

As used herein, genetically engineered bacteria that "overproduce" arginine or an intermediate byproduct, e.g., citrulline, refer to bacteria that comprise a mutant arginine regulon. For example, the engineered bacteria may comprise a feedback resistant form of ArgA, and when the arginine feedback resistant ArgA is expressed, are capable of producing more arginine and/or intermediate byproduct than unmodified bacteria of the same subtype under the same conditions. The genetically engineered bacteria may alternatively or further comprise a mutant arginine regulon comprising one or more nucleic acid mutations in at least one ARG box for each of the operons that encode the arginine biosynthesis enzymes. The genetically engineered bacteria may alternatively or further comprise a mutant or deleted arginine repressor. In some embodiments, the genetically engineered bacteria produce at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold more arginine than unmodified bacteria of the same subtype under the same conditions. In some embodiments, the genetically engineered bacteria produce at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold more citrulline or other intermediate byproduct than unmodified bacteria of the same subtype under the same conditions. In some embodiments, the mRNA transcript levels of one or more of the arginine biosynthesis genes in the genetically engineered bacteria are at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold higher than the mRNA transcript levels in unmodified bacteria of the same subtype under the same conditions. In certain embodiments, the unmodified bacteria will not have detectable levels of arginine, intermediate byproduct, and/or transcription of the gene(s) in such operons. However, protein and/or transcription levels of arginine and/or intermediate byproduct will be detectable in the corresponding genetically engineered bacterium having the mutant arginine regulon. Transcription levels may be detected by directly measuring mRNA levels of the genes. Methods of measuring arginine and/or intermediate byproduct levels, as well as the levels of transcript expressed from the arginine biosynthesis genes, are known in the art. Arginine and citrulline, for example, may be measured by mass spectrometry.

"Gut" refers to the organs, glands, tracts, and systems that are responsible for the transfer and digestion of food, absorption of nutrients, and excretion of waste. In humans, the gut comprises the gastrointestinal tract, which starts at the mouth and ends at the anus, and additionally comprises the esophagus, stomach, small intestine, and large intestine. The gut also comprises accessory organs and glands, such as the spleen, liver, gallbladder, and pancreas. The upper gastrointestinal tract comprises the esophagus, stomach, and duodenum of the small intestine. The lower gastrointestinal tract comprises the remainder of the small intestine, i.e., the jejunum and ileum, and all of the large intestine, i.e., the cecum, colon, rectum, and anal canal. Bacteria can be found throughout the gut, e.g., in the gastrointestinal tract, and particularly in the intestines.

"Non-pathogenic bacteria" refer to bacteria that are not capable of causing disease or harmful responses in a host. In some embodiments, non-pathogenic bacteria are commensal bacteria. Examples of non-pathogenic bacteria include, but are not limited to *Bacillus, Bacteroides, Bifidobacterium, Brevibacteria, Clostridium, Enterococcus, Escherichia coli, Lactobacillus, Lactococcus, Saccharomyces*, and *Staphylococcus*, e.g., *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Lactobacillus acidophilus, Lactobacillus bulgaricus, Lactobacillus casei, Lactobacillus johnsonii, Lactobacillus paracasei, Lactobacillus plantarum, Lactobacillus reuteri, Lactobacillus rhamnosus, Lactococcus lactis*, and *Saccharomyces boulardii* (Sonnenborn et al., 2009; Dinleyici et al., 2014; U.S. Pat. Nos. 6,835,376; 6,203,797; 5,589,168; 7,731,976).

Naturally pathogenic bacteria may be genetically engineered to provide reduce or eliminate pathogenicity.

"Probiotic" is used to refer to live, non-pathogenic microorganisms, e.g., bacteria, which can confer health benefits to a host organism that contains an appropriate amount of the microorganism. In some embodiments, the host organism is a mammal. In some embodiments, the host organism is a human. Some species, strains, and/or subtypes of non-pathogenic bacteria are currently recognized as probiotic bacteria. Examples of probiotic bacteria include, but are not limited to, *Bifidobacteria, Escherichia coli, Lactobacillus*, and *Saccharomyces*, e.g., *Bifidobacterium bifidum, Enterococcus faecium, Escherichia coli* strain Nissle, *Lactobacillus acidophilus, Lactobacillus bulgaricus, Lactobacillus paracasei, Lactobacillus plantarum*, and *Saccharomyces boulardii* (Dinleyici et al., 2014; U.S. Pat. Nos. 5,589,168; 6,203,797; 6,835,376). The probiotic may be a variant or a mutant strain of bacterium (Arthur et al., 2012; Cuevas-Ramos et al., 2010; Olier et al., 2012; Nougayrede et al., 2006). Non-pathogenic bacteria may be genetically engineered to enhance or improve desired biological properties, e.g., survivability. Non-pathogenic bacteria may be genetically engineered to provide probiotic properties. Probiotic bacteria may be genetically engineered to enhance or improve probiotic properties.

As used herein, "stably maintained" or "stable" bacterium is used to refer to a bacterial host cell carrying non-native genetic material, e.g., a feedback resistant argA gene, mutant arginine repressor, and/or other mutant arginine regulon that is incorporated into the host genome or propagated on a self-replicating extra-chromosomal plasmid, such that the non-native genetic material is retained, expressed, and propagated. The stable bacterium is capable of survival and/or growth in vitro, e.g., in medium, and/or in vivo, e.g., in the gut. For example, the stable bacterium may be a genetically engineered bacterium comprising an $argA^{fbr}$ gene, in which the plasmid or chromosome carrying the $argA^{fbr}$ gene is stably maintained in the bacterium, such that $argA^{fbr}$ can be expressed in the bacterium, and the bacterium is capable of survival and/or growth in vitro and/or in vivo.

As used herein, the term "treat" and its cognates refer to an amelioration of a disease or disorder, or at least one discernible symptom thereof. In another embodiment, "treat" refers to an amelioration of at least one measurable physical parameter, not necessarily discernible by the patient. In another embodiment, "treat" refers to inhibiting the progression of a disease or disorder, either physically (e.g., stabilization of a discernible symptom), physiologically (e.g., stabilization of a physical parameter), or both. In another embodiment, "treat" refers to slowing the progression or reversing the progression of a disease or disorder. As used herein, "prevent" and its cognates refer to delaying the onset or reducing the risk of acquiring a given disease or disorder.

Those in need of treatment may include individuals already having a particular medical disorder, as well as those at risk of having, or who may ultimately acquire the disorder. The need for treatment is assessed, for example, by the presence of one or more risk factors associated with the development of a disorder, the presence or progression of a disorder, or likely receptiveness to treatment of a subject having the disorder. Primary hyperammonemia is caused by UCDs, which are autosomal recessive or X-linked inborn errors of metabolism for which there are no known cures. Hyperammonemia can also be secondary to other disruptions of the urea cycle, e.g., toxic metabolites, infections, and/or substrate deficiencies. Treating hyperammonemia may encompass reducing or eliminating excess ammonia and/or associated symptoms, and does not necessarily encompass the elimination of the underlying hyperammonemia-associated disorder.

As used herein a "pharmaceutical composition" refers to a preparation of genetically engineered bacteria of the invention with other components such as a physiologically suitable carrier and/or excipient.

The phrases "physiologically acceptable carrier" and "pharmaceutically acceptable carrier" which may be used interchangeably refer to a carrier or a diluent that does not cause significant irritation to an organism and does not abrogate the biological activity and properties of the administered bacterial compound. An adjuvant is included under these phrases.

The term "excipient" refers to an inert substance added to a pharmaceutical composition to further facilitate administration of an active ingredient. Examples include, but are not limited to, calcium bicarbonate, calcium phosphate, various sugars and types of starch, cellulose derivatives, gelatin, vegetable oils, polyethylene glycols, and surfactants, including, for example, polysorbate 20.

The terms "therapeutically effective dose" and "therapeutically effective amount" are used to refer to an amount of a compound that results in prevention, delay of onset of symptoms, or amelioration of symptoms of a condition, e.g., hyperammonemia. A therapeutically effective amount may, for example, be sufficient to treat, prevent, reduce the severity, delay the onset, and/or reduce the risk of occurrence of one or more symptoms of a disorder associated with elevated ammonia concentrations. A therapeutically effective amount, as well as a therapeutically effective frequency of administration, can be determined by methods known in the art and discussed below.

The articles "a" and "an," as used herein, should be understood to mean "at least one," unless clearly indicated to the contrary.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

Bacteria

The genetically engineered bacteria of the invention are capable of reducing excess ammonia and converting ammonia and/or nitrogen into alternate byproducts. In some embodiments, the genetically engineered bacteria are non-pathogenic bacteria. In some embodiments, the genetically engineered bacteria are commensal bacteria. In some embodiments, the genetically engineered bacteria are probiotic bacteria. In some embodiments, the genetically engineered bacteria are naturally pathogenic bacteria that are modified or mutated to reduce or eliminate pathogenicity. Exemplary bacteria include, but are not limited to *Bacillus, Bacteroides, Bifidobacterium, Brevibacteria, Clostridium, Enterococcus, Escherichia coli, Lactobacillus, Lactococcus, Saccharomyces*, and *Staphylococcus*, e.g., *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Lactobacillus acidophilus, Lactobacillus bulgaricus, Lactobacillus casei, Lactobacillus johnsonii, Lactobacillus paracasei, Lactobacillus plantarum,*

*Lactobacillus reuteri, Lactobacillus rhamnosus, Lactococcus lactis*, and *Saccharomyces boulardii*. In certain embodiments, the genetically engineered bacteria are selected from the group consisting of *Bacteroides fragilis, Bacteroides thetaiotaomicron, Bacteroides subtilis, Bifidobacterium bifidum, Bifidobacterium infantis, Bifidobacterium lactis, Clostridium butyricum, Escherichia coli* Nissle, *Lactobacillus acidophilus, Lactobacillus plantarum, Lactobacillus reuteri*, and *Lactococcus lactis*.

In some embodiments, the genetically engineered bacteria are *Escherichia coli* strain Nissle 1917 (*E. coli* Nissle), a Gram-negative bacterium of the Enterobacteriaceae family that "has evolved into one of the best characterized probiotics" (Ukena et al., 2007). The strain is characterized by its complete harmlessness (Schultz, 2008), and has GRAS (generally recognized as safe) status (Reister et al., 2014, emphasis added). Genomic sequencing confirmed that E. coli Nissle lacks prominent virulence factors (e.g., *E. coli* α-hemolysin, P-fimbrial adhesins) (Schultz, 2008). In addition, it has been shown that *E. coli* Nissle does not carry pathogenic adhesion factors, does not produce any enterotoxins or cytotoxins, is not invasive, and not uropathogenic (Sonnenborn et al., 2009). As early as in 1917, *E. coli* Nissle was packaged into medicinal capsules, called Mutaflor, for therapeutic use. *E. coli* Nissle has since been used to treat ulcerative colitis in humans in vivo (Rembacken et al., 1999), to treat inflammatory bowel disease, Crohn's disease, and pouchitis in humans in vivo (Schultz, 2008), and to inhibit enteroinvasive *Salmonella, Legionella, Yersinia*, and *Shigella* in vitro (Altenhoefer et al., 2004). It is commonly accepted that *E. coli* Nissle's therapeutic efficacy and safety have convincingly been proven (Ukena et al., 2007).

One of ordinary skill in the art would appreciate that the genetic modifications disclosed herein may be modified and adapted for other species, strains, and subtypes of bacteria. It is known, for example, that arginine-mediated regulation is remarkably well conserved in very divergent bacteria, i.e., gram-negative bacteria, such as *E. coli, Salmonella enterica* serovar Typhimurium, *Thermotoga*, and *Moritella profunda*, and gram-positive bacteris, such as *B. subtilis, Geobacillus stearothermophilus*, and *Streptomyces clavuligerus*, as well as other bacteria (Nicoloff et al., 2004). Furthermore, the arginine repressor is universally conserved in bacterial genomes and that its recognition signal (the ARG box), a weak palindrome, is also conserved between genomes (Makarova et al., 2001).

Unmodified *E. coli* Nissle and the genetically engineered bacteria of the invention may be destroyed, e.g., by defense factors in the gut or blood serum (Sonnenborn et al., 2009). The residence time of bacteria in vivo can be determined using the methods described in Example 19. In some embodiments, the residence time is calculated for a human subject. A non-limiting example using a streptomycin-resistant *E. coli* Nissle comprising a wild-type ArgR and a wild-type arginine regulon is provided (see FIG. 27). In some embodiments, residence time in vivo is calculated for the genetically engineered bacteria of the invention.

Reduction of Excess Ammonia

Arginine Biosynthesis Pathway

In bacteria such as *Escherichia coli* (*E. coli*), the arginine biosynthesis pathway is capable of converting glutamate to arginine in an eight-step enzymatic process involving the enzymes N-acetylglutamate synthetase, N-acetylglutamate kinase, N-acetylglutamate phosphate reductase, acetylornithine aminotransferase, N-acetylornithinase, carbamoylphosphate synthase, ornithine transcarbamylase, argininosuccinate synthase, and argininosuccinate lyase (Cunin et al., 1986). The first five steps involve N-acetylation to generate an ornithine precursor. In the sixth step, ornithine transcarbamylase (also known as ornithine carbamoyltransferase) catalyzes the formation of citrulline. The final two steps involve carbamoylphosphate utilization to generate arginine from citrulline.

In some bacteria, e.g., *Bacillus stearothermophilus* and *Neisseria gonorrhoeae*, the first and fifth steps in arginine biosynthesis may be catalyzed by the bifunctional enzyme ornithine acetyltransferase. This bifunctionality was initially identified when ornithine acetyltransferase (argJ) was shown to complement both N-acetylglutamate synthetase (argA) and N-acetylornithinase (argE) auxotrophic gene mutations in *E. coli* (Mountain et al., 1984; Crabeel et al., 1997).

ArgA encodes N-acetylglutamate synthetase, argB encodes N-acetylglutamate kinase, argC encodes N-acetylglutamylphosphate reductase, argD encodes acetylornithine aminotransferase, argE encodes N-acetylornithinase, argF encodes ornithine transcarbamylase, argI also encodes ornithine transcarbamylase, argG encodes argininosuccinate synthase, argH encodes argininosuccinate lyase, and argJ encodes ornithine acetyltransferase. CarA encodes the small A subunit of carbamoylphosphate synthase having glutaminase activity, and carB encodes the large B subunit of carbamoylphosphate synthase that catalyzes carbamoylphosphate synthesis from ammonia. Different combinations of one or more of these arginine biosynthesis genes (i.e., argA, argB, argC, argD, argE, argF, argG, argH, argI, argJ, carA, and carB) may be organized, naturally or synthetically, into one or more operons, and such organization may vary between bacterial species, strains, and subtypes (see, e.g., Table 2). The regulatory region of each operon contains at least one ARG box, and the number of ARG boxes per regulatory region may vary between operons and bacteria.

All of the genes encoding these enzymes are subject to repression by arginine via its interaction with ArgR to form a complex that binds to the regulatory region of each gene and inhibits transcription. N-acetylglutamate synthetase is also subject to allosteric feedback inhibition at the protein level by arginine alone (Tuchman et al., 1997; Caldara et al., 2006; Caldara et al., 2008; Caldovic et al., 2010).

The genes that regulate arginine biosynthesis in bacteria are scattered across the chromosome and organized into multiple operons that are controlled by a single repressor, which Maas and Clark (1964) termed a "regulon." Each operon is regulated by a regulatory region comprising at least one 18-nucleotide imperfect palindromic sequence, called an ARG box, that overlaps with the promoter and to which the repressor protein binds (Tian et al., 1992; Tian et al., 1994). The argR gene encodes the repressor protein, which binds to one or more ARG boxes (Lim et al., 1987). Arginine functions as a corepressor that activates the arginine repressor. The ARG boxes that regulate each operon may be non-identical, and the consensus ARG box sequence is A/T nTGAAT A/T A/T T/A T/A ATTCAn T/A (Maas, 1994). In addition, the regulatory region of argR contains two promoters, one of which overlaps with two ARG boxes and is autoregulated.

In some embodiments, the genetically engineered bacteria comprise a mutant arginine regulon and produce more arginine and/or an intermediate byproduct, e.g., citrulline, than unmodified bacteria of the same subtype under the same conditions. The mutant arginine regulon comprises one or more nucleic acid mutations that reduce or prevent arginine-mediated repression—via ArgR binding to ARG boxes and/or arginine binding to N-acetylglutamate synthetase—of one or more of the operons that encode the enzymes responsible for converting glutamate to arginine in the arginine biosynthesis pathway, thereby enhancing arginine and/or intermediate byproduct biosynthesis.

In alternate embodiments, the bacteria are genetically engineered to consume excess ammonia via another metabolic pathway, e.g., a histidine biosynthesis pathway, a methionine biosynthesis pathway, a lysine biosynthesis pathway, an asparagine biosynthesis pathway, a glutamine biosynthesis pathway, and a tryptophan biosynthesis pathway.

Histidine Biosynthesis Pathway

Histidine biosynthesis, for example, is carried out by eight genes located within a single operon in *E. coli*. Three of the eight genes of the operon (hisD, hisB, and hisI) encode bifunctional enzymes, and two (hisH and hisF) encode polypeptide chains which together form one enzyme to catalyze a single step, for a total of 10 enzymatic reactions (Alifano et al., 1996). The product of the hisG gene, ATP phosphoribosyltransferase, is inhibited at the protein level by histidine. In some embodiments, the genetically engineered bacteria of the invention comprise a feedback-resistant hisG. Bacteria may be mutagenized and/or screened for feedback-resistant hisG mutants using techniques known in the art. Bacteria engineered to comprise a feedback-resistant hisG would have elevated levels of histidine production, thus increasing ammonia consumption and reducing hyperammonemia. Alternatively, one or more genes required for histidine biosynthesis could be placed under the control of an inducible promoter, such as a FNR-inducible promoter, and allow for increased production of rate-limiting enzymes. Any other suitable modification(s) to the histidine biosynthesis pathway may be used to increase ammonia consumption.

Methionine Biosynthesis Pathway

The bacterial methionine regulon controls the three-step synthesis of methionine from homoserine (i.e., acylation, sulfurylation, and methylation). The metJ gene encodes a regulatory protein that, when combined with methionine or a derivative thereof, causes repression of genes within the methionine regulon at the transcriptional level (Saint-Girons et al., 1984; Shoeman et al., 1985). In some embodiments, the genetically engineered bacteria of the invention comprise deleted, disrupted, or mutated metJ. Bacteria engineered to delete, disrupt, or mutate metJ would have elevated levels of methionine production, thus increasing ammonia consumption and reducing hyperammonemia. Any other suitable modification(s) to the methionine biosynthesis pathway may be used to increase ammonia consumption.

Lysine Biosynthesis Pathway

Microorganisms synthesize lysine by one of two pathways. The diaminopimelate (DAP) pathway is used to synthesize lysine from aspartate and pyruvate (Dogovski et al., 2012), and the aminoadipic acid pathway is used to synthesize lysine from alpha-ketoglutarate and acetyl coenzyme A. The dihydrodipicolinate synthase (DHDPS) enzyme catalyzes the first step of the DAP pathway, and is subject to feedback inhibition by lysine (Liu et al., 2010; Reboul et al., 2012). In some embodiments, the genetically engineered bacteria of the invention comprise a feedback-resistant DHDPS. Bacteria engineered to comprise a feedback-resistant DHDPS would have elevated levels of histidine production, thus increasing ammonia consumption and reducing hyperammonemia. Alternatively, lysine production could be optimized by placing one or more genes required for lysine biosynthesis under the control of an inducible promoter, such as a FNR-inducible promoter. Any other suitable modification(s) to the lysine biosynthesis pathway may be used to increase ammonia consumption.

Asparagine Biosynthesis Pathway

Asparagine is synthesized directly from oxaloacetate and aspartic acid via the oxaloacetate transaminase and asparagine synthetase enzymes, respectively. In the second step of this pathway, either L-glutamine or ammonia serves as the amino group donor. In some embodiments, the genetically engineered bacteria of the invention overproduce asparagine as compared to unmodified bacteria of the same subtype under the same conditions, thereby consuming excess ammonia and reducing hyperammonemia. Alternatively, asparagine synthesis may be optimized by placing one or both of these genes under the control of an inducible promoter, such as a FNR-inducible promoter. Any other suitable modification(s) to the asparagine biosynthesis pathway may be used to increase ammonia consumption.

Glutamine Biosynthesis Pathway

The synthesis of glutamine and glutamate from ammonia and oxoglutarate is tightly regulated by three enzymes. Glutamate dehydrogenase catalyzes the reductive amination of oxoglutarate to yield glutamate in a single step. Glutamine synthetase catalyzes the ATP-dependent condensation of glutamate and ammonia to form glutamine (Lodeiro et al., 2008). Glutamine synthetase also acts with glutamine—oxoglutarate amino transferase (also known as glutamate synthase) in a cyclic reaction to produce glutamate from glutamine and oxoglutarate. In some embodiments, the genetically engineered bacteria of the invention express glutamine synthetase at elevated levels as compared to unmodified bacteria of the same subtype under the same conditions. Bacteria engineered to have increased expression of glutamine synthetase would have elevated levels of glutamine production, thus increasing ammonia consumption and reducing hyperammonemia. Alternatively, expression of glutamate dehydrogenase and/or glutamine-oxoglutarate amino transferase could be modified to favor the consumption of ammonia. Since the production of glutamine synthetase is regulated at the transcriptional level by nitrogen (Feng et al., 1992; van Heeswijk et al., 2013), placing the glutamine synthetase gene under the control of different inducible promoter, such as a FNR-inducible promoter, may also be used to improve glutamine production. Any other suitable modification(s) to the glutamine and glutamate biosynthesis pathway may be used to increase ammonia consumption.

Tryptophan Biosynthesis Pathway

In most bacteria, the genes required for the synthesis of tryptophan from a chorismate precursor are organized as a single transcriptional unit, the trp operon. The trp operon is under the control of a single promoter that is inhibited by the tryptophan repressor (TrpR) when high levels of tryptophan are present. Transcription of the trp operon may also be terminated in the presence of high levels of charged tryptophan tRNA. In some embodiments, the genetically engineered bacteria of the invention comprise a deleted, disrupted, or mutated trpR gene. The deletion, disruption, or mutation of the trpR gene, and consequent inactivation of TrpR function, would result in elevated levels of both tryptophan production and ammonia consumption. Alternatively, one or more enzymes required for tryptophan biosynthesis could be placed under the control of an inducible promoter, such as a FNR-inducible promoter. Any other suitable modification(s) to the tryptophan biosynthesis pathway may be used to increase ammonia consumption.

Engineered Bacteria Comprising a Mutant Arginine Regulon

In some embodiments, the genetically engineered bacteria comprise an arginine biosynthesis pathway and are capable of reducing excess ammonia. In a more specific aspect, the genetically engineered bacteria comprise a mutant arginine regulon in which one or more operons encoding arginine biosynthesis enzyme(s) is derepressed to produce more arginine or an intermediate byproduct, e.g., citrulline, than unmodified bacteria of the same subtype under the same conditions. In some embodiments, the genetically engineered bacteria overproduce arginine. In some embodiments, the genetically engineered bacteria overproduce citrulline; this may be additionally beneficial, because citrulline is currently used as a therapeutic for particular urea cycle disorders (National Urea Cycle Disorders Foundation). In some embodiments, the genetically engineered bacteria overproduce an alternate intermediate byproduct in the arginine biosynthesis pathway, such as any of the intermediates described herein. In some embodiments, the genetically engineered bacterium consumes excess ammonia by producing more arginine, citrulline, and/or other intermediate byproduct than an unmodified bacterium of the same bacterial subtype under the same conditions. Enhancement of arginine and/or intermediate byproduct biosynthesis may be used to incorporate excess nitrogen in the body into non-toxic molecules in order to treat conditions associated with hyperammonemia, including urea cycle disorders and hepatic encephalopathy.

One of skill in the art would appreciate that the organization of arginine biosynthesis genes within an operon varies across species, strains, and subtypes of bacteria, e.g., bipolar argECBH in *E. coli* K12, argCAEBD-carAB-argF in *B. subtilis*, and bipolar carAB-argCJBDF in *L. plantarum*. Non-limiting examples of operon organization from different bacteria are shown in Table 2 (in some instances, the genes are putative and/or identified by sequence homology to known sequences in *Escherichia coli*; in some instances, not all of the genes in the arginine regulon are known and/or shown below). In certain instances, the arginine biosynthesis enzymes vary across species, strains, and subtypes of bacteria.

TABLE 2

Examples of arg operon organization

| Bacteria | Operon organization | | | | | |
|---|---|---|---|---|---|---|
| *Escherichia coli* Nissle | argA | bipolar argECBH | argD | argI | argG | carAB |
| Bacteroides | argRGCD | argF | argB | argE | carAB | |
| *Clostridium* | argR | argGH | | | argI | |
| *Bacillus subtilis* | argGH | argCAEBD-carAB-argF | | | | |
| *Bacillus subtilis* | argGH | argCJBD-carAB-argF | | | | |
| *Lactobacillus plantarum* | argGH | bipolar carAB-argCJBDF | | | | |
| *Lactococcus* | argE | carA | carB | argGH | argFBDJC | |

Each operon is regulated by a regulatory region comprising at least one promoter and at least one ARG box, which control repression and expression of the arginine biosynthesis genes in said operon.

In some embodiments, the genetically engineered bacteria of the invention comprise an arginine regulon comprising one or more nucleic acid mutations that reduce or eliminate arginine-mediated repression of one or more of the operons that encode the enzymes responsible for converting glutamate to arginine and/or an intermediate byproduct in the arginine biosynthesis pathway. Reducing or eliminating arginine-mediated repression may be achieved by reducing or eliminating ArgR repressor binding (e.g., by mutating or deleting the arginine repressor or by mutating at least one ARG box for each of the operons that encode the arginine biosynthesis enzymes) and/or arginine binding to N-acetylglutamate synthetase (e.g., by mutating the N-acetylglutamate synthetase to produce an arginine feedback resistant N-acetylglutamate synthase mutant, e.g., arg$A^{fbr}$).

ARG Box

In some embodiments, the genetically engineered bacteria comprise a mutant arginine regulon comprising one or more nucleic acid mutations in at least one ARG box for one or more of the operons that encode the arginine biosynthesis enzymes N-acetylglutamate kinase, N-acetylglutamylphosphate reductase, acetylornithine aminotransferase, N-acetylornithinase, ornithine transcarbamylase, argininosuccinate synthase, argininosuccinate lyase, and carbamoylphosphate synthase, thereby derepressing the regulon and enhancing arginine and/or intermediate byproduct biosynthesis. In some embodiments, the genetically engineered bacteria comprise a mutant arginine repressor comprising one or more nucleic acid mutations such that arginine repressor function is decreased or inactive, or the genetically engineered bacteria do not have an arginine repressor (e.g., the arginine repressor gene has been deleted), resulting in derepression of the regulon and enhancement of arginine and/or intermediate byproduct biosynthesis. In either of these embodiments, the genetically engineered bacteria may further comprise an arginine feedback resistant N-acetylglutamate synthase mutant, e.g., arg$A^{fbr}$. Thus, in some embodiments, the genetically engineered bacteria comprise a mutant arginine regulon comprising one or more nucleic acid mutations in at least one ARG box for one or more of the operons that encode the arginine biosynthesis enzymes and an arginine feedback resistant N-acetylglutamate synthase mutant, e.g., arg$A^{fbr}$. In some embodiments, the genetically engineered bacteria comprise a mutant or deleted arginine repressor and an arginine feedback resistant N-acetylglutamate synthase mutant, e.g., arg$A^{fbr}$. In some embodiments, the genetically engineered bacteria comprise an arginine feedback resistant N-acetylglutamate synthase mutant, e.g., arg$A^{fbr}$, a mutant arginine regulon comprising one or more nucleic acid mutations in at least one ARG box for each of the operons that encode the arginine biosynthesis enzymes, and/or a mutant or deleted arginine repressor.

In some embodiments, the genetically engineered bacteria encode an arginine feedback resistant N-acetylglutamate synthase and further comprise a mutant arginine regulon comprising one or more nucleic acid mutations in each ARG box for one or more of the operons that encode N-acetylglutamate kinase, N-acetylglutamylphosphate reductase, acetylornithine aminotransferase, N-acetylornithinase, ornithine transcarbamylase, argininosuccinate synthase, argininosuccinate lyase, carbamoylphosphate synthase, and wild-type N-acetylglutamate synthetase, such that ArgR binding is reduced or eliminated, thereby derepressing the regulon and enhancing arginine and/or intermediate byproduct biosynthesis.

In some embodiments, the ARG boxes for the operon encoding argininosuccinate synthase (argG) maintain the ability to bind to ArgR, thereby driving citrulline biosynthesis. For example, the regulatory region of the operon encoding argininosuccinate synthase (argG) may be a constitutive, thereby driving arginine biosynthesis. In alternate embodiments, the regulatory region of one or more alternate operons may be constitutive. In certain bacteria, however, genes encoding multiple enzymes may be organized in bipolar operons or under the control of a shared regulatory region; in these instances, the regulatory regions may need to be deconvoluted in order to engineer constitutively active regulatory regions. For example, in *E. coli* K12 and Nissle, argE and argCBH are organized in two bipolar operons, argECBH, and those regulatory regions may be deconvoluted in order to generate constitutive versions of argE and/or argCBH.

In some embodiments, all ARG boxes in one or more operons that comprise an arginine biosynthesis gene are mutated to reduce or eliminate ArgR binding. In some embodiments, all ARG boxes in one or more operons that encode an arginine biosynthesis enzyme are mutated to reduce or eliminate ArgR binding. In some embodiments, all ARG boxes in each operon that comprises an arginine biosynthesis gene are mutated to reduce or eliminate ArgR binding. In some embodiments, all ARG boxes in each operon that encodes an arginine biosynthesis enzyme are mutated to reduce or eliminate ArgR binding.

In some embodiments, the genetically engineered bacteria encode an arginine feedback resistant N-acetylglutamate synthase, argininosuccinate synthase driven by a ArgR-repressible regulatory region, and further comprise a mutant arginine regulon comprising one or more nucleic acid mutations in each ARG box for each of the operons that encode N-acetylglutamate kinase, N-acetylglutamylphosphate reductase, acetylornithine am inotransferase, N-acetylornithinase, ornithine transcarbamylase, argininosuccinate synthase, argininosuccinate lyase, carbamoylphosphate synthase, and optionally, wild-type N-acetylglutamate synthetase, such that ArgR binding is reduced or eliminated, thereby derepressing the regulon and enhancing citrulline biosynthesis. In some embodiments, the genetically engineered bacteria capable of producing citrulline is particularly advantageous, because citrulline further serves as a therapeutically effective supplement for the treatment of certain urea cycle disorders (National Urea Cycle Disorders Foundation).

In some embodiments, the genetically engineered bacteria encode an arginine feedback resistant N-acetylglutamate synthase, argininosuccinate synthase driven by a constitutive promoter, and further comprise a mutant arginine regulon comprising one or more nucleic acid mutations in each ARG box for each of the operons that encode N-acetylglutamate kinase, N-acetylglutamylphosphate reductase, acetylornithine am inotransferase, N-acetylornithinase, ornithine transcarbamylase, argininosuccinate lyase, carbamoylphosphate synthase, and optionally, wild-type N-acetylglutamate synthetase, such that ArgR binding is reduced or eliminated, thereby derepressing the regulon and enhancing arginine biosynthesis.

In some embodiments, the genetically engineered bacteria comprise a mutant arginine regulon and a feedback resistant ArgA, and when the arginine feedback resistant ArgA is expressed, are capable of producing more arginine and/or an intermediate byproduct than unmodified bacteria of the same subtype under the same conditions.

Arginine Repressor Binding Sites (ARG Boxes)

In some embodiments, the genetically engineered bacteria additionally comprise a mutant arginine regulon comprising one or more nucleic acid mutations in at least one ARG box for one or more of the operons that encode the arginine biosynthesis enzymes N-acetylglutamate kinase, N-acetylglutamylphosphate reductase, acetylornithine am inotransferase, N-acetylornithinase, ornithine transcarbamylase, argininosuccinate synthase, argininosuccinate lyase, and carbamoylphosphate synthase, such that the arginine regulon is derepressed and biosynthesis of arginine and/or an intermediate byproduct, e.g., citrulline, is enhanced.

In some embodiments, the mutant arginine regulon comprises an operon encoding ornithine acetyltransferase and one or more nucleic acid mutations in at least one ARG box for said operon. The one or more nucleic acid mutations results in the disruption of the palindromic ARG box sequence, such that ArgR binding to that ARG box and to the regulatory region of the operon is reduced or eliminated, as compared to ArgR binding to an unmodified ARG box and regulatory region in bacteria of the same subtype under the same conditions. In some embodiments, nucleic acids that are protected from DNA methylation and hydroxyl radical attack during ArgR binding are the primary targets for mutations to disrupt ArgR binding. In some embodiments, the mutant arginine regulon comprises at least three nucleic acid mutations in one or more ARG boxes for each of the operons that encode the arginine biosynthesis enzymes described above. The ARG box overlaps with the promoter, and in the mutant arginine regulon, the G/C:A/T ratio of the mutant promoter region differs by no more than 10% from the G/C:A/T ratio of the wild-type promoter region (FIG. 6). The promoter retains sufficiently high homology to the non-mutant promoter such that RNA polymerase binds with sufficient affinity to promote transcription.

The wild-type genomic sequences comprising ARG boxes and mutants thereof for each arginine biosynthesis operon in *E. coli* Nissle are shown in FIG. 6. For exemplary wild-type sequences, the ARG boxes are indicated in italics, and the start codon of each gene is boxed. The RNA polymerase binding sites are underlined (Cunin, 1983; Maas, 1994). In some embodiments, the underlined sequences are not altered. Bases that are protected from DNA methylation during ArgR binding are highlighted, and bases that are protected from hydroxyl radical attack during ArgR binding are bolded (Charlier et al., 1992). The highlighted and bolded bases are the primary targets for mutations to disrupt ArgR binding.

In some embodiments, more than one ARG box may be present in a single operon. In one aspect of these embodiments, at least one of the ARG boxes in an operon is mutated to produce the requisite reduced ArgR binding to the regulatory region of the operon. In an alternate aspect of these embodiments, each of the ARG boxes in an operon is mutated to produce the requisite reduced ArgR binding to the regulatory region of the operon. For example, the carAB operon in *E. coli* Nissle comprises two ARG boxes, and one or both ARG box sequences may be mutated. The argG operon in *E. coli* Nissle comprises three ARG boxes, and one, two, or three ARG box sequences may be mutated, disrupted, or deleted. In some embodiments, all three ARG box sequences are mutated, disrupted, or deleted, and a constitutive promoter, e.g., BBa_J23100, is inserted in the regulatory region of the argG operon. One of skill in the art would appreciate that the number of ARG boxes per regulatory region may vary across bacteria, and the nucleotide sequences of the ARG boxes may vary for each operon.

In some embodiments, the ArgR binding affinity to a mutant ARG box or regulatory region of an operon is at least about 50% lower, at least about 60% lower, at least about 70% lower, at least about 80% lower, at least about 90% lower, or at least about 95% lower than the ArgR binding affinity to an unmodified ARG box and regulatory region in bacteria of the same subtype under the same conditions. In some embodiments, the reduced ArgR binding to a mutant ARG box and regulatory region increases mRNA expression of the gene(s) in the associated operon by at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold.

In some embodiments, quantitative PCR (qPCR) is used to amplify, detect, and/or quantify mRNA expression levels of the arginine biosynthesis genes. Primers specific for arginine biosynthesis genes, e.g., argA, argB, argC, argD, argE, argF, argG, argH, argI, argJ, carA, and care, may be designed and used to detect mRNA in a sample according to methods known in the art (Fraga et al., 2008). In some embodiments, a fluorophore is added to a sample reaction mixture that may contain arg mRNA, and a thermal cycler is used to illuminate the sample reaction mixture with a specific wavelength of light and detect the subsequent emission by the fluorophore. The reaction mixture is heated and cooled to predetermined temperatures for predetermined time periods. In certain embodiments, the heating and cooling is repeated for a predetermined number of cycles. In some embodiments, the reaction mixture is heated and cooled to 90-100° C., 60-70° C., and 30-50° C. for a predetermined number of cycles. In a certain embodiment, the reaction mixture is heated and cooled to 93-97° C., 55-65° C., and 35-45° C. for a predetermined number of cycles. In some embodiments, the accumulating amplicon is quantified after each cycle of the qPCR. The number of cycles at which fluorescence exceeds the threshold is the threshold cycle ($C_T$). At least one $C_T$ result for each sample is generated, and the $C_T$ result(s) may be used to determine mRNA expression levels of the arginine biosynthesis genes.

In some embodiments, the genetically engineered bacteria comprising one or more nucleic acid mutations in at least one ARG box for one or more of the operons that encode the arginine biosynthesis enzymes N-acetylglutamate kinase, N-acetylglutamylphosphate reductase, acetylornithine aminotransferase, N-acetylornithinase, ornithine transcarbamylase, argininosuccinate synthase, argininosuccinate lyase, and carbamoylphosphate synthase additionally comprise an arginine feedback resistant N-acetylglutamate synthase mutant, e.g., argA$^{fbr}$.

In some embodiments, the genetically engineered bacteria comprise a feedback resistant form of ArgA, as well as one or more nucleic acid mutations in each ARG box of one or more of the operons that encode the arginine biosynthesis enzymes N-acetylglutamate kinase, N-acetylglutamylphosphate reductase, acetylornithine aminotransferase, N-acetylornithinase, ornithine transcarbamylase, argininosuccinate synthase, argininosuccinate lyase, ornithine acetyltransferase, and carbamoylphosphate synthase.

In some embodiments, the genetically engineered bacteria comprise a feedback resistant form of ArgA, argininosuccinate synthase driven by a ArgR-repressible regulatory region, as well as one or more nucleic acid mutations in each ARG box of each of the operons that encode the arginine biosynthesis enzymes N-acetylglutamate kinase, N-acetylglutamylphosphate reductase, acetylornithine aminotransferase, N-acetylornithinase, ornithine transcarbamylase, argininosuccinate lyase, ornithine acetyltransferase, and carbamoylphosphate synthase. In these embodiments, the bacteria are capable of producing citrulline.

In some embodiments, the genetically engineered bacteria comprise a feedback resistant form of ArgA, argininosuccinate synthase expressed from a constitutive promoter, as well as one or more nucleic acid mutations in each ARG box of each of the operons that encode the arginine biosynthesis enzymes N-acetylglutamate kinase, N-acetylglutamylphosphate reductase, acetylornithine aminotransferase, N-acetylornithinase, ornithine transcarbamylase, argininosuccinate synthase, argininosuccinate lyase, ornithine acetyltransferase, and carbamoylphosphate synthase. In these embodiments, the bacteria are capable of producing arginine.

Table 3 shows examples of mutant constructs in which one or more nucleic acid mutations reduce or eliminate arginine-mediated repression of each of the arginine operons. The mutant constructs comprise feedback resistant form of ArgA driven by an oxygen level-dependent promoter, e.g., a FNR promoter. Each mutant arginine regulon comprises one or more nucleic acid mutations in at least one ARG box for one or more of the operons that encode N-acetylglutamate kinase, N-acetylglutamylphosphate reductase, acetylornithine aminotransferase, N-acetylornithinase, ornithine transcarbamylase, argininosuccinate synthase, argininosuccinate lyase, carbamoylphosphate synthase, and wild-type N-acetylglutamate synthetase, such that ArgR binding is reduced or eliminated, thereby enhancing arginine and/or intermediate byproduct biosynthesis. Non-limiting examples of mutant arginine regulon constructs are shown in Table 3.

TABLE 3

Examples of ARG Box Mutant Constructs

| Mutant construct comprises: | | Exemplary Constructs (* indicates constitutive): Construct 1 | Construct 2 | Construct 3 | Construct 4 | Construct 5 | Construct 6 |
|---|---|---|---|---|---|---|---|
| Arginine feedback resistant N-acetylglutamate synthetase driven by an oxygen level-dependent promoter | | ✓ | ✓ | ✓ | ✓ | ✓ | ✓ |
| Wild-type N-acetylglutamate synthetase | | ✓ | ✓ | | ✓ | ✓ | |
| Mutation(s) in at least one ARG box for the operon encoding: | Wild-type N-acetylglutamate synthetase | ✓ | | ✓ | ✓ | | ✓ |
| | N-acetylglutamate kinase | ✓ | ✓ | ✓ | ✓ | ✓ | ✓ |
| | N- | ✓ | ✓ | ✓ | ✓ | ✓ | ✓ |

TABLE 3-continued

Examples of ARG Box Mutant Constructs

| Mutant construct comprises: | Exemplary Constructs (* indicates constitutive): Construct 1 | Construct 2 | Construct 3 | Construct 4 | Construct 5 | Construct 6 |
|---|---|---|---|---|---|---|
| acetylglutamylphosphate reductase | | | | | | |
| acetylornithine aminotransferase | ✓ | ✓ | ✓ | ✓ | ✓ | ✓ |
| N-acetylornithinase | ✓ | ✓ | ✓ | ✓ | ✓ | ✓ |
| ornithine transcarbamylase | ✓ | ✓ | ✓ | ✓ | ✓ | ✓ |
| argininosuccinate synthase | ✓ | ✓ | ✓ | ✓* | ✓* | ✓* |
| argininosuccinate lyase | ✓ | ✓ | ✓ | ✓ | ✓ | ✓ |
| ornithine acetyltransferase | ✓ | ✓ | ✓ | ✓ | ✓ | ✓ |
| carbamoylphosphate synthase | ✓ | ✓ | ✓ | ✓ | ✓ | ✓ |

The mutations may be present on a plasmid or chromosome. In some embodiments, the arginine regulon is regulated by a single repressor protein. In particular species, strains, and/or subtypes of bacteria, it has been proposed that the arginine regulon may be regulated by two putative repressors (Nicoloff et al., 2004). Thus, in certain embodiments, the arginine regulon of the invention is regulated by more than one repressor protein.

In certain embodiments, the mutant arginine regulon is expressed in one species, strain, or subtype of genetically engineered bacteria. In alternate embodiments, the mutant arginine regulon is expressed in two or more species, strains, and/or subtypes of genetically engineered bacteria.

Arginine Repressor (ArgR)

The genetically engineered bacteria of the invention comprise an arginine regulon comprising one or more nucleic acid mutations that reduce or eliminate arginine-mediated repression of one or more of the operons that encode the enzymes responsible for converting glutamate to arginine and/or an intermediate byproduct in the arginine biosynthesis pathway. In some embodiments, the reduction or elimination of arginine-mediated repression may be achieved by reducing or eliminating ArgR repressor binding, e.g., by mutating at least one ARG box for one or more of the operons that encode the arginine biosynthesis enzymes (as discussed above) or by mutating or deleting the arginine repressor (discussed here) and/or by reducing or eliminating arginine binding to N-acetylglutamate synthetase (e.g., by mutating the N-acetylglutamate synthetase to produce an arginine feedback resistant N-acetylglutamate synthase mutant, e.g., argA$^{fbr}$).

Thus, in some embodiments, the genetically engineered bacteria lack a functional ArgR repressor and therefore ArgR repressor-mediated transcriptional repression of each of the arginine biosynthesis operons is reduced or eliminated. In some embodiments, the engineered bacteria comprise a mutant arginine repressor comprising one or more nucleic acid mutations such that arginine repressor function is decreased or inactive. In some embodiments, the genetically engineered bacteria do not have an arginine repressor (e.g., the arginine repressor gene has been deleted), resulting in derepression of the regulon and enhancement of arginine and/or intermediate byproduct biosynthesis. In some embodiments, each copy of a functional argR gene normally present in a corresponding wild-type bacterium is independently deleted or rendered inactive by one or more nucleotide deletions, insertions, or substitutions. In some embodiments, each copy of the functional argR gene normally present in a corresponding wild-type bacterium is deleted.

In some embodiments, the arginine regulon is regulated by a single repressor protein. In particular species, strains, and/or subtypes of bacteria, it has been proposed that the arginine regulon may be regulated by two distinct putative repressors (Nicoloff et al., 2004). Thus, in certain embodiments, two distinct ArgR proteins each comprising a different amino acid sequence are mutated or deleted in the genetically engineered bacteria.

In some embodiments, the genetically modified bacteria comprising a mutant or deleted arginine repressor additionally comprise an arginine feedback resistant N-acetylglutamate synthase mutant, e.g., argA$^{fbr}$. In some embodiments, the genetically engineered bacteria comprise a feedback resistant form of ArgA, lack any functional arginine repressor, and are capable of producing arginine. In certain embodiments, the genetically engineered bacteria further lack functional ArgG and are capable of producing citrulline. In some embodiments, the argR gene is deleted in the genetically engineered bacteria. In some embodiments, the argR gene is mutated to inactivate ArgR function. In some embodiments, the argG gene is deleted in the genetically engineered bacteria. In some embodiments, the argG gene is mutated to inactivate ArgR function. In some embodiments, the genetically engineered bacteria comprise argA$^{fbr}$ and deleted ArgR. In some embodiments, the genetically engineered bacteria comprise argA$^{fbr}$, deleted ArgR, and deleted argG. In some embodiments, the deleted ArgR and/or the deleted argG is deleted from the bacterial genome and the argA$^{fbr}$ is present in a plasmid. In some embodiments, the deleted ArgR and/or the deleted argG is deleted from the bacterial genome and the argA$^{fbr}$is chromosomally integrated. In one specific embodiment, the genetically modified bacteria comprise chromosomally integrated argA$^{fbr}$, deleted genomic ArgR, and deleted genomic argG. In another specific embodiment, the genetically modified bacteria comprise argA$^{fbr}$ present on a plasmid, deleted genomic ArgR, and deleted genomic argG. In any of the embodiments in which argG is deleted, citrulline rather than arginine is produced In some embodiments, under conditions where a feedback resistant form of ArgAis expressed, the genetically engineered bacteria of the invention produce at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold more arginine, citrulline, other intermediate byproduct, and/or transcript of the gene(s) in the operon as compared to unmodified bacteria of the same subtype under the same conditions.

In some embodiments, quantitative PCR (qPCR) is used to amplify, detect, and/or quantify mRNA expression levels of the arginine biosynthesis genes. Primers specific for arginine biosynthesis genes, e.g., argA, argB, argC, argD, argE, argF, argG, argH, argl, argJ, carA, and care, may be designed and used to detect mRNA in a sample according to methods known in the art (Fraga et al., 2008). In some embodiments, a fluorophore is added to a sample reaction mixture that may contain arg mRNA, and a thermal cycler is used to illuminate the sample reaction mixture with a specific wavelength of light and detect the subsequent emission by the fluorophore. The reaction mixture is heated and cooled to predetermined temperatures for predetermined time periods. In certain embodiments, the heating and cooling is repeated for a predetermined number of cycles. In some embodiments, the reaction mixture is heated and cooled to 90-100° C., 60-70° C., and 30-50° C. for a predetermined number of cycles. In a certain embodiment, the reaction mixture is heated and cooled to 93-97° C., 55-65° C., and 35-45° C. for a predetermined number of cycles. In some embodiments, the accumulating amplicon is quantified after each cycle of the qPCR. The number of cycles at which fluorescence exceeds the threshold is the threshold cycle ($C_T$). At least one $C_T$ result for each sample is generated, and the $C_T$ result(s) may be used to determine mRNA expression levels of the arginine biosynthesis genes.

Feedback Resistant N-acetylglutamate Synthetase

In some embodiments, the genetically engineered bacteria comprise an arginine feedback resistant N-acetylglutamate synthase mutant, e.g., argA$^{fbr}$. In some embodiments, the genetically engineered bacteria comprise a mutant arginine regulon comprising an arginine feedback resistant ArgA, and when the arginine feedback resistant ArgA is expressed, are capable of producing more arginine and/or an intermediate byproduct than unmodified bacteria of the same subtype under the same conditions. The arginine feedback resistant N-acetylglutamate synthetase protein (argA$^{fbr}$) is significantly less sensitive to L-arginine than the enzyme from the feedback sensitive parent strain (see, e.g., Eckhardt et al., 1975; Rajagopal et al., 1998). The feedback resistant argA gene can be present on a plasmid or chromosome. In some embodiments, expression from the plasmid may be useful for increasing argA$^{fbr}$ expression. In some embodiments, expression from the chromosome may be useful for increasing stability of argA$^{fbr}$ expression.

In some embodiments, any of the genetically engineered bacteria of the present disclosure are integrated into the bacterial chromosome at one or more integration sites. For example, one or more copies of the sequence encoding the arginine feedback resistant N-acetylglutamate synthase may be integrated into the bacterial chromosome. Having multiple copies of the arginine feedback resistant N-acetylglutamate synthase integrated into the chromosome allows for greater production of the N-acetylglutamate synthase and also permits fine-tuning of the level of expression. Alternatively, different circuits described herein, such as any of the kill-switch circuits, in addition to the arginine feedback resistant N-acetylglutamate synthase could be integrated into the bacterial chromosome at one or more different integration sites to perform multiple different functions.

Multiple distinct feedback resistant N-acetylglutamate synthetase proteins are known in the art and may be combined in the genetically engineered bacteria. In some embodiments, the argA$^{fbr}$ gene is expressed under the control of a constitutive promoter. In some embodiments, the argA$^{fbr}$ gene is expressed under the control of a promoter that is induced by exogenous environmental conditions. In some embodiments, the exogenous environmental conditions are specific to the gut of a mammal. In some embodiments, exogenous environmental conditions are molecules or metabolites that are specific to the mammalian gut, e.g., propionate or bilirubin. In some embodiments, the exogenous environmental conditions are low-oxygen or anaerobic conditions, such as the environment of the mammalian gut.

Bacteria have evolved transcription factors that are capable of sensing oxygen levels. Different signaling pathways may be triggered by different oxygen levels and occur with different kinetics. An oxygen level-dependent promoter is a nucleic acid sequence to which one or more oxygen level-sensing transcription factors is capable of binding, wherein the binding and/or activation of the corresponding transcription factor activates downstream gene expression. In one embodiment, the argA$^{fbr}$ gene is under control of an oxygen level-dependent promoter. In a more specific aspect, the argA$^{fbr}$ gene is under control of an oxygen level-dependent promoter that is activated under low-oxygen or anaerobic environments, such as the environment of the mammalian gut.

In certain embodiments, the genetically engineered bacteria comprise argA$^{fbr}$ expressed under the control of the fumarate and nitrate reductase regulator (FNR) promoter. In E. coli, FNR is a major transcriptional activator that controls the switch from aerobic to anaerobic metabolism (Unden et al., 1997). In the anaerobic state, FNR dimerizes into an active DNA binding protein that activates hundreds of genes responsible for adapting to anaerobic growth. In the aerobic state, FNR is prevented from dimerizing by oxygen and is inactive. In alternate embodiments, the genetically engineered bacteria comprise argA$^{fbr}$ expressed under the control of an alternate oxygen level-dependent promoter, e.g., an anaerobic regulation of arginine deiminiase and nitrate reduction ANR promoter (Ray et al., 1997), a dissimilatory nitrate respiration regulator DNR promoter (Trunk et al., 2010). In these embodiments, the arginine biosynthesis pathway is particularly activated in a low-oxygen or anaerobic environment, such as in the gut.

In *P. aeruginosa*, the anaerobic regulation of arginine deiminiase and nitrate reduction (ANR) transcriptional regulator is "required for the expression of physiological functions which are inducible under oxygen-limiting or anaerobic conditions" (Winteler et al., 1996; Sawers 1991). *P. aeruginosa* ANR is homologous with *E. coli* FNR, and the consensus FNR site (TTGAT-ATCAA) was recognized efficiently by ANR and FNR" (Winteler et al., 1996). Like FNR, in the anaerobic state, ANR activates numerous genes responsible for adapting to anaerobic growth. In the aerobic state, ANR is inactive. *Pseudomonas fluorescens, Pseudomonas putida, Pseudomonas syringae*, and *Pseudomonas mendocina* all have functional analogs of ANR (Zimmermann et al., 1991). Promoters that are regulated by ANR are known in the art, e.g., the promoter of the arcDABC operon (see, e.g., Hasegawa et al., 1998).

The FNR family also includes the dissimilatory nitrate respiration regulator (DNR) (Arai et al., 1995), a transcriptional regulator that is required in conjunction with ANR for "anaerobic nitrate respiration of *Pseudomonas aeruginosa*" (Hasegawa et al., 1998). For certain genes, the FNR-binding motifs are probably recognized only by DNR" (Hasegawa et al., 1998). Any suitable transcriptional regulator that is controlled by exogenous environmental conditions and corresponding regulatory region may be used. Non-limiting examples include ArcA/B, ResD/E, NreA/B/C, and AirSR, and others are known in the art.

In some embodiments, argA$^{fbr}$ is expressed under the control of an inducible promoter that is responsive to specific molecules or metabolites in the environment, e.g., the mammalian gut. For example, the short-chain fatty acid propionate is a major microbial fermentation metabolite localized to the gut (Hosseini et al., 2011). In one embodiment, argA$^{fbr}$ gene expression is under the control of a propionate-inducible promoter. In a more specific embodiment, argA$^{fbr}$ gene expression is under the control of a propionate-inducible promoter that is activated by the presence of propionate in the mammalian gut. Any molecule or metabolite found in the mammalian gut, in a healthy and/or disease state, may be used to induce argA$^{fbr}$ expression. Non-limiting examples include propionate, bilirubin, aspartate aminotransferase, alanine aminotransferase, blood coagulation factors II, VII, IX, and X, alkaline phosphatase, gamma glutamyl transferase, hepatitis antigens and antibodies, alpha fetoprotein, anti-mitochondrial, smooth muscle, and anti-nuclear antibodies, iron, transferrin, ferritin, copper, ceruloplasmin, ammonia, and manganese. In alternate embodiments, argA$^{fbr}$ gene expression is under the control of a pBAD promoter, which is activated in the presence of the sugar arabinose (see, e.g., FIG. 18).

Subjects with hepatic encephalopathy (HE) and other liver disease or disorders have chronic liver damage that results in high ammonia levels in their blood and intestines. In addition to ammonia, these patients also have elevated levels of bilirubin, aspartate aminotransferase, alanine aminotransferase, blood coagulation factors II, VII, IX, and X, alkaline phosphatase, gamma glutamyl transferase, hepatitis antigens and antibodies, alpha fetoprotein, anti-mitochondrial, smooth muscle, and anti-nuclear antibodies, iron, transferrin, ferritin, copper, ceruloplasmin, ammonia, and manganese in their blood and intestines. Promoters that respond to one of these HE-related molecules or their metabolites can be used to engineer bacteria of the present disclosure that would only be induced to express argA$^{fbr}$ in the intestines of HE patients. These promoters would not be expected to be induced in UCD patients.

In some embodiments, the argA$^{fbr}$ gene is expressed under the control of a promoter that is induced by exposure to tetracycline. In some embodiments, gene expression is further optimized by methods known in the art, e.g., by optimizing ribosomal binding sites, manipulating transcriptional regulators, and/or increasing mRNA stability.

In some embodiments, arginine feedback inhibition of N-acetylglutamate synthetase is reduced by at least about 50%, at least about 60%, at least about 70%, at least about 80%, at least about 90%, or at least about 95% in the genetically engineered bacteria when the arginine feedback resistant N-acetylglutamate synthetase is active, as compared to a wild-type N-acetylglutamate synthetase from bacteria of the same subtype under the same conditions.

Figure 22:
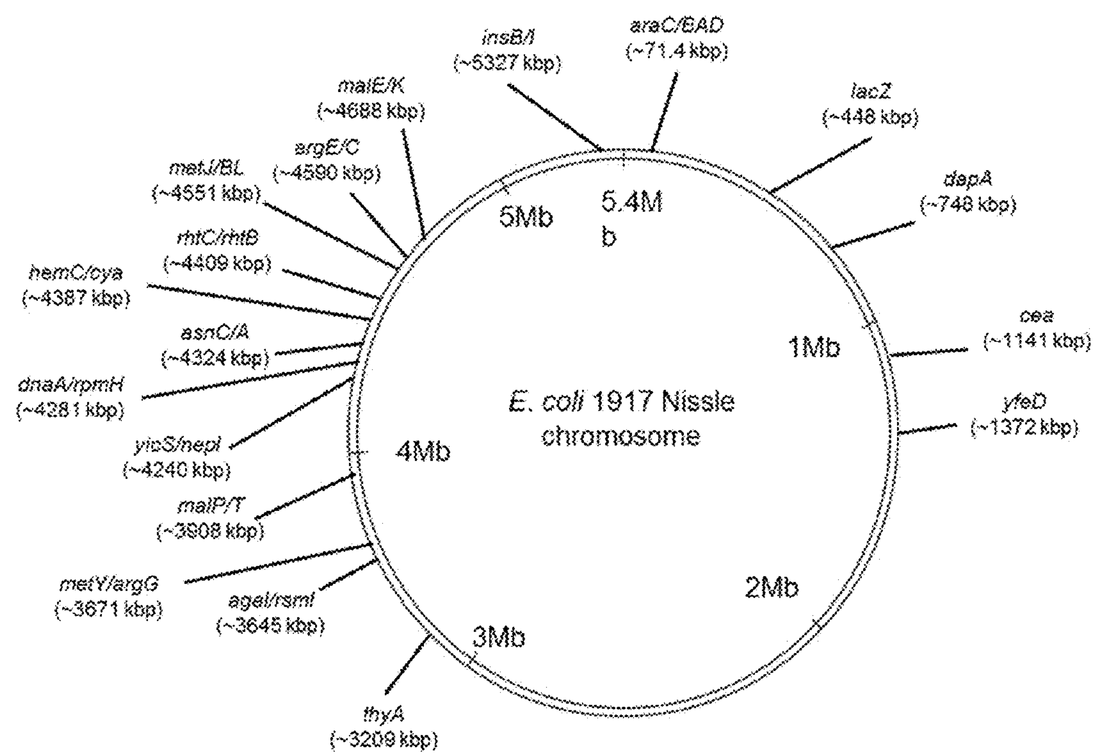
FIG. 22 depicts a map of exemplary integration sites within the *E. coli* 1917 Nissle chromosome. These sites indicate regions where circuit components may be inserted into the chromosome without interfering with essential gene expression. Backslashes (/) are used to show that the insertion will occur between divergently or convergently expressed genes. Insertions within biosynthetic genes, such as thyA, can be useful for creating nutrient auxotrophies. In some embodiments, an individual circuit component is inserted into more than one of the indicated sites.
Figure 23:
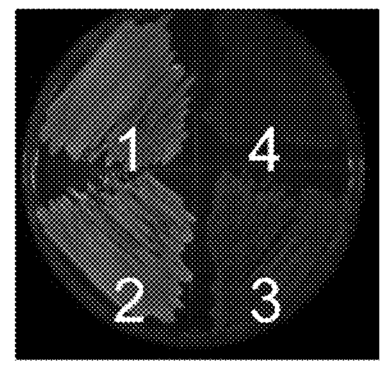
FIG. 23 depicts three bacterial strains which constitutively express red fluorescent protein (RFP). In strains 1-3, the rfp gene has been inserted into different sites within the bacterial chromosome, and results in varying degrees of brightness under fluorescent light. Unmodified *E. coli* Nissle (strain 4) is non-fluorescent.

In some embodiments, the genetically engineered bacteria comprise a stably maintained plasmid or chromosome carrying the argA$^{fbr}$ gene, such that argA$^{fbr}$ can be expressed in the host cell, and the host cell is capable of survival and/or growth in vitro, e.g., in medium, and/or in vivo, e.g., in the gut. In some embodiments, a bacterium may comprise multiple copies of the feedback resistant argA gene. In some embodiments, the feedback resistant argA gene is expressed on a low-copy plasmid. In some embodiments, the low-copy plasmid may be useful for increasing stability of expression. In some embodiments, the low-copy plasmid may be useful for decreasing leaky expression under non-inducing conditions. In some embodiments, the feedback resistant argA gene is expressed on a high-copy plasmid. In some embodiments, the high-copy plasmid may be useful for increasing argA$^{fbr}$ expression. In some embodiments, the feedback resistant argA gene is expressed on a chromosome. In some embodiments, the bacteria are genetically engineered to include multiple mechanisms of action (MOAs), e.g., circuits producing multiple copies of the same product or circuits performing multiple different functions. Examples of insertion sites include, but are not limited to, malE/K, insB/I, araC/BAD, lacZ, dapA, cea, and other shown in FIG. 22. For example, the genetically engineered bacteria may include four copies of argA$^{fbr}$ inserted at four different insertion sites, e.g., malE/K, insB/I, araC/BAD, and lacZ. Alternatively, the genetically engineered bacteria may include three copies of argA$^{fbr}$ inserted at three different insertion sites, e.g., malE/K, insB/I, and lacZ, and three mutant arginine regulons, e.g., two producing citrulline and one producing arginine, inserted at three different insertion sites dapA, cea, and araC/BAD.

In some embodiments, the plasmid or chromosome also comprises wild-type ArgR binding sites, e.g., ARG boxes. In some instances, the presence and/or build-up of functional ArgR may result in off-target binding at sites other than the ARG boxes, which may cause off-target changes in gene expression. A plasmid or chromosome that further comprises functional ARG boxes may be used to reduce or eliminate off-target ArgR binding, i.e., by acting as an ArgR sink. In some embodiments, the plasmid or chromosome does not comprise functional ArgR binding sites, e.g., the plasmid or chromosome comprises modified ARG boxes or does not comprise ARG boxes.

In some embodiments, the feedback resistant argA gene is present on a plasmid and operably linked to a promoter that is induced under low-oxygen or anaerobic conditions. In some embodiments, the feedback resistant argA gene is present in the chromosome and operably linked to a promoter that is induced under low-oxygen or anaerobic conditions. In some embodiments, the feedback resistant argA gene is present on a plasmid and operably linked to a promoter that is induced by molecules or metabolites that are specific to the mammalian gut. In some embodiments, the feedback resistant argA gene is present on a chromosome and operably linked to a promoter that is induced by molecules or metabolites that are specific to the mammalian gut. In some embodiments, the feedback resistant argA gene is present on a chromosome and operably linked to a promoter that is induced by exposure to tetracycline. In some embodiments, the feedback resistant argA gene is present on a plasmid and operably linked to a promoter that is induced by exposure to tetracycline.

In some embodiments, the genetically engineered bacteria comprise multiple mechanisms of action (MOAs), e.g., circuits producing multiple copies of the same product (to enhance copy number) or circuits performing multiple different functions. Examples of insertion sites include, but are not limited to, malE/K, insB/I, araC/BAD, lacZ, dapA, cea, and other shown in FIG. 22.

In some embodiments, the genetically engineered bacteria comprise a variant or mutated oxygen level-dependent transcriptional regulator, e.g., FNR, ANR, or DNR, in addition to the corresponding oxygen level-dependent promoter. The variant or mutated oxygen level-dependent transcriptional regulator increases the transcription of operably linked genes in a low-oxygen or anaerobic environment. In some embodiments, the corresponding wild-type transcriptional regulator retains wild-type activity. In alternate embodiments, the corresponding wild-type transcriptional regulator is deleted or mutated to reduce or eliminate wild-type activity. In certain embodiments, the mutant oxygen level-dependent transcriptional regulator is a FNR protein comprising amino acid substitutions that enhance dimerization and FNR activity (see, e.g., Moore et al., 2006).

In some embodiments, the genetically engineered bacteria comprise an oxygen level-dependent transcriptional regulator from a different bacterial species that reduces and/or consumes ammonia in low-oxygen or anaerobic environments. In certain embodiments, the mutant oxygen level-dependent transcriptional regulator is a FNR protein from *N. gonorrhoeae* (see, e.g., Isabella et al., 2011). In some embodiments, the corresponding wild-type transcriptional regulator is left intact and retains wild-type activity. In alternate embodiments, the corresponding wild-type transcriptional regulator is deleted or mutated to reduce or eliminate wild-type activity.

In some embodiments, the genetically engineered bacteria comprise argA$^{fbr}$ expressed under the control of an oxygen level-dependent promoter, e.g., a FNR promoter, as well as wild-type argA expressed under the control of a mutant regulatory region comprising one or more ARG box mutations as discussed above. In certain embodiments, the genetically engineered bacteria comprise argA$^{fbr}$ expressed under the control of an oxygen level-dependent promoter, e.g., a FNR promoter and do not comprise wild-type argA. In still other embodiments, the mutant arginine regulon comprises argA$^{fbr}$ expressed under the control of an oxygen level-dependent promoter, e.g., a FNR promoter, and further comprises wild-type argA without any ARG box mutations.

In some embodiments, the genetically engineered bacteria express ArgA$^{fbr}$ from a plasmid and/or chromosome. In some embodiments, the argA$^{fbr}$ gene is expressed under the control of a constitutive promoter. In some embodiments, the argA$^{fbr}$ gene is expressed under the control of an inducible promoter. In one embodiment, argA$^{fbr}$ is expressed under the control of an oxygen level-dependent promoter that is activated under low-oxygen or anaerobic environments, e.g., a FNR promoter. The nucleic acid sequence of a FNR promoter-driven argA$^{fbr}$ plasmid is shown in FIG. 8, with the FNR promoter sequence bolded and argA$^{fbr}$ sequence boxed.

FNR promoter sequences are known in the art, and any suitable FNR promoter sequence(s) may be used in the genetically engineered bacteria of the invention. Any suitable FNR promoter(s) may be combined with any suitable feedback-resistant ArgA (exemplary sequence, SEQ ID NO: 8A). Non-limiting FNR promoter sequences are provided in FIG. 7. In some embodiments, the genetically engineered bacteria of the invention comprise one or more of: SEQ ID NO: 16, SEQ ID NO: 17, nirB1 promoter (SEQ ID NO: 18), nirB2 promoter (SEQ ID NO: 19), nirB3 promoter (SEQ ID NO: 20), ydfZ promoter (SEQ ID NO: 21), nirB promoter fused to a strong ribosome binding site (SEQ ID NO: 22), ydfZ promoter fused to a strong ribosome binding site (SEQ ID NO: 23), fnrS, an anaerobically induced small RNA gene (fnrS1 promoter SEQ ID NO: 24 or fnrS2 promoter SEQ ID NO: 25), nirB promoter fused to a crp binding site (SEQ ID NO: 26), and fnrS fused to a crp binding site (SEQ ID NO: 27).

In some embodiments, the genetically engineered bacteria comprise the nucleic acid sequence of SEQ ID NO: 28 or a functional fragment thereof. In some embodiments, the genetically engineered bacteria comprise a nucleic acid sequence that, but for the redundancy of the genetic code, encodes the same polypeptide as SEQ ID NO: 28. In some embodiments, genetically engineered bacteria comprise a nucleic acid sequence that is at least about 80%, at least about 85%, at least about 90%, at least about 95%, or at least about 99% homologous to the DNA sequence of SEQ ID NO: 28, or a nucleic acid sequence that, but for the redundancy of the genetic code, encodes the same polypeptide as SEQ ID NO: 28.

In other embodiments, argA$^{fbr}$ is expressed under the control of an oxygen level-dependent promoter fused to a binding site for a transcriptional activator, e.g., CRP. CRP (cyclic AMP receptor protein or catabolite activator protein or CAP) plays a major regulatory role in bacteria by repressing genes responsible for the uptake, metabolism and assimilation of less favorable carbon sources when rapidly metabolizable carbohydrates, such as glucose, are present (Wu et al., 2015). This preference for glucose has been termed glucose repression, as well as carbon catabolite repression (Deutscher, 2008; Görke and Stülke, 2008). In some embodiments, argA$^{fbr}$ expression is controlled by an oxygen level-dependent promoter fused to a CRP binding site. In some embodiments, argA$^{fbr}$ expression is controlled by a FNR promoter fused to a CRP binding site. In these embodiments, cyclic AMP binds to CRP when no glucose is present in the environment. This binding causes a conformational change in CRP, and allows CRP to bind tightly to its binding site. CRP binding then activates transcription of the argA$^{fbr}$ gene by recruiting RNA polymerase to the FNR promoter via direct protein-protein interactions. In the presence of glucose, cyclic AMP does not bind to CRP and argA$^{fbr}$ gene transcription is repressed. In some embodiments, an oxygen level-dependent promoter (e.g., a FNR promoter) fused to a binding site for a transcriptional activator is used to ensure that argA$^{fbr}$ is not expressed under anaerobic conditions when sufficient amounts of glucose are present, e.g., by adding glucose to growth media in vitro.

Arginine Catabolism

An important consideration in practicing the invention is to ensure that ammonia is not overproduced as a byproduct of arginine and/or citrulline catabolism. In the final enzymatic step of the urea cycle, arginase catalyzes the hydrolytic cleavage of arginine into ornithine and urea (Cunin et al., 1986). Urease, which may be produced by gut bacteria, catalyzes the cleavage of urea into carbon dioxide and ammonia (Summerskill, 1966; Aoyagi et al., 1966; Cunin et al., 1986). Thus, urease activity may generate ammonia that can be "toxic for human tissue" (Konieczna et al., 2012). In some bacteria, including *E. coli* Nissle, the gene arcD encodes an arginine/ornithine antiporter, which may also liberate ammonia (Vander Wauven et al., 1984; Gamper et al., 1991; Meng et al., 1992).

AstA is an enzyme involved in the conversion of arginine to succinate, which liberates ammonia. SpeA is an enzyme involved in the conversion of arginine to agmatine, which can be further catabolized to produce ammonia. Thus, in some instances, it may be advantageous to prevent the breakdown of arginine. In some embodiments, the genetically engineered bacteria comprising a mutant arginine regulon additionally includes mutations that reduce or eliminate arginine catabolism, thereby reducing or eliminating further ammonia production. In some embodiments, the genetically engineered bacteria also comprise mutations that reduce or eliminate ArcD activity. In certain embodiments, ArcD is deleted. In some embodiments, the genetically engineered bacteria also comprise mutations that reduce or eliminate AstA activity. In certain embodiments, AstA is deleted. In some embodiments, the genetically engineered bacteria also comprise mutations that reduce or eliminate SpeA activity. In certain embodiments, SpeA is deleted. In some embodiments, the genetically engineered bacteria also comprise mutations that reduce or eliminate arginase activity. In certain embodiments, arginase is deleted. In some embodiments, the genetically engineered bacteria also comprise mutations that reduce or eliminate urease activity. In certain embodiments, urease is deleted. In some embodiments, one or more other genes involved in arginine catabolism are mutated or deleted.

Essential Genes and Auxotrophs

As used herein, the term "essential gene" refers to a gene which is necessary to for cell growth and/or survival. Bacterial essential genes are well known to one of ordinary skill in the art, and can be identified by directed deletion of genes and/or random mutagenesis and screening (see, for example, Zhang and Lin, 2009, DEG 5.0, a database of essential genes in both prokaryotes and eukaryotes, Nucl. Acids Res., 37:D455-D458 and Gerdes et al., Essential genes on metabolic maps, Curr. Opin. Biotechnol., 17(5): 448-456, the entire contents of each of which are expressly incorporated herein by reference).

An "essential gene" may be dependent on the circumstances and environment in which an organism lives. For example, a mutation of, modification of, or excision of an essential gene may result in the recombinant bacteria of the disclosure becoming an auxotroph. An auxotrophic modification is intended to cause bacteria to die in the absence of an exogenously added nutrient essential for survival or growth because they lack the gene(s) necessary to produce that essential nutrient.

An auxotrophic modification is intended to cause bacteria to die in the absence of an exogenously added nutrient essential for survival or growth because they lack the gene(s) necessary to produce that essential nutrient. In some embodiments, any of the genetically engineered bacteria described herein also comprise a deletion or mutation in a gene required for cell survival and/or growth. In one embodiment, the essential gene is a DNA synthesis gene, for example, thyA. In another embodiment, the essential gene is a cell wall synthesis gene, for example, dapA. In yet another embodiment, the essential gene is an amino acid gene, for example, serA or MetA. Any gene required for cell survival and/or growth may be targeted, including but not limited to, cysE, glnA, ilvD, leuB, lysA, serA, metA, glyA, hisB, ilvA, pheA, proA, thrC, trpC, tyrA, thyA, uraA, dapA, dapB, dapD, dapE, dapF, flhD, metB, metC, proAB, and thi1, as long as the corresponding wild-type gene product is not produced in the bacteria. For example, thymine is a nucleic acid that is required for bacterial cell growth; in its absence, bacteria undergo cell death. The thyA gene encodes thimidylate synthetase, an enzyme that catalyzes the first step in thymine synthesis by converting dUMP to dTMP (Sat et al., 2003). In some embodiments, the bacterial cell of the disclosure is a thyA auxotroph in which the thyA gene is deleted and/or replaced with an unrelated gene. A thyA auxotroph can grow only when sufficient amounts of thymine are present, e.g., by adding thymine to growth media in vitro, or in the presence of high thymine levels found naturally in the human gut in vivo. In some embodiments, the bacterial cell of the disclosure is auxotrophic in a gene that is complemented when the bacterium is present in the mammalian gut. Without sufficient amounts of thymine, the thyA auxotroph dies. In some embodiments, the auxotrophic modification is used to ensure that the bacterial cell does not survive in the absence of the auxotrophic gene product (e.g., outside of the gut).

Diaminopimelic acid (DAP) is an amino acid synthetized within the lysine biosynthetic pathway and is required for bacterial cell wall growth (Meadow et al., 1959; Clarkson et al., 1971). In some embodiments, any of the genetically engineered bacteria described herein is a dapD auxotroph in which dapD is deleted and/or replaced with an unrelated gene. A dapD auxotroph can grow only when sufficient amounts of DAP are present, e.g., by adding DAP to growth media in vitro. Without sufficient amounts of DAP, the dapD auxotroph dies. In some embodiments, the auxotrophic modification is used to ensure that the bacterial cell does not survive in the absence of the auxotrophic gene product (e.g., outside of the gut).

In other embodiments, the genetically engineered bacterium of the present disclosure is a uraA auxotroph in which uraA is deleted and/or replaced with an unrelated gene. The uraA gene codes for UraA, a membrane-bound transporter that facilitates the uptake and subsequent metabolism of the pyrimidine uracil (Andersen et al., 1995). A uraA auxotroph can grow only when sufficient amounts of uracil are present, e.g., by adding uracil to growth media in vitro. Without sufficient amounts of uracil, the uraA auxotroph dies. In some embodiments, auxotrophic modifications are used to ensure that the bacteria do not survive in the absence of the auxotrophic gene product (e.g., outside of the gut).

In complex communities, it is possible for bacteria to share DNA. In very rare circumstances, an auxotrophic bacterial strain may receive DNA from a non-auxotrophic strain, which repairs the genomic deletion and permanently rescues the auxotroph. Therefore, engineering a bacterial strain with more than one auxotroph may greatly decrease the probability that DNA transfer will occur enough times to rescue the auxotrophy. In some embodiments, the genetically engineered bacteria of the invention comprise a deletion or mutation in two or more genes required for cell survival and/or growth.

Other examples of essential genes include, but are not limited to yhbV, yagG, hemB, secD, secF, ribD, ribE, thiL, dxs, ispA, dnaX, adk, hemH, lpxH, cysS, fold, rplT, infC, thrS, nadE, gapA, yeaZ, aspS, argS, pgsA, yefM, metG, folE, yejM, gyrA, nrdA, nrdB, folC, accD, fabB, gltX, ligA, zipA, dapE, dapA, der, hisS, ispG, suhB, tadA, acpS, era, rnc, ftsB, eno, pyrG, chpR, lgt, fbaA, pgk, yqgD, metK, yqgF, plsC, ygiT, pare, ribB, cca, ygjD, tdcF, yraL, yihA, ftsN, murl, murB, birA, secE, nusG, rplJ, rplL, rpoB, rpoC, ubiA, plsB, lexA, dnaB, ssb, alsK, groS, psd, orn, yjeE, rpsR, chpS, ppa, valS, yjgP, yjgQ, dnaC, ribF, lspA, ispH, dapB, folA, imp, yabQ, ftsL, ftsI, murE, murF, mraY, murD, ftsW, murG, murC, ftsQ, ftsA, ftsZ, IpxC, secM, secA, can, folK, hemL, yadR, dapD, map, rpsB, infB ,nusA, ftsH, obgE, rpmA, rplU, ispB, murA, yrbB, yrbK, yhbN, rpsl, rplM, degS, mreD, mreC, mreB, accB, accC, yrdC, def, fmt, rplQ, rpoA, rpsD, rpsK, rpsM, entD, mrdB, mrdA, nadD, hlepB, rpoE, pssA, yfiO, rplS, trmD, rpsP, ffh, grpE, yfjB, csrA, ispF, ispD, rplW, rplD, rplC, rpsJ, fusA, rpsG, rpsL, trpS, yrfF, asd, rpoH, ftsX, ftsE, ftsY, frr, dxr, ispU, rfaK, kdtA, coaD, rpmB, dfp, dut, gmk, spot, gyrB, dnaN, dnaA, rpmH, rnpA, yidC, tnaB, glmS, glmU, wzyE, hemD, hemC, yigP, ubiB, ubiD, hemG, secY, rplO, rpmD, rpsE, rplR, rplF, rpsH, rpsN, rplE, rplX, rplN, rpsQ, rpmC, rplP, rpsC, rplV, rpsS, rplB, cdsA, yaeL, yaeT, lpxD, fabZ, lpxA, lpxB, dnaE, accA, tilS, proS, yafF, tsf, pyrH, olA, rlpB, leuS, Int, glnS, fldA, cydA, infA, cydC, ftsK, lolA, serS, rpsA, msbA, IpxK, kdsB, mukF, mukE, mukB, asnS, fabA, mviN, rne, yceQ, fabD, fabG, acpP, tmk, holB, lolC, lolD, lolE, purB, ymfK, minE, mind, pth, rsA, ispE, loIB, hemA, prfA, prmC, kdsA, topA, ribA, fabl, racR, dicA, ydfB, tyrS, ribC, ydiL, pheT, pheS, yhhQ, bcsB, glyQ, yibJ, and gpsA. Other essential genes are known to those of ordinary skill in the art.

In some embodiments, the genetically engineered bacterium of the present disclosure is a synthetic ligand-dependent essential gene (SLiDE) bacterial cell. SLiDE bacterial cells are synthetic auxotrophs with a mutation in one or more essential genes that only grow in the presence of a particular ligand (see Lopez and Anderson "Synthetic Auxotrophs with Ligand-Dependent Essential Genes for a BL21 (DE3 Biosafety Strain, "ACS Synthetic Biology (2015) DOI: 10.1021/acssynbio.5b00085, the entire contents of which are expressly incorporated herein by reference).

In some embodiments, the SLiDE bacterial cell comprises a mutation in an essential gene. In some embodiments, the essential gene is selected from the group consisting of pheS, dnaN, tyrS, metG and adk. In some embodiments, the essential gene is dnaN comprising one or more of the following mutations: H191N, R240C, I317S, F319V, L340T, V347I, and S345C. In some embodiments, the essential gene is dnaN comprising the mutations H191N, R240C, I317S, F319V, L340T, V347I, and S345C. In some embodiments, the essential gene is pheS comprising one or more of the following mutations: F125G, P183T, P184A, R186A, and I188L. In some embodiments, the essential gene is pheS comprising the mutations F125G, P183T, P184A, R186A, and I188L. In some embodiments, the essential gene is tyrS comprising one or more of the following mutations: L36V, C38A and F40G. In some embodiments, the essential gene is tyrS comprising the mutations L36V, C38A and F40G. In some embodiments, the essential gene is metG comprising one or more of the following mutations: E45Q, N47R, I49G, and A51C. In some embodiments, the essential gene is metG comprising the mutations E45Q, N47R, I49G, and A51 C. In some embodiments, the essential gene is adk comprising one or more of the following mutations: I4L, L5I and L6G. In some embodiments, the essential gene is adk comprising the mutations I4L, L5I and L6G.

In some embodiments, the genetically engineered bacterium is complemented by a ligand. In some embodiments, the ligand is selected from the group consisting of benzothiazole, indole, 2-aminobenzothiazole, indole-3-butyric acid, indole-3-acetic acid, and L-histidine methyl ester. For example, bacterial cells comprising mutations in metG (E45Q, N47R, I49G, and A51 C) are complemented by benzothiazole, indole, 2-aminobenzothiazole, indole-3-butyric acid, indole-3-acetic acid or L-histidine methyl ester. Bacterial cells comprising mutations in dnaN (H191N, R240C, I317S, F319V, L340T, V347I, and S345C) are complemented by benzothiazole, indole or 2-am inobenzothiazole. Bacterial cells comprising mutations in pheS (F125G, P183T, P184A, R186A, and I188L) are complemented by benzothiazole or 2-aminobenzothiazole. Bacterial cells comprising mutations in tyrS (L36V, C38A, and F40G) are complemented by benzothiazole or 2-aminobenzothiazole. Bacterial cells comprising mutations in adk (I4L, L5I and L6G) are complemented by benzothiazole or indole.

In some embodiments, the genetically engineered bacterium comprises more than one mutant essential gene that renders it auxotrophic to a ligand. In some embodiments, the bacterial cell comprises mutations in two essential genes. For example, in some embodiments, the bacterial cell comprises mutations in tyrS (L36V, C38A, and F40G) and metG (E45Q, N47R, I49G, and A51 C). In other embodiments, the bacterial cell comprises mutations in three essential genes. For example, in some embodiments, the bacterial cell comprises mutations in tyrS (L36V, C38A, and F40G), metG (E45Q, N47R, I49G, and A51C), and pheS (F125G, P183T, P184A, R186A, and I188L).

In some embodiments, the genetically engineered bacterium is a conditional auxotroph whose essential gene(s) is replaced using the arabinose system shown in FIGS. 38, 48, 61, and 62.

Figure 39:
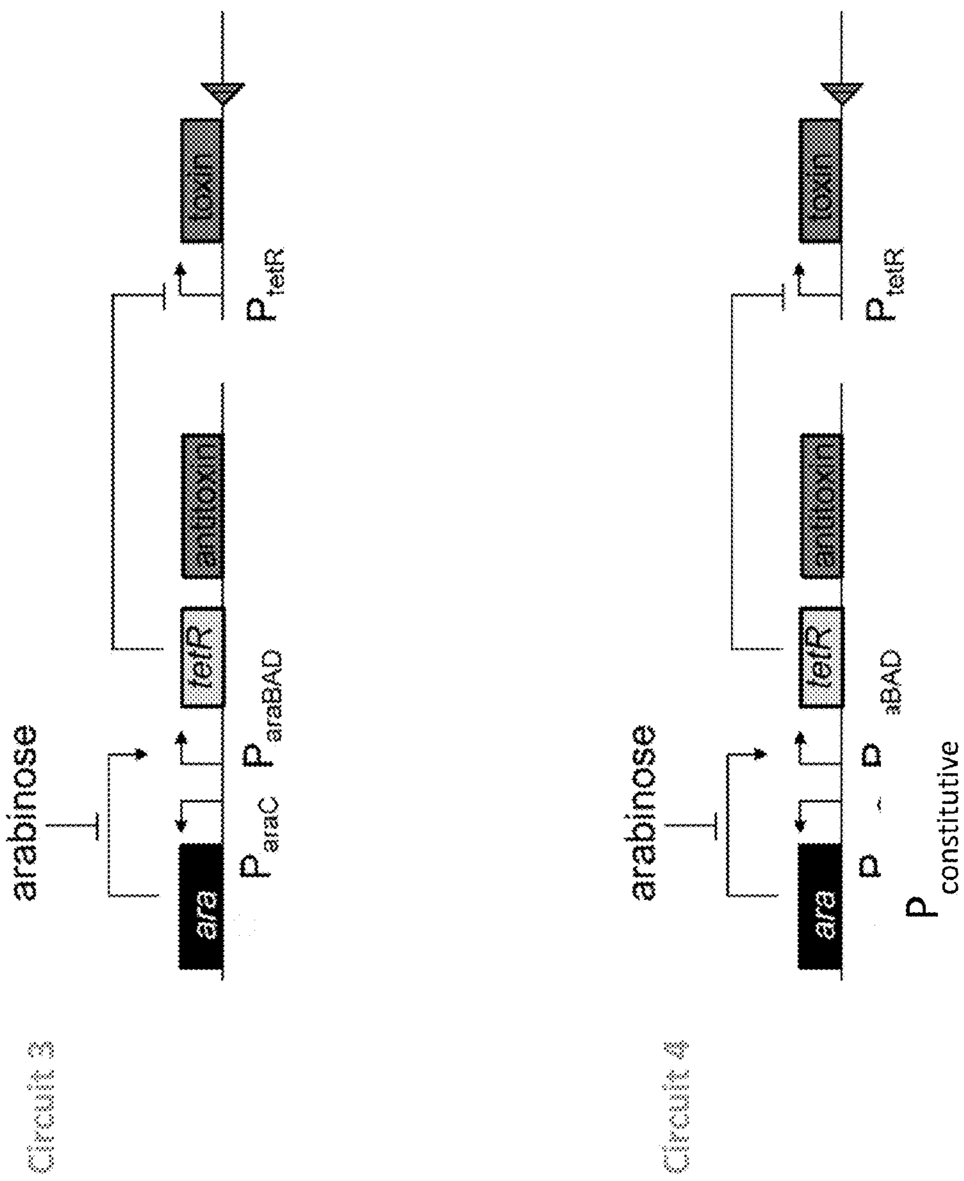
FIG. 39 depicts another non-limiting embodiment of the disclosure, wherein the expression of a heterologous gene is activated by an exogenous environmental signal. In the absence of arabinose, the AraC transcription factor adopts a conformation that represses transcription. In the presence of arabinose, the AraC transcription factor undergoes a conformational change that allows it to bind to and activate the AraBAD promoter, which induces expression of TetR (tet repressor) and an antitoxin. The antitoxin builds up in the recombinant bacterial cell, while TetR prevents expression of a toxin (which is under the control of a promoter having a TetR binding site). However, when arabinose is not present, both the antitoxin and TetR are not expressed. Since TetR is not present to repress expression of the toxin, the toxin is expressed and kills the cell. The AraC is under the control of a constitutive promoter in this circuit.
Figure 40:
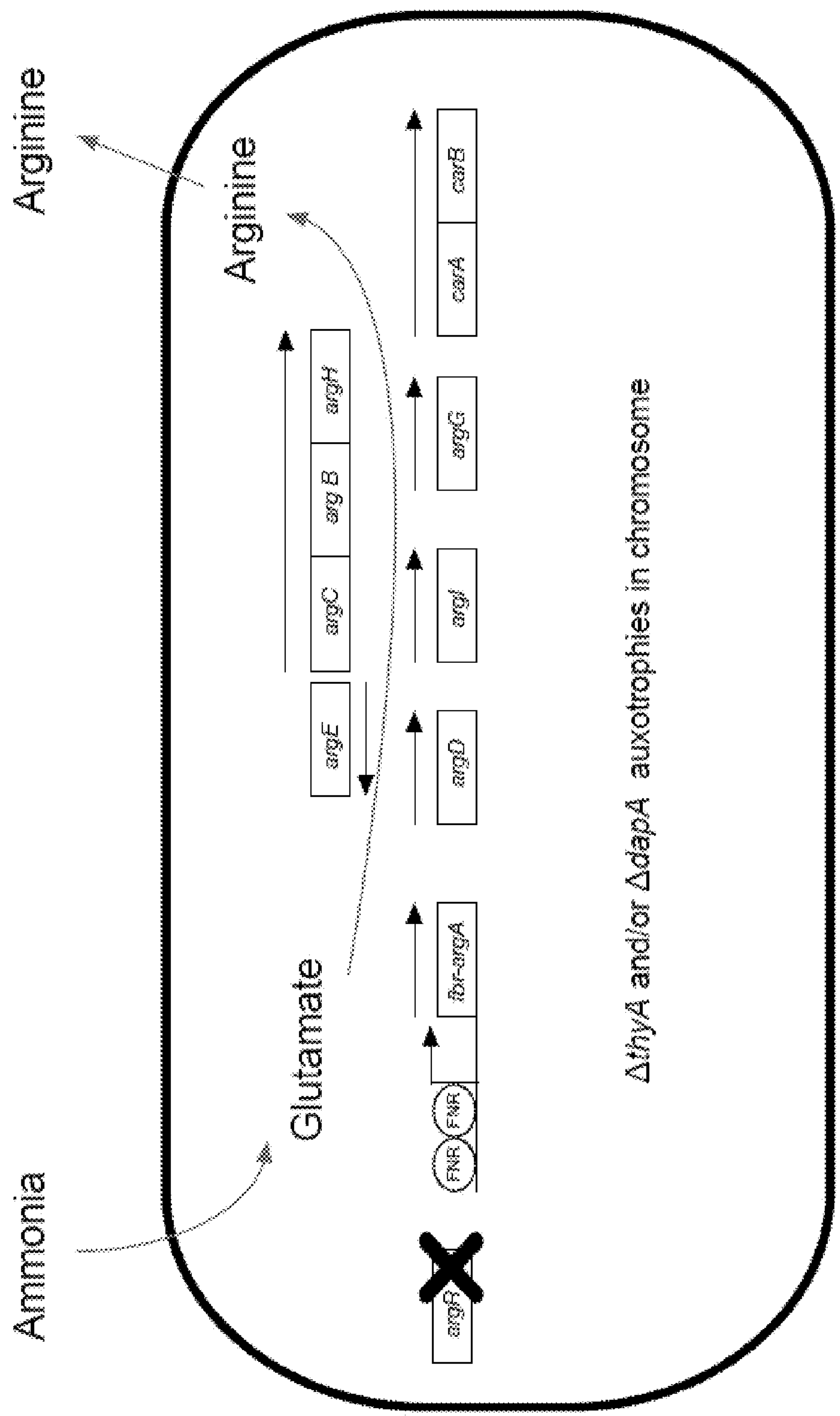
FIG. 40 depicts an exemplary embodiment of an engineered bacterial strain deleted for the argR gene and expressing the feedback-resistant $argA^{fbr}$ gene. This strain is useful for the consumption of ammonia and the production of arginine.
Figure 41:
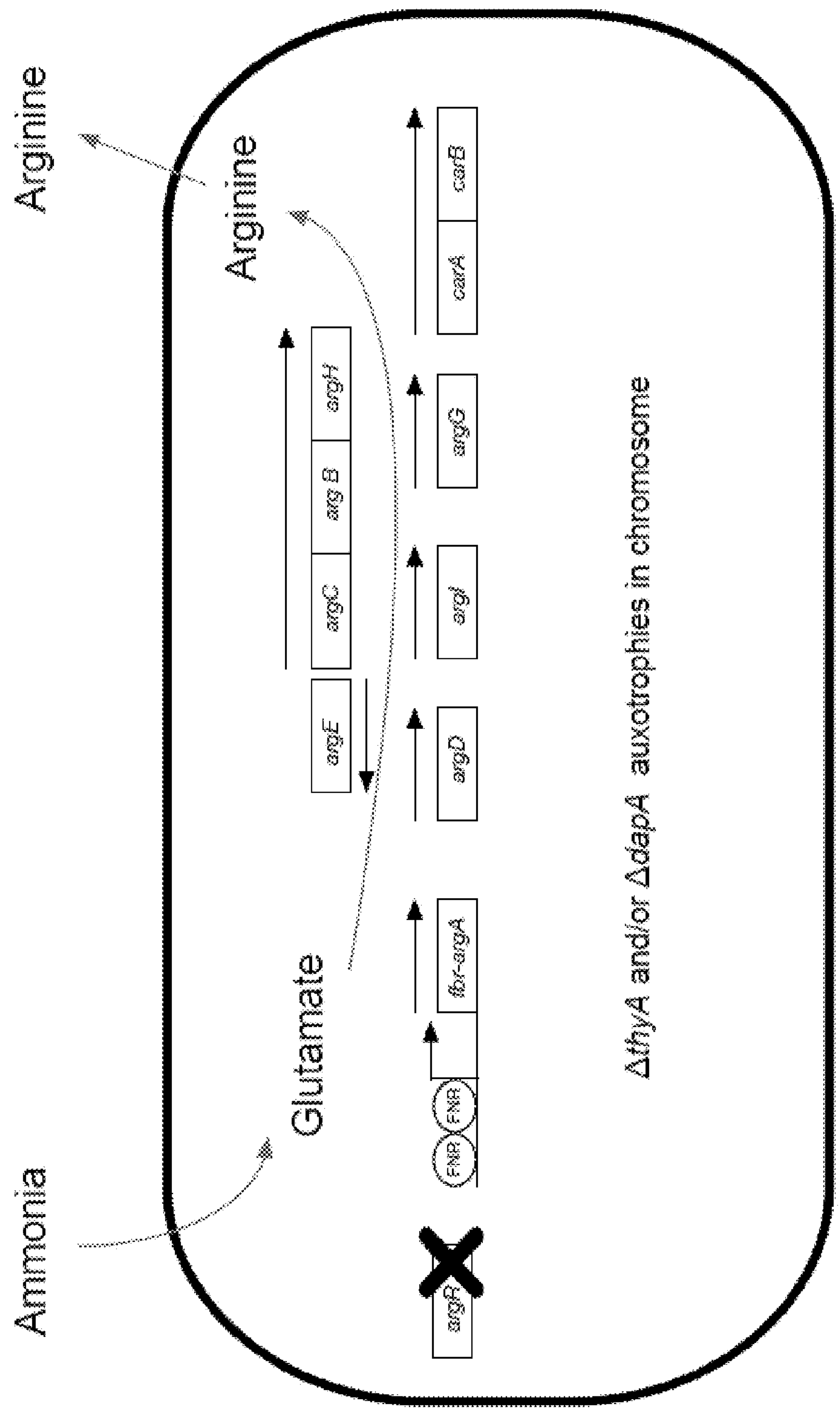
FIG. 41 depicts an exemplary embodiment of an engineered bacterial strain deleted for the argR gene and expressing the feedback-resistant $argA^{fbr}$ gene. This strain further comprises one or more auxotrophic modifications on the chromosome. This strain is useful for the consumption of ammonia and the production of arginine.
Figure 42:
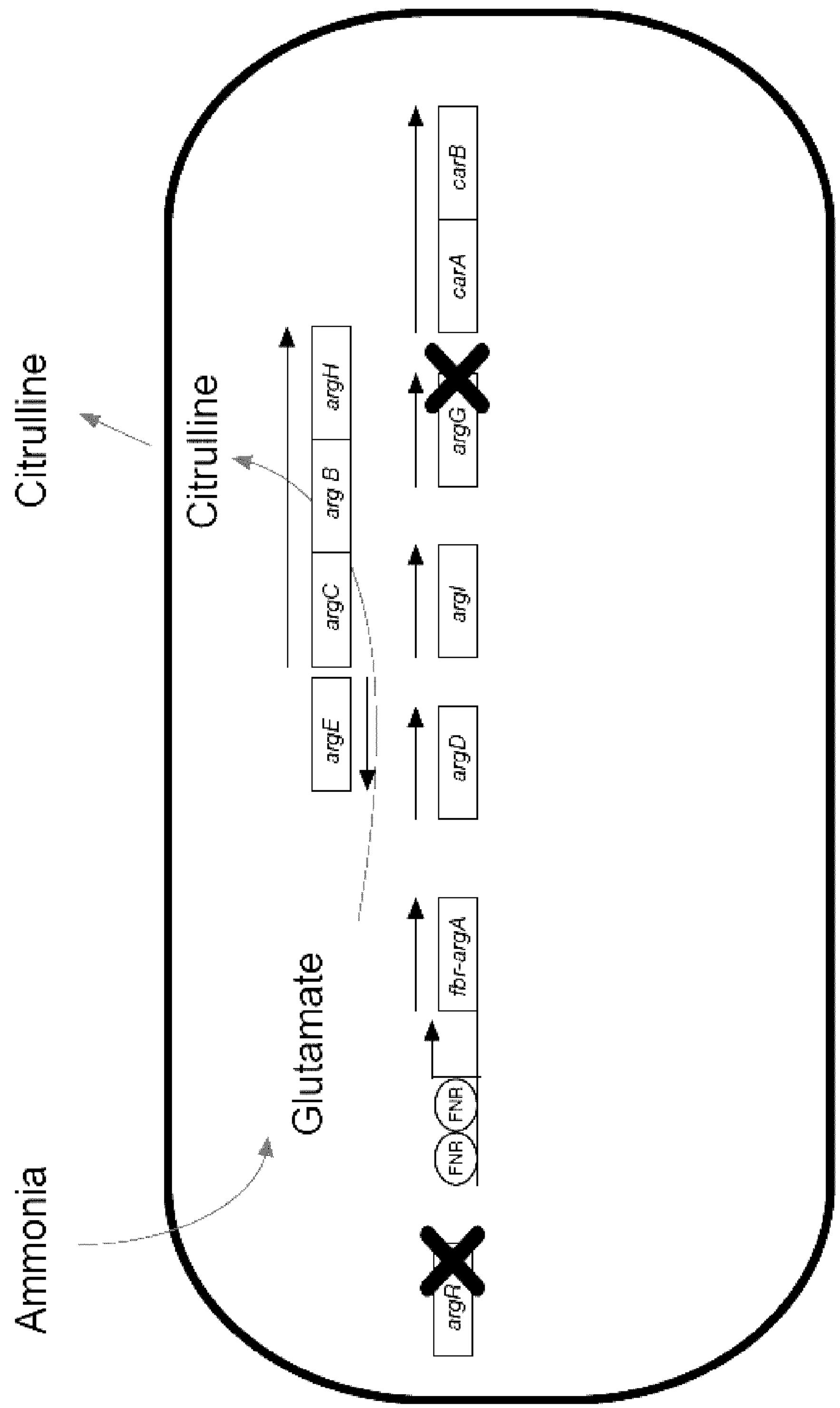
FIG. 42 depicts an exemplary embodiment of an engineered bacterial strain deleted for the argR and argG genes, and expressing the feedback-resistant $argA^{fbr}$ gene. This strain is useful for the consumption of ammonia and the production of citrulline.
Figure 43:
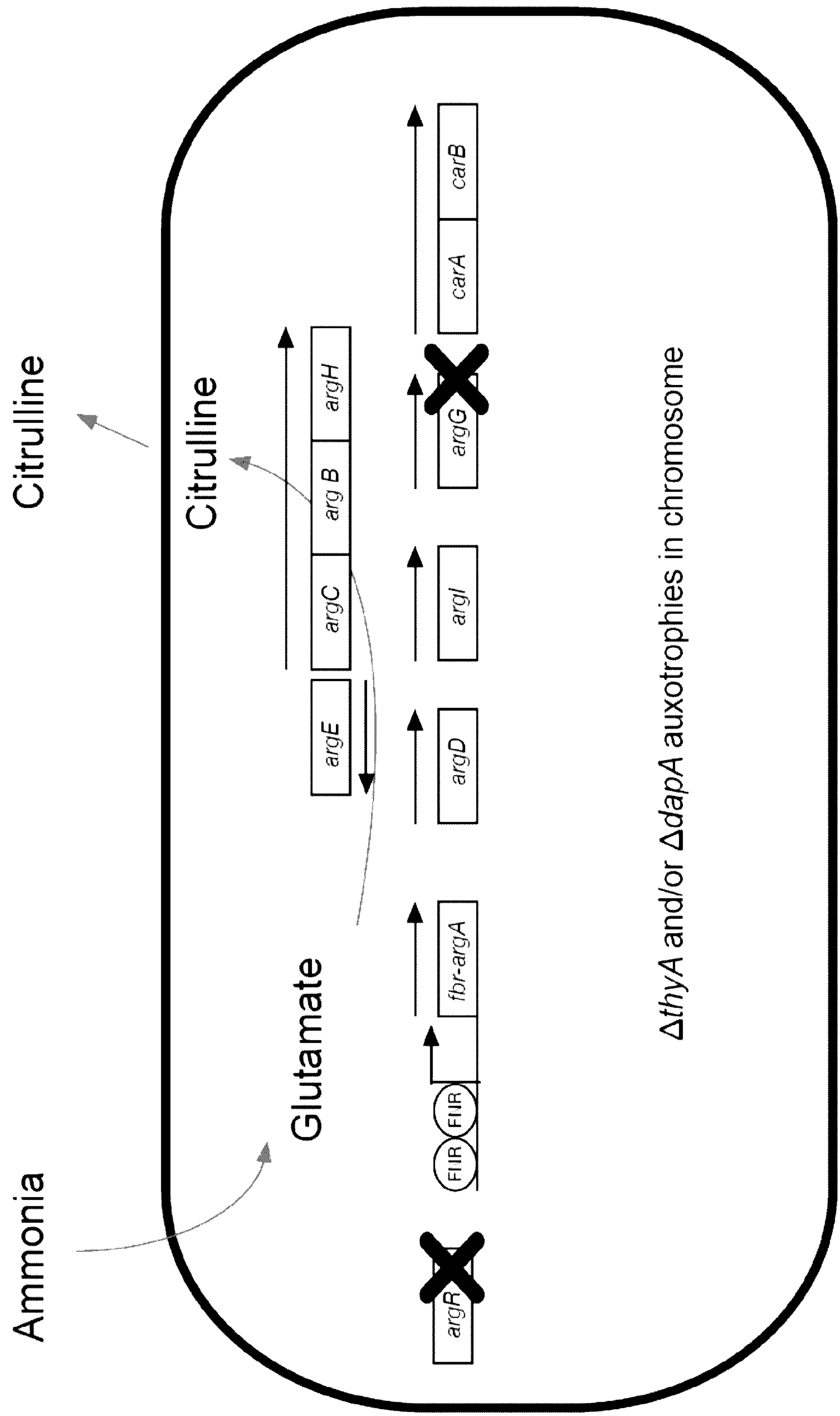
FIG. 43 depicts an exemplary embodiment of an engineered bacterial strain deleted for the argR and argG genes, and expressing the feedback-resistant $argA^{fbr}$ gene. This strain further comprises one or more auxotrophic modifications on the chromosome. This strain is useful for the consumption of ammonia and the production of citrulline.
Figure 44:
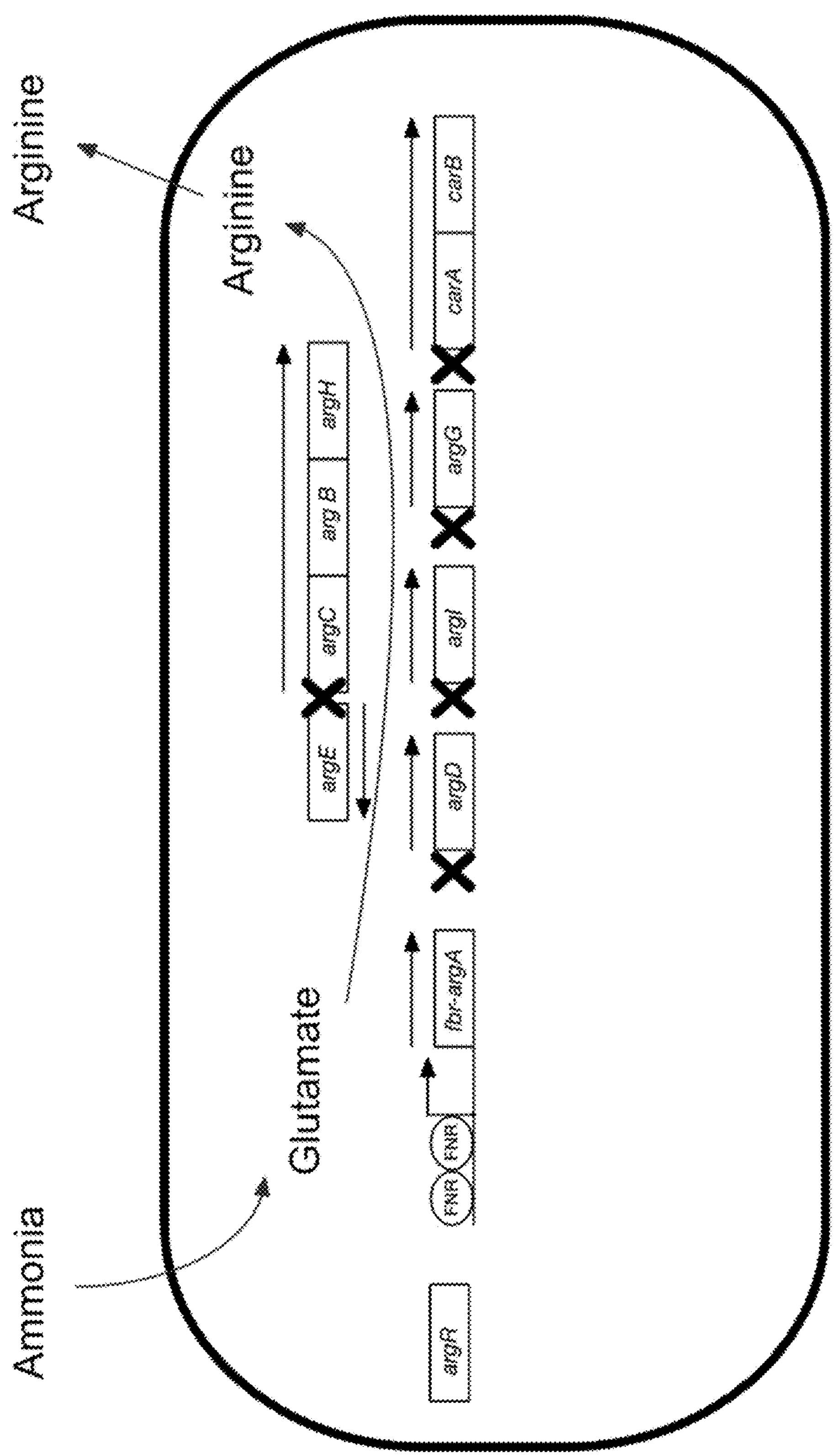
FIG. 44 depicts an exemplary embodiment of an engineered bacterial strain which lacks ArgR binding sites and expresses the feedback-resistant $argA^{fbr}$ gene. This strain is useful for the consumption of ammonia and the production of arginine.
Figure 45:
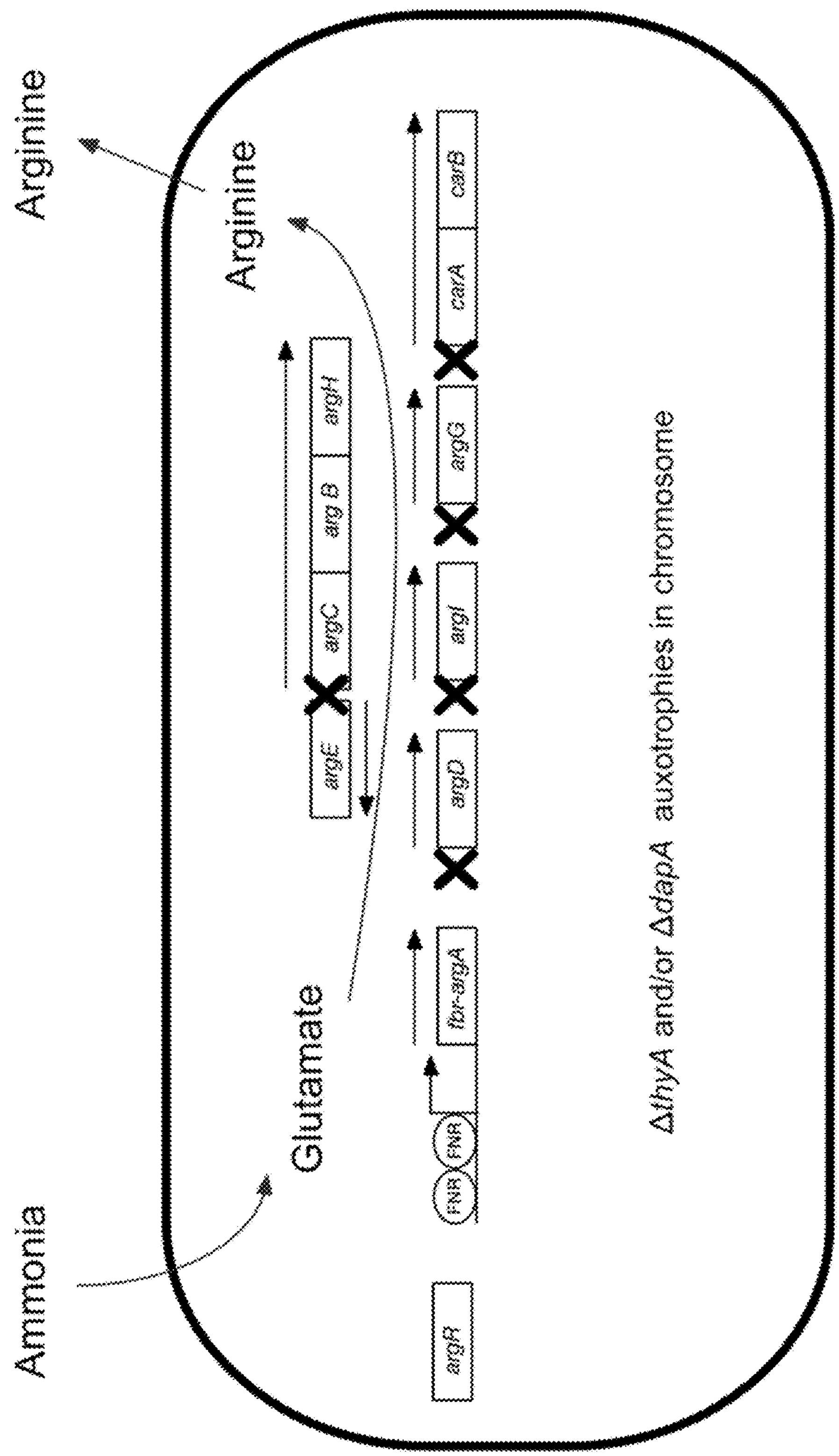
FIG. 45 depicts an exemplary embodiment of an engineered bacterial strain which lacks ArgR binding sites and expresses the feedback-resistant argA$^{fbr}$ gene. This strain further comprises one or more auxotrophic modifications on the chromosome. This strain is useful for the consumption of ammonia and the production of arginine.
Figure 46:
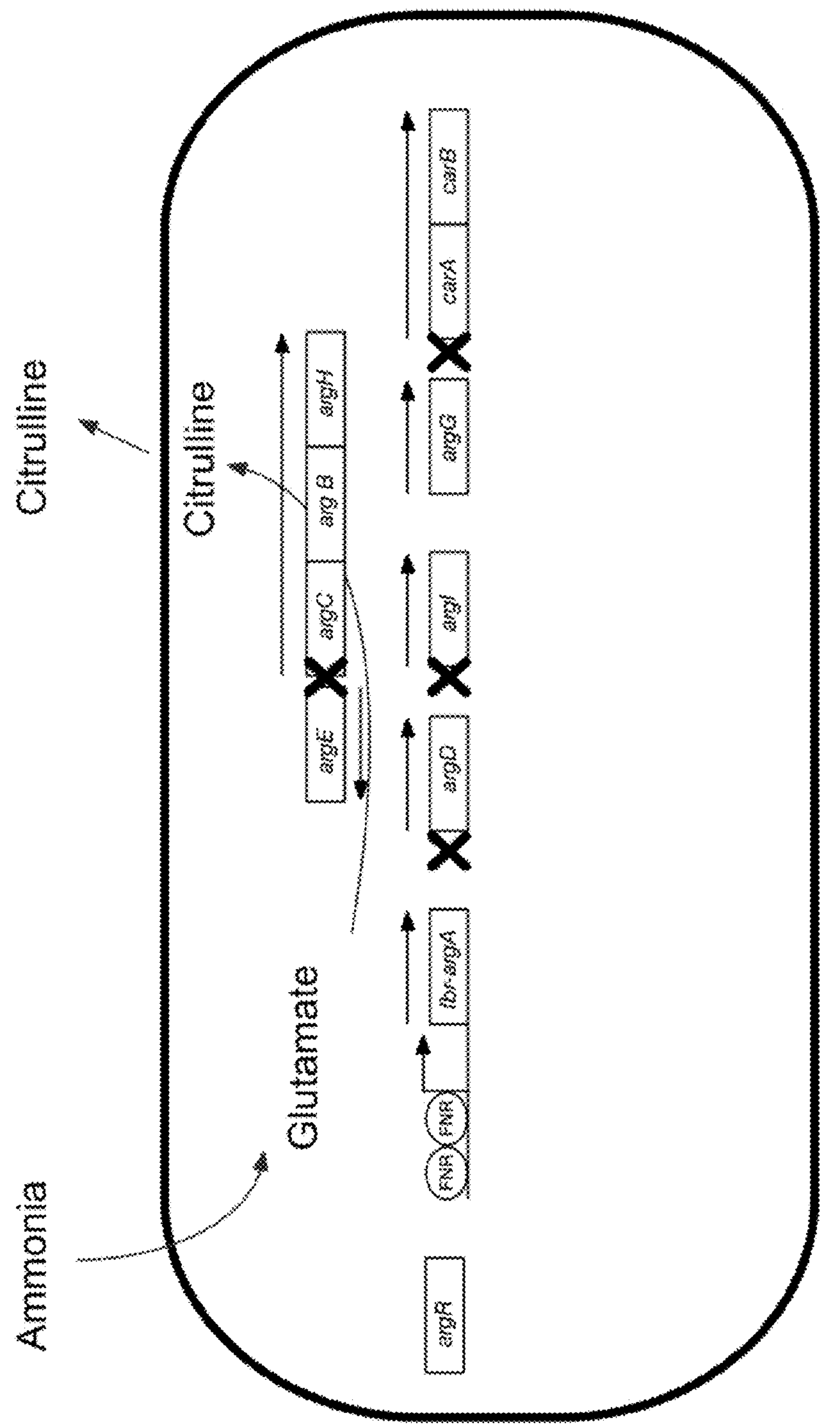
FIG. 46 depicts an exemplary embodiment of an engineered bacterial strain which lacks ArgR binding sites in all of the arginine biosynthesis operons except for argG, and expresses the feedback-resistant argA$^{fbr}$ gene. This strain is useful for the consumption of ammonia and the production of citrulline.
Figure 47:
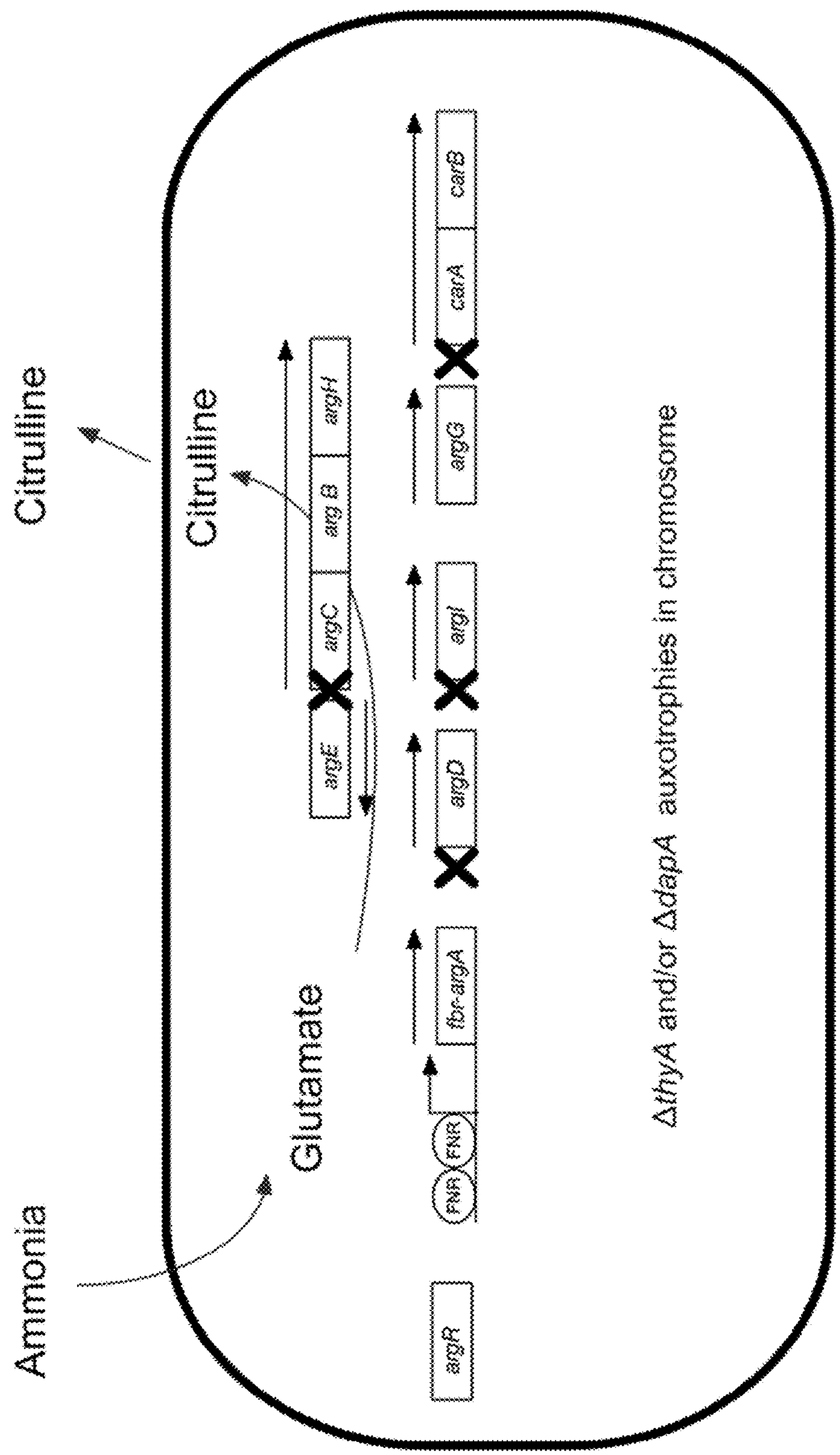
FIG. 47 depicts an exemplary embodiment of an engineered bacterial strain which lacks ArgR binding sites in all of the arginine biosynthesis operons except for argG, and expresses the feedback-resistant argA$^{fbr}$ gene. This strain further comprises one or more auxotrophic modifications on the chromosome. This strain is useful for the consumption of ammonia and the production of citrulline.
Figure 48A:
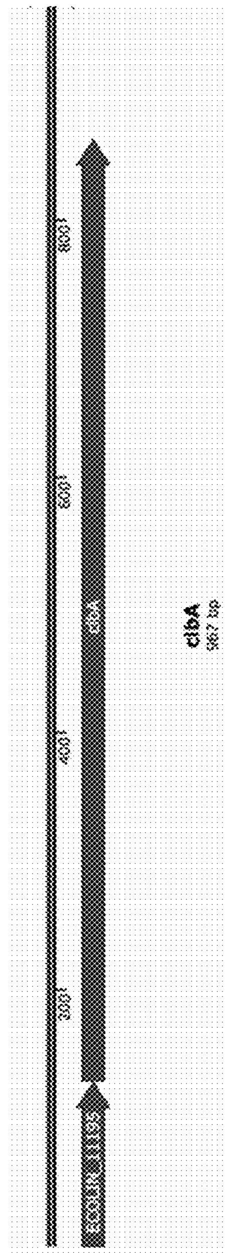
FIG. 48A depicts a schematic diagram of a wild-type clbA construct.
Figure 48B:
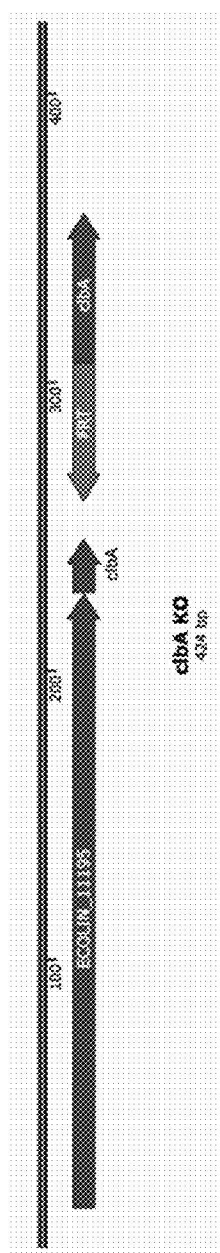
FIG. 48B depicts a schematic diagram of a clbA knockout construct.

In some embodiments, the genetically engineered bacterium of the disclosure is an auxotroph and also comprises kill-switch circuitry, such as any of the kill-switch components and systems described herein. For example, the recombinant bacteria may comprise a deletion or mutation in an essential gene required for cell survival and/or growth, for example, in a DNA synthesis gene, for example, thyA, cell wall synthesis gene, for example, dapA and/or an amino acid gene, for example, serA or MetA and may also comprise a toxin gene that is regulated by one or more transcriptional activators that are expressed in response to an environmental condition(s) and/or signal(s) (such as the described arabinose system) or regulated by one or more recombinases that are expressed upon sensing an exogenous environmental condition(s) and/or signal(s) (such as the recombinase systems described herein and in FIGS. 38, 39, and 49). Other embodiments are described in Wright et al., "GeneGuard: A Modular Plasmid System Designed for Biosafety," ACS Synthetic Biology (2015) 4: 307-16, the entire contents of which are expressly incorporated herein by reference). In some embodiments, the genetically engineered bacterium of the disclosure is an auxotroph and also comprises kill-switch circuitry, such as any of the kill-switch components and systems described herein, as well as another biosecurity system, such a conditional origin of replication (see Wright et al., supra).

Figures 32A, 32B:
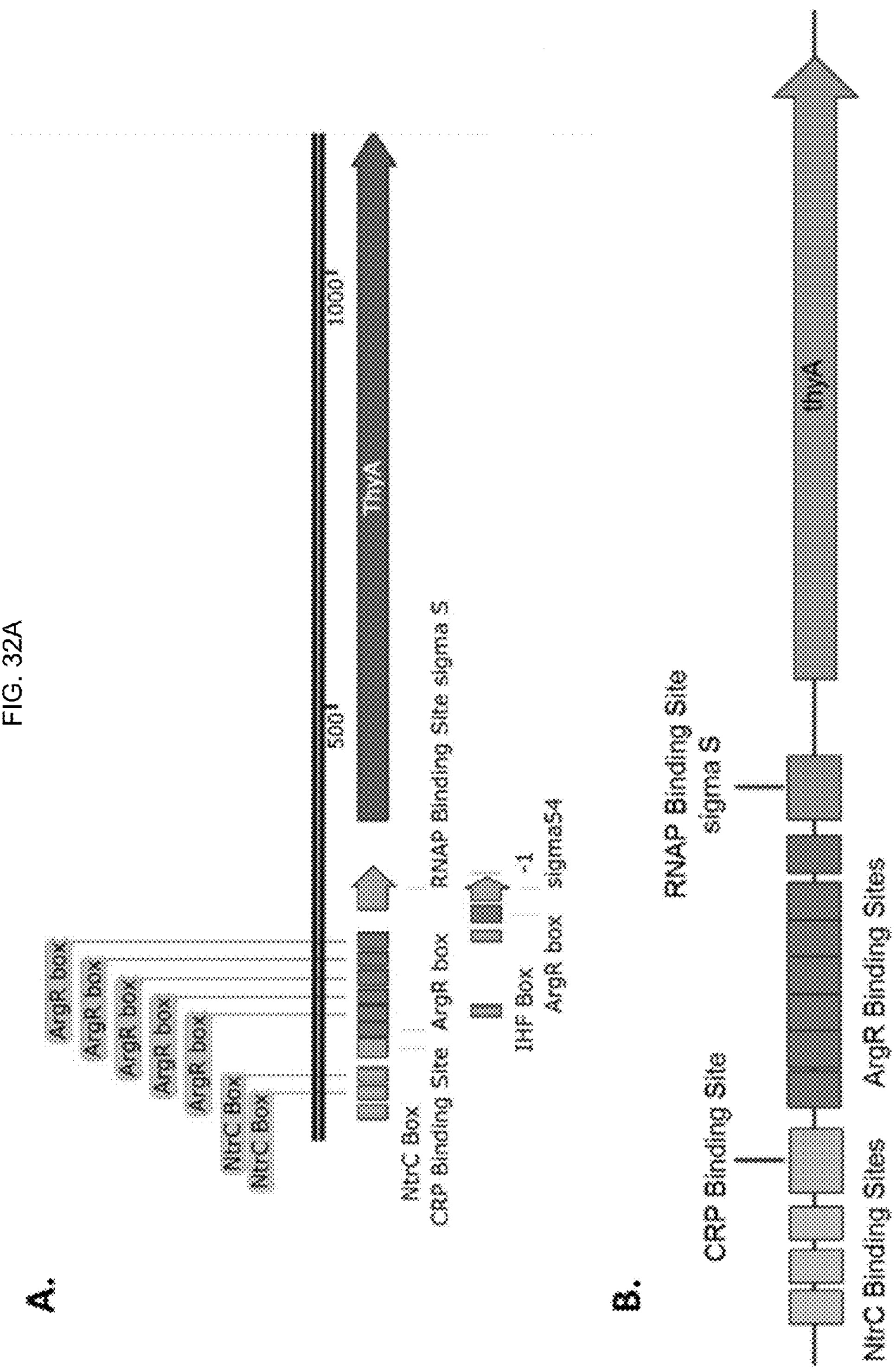
FIGS. 32A and 32B depict diagrams of exemplary constructs which may be used to produce a positive feedback auxotroph and select for high arginine production.
Figure 35:
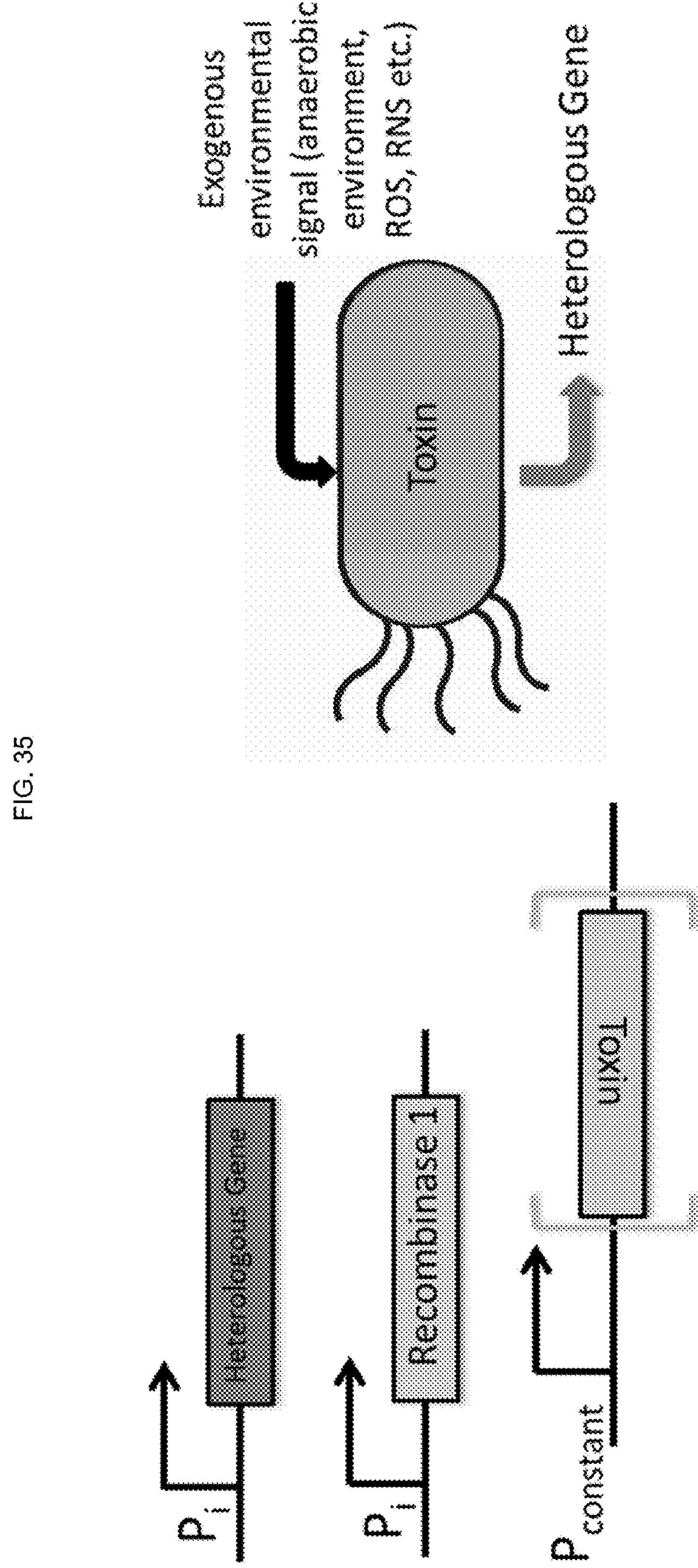
FIG. 35 depicts one non-limiting embodiment of the disclosure, where an exogenous environmental condition or one or more environmental signals activates expression of a heterologous gene and at least one recombinase from an inducible promoter or inducible promoters. The recombinase then flips a toxin gene into an activated conformation, and the natural kinetics of the recombinase create a time delay in expression of the toxin, allowing the heterologous gene to be fully expressed. Once the toxin is expressed, it kills the cell.
Figure 36:
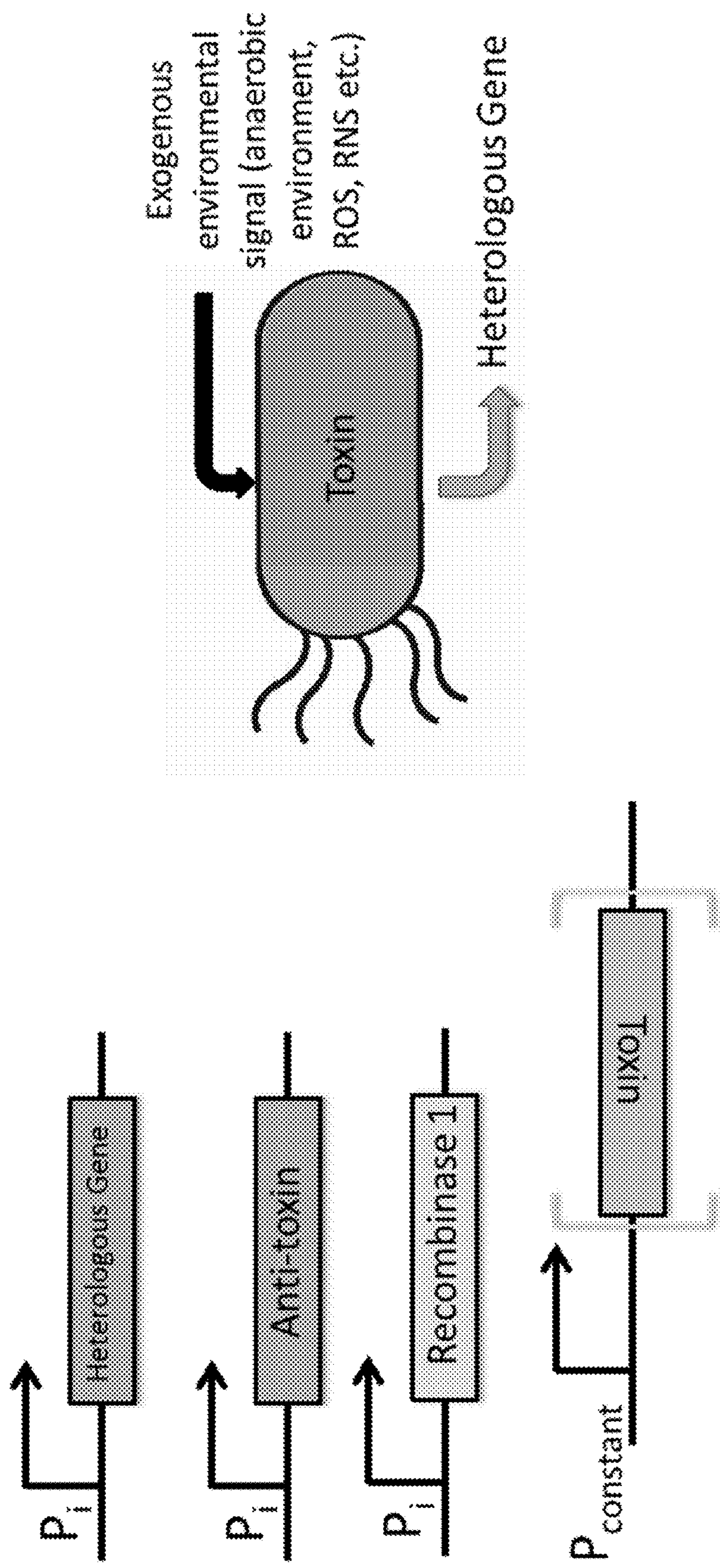
FIG. 36 depicts another non-limiting embodiment of the disclosure, where an exogenous environmental condition or one or more environmental signals activates expression of a heterologous gene, an anti-toxin, and at least one recombinase from an inducible promoter or inducible promoters. The recombinase then flips a toxin gene into an activated conformation, but the presence of the accumulated anti-toxin suppresses the activity of the toxin. Once the exogenous environmental condition or cue(s) is no longer present, expression of the anti-toxin is turned off. The toxin is constitutively expressed, continues to accumulate, and kills the bacterial cell.
Figure 37:
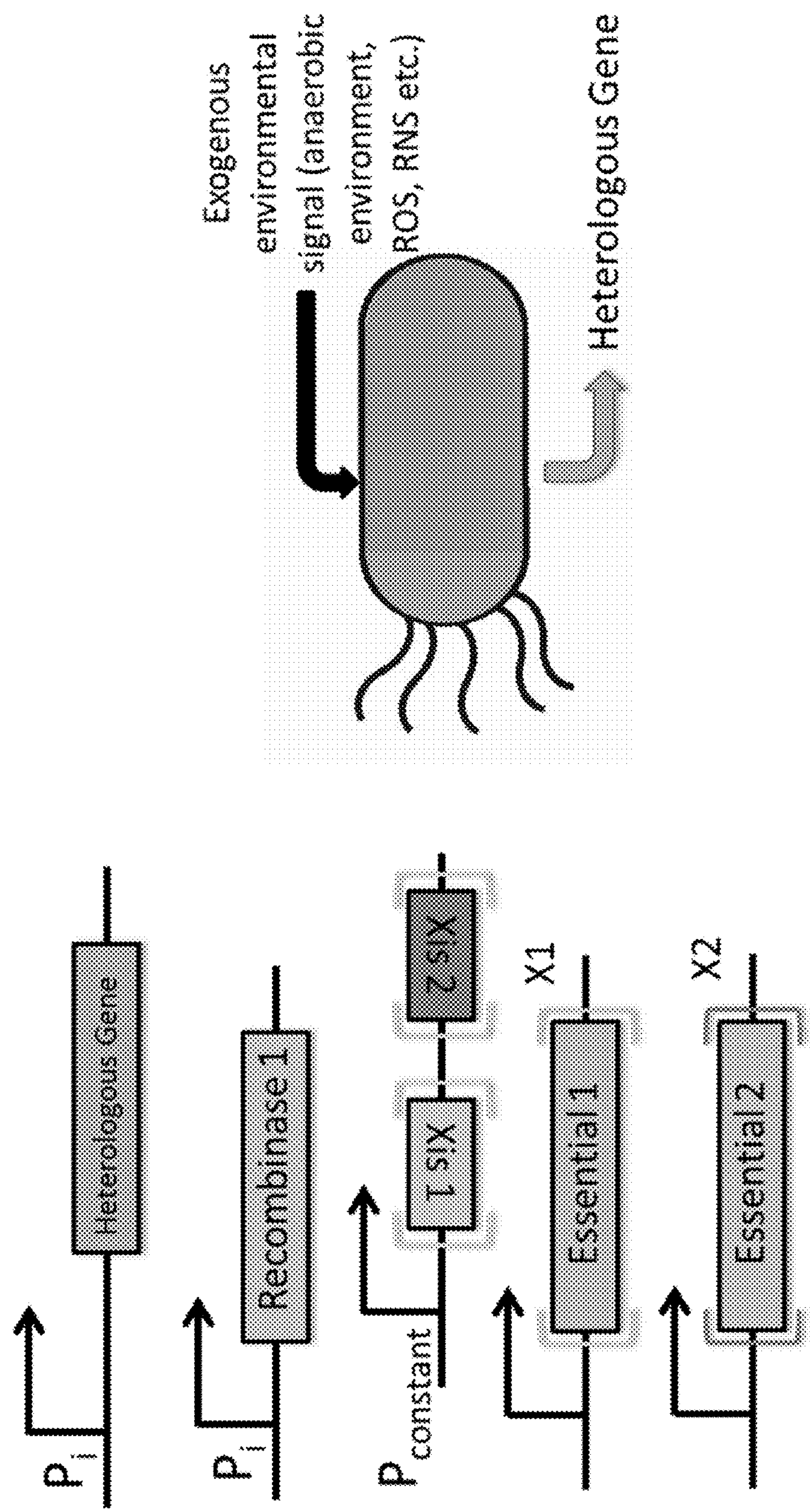
FIG. 37 depicts another non-limiting embodiment of the disclosure, where an exogenous environmental condition or one or more environmental signals activates expression of a heterologous gene and at least one recombinase from an inducible promoter or inducible promoters. The recombinase then flips at least one excision enzyme into an activated conformation. The at least one excision enzyme then excises one or more essential genes, leading to senescence, and eventual cell death. The natural kinetics of the recombinase and excision genes cause a time delay, the kinetics of which can be altered and optimized depending on the number and choice of essential genes to be excised, allowing cell death to occur within a matter of hours or days. The presence of multiple nested recombinases (as shown in FIG. 59) can be used to further control the timing of cell death.
Figure 38:
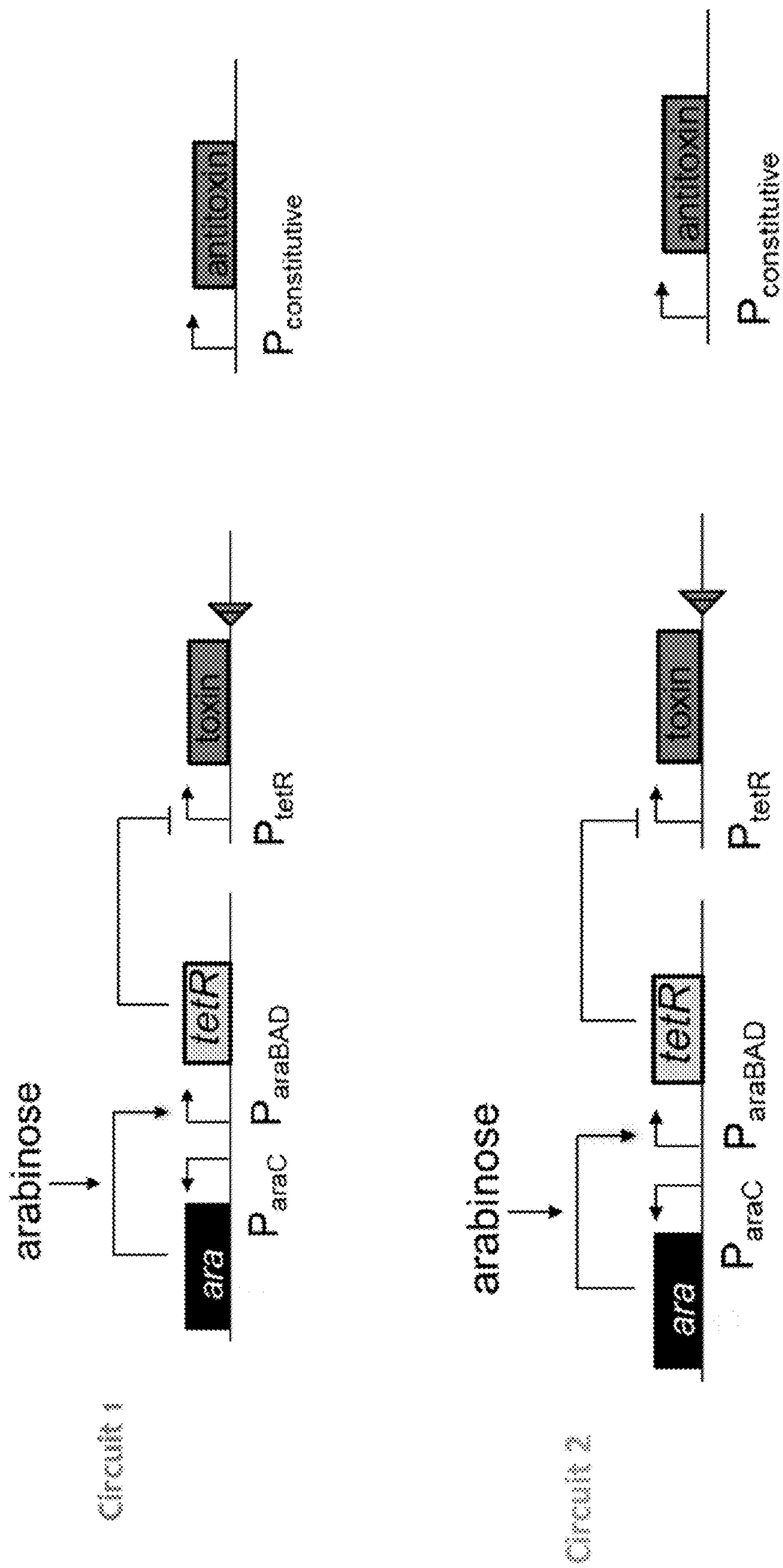
FIG. 38 depicts a non-limiting embodiment of the disclosure, where an anti-toxin is expressed from a constitutive promoter, and expression of a heterologous gene is activated by an exogenous environmental signal. In the absence of arabinose, the AraC transcription factor adopts a conformation that represses transcription. In the presence of arabinose, the AraC transcription factor undergoes a conformational change that allows it to bind to and activate the AraBAD promoter, which induces expression of TetR, thus preventing expression of a toxin. However, when arabinose is not present, TetR is not expressed, and the toxin is expressed, eventually overcoming the antitoxin and killing the cell. The constitutive promoter regulating expression of the anti-toxin should be a weaker promoter than the promoter driving expression of the toxin. The AraC is under the control of a constitutive promoter in this circuit.

In other embodiments, auxotrophic modifications may also be used to screen for mutant bacteria that consume excess ammonia. In a more specific aspect, auxotrophic modifications may be used to screen for mutant bacteria that consume excess ammonia by overproducing arginine. As described herein, many genes involved in arginine metabolism are subject to repression by arginine via its interaction with ArgR. The astC gene promoter is unique in that the arginine-ArgR complex acts as a transcriptional activator, as opposed to a transcriptional repressor. AstC encodes succinylornithine aminotransferase, the third enzyme of the ammonia-producing arginine succinyltransferase (AST) pathway and the first of the astCADBE operon in *E. coli* (Schneider et al., 1998). In certain embodiments, the genetically engineered bacteria are auxotrophic for a gene, and express the auxotrophic gene product under the control of an astC promoter. In these embodiments, the auxotrophy is subject to a positive feedback mechanism and used to select for mutant bacteria which consume excess ammonia by overproducing arginine. A non-limiting example of a positive feedback auxotroph is shown in FIGS. 32A and 32B.

Genetic Regulatory Circuits

In some embodiments, the genetically engineered bacteria comprise multi-layered genetic regulatory circuits for expressing the constructs described herein (see, e.g., U.S. Provisional Application No. 62/184,811, incorporated herein by reference in its entirety).

In certain embodiments, the invention provides methods for selecting genetically engineered bacteria that overproduce arginine. In some embodiments, the invention provides methods for selecting genetically engineered bacteria that consume excess ammonia via an alternative metabolic pathway, e.g., a histidine biosynthesis pathway, a methionine biosynthesis pathway, a lysine biosynthesis pathway, an asparagine biosynthesis pathway, a glutamine biosynthesis pathway, and a tryptophan biosynthesis pathway. In some embodiments, the invention provides genetically engineered bacteria comprising a mutant arginine regulon and an ArgR-regulated two-repressor activation genetic regulatory circuit. The two-repressor activation genetic regulatory circuit is useful to screen for mutant bacteria that reduce ammonia or rescue an auxotroph. In some constructs, high levels of arginine and the resultant activation of ArgR by arginine can cause expression of a detectable label or an essential gene that is required for cell survival.

The two-repressor activation regulatory circuit comprises a first ArgR and a second repressor, e.g., the Tet repressor. In one aspect of these embodiments, ArgR inhibits transcription of a second repressor, which inhibits the transcription of a particular gene of interest, e.g., a detectable product, which may be used to screen for mutants that consume excess ammonia, and/or an essential gene that is required for cell survival. Any detectable product may be used, including but not limited to, luciferase, β-galactosidase, and fluorescent proteins such as GFP. In some embodiments, the second repressor is a Tet repressor protein (TetR). In this embodiment, an ArgR-repressible promoter comprising wild-type ARG boxes drives the expression of TetR, and a TetR-repressible promoter drives the expression of at least one gene of interest, e.g., GFP. In the absence of ArgR binding (which occurs at low arginine concentrations), tetR is transcribed, and TetR represses GFP expression. In the presence of ArgR binding (which occurs at high arginine concentrations), tetR expression is repressed, and GFP is generated. Examples of other second repressors useful in these embodiments include, but are not limited to, ArsR, AscG, LacI, CscR, DeoR, DgoR, FruR, GaIR, GatR, CI, LexA, RafR, QacR, and PtxS (US20030166191). In some embodiments, the mutant arginine regulon comprising a switch is subjected to mutagenesis, and mutants that reduce ammonia by overproducing arginine are selected based upon the level of detectable product, e.g., by flow cytometry, fluorescence-activated cell sorting (FACS) when the detectable product fluoresces.

In some embodiments, the gene of interest is one required for survival and/or growth of the bacteria. Any such gene may be used, including but not limited to, cysE, glnA, ilvD, leuB, lysA, serA, metA, glyA, hisB, ilvA, pheA, proA, thrC, trpC, tyrA, thyA, uraA, dapA, dapB, dapD, dapE, dapF, flhD, metB, metC, proAB, and thi1, as long as the corresponding wild-type gene has been removed or mutated so as not to produce the gene product except under control of ArgR. In some embodiments, an ArgR-repressible promoter comprising wild-type ARG boxes drives the expression of a TetR protein, and a TetR-repressible promoter drives the expression of at least one gene required for survival and/or growth of the bacteria, e.g., thyA, uraA (Sat et al., 2003). In some embodiments, the genetically engineered bacterium is auxotrophic in a gene that is not complemented when the bacterium is present in the mammalian gut, wherein said gene is complemented by an second inducible gene present in the bacterium; transcription of the second gene is ArgR-repressible and induced in the presence of sufficiently high concentrations of arginine (thus complementing the auxotrophic gene). In some embodiments, the mutant arginine regulon comprising a two-repressor activation circuit is subjected to mutagenesis, and mutants that reduce excess ammonia are selected by growth in the absence of the gene product required for survival and/or growth. In some embodiments, the mutant arginine regulon comprising a two-repressor activation circuit is used to ensure that the bacteria do not survive in the absence of high levels of arginine (e.g., outside of the gut).

Host-Plasmid Mutual Dependency

In some embodiments, the genetically engineered bacteria of the invention also comprise a plasmid that has been modified to create a host-plasmid mutual dependency. In certain embodiments, the mutually dependent host-plasmid platform is GeneGuard (Wright et al., 2015). In some embodiments, the GeneGuard plasmid comprises (i) a conditional origin of replication, in which the requisite replication initiator protein is provided in trans; (ii) an auxotrophic modification that is rescued by the host via genomic translocation and is also compatible for use in rich media; and/or (iii) a nucleic acid sequence which encodes a broad-spectrum toxin. The toxin gene may be used to select against plasmid spread by making the plasmid DNA itself disadvantageous for strains not expressing the anti-toxin (e.g., a wild-type bacterium). In some embodiments, the GeneGuard plasmid is stable for at least 100 generations without antibiotic selection. In some embodiments, the GeneGuard plasmid does not disrupt growth of the host. The GeneGuard plasmid is used to greatly reduce unintentional plasmid propagation in the genetically engineered bacteria of the invention.

The mutually dependent host-plasmid platform may be used alone or in combination with other biosafety mechanisms, such as those described herein (e.g., kill switches, auxotrophies). In some embodiments, the genetically engineered bacteria comprise a GeneGuard plasmid. In other embodiments, the genetically engineered bacteria comprise a GeneGuard plasmid and/or one or more kill switches. In other embodiments, the genetically engineered bacteria comprise a GeneGuard plasmid and/or one or more auxotrophies. In still other embodiments, the genetically engineered bacteria comprise a GeneGuard plasmid, one or more kill switches, and/or one or more auxotrophies.

Kill Switch

In some embodiments, the genetically engineered bacteria of the invention also comprise a kill switch (see, e.g., U.S. Provisional Application Nos. 62/183,935 and 62/263,329 incorporated herein by reference in their entireties). The kill switch is intended to actively kill engineered microbes in response to external stimuli. As opposed to an auxotrophic mutation where bacteria die because they lack an essential nutrient for survival, the kill switch is triggered by a particular factor in the environment that induces the production of toxic molecules within the microbe that cause cell death.

Bacteria engineered with kill switches have been engineered for in vitro research purposes, e.g., to limit the spread of a biofuel-producing microorganism outside of a laboratory environment. Bacteria engineered for in vivo administration to treat a disease or disorder may also be programmed to die at a specific time after the expression and delivery of a heterologous gene or genes, for example, a therapeutic gene(s) or after the subject has experienced the therapeutic effect. For example, in some embodiments, the kill switch is activated to kill the bacteria after a period of time following oxygen level-dependent expression of $arg^{Afbr}$. In some embodiments, the kill switch is activated in a delayed fashion following oxygen level-dependent expression of $arg^{Afbr}$, for example, after the production of arginine or citrulline. Alternatively, the bacteria may be engineered to die after the bacteria has spread outside of a disease site. Specifically, it may be useful to prevent long-term colonization of subjects by the microorganism, spread of the microorganism outside the area of interest (for example, outside the gut) within the subject, or spread of the microorganism outside of the subject into the environment (for example, spread to the environment through the stool of the subject).Examples of such toxins that can be used in kill-switches include, but are not limited to, bacteriocins, lysins, and other molecules that cause cell death by lysing cell membranes, degrading cellular DNA, or other mechanisms. Such toxins can be used individually or in combination. The switches that control their production can be based on, for example, transcriptional activation (toggle switches; see, e.g., Gardner et al., 2000), translation (riboregulators), or DNA recombination (recombinase-based switches), and can sense environmental stimuli such as anaerobiosis or reactive oxygen species. These switches can be activated by a single environmental factor or may require several activators in AND, OR, NAND and NOR logic configurations to induce cell death. For example, an AND riboregulator switch is activated by tetracycline, isopropyl β-D-1-thiogalactopyranoside (IPTG), and arabinose to induce the expression of lysins, which permeabilize the cell membrane and kill the cell. IPTG induces the expression of the endolysin and holin mRNAs, which are then derepressed by the addition of arabinose and tetracycline. All three inducers must be present to cause cell death. Examples of kill switches are known in the art (Callura et al., 2010). In some embodiments, the kill switch is activated to kill the bacteria after a period of time following oxygen level-dependent expression of $arg^{Afbr}$. In some embodiments, the kill switch is activated in a delayed fashion following oxygen level-dependent expression of $arg^{Afbr}$.

Kill-switches can be designed such that a toxin is produced in response to an environmental condition or external signal (e.g., the bacteria is killed in response to an external cue) or, alternatively designed such that a toxin is produced once an environmental condition no longer exists or an external signal is ceased.

Thus, in some embodiments, the genetically engineered bacteria of the disclosure are further programmed to die after sensing an exogenous environmental signal, for example, in a low oxygen environment. In some embodiments, the genetically engineered bacteria of the present disclosure, e.g., bacteria expressing $arg^{Afbr}$ and repressor ArgR ,comprise one or more genes encoding one or more recombinase(s), whose expression is induced in response to an environmental condition or signal and causes one or more recombination events that ultimately leads to the expression of a toxin which kills the cell. In some embodiments, the at least one recombination event is to flipping of an inverted heterologous gene encoding a bacterial toxin which is then constitutively expressed after it is flipped by the first recombinase. In one embodiment, constitutive expression of the bacterial toxin kills the genetically engineered bacterium. In these types of kill-switch systems once the engineered bacterial cell senses the exogenous environmental condition and expresses the heterologous gene of interest, the recombinant bacterial cell is no longer viable.

In another embodiment in which the genetically engineered bacteria of the present disclosure, e.g., bacteria expressing $arg^{Afbr}$ and repressor ArgR , express one or more recombinase(s) in response to an environmental condition or signal causing at least one recombination event, the genetically engineered bacterium further expresses a heterologous gene encoding an anti-toxin in response to an exogenous environmental condition or signal. In one embodiment, the at least one recombination event is flipping of an inverted heterologous gene encoding a bacterial toxin by a first recombinase. In one embodiment, the inverted heterologous gene encoding the bacterial toxin is located between a first forward recombinase recognition sequence and a first reverse recombinase recognition sequence. In one embodiment, the heterologous gene encoding the bacterial toxin is constitutively expressed after it is flipped by the first recombinase. In one embodiment, the anti-toxin inhibits the activity of the toxin, thereby delaying death of the genetically engineered bacterium. In one embodiment, the genetically engineered bacterium is killed by the bacterial toxin when the heterologous gene encoding the anti-toxin is no longer expressed when the exogenous environmental condition is no longer present.

In another embodiment, the at least one recombination event is flipping of an inverted heterologous gene encoding a second recombinase by a first recombinase, followed by the flipping of an inverted heterologous gene encoding a bacterial toxin by the second recombinase. In one embodiment, the inverted heterologous gene encoding the second recombinase is located between a first forward recombinase recognition sequence and a first reverse recombinase recognition sequence. In one embodiment, the inverted heterologous gene encoding the bacterial toxin is located between a second forward recombinase recognition sequence and a second reverse recombinase recognition sequence. In one embodiment, the heterologous gene encoding the second recombinase is constitutively expressed after it is flipped by the first recombinase. In one embodiment, the heterologous gene encoding the bacterial toxin is constitutively expressed after it is flipped by the second recombinase. In one embodiment, the genetically engineered bacterium is killed by the bacterial toxin. In one embodiment, the genetically engineered bacterium further expresses a heterologous gene encoding an anti-toxin in response to the exogenous environmental condition. In one embodiment, the anti-toxin inhibits the activity of the toxin when the exogenous environmental condition is present, thereby delaying death of the genetically engineered bacterium. In one embodiment, the genetically engineered bacterium is killed by the bacterial toxin when the heterologous gene encoding the anti-toxin is no longer expressed when the exogenous environmental condition is no longer present.

In one embodiment, the at least one recombination event is flipping of an inverted heterologous gene encoding a second recombinase by a first recombinase, followed by flipping of an inverted heterologous gene encoding a third recombinase by the second recombinase, followed by flipping of an inverted heterologous gene encoding a bacterial toxin by the third recombinase.

In one embodiment, the at least one recombination event is flipping of an inverted heterologous gene encoding a first excision enzyme by a first recombinase. In one embodiment, the inverted heterologous gene encoding the first excision enzyme is located between a first forward recombinase recognition sequence and a first reverse recombinase recognition sequence. In one embodiment, the heterologous gene encoding the first excision enzyme is constitutively expressed after it is flipped by the first recombinase. In one embodiment, the first excision enzyme excises a first essential gene. In one embodiment, the programmed recombinant bacterial cell is not viable after the first essential gene is excised.

In one embodiment, the first recombinase further flips an inverted heterologous gene encoding a second excision enzyme. In one embodiment, the wherein the inverted heterologous gene encoding the second excision enzyme is located between a second forward recombinase recognition sequence and a second reverse recombinase recognition sequence. In one embodiment, the heterologous gene encoding the second excision enzyme is constitutively expressed after it is flipped by the first recombinase. In one embodiment, the genetically engineered bacterium dies or is no longer viable when the first essential gene and the second essential gene are both excised. In one embodiment, the genetically engineered bacterium dies or is no longer viable when either the first essential gene is excised or the second essential gene is excised by the first recombinase.

In one embodiment, the genetically engineered bacterium dies after the at least one recombination event occurs. In another embodiment, the genetically engineered bacterium is no longer viable after the at least one recombination event occurs.

In any of these embodiment, the recombinase can be a recombinase selected from the group consisting of: Bxbl, PhiC31, TP901, Bxbl, PhiC31, TP901, HK022, HP1, R4, Int1, Int2, Int3, Int4, Int5, Int6, Int7, Int8, Int9, Int10 , Int11, Int12, Int13, Int14, Int15, Int16, Int17, Int18, Int19, Int20, Int21, Int22, Int23, Int24, Int25, Int26, Int27, Int28, Int29, Int30, Int31, Int32, Int33, and Int34, or a biologically active fragment thereof.

In the above-described kill-switch circuits, a toxin is produced in the presence of an environmental factor or signal. In another aspect of kill-switch circuitry, a toxin may be repressed in the presence of an environmental factor (not produced) and then produced once the environmental condition or external signal is no longer present. An exemplary kill-switch in which the toxin is repressed in the presence of an external factor or signal (and activated once the external signal is removed) is shown in FIGS. 38, 39, 61, and 62. The disclosure provides recombinant bacterial cells which express one or more heterologous gene(s) upon sensing arabinose or other sugar in the exogenous environment. In this aspect, the recombinant bacterial cells contain the araC gene, which encodes the AraC transcription factor, as well as one or more genes under the control of the araBAD promoter. In the absence of arabinose, the AraC transcription factor adopts a conformation that represses transcription of genes under the control of the araBAD promoter. In the presence of arabinose, the AraC transcription factor undergoes a conformational change that allows it to bind to and activate the AraBAD promoter, which induces expression of the desired gene.

Thus, in some embodiments in which one or more heterologous gene(s) are expressed upon sensing arabinose in the exogenous environment, the one or more heterologous genes are directly or indirectly under the control of the araBAD promoter. In some embodiments, the expressed heterologous gene is selected from one or more of the following: a heterologous therapeutic gene, a heterologous gene encoding an antitoxin, a heterologous gene encoding a repressor protein or polypeptide, for example, a TetR repressor, a heterologous gene encoding an essential protein not found in the bacterial cell, and/or a heterologous encoding a regulatory protein or polypeptide.

Arabinose inducible promoters are known in the art, including $P_{ara}$, $P_{araB}$, $P_{araC}$, and $P_{araBAD}$. In one embodiment, the arabinose inducible promoter is from *E. coli*. In some embodiments, the $P_{araC}$ promoter and the $P_{araBAD}$ promoter operate as a bidirectional promoter, with the $P_{araBAD}$ promoter controlling expression of a heterologous gene(s) in one direction, and the $P_{araC}$ (in close proximity to, and on the opposite strand from the $P_{araBAD}$ promoter), controlling expression of a heterologous gene(s) in the other direction. In the presence of arabinose, transcription of both heterologous genes from both promoters is induced. However, in the absence of arabinose, transcription of both heterologous genes from both promoters is not induced.

In one exemplary embodiment of the disclosure, the engineered bacteria of the present dicslosure contains a kill-switch having at least the following sequences: a $P_{araBAD}$ promoter operably linked to a heterologous gene encoding a Tetracycline Repressor Protein (TetR), a $P_{araC}$ promoter operably linked to a heterologous gene encoding AraC transcription factor, and a heterologous gene encoding a bacterial toxin operably linked to a promoter which is repressed by the Tetracycline Repressor Protein ($P_{TetR}$). In the presence of arabinose, the AraC transcription factor activates the $P_{araBAD}$ promoter, which activates transcription of the TetR protein which, in turn, represses transcription of the toxin. In the absence of arabinose, however, AraC suppresses transcription from the the $P_{araBAD}$ promoter and no TetR protein is expressed. In this case, expression of the heterologous toxin gene is activated, and the toxin is expressed. The toxin builds up in the recombinant bacterial cell, and the recombinant bacterial cell is killed. In one embodiment, the AraC gene encoding the AraC transcription factor is under the control of a constitutive promoter and is therefore constitutively expressed.

In one embodiment of the disclosure, the recombinant bacterial cell further comprises an antitoxin under the control of a constitutive promoter. In this situation, in the presence of arabinose, the toxin is not expressed due to repression by TetR protein, and the antitoxin protein builds-up in the cell. However, in the absence of arabinose, TetR protein is not expressed, and expression of the toxin is induced. The toxin begins to build-up within the recombinant bacterial cell. The recombinant bacterial cell is no longer viable once the toxin protein is present at either equal or greater amounts than that of the anti-toxin protein in the cell, and the recombinant bacterial cell will be killed by the toxin.

In another embodiment of the disclosure, the recombinant bacterial cell further comprises an antitoxin under the control of the $P_{araBAD}$ promoter. In this situation, in the presence of arabinose, TetR and the anti-toxin are expressed, the anti-toxin builds up in the cell, and the toxin is not expressed due to repression by TetR protein. However, in the absence of arabinose, both the TetR protein and the anti-toxin are not expressed, and expression of the toxin is induced. The toxin begins to build-up within the recombinant bacterial cell. The recombinant bacterial cell is no longer viable once the toxin protein is expressed, and the recombinant bacterial cell will be killed by the toxin.

In another exemplary embodiment of the disclosure, the engineered bacteria of the present disclosure contains a kill-switch having at least the following sequences: a $P_{araBAD}$ promoter operably linked to a heterologous gene encoding an essential polypeptide not found in the recombinant bacterial cell (and required for survival), and a $P_{araC}$ promoter operably linked to a heterologous gene encoding AraC transcription factor. In the presence of arabinose, the AraC transcription factor activates the $P_{araBAD}$ promoter, which activates transcription of the heterologous gene encoding the essential polypeptide, allowing the recombinant bacterial cell to survive. In the absence of arabinose, however, AraC suppresses transcription from the the $P_{araBAD}$ promoter and the essential protein required for survival is not expressed. In this case, the recombinant bacterial cell dies in the absence of arabinose. In some embodiments, the sequence of $P_{araBAD}$ promoter operably linked to a heterologous gene encoding an essential polypeptide not found in the recombinant bacterial cell can be present in the bacterial cell in conjunction with the TetR/toxin kill-switch system described directly above. In some embodiments, the sequence of $P_{araBAD}$ promoter operably linked to a heterologous gene encoding an essential polypeptide not found in the recombinant bacterial cell can be present in the bacterial cell in conjunction with the TetR/toxin/anto-toxin kill-switch system described directly above.

In some embodiments, the engineered bacteria of the present disclosure, for example, bacteria expressing $arg^{Afbr}$ and repressor ArgR further comprise the gene(s) encoding the components of any of the above-described kill-switch circuits.

In any of the above-described embodiments, the bacterial toxin is selected from the group consisting of a lysin, Hok, Fst, TisB, LdrD, Kid, SymE, MazF, FlmA, lbs, XCV2162, dinJ, CcdB, MazF, ParE, YafO, Zeta, hicB, relB, yhaV, yoeB, chpBK, hipA, microcin B, microcin B17, microcin C, microcin C7-051, microcin J25, microcin ColV, microcin 24, microcin L, microcin D93, microcin L, microcin E492, microcin H47, microcin 147, microcin M, colicin A, colicin E1, colicin K, colicin N, colicin U, colicin B, colicin Ia, colicin Ib, colicin 5, colicin10, colicin S4, colicin Y, colicin E2, colicin E7, colicin E8, colicin E9, colicin E3, colicin E4, colicin E6; colicin E5, colicin D, colicin M, and cloacin DF13, or a biologically active fragment thereof.

In any of the above-described embodiments, the anti-toxin is selected from the group consisting of an anti-lysin, Sok, RNAII, IstR, RdlD, Kis, SymR, MazE, FlmB, Sib, ptaRNA1, yafQ, CcdA, MazE, ParD, yafN, Epsilon, HicA, relE, prlF, yefM, chpBI, hipB, MccE, $MccE^{CTD}$, MccF, Cai, ImmE1, Cki, Cni, Cui, Cbi, Iia, Imm, Cfi, Im10, Csi, Cyi, Im2, Im7, Im8, Im9, Im3, Im4, ImmE6, cloacin immunity protein (Cim), ImmE5, ImmD, and Cmi, or a biologically active fragment thereof.

In one embodiment, the bacterial toxin is bactericidal to the genetically engineered bacterium. In one embodiment, the bacterial toxin is bacteriostatic to the genetically engineered bacterium.

In some embodiments, the engineered bacteria provided herein have an arginine regulon comprising one or more nucleic acid mutations that reduce or eliminate arginine-mediated repression of each of the operons that encode the enzymes responsible for converting glutamate to arginine and/or an intermediate byproduct, e.g., citrulline, in the arginine biosynthesis pathway, such that the mutant arginine regulon produces more arginine and/or intermediate byproduct than an unmodified regulon from the same bacterial subtype under the same conditions. In some embodiments, the genetically engineered bacteria comprise an arginine feedback resistant N-acetylglutamate synthase mutant, e.g., $argA^{fbr}$. In some embodiments, the genetically engineered bacteria comprise a mutant arginine regulon comprising one or more nucleic acid mutations in at least one ARG box for each of the operons that encode the arginine biosynthesis enzymes N-acetylglutamate kinase, N-acetylglutamylphosphate reductase, acetylornithine am inotransferase, N-acetylornithinase, ornithine transcarbamylase, argininosuccinate synthase, argininosuccinate lyase, and carbamoylphosphate synthase, thereby derepressing the regulon and enhancing arginine and/or intermediate byproduct biosynthesis. In some embodiments, the genetically engineered bacteria further comprise an arginine feedback resistant N-acetylglutamate synthase mutant. In some embodiments, the arginine feedback resistant N-acetylglutamate synthase mutant is controlled by an oxygen level-dependent promoter. In some embodiments, the arginine feedback resistant N-acetylglutamate synthase mutant is controlled by a promoter that is induced under low-oxygen or anaerobic conditions. In some embodiments, the promoter is selected from the fumarate and nitrate reductase regulator (FNR) promoter, arginine deiminiase and nitrate reduction (ANR) promoter, and dissimilatory nitrate respiration regulator (DNR) promoter. In some embodiments, the arginine feedback resistant N-acetylglutamate synthase mutant is $argA^{fbr}$.

In some embodiments, the genetically engineered bacteria comprise a mutant arginine regulon comprising one or more nucleic acid mutations in at least one ARG box for each of the operons that encode the arginine biosynthesis enzymes and an arginine feedback resistant N-acetylglutamate synthase mutant. In some embodiments, the genetically engineered bacteria comprise a mutant arginine regulon, wherein the bacterium comprises a gene encoding a functional N-acetylglutamate synthetase that is mutated to reduce arginine feedback inhibition as compared to a wild-type N-acetylglutamate synthetase from the same bacterial subtype under the same conditions, wherein expression of the gene encoding the mutated N-acetylglutamate synthetase is controlled by a promoter that is induced under low-oxygen or anaerobic conditions, wherein the mutant arginine regulon comprises one or more operons comprising genes that encode arginine biosynthesis enzymes N-acetylglutamate kinase, N-acetylglutamate phosphate reductase, acetylornithine aminotransferase, N-acetylornithinase, carbamoylphosphate synthase, ornithine transcarbamylase, argininosuccinate synthase, and argininosuccinate lyase, and wherein each operon comprises one or more mutated ARG box(es) characterized by one or more nucleic acid mutations that reduces arginine-mediated repression of the operon via ArgR repressor binding, and retains RNA polymerase binding with sufficient affinity to promote transcription of the genes in the operon In some embodiments, the genetically engineered bacteria is an auxotroph comprising a mutant arginine regulon comprising one or more nucleic acid mutations in at least one ARG box for each of the operons that encode the arginine biosynthesis enzymes and an arginine feedback resistant N-acetylglutamate synthase mutant. In one embodiment, the genetically engineered bacteria comprising a mutant arginine regulon comprising one or more nucleic acid mutations in at least one ARG box for each of the operons that encode the arginine biosynthesis enzymes and an arginine feedback resistant N-acetylglutamate synthase mutant is an auxotroph selected from a cysE, glnA, ilvD, leuB, lysA, serA, metA, glyA, hisB, ilvA, pheA, proA, thrC, trpC, tyrA, thyA, uraA, dapA, dapB, dapD, dapE, dapF, flhD, metB, metC, proAB, and thi1 auxotroph. In some embodiments, the engineered bacteria have more than one auxotrophy, for example, they may be a ΔthyA and ΔdapA auxotroph.

In some embodiments, the genetically engineered bacteria comprising a mutant arginine regulon comprising one or more nucleic acid mutations in at least one ARG box for each of the operons that encode the arginine biosynthesis enzymes and an arginine feedback resistant N-acetylglutamate synthase mutant further comprises a kill-switch circuit, such as any of the kill-switch circuits provided herein. For example, in some embodiments, the genetically engineered bacteria further comprise one or more genes encoding one or more recombinase(s) under the control of an inducible promoter and an inverted toxin sequence. In some embodiments, the genetically engineered bacteria further comprise one or more genes encoding an antitoxin. In some embodiments, the engineered bacteria further comprise one or more genes encoding one or more recombinase(s) under the control of an inducible promoter and one or more inverted excision genes, wherein the excision gene(s) encode an enzyme that deletes an essential gene. In some embodiments, the genetically engineered bacteria further comprise one or more genes encoding an antitoxin. In some embodiments, the engineered bacteria further comprise one or more genes encoding a toxin under the control of a promoter having a TetR repressor binding site and a gene encoding the TetR under the control of an inducible promoter that is induced by arabinose, such as ParaBAD. In some embodiments, the genetically engineered bacteria further comprise one or more genes encoding an antitoxin.

In some embodiments, the genetically engineered bacteria is an auxotroph comprising a mutant arginine regulon comprising one or more nucleic acid mutations in at least one ARG box for each of the operons that encode the arginine biosynthesis enzymes and an arginine feedback resistant N-acetylglutamate synthase mutant and further comprises a kill-switch circuit, such as any of the kill-switch circuits described herein.

In some embodiments of the above described genetically engineered bacteria, the gene encoding the arginine feedback resistant N-acetylglutamate synthetase is present on a plasmid in the bacterium and operatively linked on the plasmid to the promoter that is induced under low-oxygen or anaerobic conditions. In other embodiments, the gene encoding the arginine feedback resistant N-acetylglutamate synthetase is present in the bacterial chromosome and is operatively linked in the chromosome to the promoter that is induced under low-oxygen or anaerobic conditions.

In some embodiments, the genetically engineered bacteria comprise a mutant arginine repressor comprising one or more nucleic acid mutations such that arginine repressor function is decreased or inactive, or the genetically engineered bacteria do not have an arginine repressor (e.g., the arginine repressor gene has been deleted), resulting in derepression of the regulon and enhancement of arginine and/or intermediate byproduct biosynthesis. In some embodiments, the genetically engineered bacteria further comprise an arginine feedback resistant N-acetylglutamate synthase mutant. In some embodiments, the arginine feedback resistant N-acetylglutamate synthase mutant is controlled by an oxygen level-dependent promoter. In some embodiments, the arginine feedback resistant N-acetylglutamate synthase mutant is controlled by a promoter that is induced under low-oxygen or anaerobic conditions. In some embodiments, the promoter is selected from the fumarate and nitrate reductase regulator (FNR) promoter, arginine deiminiase and nitrate reduction (ANR) promoter, and dissimilatory nitrate respiration regulator (DNR) promoter. In some embodiments, the arginine feedback resistant N-acetylglutamate synthase mutant is argA$^{fbr}$.

In some embodiments, the genetically engineered bacteria comprise a mutant or deleted arginine repressor and an arginine feedback resistant N-acetylglutamate synthase mutant. In some embodiments, the genetically engineered bacterium comprise an arginine regulon, wherein the bacterium comprises a gene encoding a functional N-acetylglutamate synthetase with reduced arginine feedback inhibition as compared to a wild-type N-acetylglutamate synthetase from the same bacterial subtype under the same conditions, wherein expression of the gene encoding arginine feedback resistant N-acetylglutamate synthetase is controlled by a promoter that is induced by exogenous environmental conditions and wherein the bacterium has been genetically engineered to lack a functional ArgR repressor.

In some embodiments, the genetically engineered bacteria comprising a mutant or deleted arginine repressor and an arginine feedback resistant N-acetylglutamate synthase mutant is an auxotroph. In one embodiment, the genetically engineered bacteria comprising a mutant or deleted arginine repressor and an arginine feedback resistant N-acetylglutamate synthase mutant is an auxotroph selected from a cysE, glnA, ilvD, leuB, lysA, serA, metA, glyA, hisB, ilvA, pheA, proA, thrC, trpC, tyrA, thyA, uraA, dapA, dapB, dapD, dapE, dapF, flhD, metB, metC, proAB, and thi1 auxotroph. In some embodiments, the engineered bacteria have more than one auxotrophy, for example, they may be a ΔthyA and ΔdapA auxotroph.

In some embodiments, the genetically engineered bacteria comprising a mutant or deleted arginine repressor and an arginine feedback resistant N-acetylglutamate synthase mutant further comprise a kill-switch circuit, such as any of the kill-switch circuits provided herein. For example, in some embodiments, the genetically engineered bacteria further comprise one or more genes encoding one or more recombinase(s) under the control of an inducible promoter, and an inverted toxin sequence. In some embodiments, the genetically engineered bacteria further comprise one or more genes encoding an antitoxin. In some embodiments, the engineered bacteria further comprise one or more genes encoding one or more recombinase(s) under the control of an inducible promoter and one or more inverted excision genes, wherein the excision gene(s) encode an enzyme that deletes an essential gene. In some embodiments, the genetically engineered bacteria further comprise one or more genes encoding an antitoxin. In some embodiments, the engineered bacteria further comprise one or more genes encoding a toxin under the control of an promoter having a TetR repressor binding site and a gene encoding the TetR under the control of an inducible promoter that is induced by arabinose, such as ParaBAD. In some embodiments, the genetically engineered bacteria further comprise one or more genes encoding an antitoxin.

In some embodiments, the genetically engineered bacteria is an auxotroph comprising a mutant or deleted arginine repressor and an arginine feedback resistant N-acetylglutamate synthase mutant and further comprises a kill-switch circuit, such as any of the kill-switch circuits described herein.

In some embodiments of the above described genetically engineered bacteria, the gene encoding the arginine feedback resistant N-acetylglutamate synthetase is present on a plasmid in the bacterium and operatively linked on the plasmid to the promoter that is induced under low-oxygen or anaerobic conditions. In other embodiments, the gene encoding the arginine feedback resistant N-acetylglutamate synthetase is present in the bacterial chromosome and is operatively linked in the chromosome to the promoter that is induced under low-oxygen or anaerobic conditions.

Ammonia Transport

Ammonia transporters may be expressed or modified in the genetically engineered bacteria of the invention in order to enhance ammonia transport into the cell. AmtB is a membrane transport protein that transports ammonia into bacterial cells. In some embodiments, the genetically engineered bacteria of the invention also comprise multiple copies of the native amtB gene. In some embodiments, the genetically engineered bacteria of the invention also comprise an amtB gene from a different bacterial species. In some embodiments, the genetically engineered bacteria of the invention comprise multiple copies of an amtB gene from a different bacterial species. In some embodiments, the native amtB gene in the genetically engineered bacteria of the invention is not modified. In some embodiments, the genetically engineered bacteria of the invention comprise an amtB gene that is controlled by its native promoter, an inducible promoter, or a promoter that is stronger than the native promoter, e.g., a GlnRS promoter, a P(Bla) promoter, or a constitutive promoter.

In some embodiments, the native amtB gene in the genetically engineered bacteria is not modified, and one or more additional copies of the native amtB gene are inserted into the genome under the control of the same inducible promoter that controls expression of $argA^{fbr}$, e.g., a FNR promoter, or a different inducible promoter than the one that controls expression of $argA^{fbr}$ or a constitutive promoter. In alternate embodiments, the native amtB gene is not modified, and a copy of a non-native amtB gene from a different bacterial species is inserted into the genome under the control of the same inducible promoter that controls expression of $argA^{fbr}$, e.g., a FNR promoter, or a different inducible promoter than the one that controls expression of $argA^{fbr}$ or a constitutive promoter.

In some embodiments, the native amtB gene in the genetically engineered bacteria is not modified, and one or more additional copies of the native amtB gene are present in the bacteria on a plasmid and under the control of the same inducible promoter that controls expression of $argA^{fbr}$, e.g., a FNR promoter, or a different inducible promoter than the one that controls expression of $argA^{fbr}$ or a constitutive promoter. In alternate embodiments, the native amtB gene is not modified, and a copy of a non-native amtB gene from a different bacterial species is present in the bacteria on a plasmid and under the control of the same inducible promoter that controls expression of $argA^{fbr}$, e.g., a FNR promoter, or a different inducible promoter than the one that controls expression of $argA^{fbr}$ or a constitutive promoter.

In some embodiments, the native amtB gene is mutagenized, the mutants exhibiting increased ammonia transport are selected, and the mutagenized amtB gene is isolated and inserted into the genetically engineered bacteria. In some embodiments, the native amtB gene is mutagenized, mutants exhibiting increased ammonia transport are selected, and those mutants are used to produce the bacteria of the invention. The ammonia transporter modifications described herein may be present on a plasmid or chromosome.

In some embodiments, the genetically engineered bacterium is *E. coli* Nissle, and the native amtB gene in *E. coli* Nissle is not modified; one or more additional copies the native *E. coli* Nissle amtB genes are inserted into the *E. coli* Nissle genome under the control of the same inducible promoter that controls expression of $argA^{fbr}$, e.g., a FNR promoter, or a different inducible promoter than the one that controls expression of $argA^{fbr}$ or a constitutive promoter. In an alternate embodiment, the native amtB gene in *E. coli* Nissle is not modified, and a copy of a non-native amtB gene from a different bacterium, e.g., *Lactobacillus plantarum*, is inserted into the *E. coli* Nissle genome under the control of the same inducible promoter that controls expression of $argA^{fbr}$, e.g., a FNR promoter, or a different inducible promoter than the one that controls expression of $argA^{fbr}$ or a constitutive promoter.

In some embodiments, the genetically engineered bacterium is *E. coli* Nissle, and the native amtB gene in *E. coli* Nissle is not modified; one or more additional copies the native *E. coli* Nissle amtB genes are present in the bacterium on a plasmid and under the control of the same inducible promoter that controls expression of $argA^{fbr}$, e.g., a FNR promoter, or a different inducible promoter than the one that controls expression of $argA^{fbr}$, or a constitutive promoter. In an alternate embodiment, the native amtB gene in *E. coli* Nissle is not modified, and a copy of a non-native amtB gene from a different bacterium, e.g., *Lactobacillus plantarum*, are present in the bacterium on a plasmid and under the control of the same inducible promoter that controls expression of $argA^{fbr}$, e.g., a FNR promoter, or a different inducible promoter than the one that controls expression of $argA^{fbr}$, or a constitutive promoter.

Pharmaceutical Compositions and Formulations

Pharmaceutical compositions comprising the genetically engineered bacteria of the invention may be used to treat, manage, ameliorate, and/or prevent a disorder associated with hyperammonemia or symptom(s) associated with hyperammonemia. Pharmaceutical compositions of the invention comprising one or more genetically engineered bacteria, alone or in combination with prophylactic agents, therapeutic agents, and/or pharmaceutically acceptable carriers are provided.

In certain embodiments, the pharmaceutical composition comprises one species, strain, or subtype of bacteria that are engineered to comprise the genetic modifications described herein, e.g., the mutant arginine regulon. In alternate embodiments, the pharmaceutical composition comprises two or more species, strains, and/or subtypes of bacteria that are each engineered to comprise the genetic modifications described herein, e.g., the mutant arginine regulon.

The pharmaceutical compositions of the invention may be formulated in a conventional manner using one or more physiologically acceptable carriers comprising excipients and auxiliaries, which facilitate processing of the active ingredients into compositions for pharmaceutical use. Methods of formulating pharmaceutical compositions are known in the art (see, e.g., "Remington's Pharmaceutical Sciences," Mack Publishing Co., Easton, Pa.). In some embodiments, the pharmaceutical compositions are subjected to tabletting, lyophilizing, direct compression, conventional mixing, dissolving, granulating, levigating, emulsifying, encapsulating, entrapping, or spray drying to form tablets, granulates, nanoparticles, nanocapsules, microcapsules, microtablets, pellets, or powders, which may be enterically coated or uncoated. Appropriate formulation depends on the route of administration.

The genetically engineered bacteria of the invention may be formulated into pharmaceutical compositions in any suitable dosage form (e.g., liquids, capsules, sachet, hard capsules, soft capsules, tablets, enteric coated tablets, suspension powders, granules, or matrix sustained release formations for oral administration) and for any suitable type of administration (e.g., oral, topical, immediate-release, pulsatile-release, delayed-release, or sustained release). Suitable dosage amounts for the genetically engineered bacteria may range from about $10^5$ to $10^{12}$ bacteria. The composition may be administered once or more daily, weekly, or monthly. The genetically engineered bacteria may be formulated into pharmaceutical compositions comprising one or more pharmaceutically acceptable carriers, thickeners, diluents, buffers, surface active agents, neutral or cationic lipids, lipid complexes, liposomes, penetration enhancers, carrier compounds, and other pharmaceutically acceptable carriers or agents.

The genetically engineered bacteria of the invention may be administered topically and formulated in the form of an ointment, cream, transdermal patch, lotion, gel, shampoo, spray, aerosol, solution, emulsion, or other form well-known to one of skill in the art. See, e.g., "Remington's Pharmaceutical Sciences," Mack Publishing Co., Easton, Pa. In an embodiment, for non-sprayable topical dosage forms, viscous to semi-solid or solid forms comprising a carrier or one or more excipients compatible with topical application and having a dynamic viscosity greater than water are employed. Suitable formulations include, but are not limited to, solutions, suspensions, emulsions, creams, ointments, powders, liniments, salves, etc., which may be sterilized or mixed with auxiliary agents (e.g., preservatives, stabilizers, wetting agents, buffers, or salts) for influencing various properties, e.g., osmotic pressure. Other suitable topical dosage forms include sprayable aerosol preparations wherein the active ingredient in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms. Examples of such additional ingredients are well known in the art.

The genetically engineered bacteria of the invention may be administered orally and formulated as tablets, pills, dragees, capsules, liquids, gels, syrups, slurries, suspensions, etc. Pharmacological compositions for oral use can be made using a solid excipient, optionally grinding the resulting mixture, and processing the mixture of granules, after adding suitable auxiliaries if desired, to obtain tablets or dragee cores. Suitable excipients include, but are not limited to, fillers such as sugars, including lactose, sucrose, mannitol, or sorbitol; cellulose compositions such as maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP) or polyethylene glycol (PEG). Disintegrating agents may also be added, such as cross-linked polyvinylpyrrolidone, agar, alginic acid or a salt thereof such as sodium alginate.

Tablets or capsules can be prepared by conventional means with pharmaceutically acceptable excipients such as binding agents (e.g., pregelatinised maize starch, polyvinylpyrrolidone, hydroxypropyl methylcellulose, carboxymethylcellulose, polyethylene glycol, sucrose, glucose, sorbitol, starch, gum, kaolin, and tragacanth); fillers (e.g., lactose, microcrystalline cellulose, or calcium hydrogen phosphate); lubricants (e.g., calcium, aluminum, zinc, stearic acid, polyethylene glycol, sodium lauryl sulfate, starch, sodium benzoate, L-leucine, magnesium stearate, talc, or silica); disintegrants (e.g., starch, potato starch, sodium starch glycolate, sugars, cellulose derivatives, silica powders); or wetting agents (e.g., sodium lauryl sulphate). The tablets may be coated by methods well known in the art. A coating shell may be present, and common membranes include, but are not limited to, polylactide, polyglycolic acid, polyanhydride, other biodegradable polymers, alginate-polylysine-alginate (APA), alginate-polymethylene-co-guanidine-alginate (A-PMCG-A), hydroymethylacrylate-methyl methacrylate (HEMA-MMA), multilayered HEMA-MMA-MAA, polyacrylonitrilevinylchloride (PAN-PVC), acrylonitrile/sodium methallylsulfonate (AN-69), polyethylene glycol/poly pentamethylcyclopentasiloxane/polydimethylsiloxane (PEG/PD5/PDMS), poly N,N- dimethyl acrylamide (PDMAAm), siliceous encapsulates, cellulose sulphate/sodium alginate/polymethylene-co-guanidine (CS/A/PMCG), cellulose acetate phthalate, calcium alginate, k-carrageenan-locust bean gum gel beads, gellan-xanthan beads, poly(lactide-co-glycolides), carrageenan, starch poly-anhydrides, starch polymethacrylates, polyamino acids, and enteric coating polymers.

In some embodiments, the genetically engineered bacteria are enterically coated for release into the gut or a particular region of the gut, for example, the large intestine. The typical pH profile from the stomach to the colon is about 1-4 (stomach), 5.5-6 (duodenum), 7.3-8.0 (ileum), and 5.5-6.5 (colon). In some diseases, the pH profile may be modified. In some embodiments, the coating is degraded in specific pH environments in order to specify the site of release. In some embodiments, at least two coatings are used. In some embodiments, the outside coating and the inside coating are degraded at different pH levels.

Liquid preparations for oral administration may take the form of solutions, syrups, suspensions, or a dry product for constitution with water or other suitable vehicle before use. Such liquid preparations may be prepared by conventional means with pharmaceutically acceptable agents such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of the genetically engineered bacteria of the invention.

In certain embodiments, the genetically engineered bacteria of the invention may be orally administered, for example, with an inert diluent or an assimilable edible carrier. The compound may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

In some embodiments, the composition is formulated for intraintestinal administration, intrajejunal administration, intraduodenal administration, intraileal administration, gastric shunt administration, or intracolic administration, via nanoparticles, nanocapsules, microcapsules, or microtablets, which are enterically coated or uncoated. The pharmaceutical compositions of the present invention may also be formulated in rectal compositions such as suppositories or retention enemas, using, e.g., conventional suppository bases such as cocoa butter or other glycerides. The compositions may be suspensions, solutions, or emulsions in oily or aqueous vehicles, and may contain suspending, stabilizing and/or dispersing agents.

The genetically engineered bacteria of the invention may be administered intranasally, formulated in an aerosol form, spray, mist, or in the form of drops, and conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). Pressurized aerosol dosage units may be determined by providing a valve to deliver a metered amount. Capsules and cartridges (e.g., of gelatin) for use in an inhaler or insufflator may be formulated containing a powder mix of the compound and a suitable powder base such as lactose or starch.

The genetically engineered bacteria of the invention may be administered and formulated as depot preparations. Such long acting formulations may be administered by implantation or by injection. For example, the compositions may be formulated with suitable polymeric or hydrophobic materials (e.g., as an emulsion in an acceptable oil) or ion exchange resins, or as sparingly soluble derivatives (e.g., as a sparingly soluble salt).

In some embodiments, the invention provides pharmaceutically acceptable compositions in single dosage forms. Single dosage forms may be in a liquid or a solid form. Single dosage forms may be administered directly to a patient without modification or may be diluted or reconstituted prior to administration. In certain embodiments, a single dosage form may be administered in bolus form, e.g., single injection, single oral dose, including an oral dose that comprises multiple tablets, capsule, pills, etc. In alternate embodiments, a single dosage form may be administered over a period of time, e.g., by infusion.

Single dosage forms of the pharmaceutical composition of the invention may be prepared by portioning the pharmaceutical composition into smaller aliquots, single dose containers, single dose liquid forms, or single dose solid forms, such as tablets, granulates, nanoparticles, nanocapsules, microcapsules, microtablets, pellets, or powders, which may be enterically coated or uncoated. A single dose in a solid form may be reconstituted by adding liquid, typically sterile water or saline solution, prior to administration to a patient.

Dosage regimens may be adjusted to provide a therapeutic response. For example, a single bolus may be administered at one time, several divided doses may be administered over a predetermined period of time, or the dose may be reduced or increased as indicated by the therapeutic situation. The specification for the dosage is dictated by the unique characteristics of the active compound and the particular therapeutic effect to be achieved. Dosage values may vary with the type and severity of the condition to be alleviated. For any particular subject, specific dosage regimens may be adjusted over time according to the individual need and the professional judgment of the treating clinician.

In another embodiment, the composition can be delivered in a controlled release or sustained release system. In one embodiment, a pump may be used to achieve controlled or sustained release. In another embodiment, polymeric materials can be used to achieve controlled or sustained release of the therapies of the present disclosure (see e.g., U.S. Pat. No. 5,989,463). Examples of polymers used in sustained release formulations include, but are not limited to, poly(2-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N- vinyl pyrrolidone), poly(vinyl alcohol), polyacrylamide, poly(ethylene glycol), polylactides (PLA), poly(lactide-co-glycolides) (PLGA), and polyorthoesters. The polymer used in a sustained release formulation may be inert, free of leachable impurities, stable on storage, sterile, and biodegradable. In some embodiments, a controlled or sustained release system can be placed in proximity of the prophylactic or therapeutic target, thus requiring only a fraction of the systemic dose. Any suitable technique known to one of skill in the art may be used.

The genetically engineered bacteria of the invention may be administered and formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The ingredients are supplied either separately or mixed together in unit dosage form, for example, as a dry lyophilized powder or water-free concentrate in a hermetically sealed container such as an ampoule or sachet indicating the quantity of active agent. If the mode of administration is by injection, an ampoule of sterile water for injection or saline can be provided so that the ingredients may be mixed prior to administration.

The pharmaceutical compositions of the invention may be packaged in a hermetically sealed container such as an ampoule or sachet indicating the quantity of the agent. In one embodiment, one or more of the pharmaceutical compositions of the invention is supplied as a dry sterilized lyophilized powder or water-free concentrate in a hermetically sealed container and can be reconstituted (e.g., with water or saline) to the appropriate concentration for administration to a subject. In an embodiment, one or more of the prophylactic or therapeutic agents or pharmaceutical compositions of the invention is supplied as a dry sterile lyophilized powder in a hermetically sealed container stored between 2° C. and 8° C. and administered within 1 hour, within 3 hours, within 5 hours, within 6 hours, within 12 hours, within 24 hours, within 48 hours, within 72 hours, or within one week after being reconstituted. Cryoprotectants can be included for a lyophilized dosage form, principally 0-10% sucrose (optimally 0.5-1.0%). Other suitable cryoprotectants include trehalose and lactose. Other suitable bulking agents include glycine and arginine, either of which can be included at a concentration of 0-0.05%, and polysorbate-80 (optimally included at a concentration of 0.005-0.01%). Additional surfactants include but are not limited to polysorbate 20 and BRIJ surfactants. The pharmaceutical composition may be prepared as an injectable solution and can further comprise an agent useful as an adjuvant, such as those used to increase absorption or dispersion, e.g., hyaluronidase.

Dosing can depend on several factors, including severity and responsiveness of the disease, route of administration, time course of treatment (days to months to years), and time to amelioration of the disease. Toxicity and therapeutic efficacy of compounds provided herein can be determined by standard pharmaceutical procedures in cell culture or animal models. For example, $LD_{50}$, $ED_{50}$, $EC_{50}$, and $IC_{50}$ may be determined, and the dose ratio between toxic and therapeutic effects ($LD_{50}/ED_{50}$) may be calculated as the therapeutic index. Compositions that exhibit toxic side effects may be used, with careful modifications to minimize potential damage to reduce side effects. Dosing may be estimated initially from cell culture assays and animal models. The data obtained from in vitro and in vivo assays and animal studies can be used in formulating a range of dosage for use in humans.

Methods of Treatment

Another aspect of the invention provides methods of treating a disease or disorder associated with hyperammonemia. In some embodiments, the invention provides methods for reducing, ameliorating, or eliminating one or more symptom(s) associated with these diseases or disorders. In some embodiments, the disorder is a urea cycle disorder such as argininosuccinic aciduria, arginase deficiency, carbamoylphosphate synthetase deficiency, citrullinemia, N-acetylglutamate synthetase deficiency, and ornithine transcarbamylase deficiency. In alternate embodiments, the disorder is a liver disorder such as hepatic encephalopathy, acute liver failure, or chronic liver failure; organic acid disorders; isovaleric aciduria; 3-methylcrotonylglycinuria; methylmalonic acidemia; propionic aciduria; fatty acid oxidation defects; carnitine cycle defects; carnitine deficiency; β-oxidation deficiency; lysinuric protein intolerance; pyrroline-5-carboxylate synthetase deficiency; pyruvate carboxylase deficiency; ornithine aminotransferase deficiency; carbonic anhydrase deficiency; hyperinsulinism-hyperammonemia syndrome; mitochondrial disorders; valproate therapy; asparaginase therapy; total parenteral nutrition; cystoscopy with glycine-containing solutions; post-lung/bone marrow transplantation; portosystemic shunting; urinary tract infections; ureter dilation; multiple myeloma; chemotherapy; infection; neurogenic bladder; or intestinal bacterial overgrowth. In some embodiments, the symptom(s) associated thereof include, but are not limited to, seizures, ataxia, stroke-like lesions, coma, psychosis, vision loss, acute encephalopathy, cerebral edema, as well as vomiting, respiratory alkalosis, and hypothermia.

The method may comprise preparing a pharmaceutical composition with at least one genetically engineered species, strain, or subtype of bacteria described herein, and administering the pharmaceutical composition to a subject in a therapeutically effective amount. In some embodiments, the genetically engineered bacteria of the invention are administered orally, e.g., in a liquid suspension. In some embodiments, the genetically engineered bacteria of the invention are lyophilized in a gel cap and administered orally. In some embodiments, the genetically engineered bacteria of the invention are administered via a feeding tube or gastric shunt. In some embodiments, the genetically engineered bacteria of the invention are administered rectally, e.g., by enema. In some embodiments, the genetically engineered bacteria of the invention are administered topically, intraintestinally, intrajejunally, intraduodenally, intraileally, and/or intracolically.

In certain embodiments, administering the pharmaceutical composition to the subject reduces ammonia concentrations in a subject. In some embodiments, the methods of the present disclosure may reduce the ammonia concentration in a subject by at least about 10%, 20%, 25%, 30%, 40%, 50%, 60%, 70%, 75%, 80%, 85%, 90%, 95%, or more as compared to levels in an untreated or control subject. In some embodiments, reduction is measured by comparing the ammonia concentration in a subject before and after administration of the pharmaceutical composition. In some embodiments, the method of treating or ameliorating hyperammonemia allows one or more symptoms of the condition or disorder to improve by at least about 10%, 20%, 30%, 40%, 50%, 60%, 70%, 80%, 90%, 95%, or more.

Before, during, and after the administration of the pharmaceutical composition, ammonia concentrations in the subject may be measured in a biological sample, such as blood, serum, plasma, urine, fecal matter, peritoneal fluid, intestinal mucosal scrapings, a sample collected from a tissue, and/or a sample collected from the contents of one or more of the following: the stomach, duodenum, jejunum, ileum, cecum, colon, rectum, and anal canal. In some embodiments, the methods may include administration of the compositions of the invention to reduce ammonia concentrations in a subject to undetectable levels, or to less than about 1%, 2%, 5%, 10%, 20%, 25%, 30%, 40%, 50%, 60%, 70%, 75%, or 80% of the subject's ammonia concentrations prior to treatment.

Figure 27:
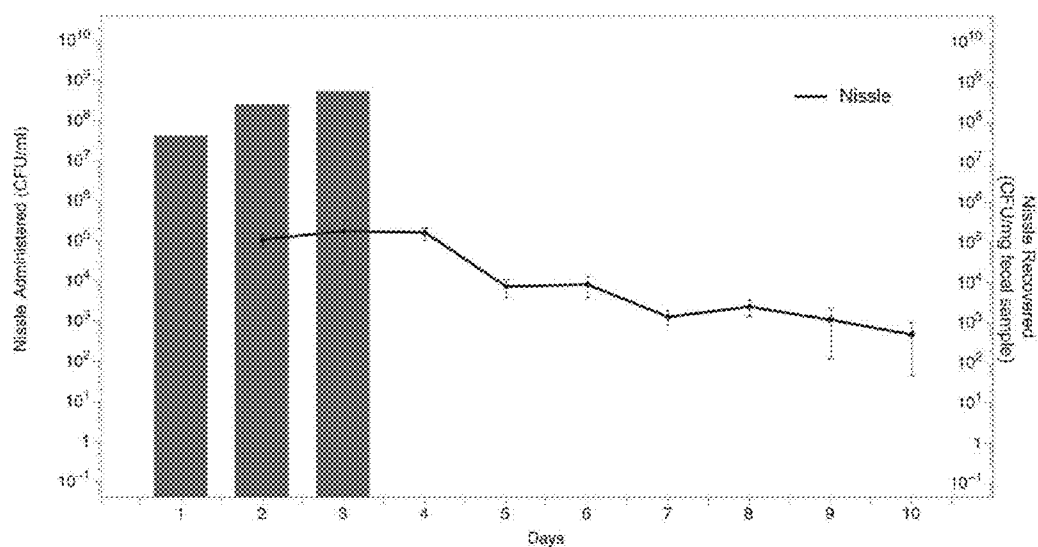
FIG. 27 depicts a graph of Nissle residence in vivo. Streptomycin-resistant Nissle was administered to mice via oral gavage without antibiotic pre-treatment. Fecal pellets from six total mice were monitored post-administration to determine the amount of administered Nissle still residing within the mouse gastrointestinal tract. The bars represent the number of bacteria administered to the mice. The line represents the number of Nissle recovered from the fecal samples each day for 10 consecutive days.

In certain embodiments, the genetically engineered bacteria comprising the mutant arginine regulon is *E. coli* Nissle. The genetically engineered bacteria may be destroyed, e.g., by defense factors in the gut or blood serum (Sonnenborn et al., 2009), or by activation of a kill switch, several hours or days after administration. Thus, the pharmaceutical composition comprising the mutant arginine regulon may be re-administered at a therapeutically effective dose and frequency. Length of Nissle residence in vivo in mice is shown in FIG. 27. In alternate embodiments, the genetically engineered bacteria are not destroyed within hours or days after administration and may propagate and colonize the gut.

The pharmaceutical composition may be administered alone or in combination with one or more additional therapeutic agents, including but not limited to, sodium phenylbutyrate, sodium benzoate, and glycerol phenylbutyrate. An important consideration in the selection of the one or more additional therapeutic agents is that the agent(s) should be compatible with the genetically engineered bacteria of the invention, e.g., the agent(s) must not kill the bacteria. In some embodiments, the pharmaceutical composition is administered with food. In alternate embodiments, the pharmaceutical composition is administered before or after eating food. The pharmaceutical composition may be administered in combination with one or more dietary modifications, e.g., low-protein diet and amino acid supplementation. The dosage of the pharmaceutical composition and the frequency of administration may be selected based on the severity of the symptoms and the progression of the disorder. The appropriate therapeutically effective dose and/or frequency of administration can be selected by a treating clinician.

Treatment In Vivo

The genetically engineered bacteria of the invention may be evaluated in vivo, e.g., in an animal model. Any suitable animal model of a disease or condition associated with hyperammonemia may be used (see, e.g., Deignan et al., 2008; Nicaise et al., 2008), for example, a mouse model of acute liver failure and hyperammonemia. This acute liver failure and hyperammonemia may be induced by treatment with thiol acetamide (TAA) (Nicaise et al., 2008). Another exemplary animal model is the $spf^{ash}$ (sparse fur with abnormal skin and hair) mouse, which displays elevated levels of plasma ammonia due to a missense mutation in the ornithine transcarbamylase gene (Doolittle et al., 1974; Hodges and Rosenberg, 1989). The genetically engineered bacteria of the invention may be administered to the animal, e.g., by oral gavage, and treatment efficacy determined, e.g., by measuring ammonia in blood samples and/or arginine, citrulline, or other byproducts in fecal samples.

Exemplary Embodiments

1. A genetically engineered bacterium comprising an arginine regulon,
   wherein the bacterium comprises a gene encoding a functional N-acetylglutamate synthetase with reduced arginine feedback inhibition as compared to a wild-type N-acetylglutamate synthetase from the same bacterial subtype under the same conditions, wherein expression of the gene encoding arginine feedback resistant N-acetylglutamate synthetase is controlled by a promoter that is induced by exogenous environmental conditions; and wherein the bacterium has been genetically engineered to lack a functional ArgR.

2. The bacterium of embodiment 1, wherein the promoter that controls expression of the arginine feedback resistant N-acetylglutamate synthetase is induced under low-oxygen or anaerobic conditions.
3. The bacterium of any one of embodiments 1 or 2, wherein each copy of a functional argR gene normally present in a corresponding wild-type bacterium has been independently deleted or rendered inactive by one or more nucleotide deletions, insertions or substitutions.
4. The bacterium of embodiment 3, wherein each copy of a functional argR gene normally present in a corresponding wild-type bacterium has been deleted.
5. The bacterium of any one of embodiments 1-4, wherein each copy of a functional argG gene normally present in a corresponding wild-type bacterium has been independently deleted or rendered inactive by one or more nucleotide deletions, insertions or substitutions.
6. The bacterium of embodiment 5, wherein each copy of the functional argG gene normally present in a corresponding wild-type bacterium has been deleted.
7. The bacterium of any one of embodiments 1-7, wherein under conditions that induce the promoter that controls expression of the arginine feedback resistant N-acetylglutamate synthetase, the transcription of each gene that is present in an operon comprising a functional ARG box and which encodes an arginine biosynthesis enzyme is increased as compared to a corresponding gene in a wild-type bacterium under the same conditions.
8. The bacterium of any one of embodiments 2-7, wherein the promoter that is induced under low-oxygen or anaerobic conditions is a FNR promoter.
9. The bacterium of any one of embodiments 2-7, wherein the arginine feedback resistant N-acetylglutamate synthetase gene has a DNA sequence selected from:
   a) SEQ ID NO:28,
   b) a DNA sequence that, but for the redundancy of the genetic code, encodes the same polypeptide as encoded by SEQ ID NO:28, and
   c) a DNA sequence having at least 80% homology to the DNA sequence of a) or b).
10. The bacterium of any one of embodiments 1-9, wherein the bacterium is a non-pathogenic bacterium.
11. The bacterium of embodiment 10, wherein the bacterium is a probiotic bacterium.
12. The bacterium of embodiment 10, wherein the bacterium is selected from the group consisting of *Bacteroides, Bifidobacterium, Clostridium, Escherichia, Lactobacillus*, and *Lactococcus*.
13. The bacterium of embodiment 12, wherein the bacterium is *Escherichia coli* strain Nissle.
14. The bacterium of any one of embodiments 2-13, wherein the gene encoding the arginine feedback resistant N-acetylglutamate synthetase is present on a plasmid in the bacterium and operably linked on the plasmid to the promoter that is induced under low-oxygen or anaerobic conditions.
15. The bacterium of any one of embodiments 2-13, wherein the gene encoding the arginine feedback resistant N-acetylglutamate synthetase is present in the bacterial chromosome and is operably linked in the chromosome to the promoter that is induced under low-oxygen or anaerobic conditions.
16. The bacterium of any one of embodiments 1-15, wherein the bacterium is an auxotroph in a gene that is complemented when the bacterium is present in a mammalian gut.
17. The bacterium of embodiment 16, wherein mammalian gut is a human gut.
18. A pharmaceutically acceptable composition comprising the bacterium of any one of embodiments 1-17; and a pharmaceutically acceptable carrier.
19. The pharmaceutically acceptable composition of embodiment 18, wherein the composition is formulated for oral or rectal administration.
20. A method of producing the pharmaceutically acceptable composition of embodiment 19, comprising the steps of:
   a) growing the bacterium of any one of embodiments 1-17 in a growth medium culture under conditions that do not induce the promoter that controls expression of the arginine feedback resistant N-acetylglutamate synthetase;
   b) isolating the resulting bacteria from the growth medium; and
   c) suspending the isolated bacteria in a pharmaceutically acceptable carrier.
21. A method of treating a hyperammonemia-associated disorder or symptom(s) thereof in a subject in need thereof comprising the step of administering to the subject the composition of embodiment 18 for a period of time sufficient to lessen the severity of the hyperammonemia-associated disorder.
22. The method of embodiment 21, wherein the hyperammonemia-associated disorder is a urea cycle disorder.
23. The method of embodiment 22, wherein the urea cycle disorder is argininosuccinic aciduria, arginase deficiency, carbamylphosphate synthetase deficiency, citrullinemia, N-acetylglutamate synthetase deficiency, or ornithine transcarbamylase deficiency.
24. The method of embodiment 21, wherein the hyperammonemia-associated disorder is a liver disorder; an organic acid disorder; isovaleric aciduria; 3-methylcrotonylglycinuria; methylmalonic acidemia; propionic aciduria; fatty acid oxidation defects; carnitine cycle defects; carnitine deficiency; β-oxidation deficiency; lysinuric protein intolerance; pyrroline-5-carboxylate synthetase deficiency; pyruvate carboxylase deficiency; ornithine aminotransferase deficiency; carbonic anhydrase deficiency; hyperinsulinism-hyperammonemia syndrome; mitochondrial disorders; valproate therapy; asparaginase therapy; total parenteral nutrition; cystoscopy with glycine-containing solutions; post-lung/bone marrow transplantation; portosystemic shunting; urinary tract infections; ureter dilation; multiple myeloma; chemotherapy; infection; neurogenic bladder; or intestinal bacterial overgrowth.
25. The method of embodiment 24, wherein the liver disorder is hepatic encephalopathy, acute liver failure, or chronic liver failure.
26. The method of embodiment 25, wherein the symptoms of the hyperammonemia-associated disorder are selected from the group consisting of seizures, ataxia, stroke-like lesions, coma, psychosis, vision loss, acute encephalopathy, cerebral edema, as well as vomiting, respiratory alkalosis, and hypothermia.
27. A genetically engineered bacterium comprising a mutant arginine regulon, wherein the bacterium comprises a gene encoding a functional N-acetylglutamate synthetase that is mutated to reduce arginine feedback inhibition as compared to a wild-type N-acetylglutamate synthetase from the same bacterial subtype under the same conditions, wherein expression of the gene encoding the mutated N-acetylglutamate synthetase is controlled by a promoter that is induced under low-oxygen or anaerobic conditions;

wherein the mutant arginine regulon comprises one or more operons comprising genes that encode arginine biosynthesis enzymes N-acetylglutamate kinase, N-acetylglutamate phosphate reductase, acetylornithine aminotransferase, N-acetylornithinase, carbamoylphosphate synthase, ornithine transcarbamylase, argininosuccinate synthase, and argininosuccinate lyase, and wherein each operon except the operon comprising the gene encoding argininosuccinate synthase comprises one or more mutated ARG box(es) characterized by one or more nucleic acid mutations that reduces arginine-mediated repression of the operon via ArgR binding, and retains RNA polymerase binding with sufficient affinity to promote transcription of the genes in the operon.

28. The genetically engineered bacterium of embodiment 27, wherein the operon comprising the gene encoding argininosuccinate synthase comprises one or more mutated ARG box(es) characterized by one or more nucleic acid mutations that reduces arginine-mediated repression of the operon via ArgR binding, and retains RNA polymerase binding with sufficient affinity to promote transcription of the argininosuccinate synthase gene.

29. The genetically engineered bacterium of embodiment 27, wherein the operon comprising the gene encoding argininosuccinate synthase comprises a constitutively active promoter that regulates transcription of the argininosuccinate synthase gene.

30. The bacterium of any one of embodiments 27-29, wherein the gene encoding the functional N-acetylglutamate synthetase is mutated to reduce arginine feedback inhibition as compared to a wild-type N-acetylglutamate synthetase from the same bacterial subtype under the same conditions.

31. The bacterium of any one of embodiments 27-30, wherein ArgR binding is reduced as compared to a bacterium from the same bacterial subtype comprising a wild-type arginine regulon under the same conditions.

32. The bacterium of any one of embodiments 27, wherein the reduced arginine-mediated repression via ArgR binding increases the transcription of each of the genes that encode arginine biosynthesis enzymes N-acetylglutamate kinase, N-acetylglutamate phosphate reductase, acetylornithine aminotransferase, N-acetylornithinase, carbamoylphosphate synthase, ornithine transcarbamylase, and argininosuccinate lyase as compared to a corresponding wild-type bacterium under the same conditions.

33. The bacterium of embodiment 28, wherein the reduced arginine-mediated repression via ArgR binding increases the transcription of each of the genes that encode arginine biosynthesis enzymes N-acetylglutamate kinase, N-acetylglutamate phosphate reductase, acetylornithine aminotransferase, N-acetylornithinase, carbamoylphosphate synthase, ornithine transcarbamylase, argininosuccinate synthase, and argininosuccinate lyase as compared to a corresponding wild-type bacterium under the same conditions.

34. The bacterium of embodiment 27, wherein each of the operons encoding the arginine biosynthesis enzymes N-acetylglutamate kinase, N-acetylglutamate phosphate reductase, acetylornithine am inotransferase, N-acetylornithinase, carbamoylphosphate synthase, ornithine transcarbamylase, and argininosuccinate lyase comprises one or more nucleic acid mutations in each ARG box in the operon.

35. The bacterium of embodiment 28, wherein each of the operons encoding the arginine biosynthesis enzymes N-acetylglutamate kinase, N-acetylglutamate phosphate reductase, acetylornithine am inotransferase, N-acetylornithinase, carbamoylphosphate synthase, ornithine transcarbamylase, argininosuccinate synthase, and argininosuccinate lyase comprises one or more nucleic acid mutations in each ARG box in the operon.

36. The bacterium of any one of embodiments 27-35, further comprising one or more operons encoding wild-type ornithine acetyltransferase, wherein each operon encoding wild-type ornithine acetyltransferase comprises one or more mutated ARG box(es) characterized by one or more nucleic acid mutations that reduces arginine-mediated repression of the operon via ArgR binding, and retains RNA polymerase binding with sufficient affinity to promote transcription of the genes in the operon.

37. The bacterium of any one of embodiments 27-36, wherein the promoter that is induced under low-oxygen or anaerobic conditions is a FNR promoter.

38. The bacterium of any one of embodiments 27-37, wherein the bacterium additionally comprises one or more operons encoding wild-type N-acetylglutamate synthetase, wherein each operon encoding wild-type N-acetylglutamate synthetase comprises one or more mutated ARG box(es) characterized by one or more nucleic acid mutations that reduces arginine-mediated repression of the operon via ArgR binding, and retains RNA polymerase binding with sufficient affinity to promote transcription of the genes in the operon; wherein the genetically engineered bacterium does not comprise a wild-type N-acetylglutamate synthetase promoter.

39. The bacterium of any one of embodiments 27-39, wherein genes encoding N-acetylglutamate kinase, N-acetylglutamate phosphate reductase, acetylornithine aminotransferase, N-acetylornithinase, carbamoylphosphate synthase, ornithine transcarbamylase, argininosuccinate synthase, and argininosuccinate lyase are grouped into operons present in *Escherichia coli* Nissle.

40. The bacterium of any one of embodiments 27-39, wherein each operon comprises a promoter region, and wherein each promoter region of the mutant arginine regulon has a G/C:A/T ratio that differs by no more than 10% from a G/C:A/T ratio found in a corresponding wild-type promoter region.

41. The bacterium of of any one of embodiments 27-40, wherein each mutated ARG box is characterized by at least three nucleotide mutations as compared to the corresponding wild-type ARG box.

42. The bacterium of any one of embodiments 27-41, wherein the mutant N-acetylglutamate synthetase gene has a DNA sequence selected from:

a) SEQ ID NO:28, b) a DNA sequence that, but for the redundancy of the genetic code, encodes the same polypeptide as SEQ ID NO:28, and c) a DNA sequence having at least 80% homology to the DNA sequence of a) or b).

43. The bacterium of any one of embodiments 27-42, comprising a single operon that encodes N-acetylglutamate kinase, N-acetylglutamylphosphate reductase, and argininosuccinate lyase, wherein the single operon comprises a mutated DNA sequence of SEQ ID NO:5, wherein the mutations are in one or more of nucleotides 37, 38, 45, 46, 47 of SEQ ID NO:5; and in one or more of nucleotides 55, 56, 57, 67, 68, 69 of SEQ ID NO:5.

44. The bacterium of embodiment 43, wherein the single operon comprises a DNA sequence of SEQ ID NO:6.

45. The bacterium of any one of embodiments 27-44, wherein the operon encoding acetylornithine aminotransferase comprises a mutated DNA sequence of SEQ ID NO:11, wherein the mutations are in one or more of nucleotides 20, 21, 29, 30, 31 of SEQ ID NO:11; and in one or more of nucleotides 41, 42, 50, 52 of SEQ ID NO:11.

46. The bacterium of embodiment 45, wherein the operon encoding acetylornithine aminotransferase comprises a DNA sequence of SEQ ID NO:12.

47. The bacterium of any one of embodiments 27-46, wherein the operon encoding N-acetylornithinase comprises a mutated DNA sequence of SEQ ID NO:7, wherein the mutations are in one or more of nucleotides 92, 93, 94, 104, 105, 106 of SEQ ID NO:7; and in one or more of nucleotides 114, 115, 116, 123, 124 of SEQ ID NO:7.

48. The bacterium of embodiment 46, wherein the operon encoding N-acetylornithinase comprises a DNA sequence of SEQ ID NO:8.

49. The bacterium of any one of embodiments 27-48, wherein the operon encoding ornithine transcarbamylase comprises a mutated DNA sequence of SEQ ID NO:3, wherein the mutations are in one or more of nucleotides 12, 13, 14, 18, 20 of SEQ ID NO:3; and in one or more of nucleotides 34, 35, 36, 45, 46 of SEQ ID NO:3.

50. The bacterium of embodiment 49, wherein the operon encoding ornithine transcarbamylase comprises a DNA sequence of SEQ ID NO:4.

51. The bacterium of any one of embodiments 27-50, wherein the mutated promoter region of an operon encoding carbamoylphosphate synthase comprises a mutated DNA sequence of SEQ ID NO:9, wherein the mutations are in one or more of nucleotides 33, 34, 35, 43, 44, 45 of SEQ ID NO:9; and in one or more of nucleotides 51, 52, 53, 60, 61, 62 of SEQ ID NO:9.

52. The bacterium of embodiment 51, wherein the operon encoding carbamoylphosphate synthase comprises a DNA sequence of SEQ ID NO:10.

53. The bacterium of any one of embodiments 27-52, wherein the mutated promoter region of an operon encoding N-acetylglutamate synthetase comprises a mutated DNA sequence of SEQ ID NO:1, wherein the mutations are in one or more of nucleotides 12, 13, 14, 21, 22, 23 of SEQ ID NO:1 and in one or more of nucleotides 33, 34, 35, 42, 43, 44 of SEQ ID NO:1.

54. The bacterium of embodiment 53, wherein the operon encoding N-acetylglutamate synthetase comprises a DNA sequence of SEQ ID NO:2.

55. The bacterium of embodiment 28, wherein the mutated promoter region of an operon encoding argininosuccinate synthase comprises a mutated DNA sequence of SEQ ID NO:13, wherein the mutations are in one or more of nucleotides 9, 11, 19, 21 of SEQ ID NO:13; in one or more of nucleotides 129, 130, 131, 140, 141, 142 of SEQ ID NO:13; and in one or more of nucleotides 150, 151, 152, 161, 162, 163 of SEQ ID NO:13.

56. The bacterium of embodiment 27, wherein the operon encoding argininosuccinate synthase comprises a DNA sequence of SEQ ID NO:31.

57. The bacterium of embodiment 28, wherein the operon encoding argininosuccinate synthase comprises a DNA sequence of SEQ ID NO:32.

58. The bacterium of any one of embodiments 27-57, wherein the bacterium is selected from the group consisting of *Bacteroides, Bifidobacterium, Clostridium, Escherichia, Lactobacillus*, and *Lactococcus*.

59. The bacterium of any one of embodiments 27-58, wherein the bacterium is *Escherichia coli* Nissle.

60. The bacterium of any one of embodiments 27-59, wherein at least one of the operons is present on a plasmid in the bacterium; and wherein all chromosomal copies of the arginine regulon genes corresponding to those on the plasmid do not encode an active enzyme.

61. The bacterium of embodiment 60, wherein the gene encoding the mutated N-acetylglutamate synthetase is present on a plasmid in the bacterium and operably linked on the plasmid to the promoter that is induced under low-oxygen or anaerobic conditions.

62. The bacterium of any one of embodiments 27-59, wherein the gene encoding the mutated N-acetylglutamate synthetase is present in the bacterial chromosome and is operably linked in the chromosome to the promoter that is induced under low-oxygen or anaerobic conditions.

63. The bacterium of any one of embodiments 27-62, wherein the bacterium is an auxotroph in a first gene that is complemented when the bacterium is present in a mammalian gut.

64. The bacterium of embodiment 63, wherein mammalian gut is a human gut.

65. The bacterium of any one of embodiments 27-64, wherein:
  a) the bacterium is auxotrophic in a second gene that is not complemented when the bacterium is present in a mammalian gut;
  b) the second gene is complemented by an inducible third gene present in the bacterium; and
  c) transcription of the third gene is induced in the presence of sufficiently high concentration of arginine thus complementing the auxotrophy in the second gene.

66. The bacterium of embodiment 65, wherein:
  a) transcription of the third gene is repressed by a second repressor;
  b) transcription of the second repressor is repressed by an arginine-arginine repressor complex.

67. The bacterium of embodiment 66, wherein the third gene and the second repressor are each present on a plasmid.

68. A pharmaceutically acceptable composition comprising the bacterium of any one of embodiments 27-67; and a pharmaceutically acceptable carrier.

69. A method of producing the pharmaceutically acceptable composition of embodiment 68, comprising the steps of:
  a) growing the bacterium of any one of embodiments 27-67 in a growth medium culture under aerobic conditions;
  b) isolating the resulting bacteria from the growth medium; and
  c) suspending the isolated bacteria in a pharmaceutically acceptable carrier.

70. A method of treating a hyperammonemia-associated disorder or symptom(s) thereof in a subject in need thereof comprising the step of administering to the subject the composition of embodiment 68 for a period of time sufficient to lessen the severity of the hyperammonemia-associated disorder.

71. The method of embodiment 70, wherein the hyperammonemia-associated disorder is a urea cycle disorder.

72. The method of embodiment 71, wherein the urea cycle disorder is argininosuccinic aciduria, arginase deficiency, carbamoylphosphate synthetase deficiency, citrullinemia, N-acetylglutamate synthetase deficiency, or ornithine transcarbamylase deficiency.
73. The method of embodiment 70, wherein the hyperammonemia-associated disorder is a liver disorder; an organic acid disorder; isovaleric aciduria; 3-methylcrotonylglycinuria; methylmalonic acidemia; propionic aciduria; fatty acid oxidation defects; carnitine cycle defects; carnitine deficiency; p-oxidation deficiency; lysinuric protein intolerance; pyrroline-5-carboxylate synthetase deficiency; pyruvate carboxylase deficiency; ornithine aminotransferase deficiency; carbonic anhydrase deficiency; hyperinsulinism-hyperammonemia syndrome; mitochondrial disorders; valproate therapy; asparaginase therapy; total parenteral nutrition; cystoscopy with glycine-containing solutions; post-lung/bone marrow transplantation; portosystemic shunting; urinary tract infections; ureter dilation; multiple myeloma; chemotherapy; infection; neurogenic bladder; or intestinal bacterial overgrowth.
74. The method of embodiment 73, wherein the liver disorder is hepatic encephalopathy, acute liver failure, or chronic liver failure.
75. The method of embodiment 70, wherein the symptoms of the hyperammonemia-associated disorder are selected from the group consisting of seizures, ataxia, stroke-like lesions, coma, psychosis, vision loss, acute encephalopathy, cerebral edema, as well as vomiting, respiratory alkalosis, and hypothermia.
76. The bacterium of any one of embodiments 27-75, wherein the bacterium additionally comprises a DNA sequence coding for a detectable product, wherein transcription of the DNA sequence coding for the detectable product is induced in the presence of arginine.
77. The bacterium of embodiment 76, wherein:
  a) transcription of the DNA sequence coding for the detectable product is repressed by a third repressor; and
  b) transcription of the third repressor is repressed by an arginine-arginine repressor complex.
78. A method of selecting for a bacterium that produces high levels of arginine comprising:
  a) providing a bacterium of embodiment 77;
  b) culturing the bacterium for a first period of time;
  c) subjecting the culture to mutagenesis;
  d) culturing the mutagenized culture for a second period of time; and
  e) selecting bacterium that express the detectable product, thereby selecting bacterium that produce high levels of arginine.
79. The method of embodiment 78, wherein the detectable product is a fluorescent protein and selection comprises the use of fluorescence-activated cell sorter.

Full citations for the references cited throughout the specification include:

1. Altenhoefer et al. The probiotic *Escherichia coli* strain Nissle 1917 interferes with invasion of human intestinal epithelial cells by different enteroinvasive bacterial pathogens. FEMS Immunol Med Microbiol. 2004 Apr. 9; 40(3):223-9. PMID: 15039098.
2. Andersen et al. Uracil uptake in *Escherichia coli* K-12: isolation of uraA mutants and cloning of the gene. J Bacteriol. 1995 April; 177(8):2008-13. PMID: 7721693.
3. Arthur et al. Intestinal inflammation targets cancer-inducing activity of the microbiota. Science. 2012 Oct. 5; 338(6103):120-3. PMID: 22903521.
4. Aoyagi et al. Gastrointestinal urease in man. Activity of mucosal urease. Gut. 1966 December; 7(6):631-5. PMID: 5957514.
5. Arai et al. Expression of the nir and nor genes for denitrification of *Pseudomonas aeruginosa* requires a novel CRP/FNR-related transcriptional regulator, DNR, in addition to ANR. FEBS Lett. 1995 Aug 28;371(1):73-6. PMID: 7664887.
6. Caldara et al. The arginine regulon of *Escherichia coli*: whole-system transcriptome analysis discovers new genes and provides an integrated view of arginine regulation. Microbiology. 2006 November; 152(Pt 11): 3343-54. PMID: 17074904.
7. Caldara et al. Arginine biosynthesis in *Escherichia coli*: experimental perturbation and mathematical modeling. J Biol Chem. 2008 Mar. 7; 283(10):6347-58. PMID: 18165237.
8. Caldovic et al. N-acetylglutamate synthase: structure, function and defects. Mol Genet Metab. 2010;100 Suppl 1:S13-9. Review. PMID: 20303810.
9. Callura et al. Tracking, tuning, and terminating microbial physiology using synthetic riboregulators. Proc Natl Acad Sci USA. 2010 Sep. 7; 107(36):15898-903. PMID: 20713708.
10. Castiglione et al. The transcription factor DNR from *Pseudomonas aeruginosa* specifically requires nitric oxide and haem for the activation of a target promoter in *Escherichia coli*. Microbiology. 2009 September; 155(Pt 9):2838-44. PMID: 19477902.
11. Charlier et al. Arginine regulon of *Escherichia coli* K-12. A study of repressor-operator interactions and of in vitro binding affinities versus in vivo repression. J Mol Biol. 1992 Jul. 20; 226(2):367-86. PMID: 1640456.
12. Crabeel et al. Characterization of the *Saccharomyces cerevisiae* ARG7 gene encoding ornithine acetyltransferase, an enzyme also endowed with acetylglutamate synthase activity. Eur J Biochem. 1997 Dec 1;250(2): 232-41. PMID: 9428669.
13. Cuevas-Ramos et al. *Escherichia coli* induces DNA damage in vivo and triggers genomic instability in mammalian cells. Proc Natl Acad Sci U S A. 2010 Jun. 22; 107(25):11537-42. PMID: 20534522.
14. Cunin et al. Molecular basis for modulated regulation of gene expression in the arginine regulon of *Escherichia coli* K-12. Nucleic Acids Res. 1983 Aug. 11; 11(15):5007-19. PMID: 6348703.
15. Cunin et al. Biosynthesis and metabolism of arginine in bacteria. Microbiol Rev. 1986 September; 50(3): 314-52. Review. Erratum in: Microbiol Rev. 1987 March; 51(1):178. PMID: 3534538.
16. Deignan et al. Contrasting features of urea cycle disorders in human patients. Mol Genet Metab. 2008 January; 93(1);7-14. PMID: 17933574.
17. Deutscher. The mechanisms of carbon catabolite repression in bacteria. Curr Opin Microbiol. 2008 April; 11(2):87-93. PMID: 18359269.
18. Diaz et al. Ammonia control and neurocognitive outcome among urea cycle disorder patients treated with glycerol phenylbutyrate. Hepatology. 2013 June; 57(6):2171-9. PMID: 22961727.

19. Dinleyici et al. Saccharomyces boulardii CNCM 1-745 in different clinical conditions. Expert Opin Biot Ther. 2014 November; 14(11):1593-609. PMID: 24995675.

20. Doolittle. A new allele of the sparse fur gene in the mouse. J Hered. 1974 May-June; 65(3):194-5. PMID: 4603259.

21. Eckhardt et al. Isolation and characterization of mutants with a feedback resistant N-acetylglutamate synthase in *Escherichia coli* K 12. Mol Gen Genet. 1975 Jun. 19; 138(3):225-32. PMID: 1102931.

22. Eiglmeier et al. Molecular genetic analysis of FNR-dependent promoters. Mol Microbiol. 1989 July; 3(7): 869-78. PMID: 2677602.

23. Fraga et al. (2008). Real-Time PCR. *Current Protocols Essential Laboratory Techniques* (10.3.1-10.3.33). John Wiley & Sons, Inc.

24. Galimand et al. Positive FNR-like control of anaerobic arginine degradation and nitrate respiration in Pseudomonas aeruginosa. J Bacteriol. 1991 March; 173(5): 1598-606. PMID: 1900277.

25. Gamper et al. Anaerobic regulation of transcription initiation in the arcDABC operon of *Pseudomonas aeruginosa*. J Bacteriol. 1991 August; 173(15):4742-50. PMID: 1906871.

26. Gardner et al. Construction of a genetic toggle switch in *Escherichia coli*. Nature. 2000;403:339-42. PMID: 10659857.

27. Görke B et al. Carbon catabolite repression in bacteria: many ways to make the most out of nutrients. Nat Rev Microbiol. 2008 August; 6(8):613-24. PMID: 18628769.

28. Häberle et al. Suggested guidelines for the diagnosis and management of urea cycle disorders. Orphanet J Rare Dis. 2012 May 29;7:32. Review. PMID: 22642880.

29. Häberle J. Clinical and biochemical aspects of primary and secondary hyperammonemic disorders. Arch Biochem Biophys. 2013 Aug. 15; 536(2):101-8. Review. PMID: 23628343.

30. Hasegawa et al. Activation of a consensus FNR-dependent promoter by DNR of *Pseudomonas aeruginosa* in response to nitrite. FEMS Microbiol Lett. 1998 Sep. 15; 166(2):213-7. PMID: 9770276.

31. Hodges et al. The spfash mouse: a missense mutation in the ornithine transcarbamylase gene also causes aberrant mRNA splicing. Proc Natl Acad Sci USA. 1989 June; 86(11):4142-6. PMID: 2471197.

32. Hoeren et al. Sequence and expression of the gene encoding the respiratory nitrous-oxide reductase from Paracoccus denitrificans. Eur J Biochem. 1993 Nov. 15; 218(1):49-57. PMID: 8243476.

33. Hoffmann et al. Defects in amino acid catabolism and the urea cycle. Handb Clin Neurol. 2013; 113:1755-73. Review. PMID: 23622399.

34. Hosseini et al. Proprionate as a health-promoting microbial metabolite in the human gut. Nutr Rev. 2011 May; 69(5):245-58. PMID: 21521227.

35. Isabella et al. Deep sequencing-based analysis of the anaerobic stimulon in *Neisseria gonorrhoeae*. BMC Genomics. 2011 Jan. 20; 12:51. PMID: 21251255.

36. Konieczna et al. Bacterial urease and its role in long-lasting human diseases. Curr Protein Pept Sci. 2012 December; 13(8):789-806. Review. PMID: 23305365.

37. Lazier et al. Hyperammonemic encephalopathy in an adenocarcinoma patient managed with carglumic acid. Curr Oncol. 2014 October; 21(5):e736-9. PMID: 25302046.

38. Leonard (2006). Disorders of the urea cycle and related enzymes. *Inborn Metabolic Diseases,* 4*th* ed (pp. 263-272). Springer Medizin Verlag Heidelberg.

39. Lim et al. Nucleotide sequence of the argR gene of *Escherichia coli* K-12 and isolation of its product, the arginine repressor. Proc Natl Acad Sci USA. 1987 October; 84(19):6697-701. PMID: 3116542.

40. Makarova et al. Conservation of the binding site for the arginine repressor in all bacterial lineages. Genome Biol. 2001; 2(4). PMID: 11305941.

41. Maas et al. Studies on the mechanism of repression of arginine biosynthesis in *Escherichia coli*. Dominance of repressibility in diploids. J Mol Biol. 1964 March; 8:365-70. PMID: 14168690.

42. Maas. The arginine repressor of *Escherichia coli*. Microbiol Rev. 1994 December; 58(4):631-40. PMID: 7854250.

43. Meng et al. Nucleotide sequence of the Escherichia coli cad operon: a system for neutralization of low extracellular pH. J Bacteriol. 1992 April; 174(8):2659-69. PMID: 1556085.

44. Moore et al. Regulation of FNR dimerization by subunit charge repulsion. J Biol Chem. 2006 Nov. 3; 281(44):33268-75. PMID: 16959764.

45. Mountain et al. Cloning of a Bacillus subtilis restriction fragment complementing auxotrophic mutants of eight Escherichia coli genes of arginine biosynthesis. Mol Gen Genet. 1984; 197(1):82-9. PMID: 6096675.

46. Nagamani et al. Optimizing therapy for argininosuccinic aciduria. Mol Genet Metab. 2012 September; 107(1-2):10-4. Review. PMID: 22841516.

47. Nicaise et al. Control of acute, chronic, and constitutive hyperammonemia by wild-type and genetically engineered Lactobacillus plantarum in rodents. Hepatology. 2008 October; 48(4):1184-92. PMID: 18697211.

48. Nicoloff et al. Two arginine repressors regulate arginine biosynthesis in *Lactobacillus plantarum*. J Bacteriol. 2004 Sep; 186(18):6059-69. PMID: 15342575.

49. Nougayrede et al. *Escherichia coli* induces DNA double-strand breaks in eukaryotic cells. Science. 2006 Aug. 11; 313(5788):848-51. PMID: 16902142.

50. Olier et al. Genotoxicity of Escherichia coli Nissle 1917 strain cannot be dissociated from its probiotic activity. Gut Microbes. 2012 November-December; 3(6):501-9. PMID: 22895085.

51. Pham et al. Multiple myeloma-induced hyperammonemic encephalopathy: an entity associated with high in-patient mortality. Leuk Res. 2013 October; 37(10): 1229-32. Review. PMID: 23932549.

52. Rajagopal et al. Use of inducible feedback-resistant N-acetylglutamate synthetase (argA) genes for enhanced arginine biosynthesis by genetically engineered *Escherichia coli* K-12 strains. Appl Environ Microbiol. 1998 May; 64(5):1805-11. PMID: 9572954.

53. Ray et al. The effects of mutation of the anr gene on the aerobic respiratory chain of Pseudomonas aeruginosa. FEMS Microbiol Lett. 1997 Nov. 15; 156(2):227-32. PMID: 9513270.

54. Reister et al. Complete genome sequence of the Gram-negative probiotic *Escherichia coli* strain Nissle 1917. J Biotechnol. 2014 Oct. 10; 187:106-7. PMID: 25093936.

55. Rembacken et al. Non-pathogenic *Escherichia coli* versus mesalazine for the treatment of ulcerative colitis: a randomised trial. Lancet. 1999 Aug. 21; 354 (9179):635-9. PMID: 10466665.

56. Remington's Pharmaceutical Sciences, 22nd ed. Mack Publishing Co.

57. Salmon et al. Global gene expression profiling in *Escherichia coli* K12. The effects of oxygen availability and FNR. J Biol Chem. 2003 Aug. 8; 278(32): 29837-55. PMID: 12754220.

58. Sat et al. The *Escherichia coli* mazEF suicide module mediates thymineless death. J Bacteriol. 2003 Mar;185 (6):1803-7. PMID: 12618443.

59. Sawers. Identification and molecular characterization of a transcriptional regulator from Pseudomonas aeruginosa PAO1 exhibiting structural and functional similarity to the FNR protein of *Escherichia coli*. Mol Microbiol. 1991 June;5(6):1469-81. PMID: 1787797.

60. Schneider et al. Arginine catabolism and the arginine succinyltransferase pathway in *Escherichia coli*. J Bacteriol. 1998 August; 180(16): 4278-86. PMID: 9696779.

61. Schultz. Clinical use of *E. coli* Nissle 1917 in inflammatory bowel disease. Inflamm Bowel Dis. 2008 July; 14(7):1012-8. Review. PMID: 18240278.

62. Sonnenborn et al. The non-pathogenic *Escherichia coli* strain Nissle 1917—features of a versatile probiotic. Microbial Ecology in Health and Disease. 2009; 21:122-58.

63. Suiter et al. Fitness consequences of a regulatory polymorphism in a seasonal environment. Proc Natl Acad Sci U S A. 2003 Oct. 28; 100(22):12782-6. PMID: 14555766.

64. Summerskill. On the origin and transfer of ammonia in the human gastrointestinal tract. Medicine (Baltimore). 1966 November; 45(6):491-6. PMID: 5925900.

65. Szwajkajzer et al. Quantitative analysis of DNA binding by the *Escherichia coli* arginine repressor. J Mol Biol. 2001 Oct. 5; 312(5):949-62. PMID: 11580241.

66. Tian et al. Binding of the arginine repressor of *Escherichia coli* K12 to its operator sites. J Mol Biol. 1992 Jul. 20; 226(2):387-97. PMID: 1640457.

67. Tian et al. Explanation for different types of regulation of arginine biosynthesis in *Escherichia coli* B and *Escherichia coli* K12 caused by a difference between their arginine repressors. J Mol Biol. 1994 Jan. 7; 235(1):221-30. PMID: 8289243.

68. Torres-Vega et al. Delivery of glutamine synthetase gene by baculovirus vectors: a proof of concept for the treatment of acute hyperammonemia. Gene Ther. 2014 Oct. 23; 22(1):58-64. PMID: 25338921.

69. Trunk et al. Anaerobic adaptation in *Pseudomonas aeruginosa*: definition of the Anr and Dnr regulons. Environ Microbiol. 2010 Jun;12(6):1719-33. PMID: 20553552.

70. Tuchman et al. Enhanced production of arginine and urea by genetically engineered Escherichia coli K-12 strains. Appl Environ Microbiol. 1997 January;63(1): 33-8. PMID: 8979336.

71. Ukena et al. Probiotic *Escherichia coli* Nissle 1917 inhibits leaky gut by enhancing mucosal integrity. PLoS One. 2007 Dec 12;2(12):e1308. PMID: 18074031.

72. Unden et al. Alternative respiratory pathways of *Escherichia coli*: energetics and transcriptional regulation in response to electron acceptors. Biochim Biophys Acta. 1997 Jul. 4;1320(3):217-34. Review. PMID: 9230919.

73. Vander Wauven et al. *Pseudomonas aeruginosa* mutants affected in anaerobic growth on arginine: evidence for a four-gene cluster encoding the arginine deiminase pathway. J Bacteriol. 1984 December; 160 (3):928-34. PMID: 6438064.

74. Walker. Severe hyperammonaemia in adults not explained by liver disease. Ann Clin Biochem. 2012 May; 49(Pt 3):214-28. Review. PMID: 22349554.

75. Winteler et al. The homologous regulators ANR of *Pseudomonas aeruginosa* and FNR of *Escherichia coli* have overlapping but distinct specificities for anaerobically inducible promoters. Microbiology. 1996 March; 142 (Pt 3):685-93. PMID: 8868444.

76. Wu et al. Direct regulation of the natural competence regulator gene tfoX by cyclic AMP (cAMP) and cAMP receptor protein in Vibrios. Sci Rep. 2015 Oct. 7; 5:14921. PMID: 26442598.

77. Zimmermann et al. Anaerobic growth and cyanide synthesis of *Pseudomonas aeruginosa* depend on anr, a regulatory gene homologous with fnr of *Escherichia coli*. Mol Microbiol. 1991 June; 5(6):1483-90. PMID: 1787798.

78. Wright O, Delmans M, Stan G B, Ellis T. GeneGuard: A modular plasmid system designed for biosafety. ACS Synth Biol. 2015 Mar. 20; 4(3):307-16. PMID: 24847673.

79. Alifano et al. Histidine biosynthetic pathway and genes: structure, regulation, and evolution. Microbiol Rev. 1996 March; 60(1):44-69. PMID: 8852895.

80. Liu Y, White R H, Whitman W B. Methanococci use the diaminopimelate aminotransferase (DapL) pathway for lysine biosynthesis. J Bacteriol. 2010 July; 192(13): 3304-10. PMID: 20418392.

81. Dogovski et al. (2012) Enzymology of Bacterial Lysine Biosynthesis, Biochemistry, Prof. Deniz Ekinci (Ed.), ISBN: 978-953-51-0076-8, InTech, Available from:

82. http://www.intechopen.com/books/biochemistry/enzymology-of-bacterial-lysine-biosynthesis.

83. Feng et al. Role of phosphorylated metabolic intermediates in the regulation of glutamine synthetase synthesis in *Escherichia coli*. J Bacteriol. 1992 October; 174(19):6061-70. PMID: 1356964.

84. Lodeiro et al. Robustness in *Escherichia coli* glutamate and glutamine synthesis studied by a kinetic model. J Biol Phys. 2008 April; 34(1-2):91-106. PMID: 19669495.

85. Reboul et al. Structural and dynamic requirements for optimal activity of the essential bacterial enzyme dihydrodipicolinate synthase. PLoS Comput Biol. 2012; 8(6):e1002537. PMID: 22685390.

86. Saint-Girons et al. Structure and autoregulation of the metJ regulatory gene in *Escherichia coli*. J Biol Chem. 1984 Nov. 25; 259(22):14282-5. PMID: 6094549.

87. Shoeman et al. Regulation of methionine synthesis in *Escherichia coli*: Effect of metJ gene product and S-adenosylmethionine on the expression of the metF gene. Proc Natl Acad Sci USA. 1985 June;82(11): 3601-5. PMID: 16593564.

88. van Heeswijk et al. Nitrogen assimilation in *Escherichia coli*: putting molecular data into a systems perspective. Microbiol Mol Biol Rev. 2013 December; 77(4):628-95. PMID: 24296575.

EXAMPLES

The following examples provide illustrative embodiments of the disclosure. One of ordinary skill in the art will recognize the numerous modifications and variations that may be performed without altering the spirit or scope of the disclosure. Such modifications and variations are encompassed within the scope of the disclosure. The Examples do not in any way limit the disclosure.

Arginine Repressor Binding Sites (ARG Boxes)

Example 1

ARG Box Mutations

The wild-type genomic sequences comprising ArgR binding sites for each arginine biosynthesis operon in *E. coli* Nissle is shown in FIG. 6. Modifications to those sequences are designed according to the following parameters. For each wild-type sequence, the ARG boxes are shown in italics. The ARG boxes of the arginine regulon overlap with the promoter region of each operon. The underlined sequences represent RNA polymerase binding sites and those sequences were not altered. Bases that are protected from DNA methylation during ArgR binding are highlighted and bases that are protected from hydroxyl radical attack during ArgR binding are bolded. The highlighted and bolded bases were the primary targets for mutations to disrupt ArgR binding.

Example 2

Lambda Red Recombination

Lambda red recombination is used to make chromosomal modifications, e.g., ARG box mutations. Lambda red is a procedure using recombination enzymes from a bacteriophage lambda to insert a piece of custom DNA into the chromosome of *E. coli*. A pKD46 plasmid is transformed into the *E. coli* Nissle host strain. *E. coli* Nissle cells are grown overnight in LB media. The overnight culture is diluted 1:100 in 5 mL of LB media and grown until it reaches an $OD_{600}$ of 0.4-0.6. All tubes, solutions, and cuvettes are pre-chilled to 4° C. The *E. coli* cells are centrifuged at 2,000 rpm for 5 min. at 4° C., the supernatant is removed, and the cells are resuspended in 1 mL of 4° C. water. The *E. coli* are centrifuged at 2,000 rpm for 5 min. at 4° C., the supernatant is removed, and the cells are resuspended in 0.5 mL of 4° C. water. The *E. coli* are centrifuged at 2,000 rpm for 5 min. at 4° C., the supernatant is removed, and the cells are resuspended in 0.1 mL of 4° C. water. The electroporator is set to 2.5 kV. 1 ng of pKD46 plasmid DNA is added to the *E. coli* cells, mixed by pipetting, and pipetted into a sterile, chilled cuvette. The dry cuvette is placed into the sample chamber, and the electric pulse is applied. 1 mL of room-temperature SOC media is immediately added, and the mixture is transferred to a culture tube and incubated at 30° C. for 1 hr. The cells are spread out on a selective media plate and incubated overnight at 30° C.

DNA sequences comprising the desired ARG box sequences shown in FIG. 6 were ordered from a gene synthesis company. For the argA operon, the mutant regulatory region comprises the following nucleic acid sequence (SEQ ID NO: 2):

```
gcaaaaaaacaCTTtaaaaaCTTaataatttcCTTtaatcaCTT
aaagaggtgtaccgtg.
```

The lambda enzymes are used to insert this construct into the genome of *E. coli* Nissle through homologous recombination. The construct is inserted into a specific site in the genome of *E. coli* Nissle based on its DNA sequence. To insert the construct into a specific site, the homologous DNA sequence flanking the construct is identified. The homologous sequence of DNA includes approximately 50 bases on either side of the mutated sequence. The homologous sequences are ordered as part of the synthesized gene. Alternatively, the homologous sequences may be added by PCR. The construct is used to replace the natural sequence upstream of argA in the *E. coli* Nissle genome. The construct includes an antibiotic resistance marker that may be removed by recombination. The resulting mutant argA construct comprises approximately 50 bases of homology upstream of argA, a kanamycin resistance marker that can be removed by recombination,

```
gcaaaaaaacaCTTtaaaaaCTTaataatttcCTTtaatcaCTT
aaagaggtgtaccgtg,
```

and approximately 50 bases of homology to argA.

In some embodiments, the ARG boxes were mutated in the argG regulatory region as described above, and a BBa_J23100 constitutive promoter was inserted into the regulatory region using lambda red recombination (SYN-UCD105). These bacteria were capable of producing arginine. In alternate embodiments, the argG regulatory region (SEQ ID NO: 31) remained ArgR-repressible (SYN-UCD104), and the bacteria were capable of producing citrulline.

Example 3

Transforming *E. coli* Nissle

The mutated ARG box construct is transformed into *E. coli* Nissle comprising pKD46. All tubes, solutions, and cuvettes are pre-chilled to 4° C. An overnight culture is diluted 1:100 in 5 mL of LB media containing ampicillin and grown until it reaches an $OD_{600}$ of 0.1. 0.05 mL of 100× L-arabinose stock solution is added to induce pKD46 lambda red expression. The culture is grown until it reaches an $OD_{600}$ of 0.4-0.6. The *E. coli* cells are centrifuged at 2,000 rpm for 5 min. at 4° C., the supernatant is removed, and the cells are resuspended in 1 mL of 4° C. water. The *E. coli* are centrifuged at 2,000 rpm for 5 min. at 4° C., the supernatant is removed, and the cells are resuspended in 0.5 mL of 4° C. water. The *E. coli* are centrifuged at 2,000 rpm for 5 min. at 4° C., the supernatant is removed, and the cells are resuspended in 0.1 mL of 4° C. water. The electroporator is set to 2.5 kV. 0.5 μg of the mutated ARG box construct is added to the cells, mixed by pipetting, and pipetted into a sterile, chilled cuvette. The dry cuvette is placed into the sample chamber, and the electric pulse is applied. 1 mL of room-temperature SOC media is immediately added, and the mixture is transferred to a culture tube and incubated at 37°

C. for 1 hr. The cells are spread out on an LB plate containing kanamycin and incubated overnight.

Example 4

Verifying Mutants

The presence of the mutation is verified by colony PCR. Colonies are picked with a pipette tip and resuspended in 20 μl of cold $ddH_2O$ by pipetting up and down. 3 μl of the suspension is pipetted onto an index plate with appropriate antibiotic for use later. The index plate is grown at 37° C. overnight. A PCR master mix is made using 5 μl of 10× PCR buffer, 0.6 μl of 10 mM dNTPs, 0.4 μl of 50 mM $Mg_2SO_4$, 6.0 μl of 10× enhancer, and 3.0 μl of $ddH_2O$ (15 μl of master mix per PCR reaction). A 10 μM primer mix is made by mixing 2 μL of primers unique to the argA mutant construct (100 μM stock) into 16 μL of $ddH_2O$. For each 20 μl reaction, 15μL of the PCR master mix, 2.0 μL of the colony suspension (template), 2.0 μL of the primer mix, and 1.0 μL of Pfx Platinum DNA Pol are mixed in a PCR tube. The PCR thermocycler is programmed as follows, with steps 2-4 repeating 34 times: 1) 94° C. at 5:00 min., 2) 94° C. at 0:15 min., 3) 55° C. at 0:30 min., 4) 68° C. at 2:00 min., 5) 68° C. at 7:00 min., and then cooled to 4° C. The PCR products are analyzed by gel electrophoresis using 10 μL of each amplicon and 2.5 μL 5× dye. The PCR product only forms if the mutation has inserted into the genome.

Example 5

Removing Selection Marker

The antibiotic resistance gene is removed with pCP20. Each strain with the mutated ARG boxes is grown in LB media containing antibiotics at 37° C. until it reaches an $OD_{600}$ of 0.4-0.6. All tubes, solutions, and cuvettes are pre-chilled to 4° C. The cells are centrifuged at 2,000 rpm for 5 min. at 4° C., the supernatant is removed, and the cells are resuspended in 1 mL of 4° C. water. The *E. coli* are centrifuged at 2,000 rpm for 5 min. at 4° C., the supernatant is removed, and the cells are resuspended in 0.5 mL of 4° C. water. The *E. coli* are centrifuged at 2,000 rpm for 5 min. at 4° C., the supernatant is removed, and the cells are resuspended in 0.1 mL of 4° C. water. The electroporator is set to 2.5 kV. 1 ng of pCP20 plasmid DNA is added to the cells, mixed by pipetting, and pipetted into a sterile, chilled cuvette. The dry cuvette was placed into the sample chamber, and the electric pulse was applied. 1 mL of room-temperature SOC media is immediately added, and the mixture is transferred to a culture tube and incubated at 30° C. for 1-3 hrs. The cells are spread out on an LB plate containing kanamycin and incubated overnight. Colonies that do not grow to a sufficient $OD_{600}$ overnight are further incubated for an additional 24 hrs. 200 μL of cells are spread on ampicillin plates, 200 μL of cells are spread on kanamycin plates, and both are grown at 37° C. overnight. The ampicillin plate contains cells with pCP20. The kanamycin plate provides an indication of how many cells survived the electroporation. Transformants from the ampicillin plate are purified non-selectively at 43° C. and allowed to grow overnight.

Example 6

Verifying Transformants

The purified transformants are tested for sensitivity to ampicillin and kanamycin. A colony from the plate grown at 43° C. is picked and and resuspended in 10 μL of LB media. 3 μL of the cell suspension is pipetted onto each of three plates: 1) an LB plate with kanamycin incubated at 37° C., which tests for the presence or absence of the KanR gene in the genome of the host strain; 2) an LB plate with ampicillin incubated at 30° C., which tests for the presence or absence of the AmpR gene from the pCP20 plasmid; and 3) an LB plate without antibiotic incubated at 37° C. If no growth is observed on the kanamycin or ampicillin plates for a particular colony, then both the KanR gene and the pCP20 plasmid were lost, and the colony is saved for further analysis. The saved colonies are restreaked onto an LB plate to obtain single colonies and grown overnight at 37° C. The presence of the mutated genomic ARG box is confirmed by sequencing the argA region of the genome.

The methods for lambda red recombination, transforming *E. coli* Nissle, verifying the mutation, removing the selection marker, and verifying/sequencing the transformants are repeated for each of the ARG box mutations and operons shown in FIG. 6. The resulting bacteria comprise mutations in each ARG box for one or more operons encoding the arginine biosynthesis enzymes, such that ArgR binding to the ARG boxes is reduced and total ArgR binding to the regulatory region of said operons is reduced.

Example 7

Arginine Feedback Resistant N-acetylglutamate Synthetase ($argA^{fbr}$)

In addition to the ARG box mutations described above, the *E. coli* Nissle bacteria further comprise an arginine feedback resistant N-acetylglutamate synthetase ($argA^{fbr}$, SEQ ID NO: 28) gene expressed under the control of each of the following promoters: tetracycline-inducible promoter, FNR promoter selected from SEQ ID NOs: 16-27. As discussed herein, other promoters may be used.

The $argA^{fbr}$ gene is expressed on a high-copy plasmid, a low-copy plasmid, or a chromosome. SYN-UCD101 comprises wild-type ArgR, wild-type ArgA, tetracycline-inducible $argA^{fbr}$ on a plasmid, and mutations in each ARG box for each arginine biosynthesis operon. The plasmid does not comprise functional ArgR binding sites, i.e., ARG boxes. SYN-UCD101 was used to generate SYN-UCD102, which comprises wild-type ArgR, wild-type ArgA, tetracycline-inducible $argA^{fbr}$ on a plasmid, and mutations in each ARG box for each arginine biosynthesis operon. The plasmid further comprises functional ArgR binding sites, i.e., ARG boxes. In some instances, the presence and/or build-up of functional ArgR may result in off-target binding at sites other than the ARG boxes. Introducing functional ARG boxes in this plasmid may be useful for reducing or eliminating off-target ArgR binding, i.e., by acting as an ArgR sink. SYN-UCD104 comprises wild-type ArgR, wild-type ArgA, tetracycline-inducibl $argA^{fbr}$ on a low-copy plasmid, tetracycline-inducible argG, and mutations in each ARG box for each arginine biosynthesis operon except for argG. SYN-UCD105 comprises wild-type ArgR, wild-type ArgA, tetracycline-inducible $argA^{fbr}$ on a low-copy plasmid, constitutively expressed argG (SEQ ID NO: 31 comprising the BBa_J23100 constitutive promoter), and mutations in each ARG box for each arginine biosynthesis operon. SYN-UCD103 is a control Nissle construct.

The $argA^{fbr}$ gene is inserted into the bacterial genome at one or more of the following insertion sites in *E. coli* Nissle: malE/K, araC/BAD, lacZ, thyA, malP/T. Any suitable insertion site may be used, see, e.g., FIG. 22. The insertion site may be anywhere in the genome, e.g., in a gene required for survival and/or growth, such as thyA (to create an auxotroph); in an active area of the genome, such as near the site of genome replication; and/or in between divergent promoters in order to reduce the risk of unintended transcription, such as between AraB and AraC of the arabinose operon. At the site of insertion, DNA primers that are homologous to the site of insertion and to the $argA^{fbr}$ construct are designed. A linear DNA fragment containing the construct with homology to the target site is generated by PCR, and lambda red recombination is performed as described above.

Figure 25:
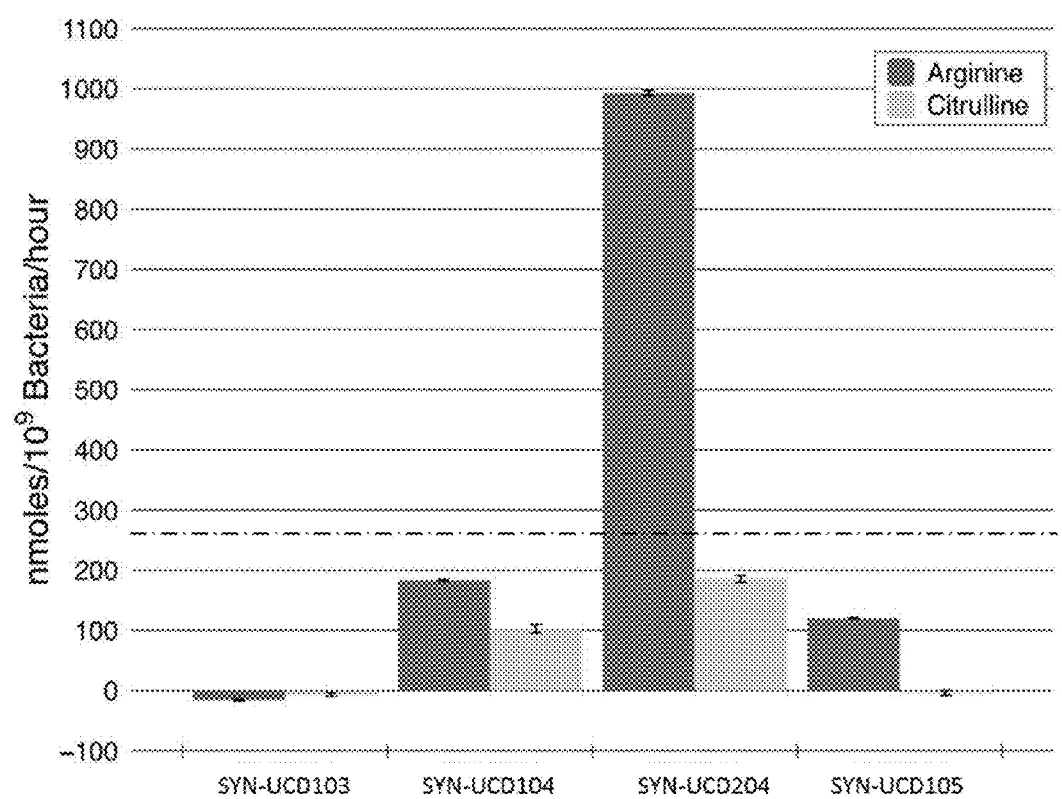
FIG. 25 depicts a bar graph of in vitro levels of arginine and citrulline produced by streptomycin-resistant control Nissle (SYN-UCD103), SYN-UCD104, SYN-UCD204, and SYN-UCD105 under inducing conditions. SYN-UCD104 comprises wild-type ArgR, tetracycline-inducible argA$^{fbr}$ on a low-copy plasmid, tetracycline-inducible argG, and mutations in each ARG box for each arginine biosynthesis operon except for argG. SYN-UCD204 comprises ΔArgR and argA$^{fbr}$ expressed under the control of a tetracycline-inducible promoter on a low-copy plasmid. SYN-UCD105 comprises wild-type ArgR, tetracycline-inducible argA$^{fbr}$ on a low-copy plasmid, constitutively expressed argG (BBa_J23100 constitutive promoter), and mutations in each ARG box for each arginine biosynthesis operon except for argG.

The resulting *E. coli* Nissle bacteria are genetically engineered to include nucleic acid mutations that reduce arginine-mediated repression—via ArgR binding and arginine binding to N-acetylglutamate synthetase—of one or more of the operons that encode the arginine biosynthesis enzymes, thereby enhancing arginine and/or citrulline biosynthesis (FIG. 25).

Arginine Repressor (ArqR)

Example 8

ArgR Sequences

The wild-type argR nucleotide sequence in *E. coli* Nissle and the nucleotide sequence following argR deletion are shown below.

| SEQ ID NO: 38 | 0123456789012345678901234567890123456789 |
|---|---|
| argR nucleotide sequence | atgcgaagctcggctaagcaagaagaactagttaaagcat<br>ttaaagcattacttaaagaagagaaatttagctcccaggg<br>cgaaatcgtcgccgcgttgcaggagcaaggctttgacaat<br>attaatcagtctaaagtctcgcggatgttgaccaagtttg<br>gtgctgtacgtacacgcaatgccaaaatggaaatggttta<br>ctgcctgccagctgaactgggtgtaccaaccacctccagt<br>ccattgaagaatctggtactggatatcgactacaacgatg<br>cagttgtcgtgattcataccagccctggtgcggcgcagtt<br>aattgctcgcctgctggactcactgggcaaagcagaaggt<br>attctgggcaccatcgctggcgatgacaccatctttacta<br>cccctgctaacggtttcaccgtcaaagagctgtacgaagc<br>gattttagagctgttcgaccaggagctttaa |

| SEQ ID NO: 39 | 0123456789012345678901234567890123456789 |
|---|---|
| argR-deleted nucleotide sequence | atgcgaagctcggctaagcaagaagagagctgttcgacca<br>ggagctttaa |

Example 9

Deleting ArgR

A pKD46 plasmid is transformed into the *E. coli* Nissle host strain. *E. coli* Nissle cells are grown overnight in LB media. The overnight culture is diluted 1:100 in 5 mL of LB media and grown until it reaches an $OD_{600}$ of 0.4-0.6. All tubes, solutions, and cuvettes are pre-chilled to 4° C. The *E. coli* cells are centrifuged at 2,000 rpm for 5 min. at 4° C., the supernatant is removed, and the cells are resuspended in 1 mL of 4° C. water. The *E. coli* are centrifuged at 2,000 rpm for 5 min. at 4° C., the supernatant is removed, and the cells are resuspended in 0.5 mL of 4° C. water. The *E. coli* are centrifuged at 2,000 rpm for 5 min. at 4° C., the supernatant is removed, and the cells are resuspended in 0.1 mL of 4° C. water. The electroporator is set to 2.5 kV. 1 ng of pKD46 plasmid DNA is added to the *E. coli* cells, mixed by pipetting, and pipetted into a sterile, chilled cuvette. The dry cuvette is placed into the sample chamber, and the electric pulse is applied. 1 mL of room-temperature SOC media is immediately added, and the mixture is transferred to a culture tube and incubated at 30° C. for 1 hr. The cells are spread out on a selective media plate and incubated overnight at 30° C.

Approximately 50 bases of homology upstream and downstream of the ArgR gene are added by PCR to the kanamycin resistance gene in the pKD4 plasmid to generate the following KanR construct: (~50 bases upstream of ArgR) (terminator) (KanR gene flanked by FRT sites from pKD4) (DNA downstream of ArgR).

In some embodiments, both argR and argG genes are deleted using lambda red recombination as described above, and the bacteria are capable of producing citrulline.

Example 10

Transforming *E. coli* Nissle

The KanR construct is transformed into *E. coli* Nissle comprising pKD46 in order to delete ArgR. All tubes, solutions, and cuvettes are pre-chilled to 4° C. An overnight culture is diluted 1:100 in 5 mL of LB media containing ampicillin and grown until it reached an $OD_{600}$ of 0.1. 0.05 mL of 100X L-arabinose stock solution is added to induce pKD46 lambda red expression. The culture is grown until it reaches an $OD_{600}$ of 0.4-0.6. The *E. coli* cells are centrifuged at 2,000 rpm for 5 min. at 4° C., the supernatant is removed, and the cells are resuspended in 1 mL of 4° C. water. The E. coli are centrifuged at 2,000 rpm for 5 min. at 4° C., the supernatant is removed, and the cells are resuspended in 0.5 mL of 4° C. water. The E. coli are centrifuged at 2,000 rpm for 5 min. at 4° C., the supernatant is removed, and the cells are resuspended in 0.1 mL of 4° C. water. The electroporator is set to 2.5 kV. 0.5 pg of the KanR construct is added to the cells, mixed by pipetting, and pipetted into a sterile, chilled cuvette. The dry cuvette is placed into the sample chamber, and the electric pulse is applied. 1 mL of room-temperature SOC media is immediately added, and the mixture is transferred to a culture tube and incubated at 37° C. for 1 hr. The cells are spread out on an LB plate containing kanamycin and incubated overnight.

Example 11

Verifying Mutants

The presence of the mutation is verified by colony PCR. Colonies are picked with a pipette tip and resuspended in 20 μl of cold $ddH_2O$ by pipetting up and down. 3 μl of the suspension is pipetted onto an index plate with appropriate antibiotic for use later. The index plate is grown at 37° C. overnight. A PCR master mix is made using 5 μl of 10× PCR buffer, 0.6 μl of 10 mM dNTPs, 0.4 μl of 50 mM $Mg_2SO_4$, 6.0 μl of 10× enhancer, and 3.0 μl of $ddH_2O$ (15 μl of master mix per PCR reaction). A 10 μM primer mix is made by mixing 2 μL of primers unique to the KanR gene (100 μM stock) into 16 μL of $ddH_2O$. For each 20 μl reaction, 15μL of the PCR master mix, 2.0 μL of the colony suspension (template), 2.0 μL of the primer mix, and 1.0 μL of Pfx Platinum DNA Pol are mixed in a PCR tube. The PCR thermocycler is programmed as follows, with steps 2-4 repeating 34 times: 1) 94° C. at 5:00 min., 2) 94° C. at 0:15 min., 3) 55° C. at 0:30 min., 4) 68° C. at 2:00 min., 5) 68° C. at 7:00 min., and then cooled to 4° C. The PCR products are analyzed by gel electrophoresis using 10 μL of each amplicon and 2.5 μL 5× dye. The PCR product only forms if the KanR gene has inserted into the genome.

Example 12

Removing Selection Marker

The antibiotic resistance gene is removed with pCP20. The strain with deleted ArgR is grown in LB media containing antibiotics at 37° C. until it reaches an $OD_{600}$ of 0.4-0.6. All tubes, solutions, and cuvettes are pre-chilled to 4° C. The cells are centrifuged at 2,000 rpm for 5 min. at 4° C., the supernatant is removed, and the cells are resuspended in 1 mL of 4° C. water. The *E. coli* are centrifuged at 2,000 rpm for 5 min. at 4° C., the supernatant is removed, and the cells are resuspended in 0.5 mL of 4° C. water. The *E. coli* are centrifuged at 2,000 rpm for 5 min. at 4° C., the supernatant is removed, and the cells are resuspended in 0.1 mL of 4° C. water. The electroporator is set to 2.5 kV. 1 ng of pCP20 plasmid DNA is added to the cells, mixed by pipetting, and pipetted into a sterile, chilled cuvette. The dry cuvette was placed into the sample chamber, and the electric pulse was applied. 1 mL of room-temperature SOC media is immediately added, and the mixture is transferred to a culture tube and incubated at 30° C. for 1-3 hrs. 200 μL of cells are spread on ampicillin plates, 200 μL of cells are spread on kanamycin plates, and both are grown at 37° C. overnight. The ampicillin plate contains cells with pCP20. The cells are incubated overnight, and colonies that do not grow to a sufficient $OD_{600}$ overnight are further incubated for an additional 24 hrs. The kanamycin plate provides an indication of how many cells survived the electroporation. Transformants from the ampicillin plate are purified non-selectively at 43° C. and allowed to grow overnight.

Example 13

Verifying Transformants

The purified transformants are tested for sensitivity to ampicillin and kanamycin. A colony from the plate grown at 43° C. is picked and resuspended in 10 μL of LB media. 3 μL of the cell suspension is pipetted onto each of three plates: 1) an LB plate with kanamycin incubated at 37° C., which tests for the presence or absence of the KanR gene in the genome of the host strain; 2) an LB plate with ampicillin incubated at 30° C., which tests for the presence or absence of the AmpR gene from the pCP20 plasmid; and 3) an LB plate without antibiotic incubated at 37° C. If no growth is observed on the kanamycin or ampicillin plates for a particular colony, then both the KanR gene and the pCP20 plasmid were lost, and the colony is saved for further analysis. The saved colonies are restreaked onto an LB plate to obtain single colonies and grown overnight at 37° C. The deletion of ArgR is confirmed by sequencing the argR region of the genome.

Example 14

Arginine Feedback Resistant N-acetylglutamate Synthetase ($argA^{fbr}$)

In addition to the ArgR deletion described above, the *E. coli* Nissle bacteria further comprise an arginine feedback resistant N-acetylglutamate synthetase ($argA^{fbr}$, SEQ ID NO: 28) gene expressed under the control of each of the following promoters: tetracycline-inducible promoter, FNR promoter selected from SEQ ID NOs: 16-27. As discussed herein, other promoters may be used.

The $argA^{fbr}$ gene is expressed on a high-copy plasmid, a low-copy plasmid, or a chromosome. ArgR is deleted (ΔArgR) in each of SYN-UCD201, SYN-UCD202, and SYN-UCD203. SYN-UCD201 further comprises wild-type argA, but lacks inducible $argA^{fbr}$. SYN-UCD202 comprises ΔArgR and $argA^{fbr}$ expressed under the control of a tetracycline-inducible promoter on a high-copy plasmid. SYN-UCD203 comprises ΔArgR and $argA^{fbr}$ expressed under the control of a tetracycline-inducible promoter on a low-copy plasmid. SYN-UCD204 comprises ΔArgR and $argA^{fbr}$ expressed under the control of a tetracycline-inducible promoter on a low-copy plasmid. SYN-UCD205 comprises ΔArgR and $argA^{fbr}$ expressed under the control of a FNR-inducible promoter (fnrS2) on a low-copy plasmid.

The $argA^{fbr}$ gene is inserted into the bacterial genome at one or more of the following insertion sites in *E. coli* Nissle: malE/K, araC/BAD, lacZ, thyA, malP/T. Any suitable insertion site may be used, see, e.g., FIG. 22. The insertion site may be anywhere in the genome, e.g., in a gene required for survival and/or growth, such as thyA (to create an auxotroph); in an active area of the genome, such as near the site of genome replication; and/or in between divergent promoters in order to reduce the risk of unintended transcription, such as between AraB and AraC of the arabinose operon. At the site of insertion, DNA primers that are homologous to the site of insertion and to the $argA^{fbr}$ construct are designed. A linear DNA fragment containing the construct with homology to the target site is generated by PCR, and lambda red recombination is performed as described above. The resulting *E. coli* Nissle bacteria have deleted ArgR and inserted feedback resistant N-acetylglutamate synthetase, thereby increasing arginine or citrulline biosynthesis.

Example 15

Quantifying Ammonia

The genetically engineered bacteria described above were grown overnight in 5 mL LB. The next day, cells were pelleted and washed in M9+ glucose, pelleted, and resuspended in 3 mL M9+ glucose. Cell cultures were incubated with shaking (250 rpm) for 4 hrs and incubated aerobically or anaerobically in a Coy anaerobic chamber (supplying 90% $N_2$, 5% $CO_2$, 5% $H_2$) at 37° C. At baseline (t=0), 2 hours, and 4 hours, the $OD_{600}$ of each cell culture was measured in order to determine the relative abundance of each cell.

At t=0, 2 hrs, and 4 hrs, a 1 mL aliquot of each cell culture was analyzed on the Nova Biomedical Bioprofile Analyzer 300 in order to determine the concentration of ammonia in the media. Both SYN-UCD101 and SYN-UCD102 were capable of consuming ammonia in vitro. FIGS. 28A, B, and C depict bar graphs of ammonia concentrations using SYN-UCD202, SYN-UCD204, SYN-UCD103, and blank controls.

Example 16

Quantifying Arginine and Citrulline

In some embodiments, the genetically engineered bacteria described above are grown overnight in LB at 37 C with shaking. The bacteria are diluted 1:100 in 5 mL LB and grown at 37 C with shaking for 1.5 hr. The bacteria cultures are induced as follows: (1) bacteria comprising FNR-inducible arg$A^{fbr}$ are induced in LB at 37 C for up to 4 hours in anaerobic conditions in a Coy anaerobic chamber (supplying 90% $N_2$, 5% $CO_2$, 5% $H_2$, and 20 mM nitrate) at 37° C.; (2) bacteria comprising tetracycline-inducible arg$A^{fbr}$ are induced with anhydrotetracycline (100 ng/mL); (3) bacteria comprising arabinose-inducible arg$A^{fbr}$ are inducedwith 1% arabinose in media lacking glucose. After induction, bacterial cells are removed from the incubator and spun down at maximum speed for 5 minutes. The cells are resuspended in 1 mL M9 glucose, and the $OD_{600}$ is measured. Cells are diluted until the $OD_{600}$ is between 0.6-0.8. Resuspended cells in M9 glucose media are grown aerobically with shaking at 37C. 100 μL of the cell resuspension is removed and the $OD_{600}$ is measured at time=0. A 100 uL aliquot is frozen at −20 C in a round-bottom 96-well plate for mass spectrometry analysis (LC-MS/MS). At each subsequent time point, 100 uL of the cell suspension is removed and the $OD_{600}$ is measured; a 100 uL aliquot is frozen at −20 C in a round-bottom 96-well plate for mass spectrometry analysis. Samples are analyzed for arginine and/or citrulline concentrations. At each time point, normalized concentrations as determined by mass spectrometry vs. $OD_{600}$ are used to determine the rate of arginine and/or citrulline production per cell per unit time.

In some embodiments, the genetically engineered bacteria described above are streaked from glycerol stocks for single colonies on agar. A colony is picked and grown in 3 mL LB for four hours or overnight, then centrifuged for 5 min. at 2,500 rcf. The cultures are washed in M9 media with 0.5% glucose. The cultures are resuspended in 3 mL of M9 media with 0.5% glucose, and the $OD_{600}$ is measured. The cultures are diluted in M9 media with 0.5% glucose, with or without ATC (100 ng/mL), with or without 20 mM glutamine, so that all of the $OD_{600}$ are between 0.4 and 0.5. A 0.5 mL aliquot of each sample is removed, centrifuged for 5 min. at 14,000 rpm, and the supernatant is removed and saved. The supernatant is frozen at −80° C., and the cell pellets are frozen at −80° C. (t=0). The remaining cells are grown with shaking (250 rpm) for 4-6 hrs and incubated aerobically or anaerobically in a Coy anaerobic chamber (supplying 90% $N_2$, 5% $CO_2$, 5% $H_2$) at 37° C. One 0.5 mL aliquot is removed from each sample every two hours and the $OD_{600}$ is measured. The aliquots are centrifuged for 5 min. at 14,000 rpm, and the supernatant is removed. The supernatant is frozen at −80° C., and the cell pellets are frozen at −80° C. (t=2, 4, and 6 hours). The samples are placed on ice, and arginine and citrulline levels are determined using mass spectrometry.

For bacterial culture supernatants, samples of 500, 100, 20, 4, and 0.8 ug/mL arginine and citrulline standards in water are prepared. In a round-bottom 96-well plate, 20 uL of sample (bacterial supernatant or standards) is added to 80 uL of water with L-Arginine-$^{13}C_6$, $^{15}N_4$ (Sigma) and L-Citrulline-2,3,3,4,4,5,5-d7 (CDN isotope) internal standards at a final 2pg/mL concentration. The plate is heat-sealed with a PierceASeal foil and mixed well. In a V-bottom 96-well polypropylene plate, 5 μL of diluted samples is added to 95 μL of derivatization mix (85 μL 10 mM $NaHCO_3$ pH 9.7 and 10 μL 10mg/mL dansyl-chloride (diluted in acetonitrile). The plate is heat-sealed with a ThermASeal foil and mixed well. The samples are incubated at 60° C. for 45 min for derivatization and centrifuged at 4000 rpm for 5 min. In a round-bottom 96-well plate, 20μL of the derivatized samples are added to 180μL of water with 0.1% formic acid. The plate is heat-sealed with a ClearASeal sheet and mixed well.

Arginine and citrulline are measured by liquid chromatography coupled to tandem mass spectrometry (LC-MS/MS) using a Thermo TSQ Quantum Max triple quadrupole mass spectrometer. The table below provides a summary of a LC-MS/MS method.

| HPLC | | | | |
|---|---|---|---|---|
| Column | Luna C18(2) column, 5 μm (50 × 2.1 mm) | | | |
| Mobile Phase A | 100% $H_2O$, 0.1% Formic Acid) | | | |
| Mobile Phase B | 100% ACN, 0.1% Formic Acid | | | |
| HPLC Method | Total Time (min) | Flow Rate (μL/min) | A % | B % |
| | 0.00 | 400 | 90.0 | 10.0 |
| | 0.50 | 400 | 90.0 | 10.0 |
| | 2.00 | 400 | 10.0 | 90.0 |
| | 3.25 | 400 | 10.0 | 90.0 |
| | 3.26 | 400 | 90.0 | 10.0 |
| | 4.30 | 400 | 90.0 | 10.0 |
| Injection Volume | 10 μL | | | |
| Tandem Mass Spectrometry | | | | |
| Ion Source | HESI-II | | | |
| Polarity | Positive | | | |
| SRM transitions | L-Arginine: 408. 1/170.1 | | | |
| | L-Arginine-$^{13}C_6$,$^{15}N_4$: 418.1/170.0 | | | |
| | L-Citrulline: 409.1/170.2 | | | |
| | L-Citrulline-2,3,3,4,4,5,5-d7: 416.1/170.1 | | | |

Figure 50:
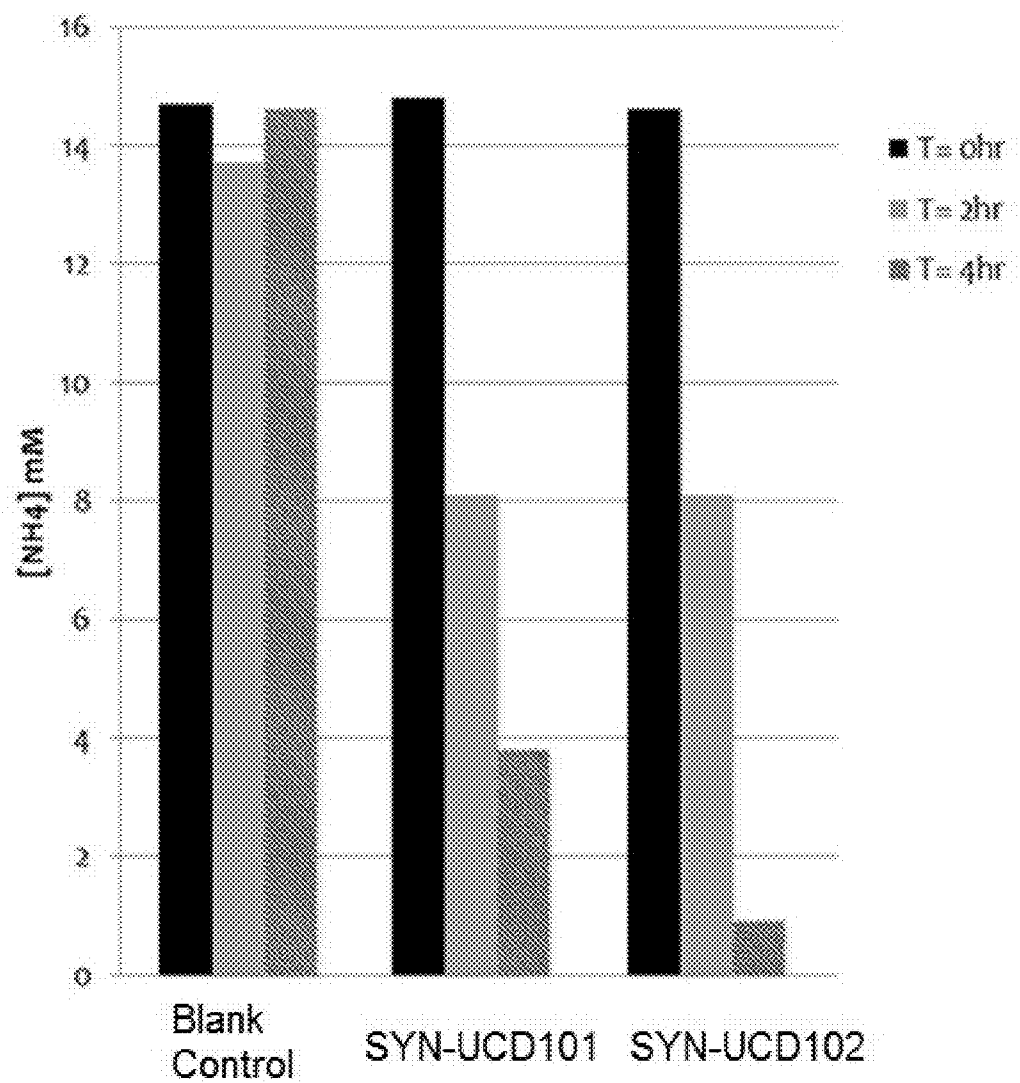
FIG. 50 depicts a bar graph of in vitro ammonia levels in culture media from SYN-UCD101, SYN-UCD102, and blank controls at baseline, two hours, and four hours. Both SYN-UCD101 and SYN-UCD102 are capable of consuming ammonia in vitro.

FIG. 50 depicts a bar graph of in vitro ammonia levels in culture media from SYN-UCD101, SYN-UCD102, and blank controls at baseline, two hours, and four hours. Both SYN-UCD101 and SYN-UCD102 are capable of consuming ammonia in vitro.

Figure 51:
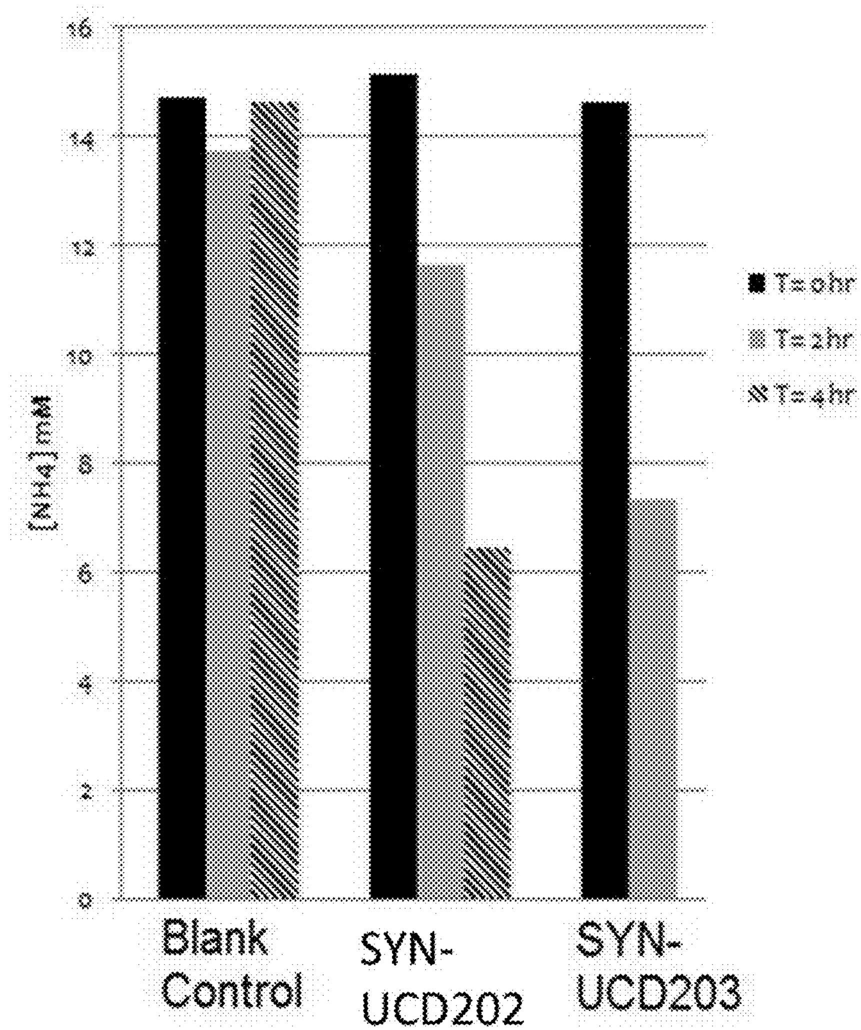
FIG. 51 depicts a bar graph of in vitro ammonia levels in culture media from SYN-UCD201, SYN-UCD203, and blank controls at baseline, two hours, and four hours. Both SYN-UCD201 and SYN-UCD203 are capable of consuming ammonia in vitro.
Figure 52:
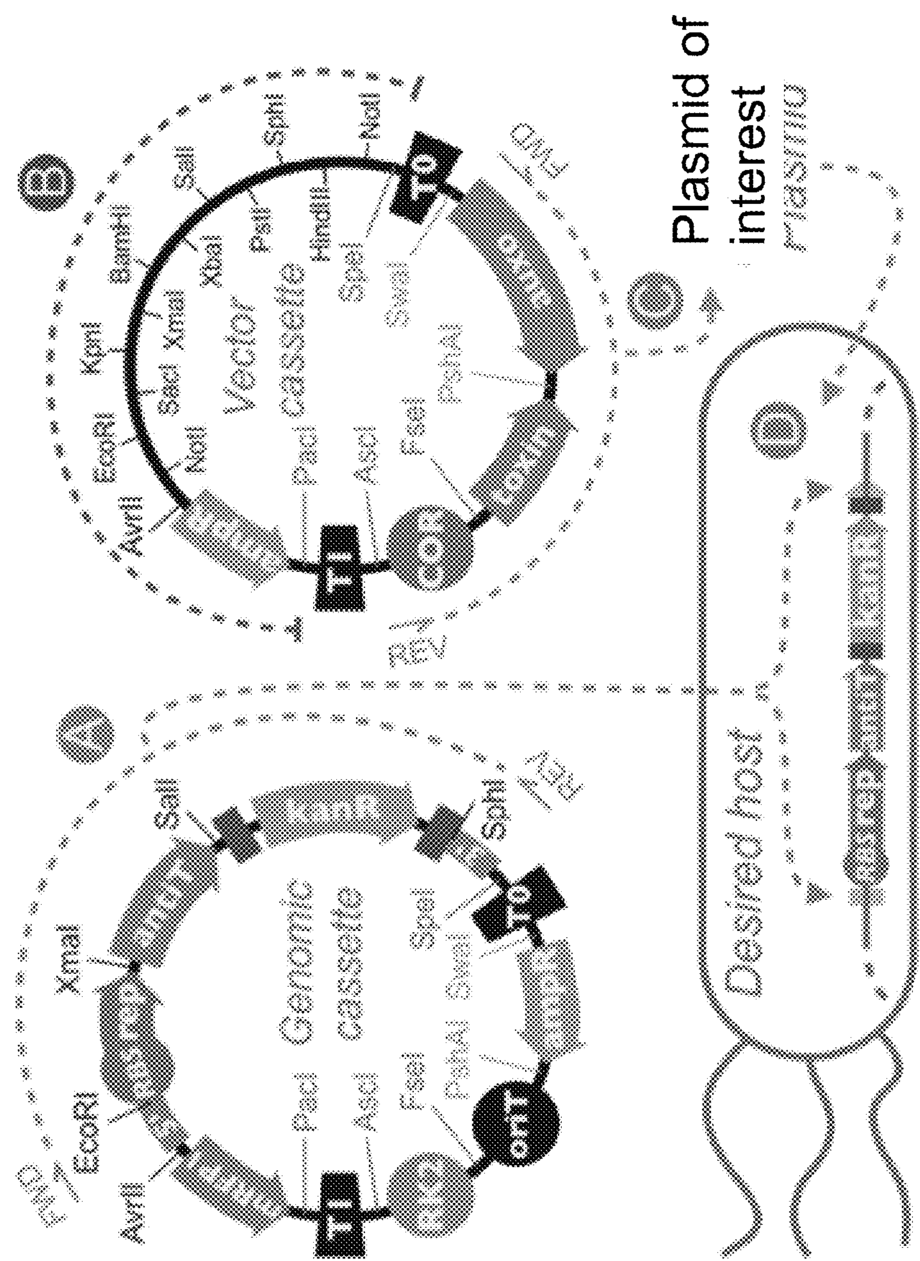
FIG. 52 depicts the use of GeneGuards as an engineered safety component. All engineered DNA is present on a plasmid which can be conditionally destroyed. See, e.g., Wright et al., "GeneGuard: A Modular Plasmid System Designed for Biosafety," ACS Synthetic Biology (2015) 4: 307-316.
Figure 53:
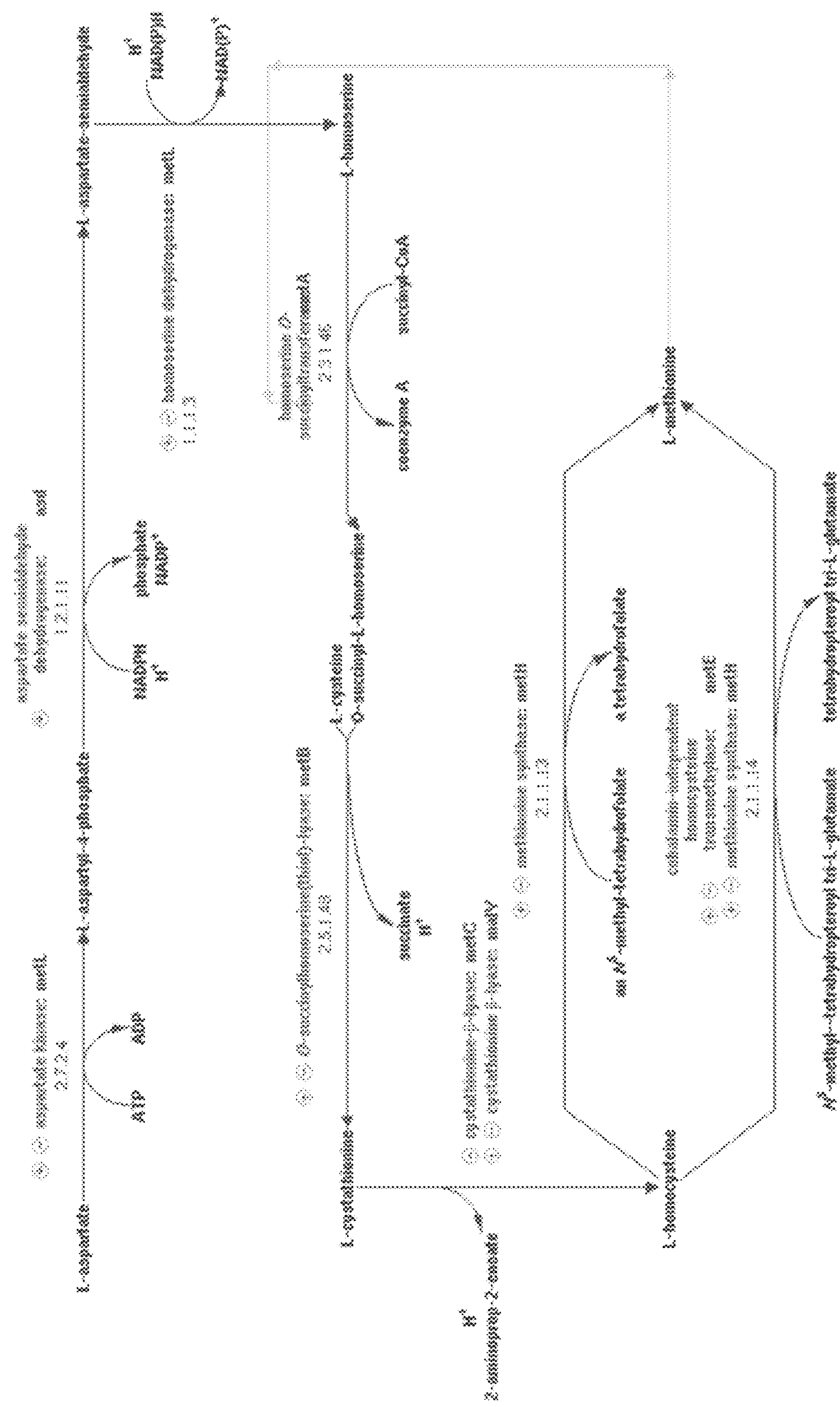
FIG. 53 depicts an exemplary L-homoserine and L-methionine biosynthesis pathway. Circles indicate genes repressed by MetJ, and deletion of metJ leads to constitutive expression of these genes and activation of the pathway.
Figure 54:
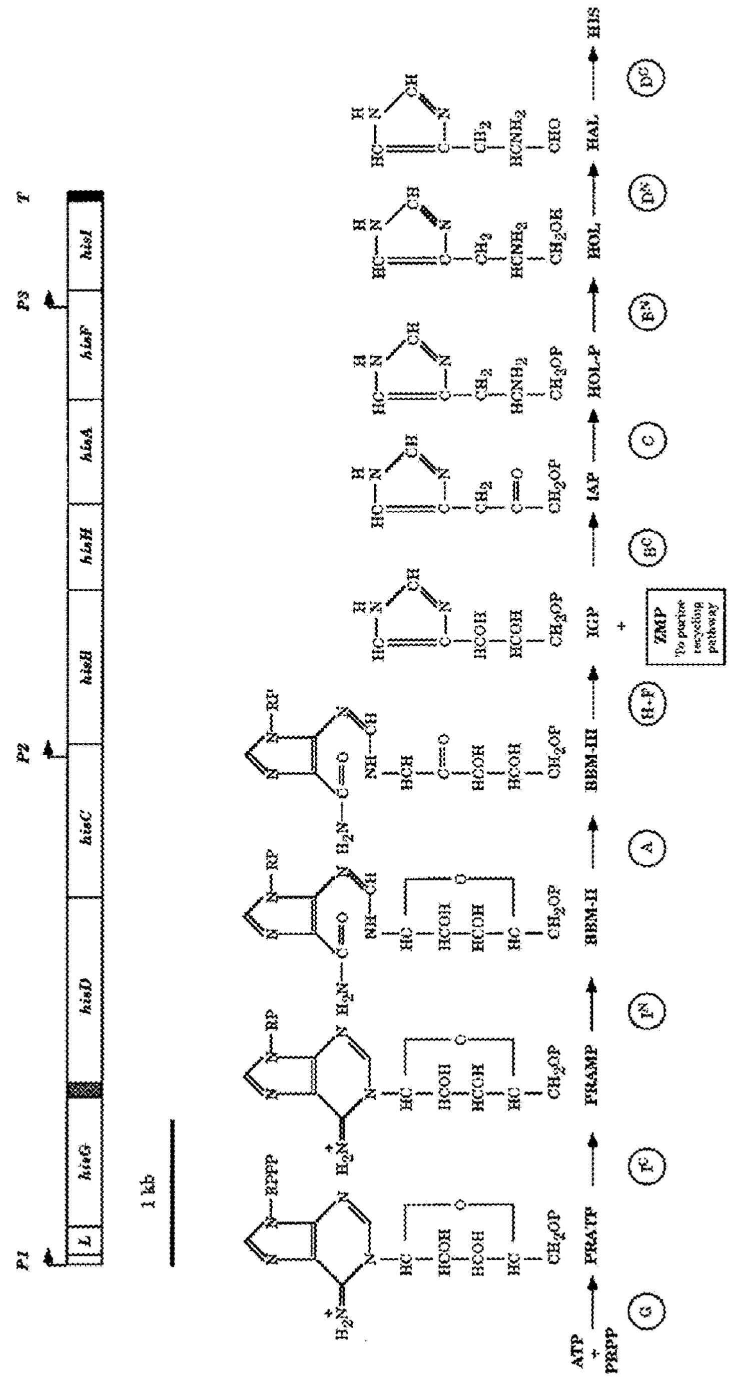
FIG. 54 depicts an exemplary histidine biosynthesis pathway.
Figure 55:
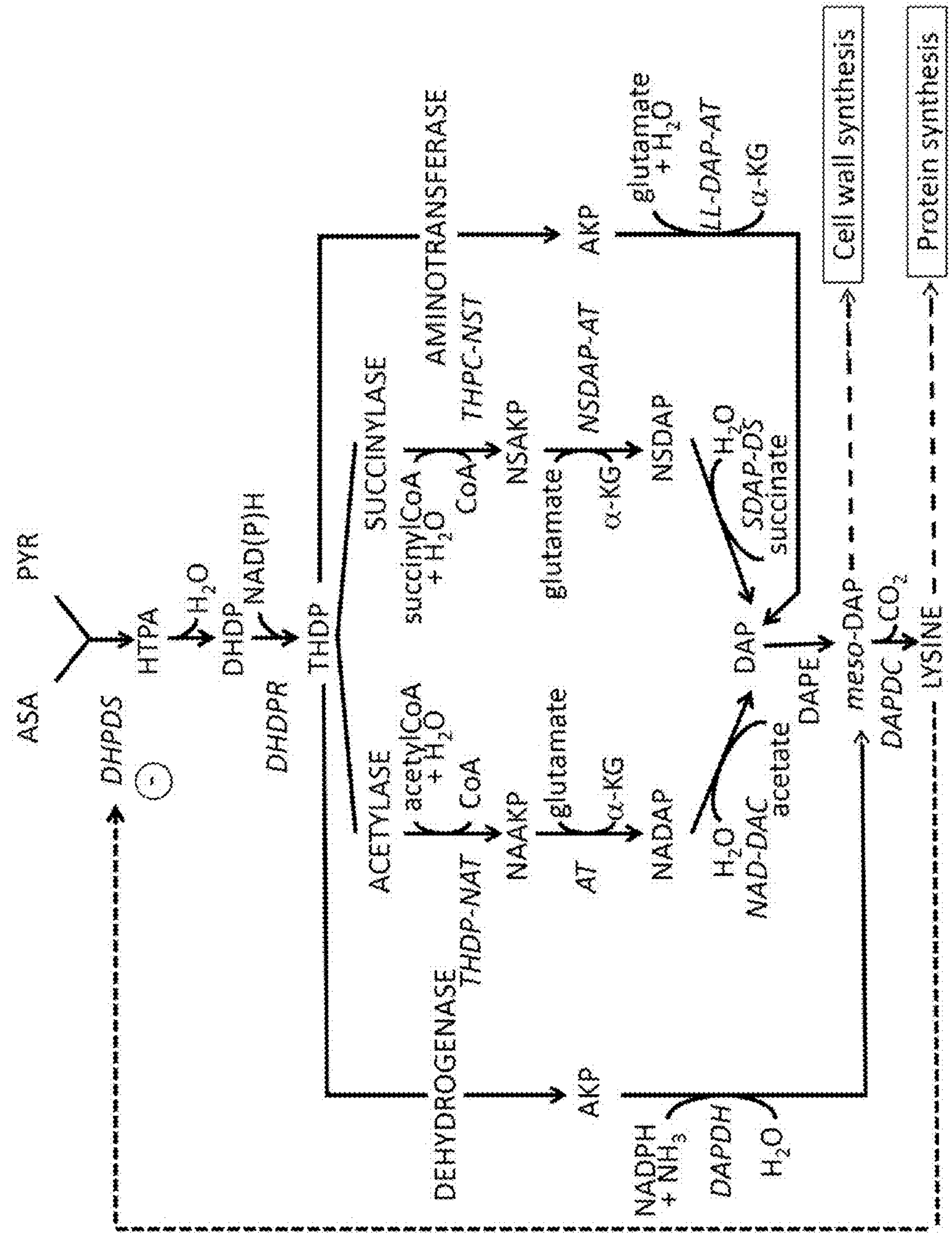
FIG. 55 depicts an exemplary lysine biosynthesis pathway.
Figure 56:
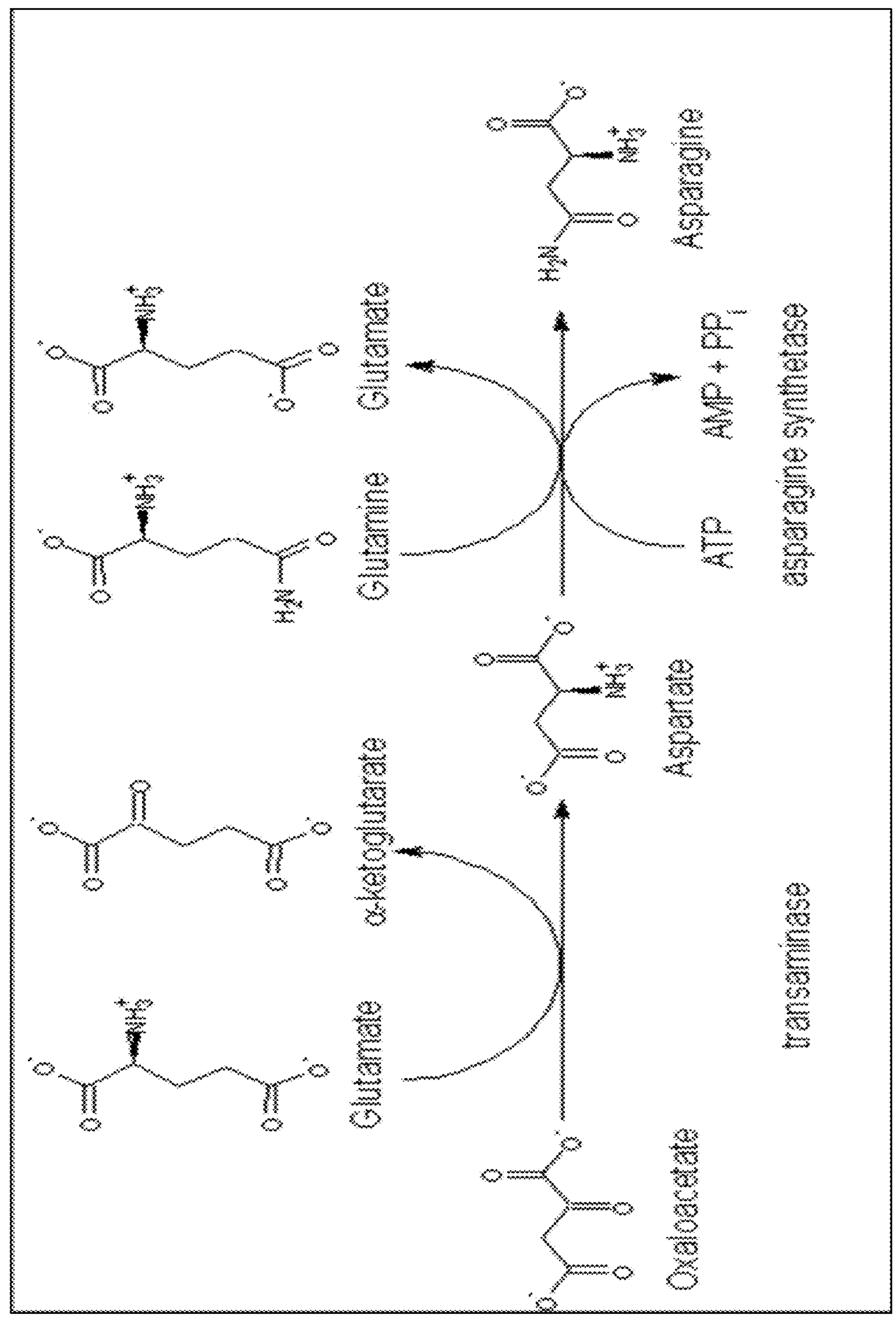
FIG. 56 depicts an exemplary asparagine biosynthesis pathway.
Figure 59:
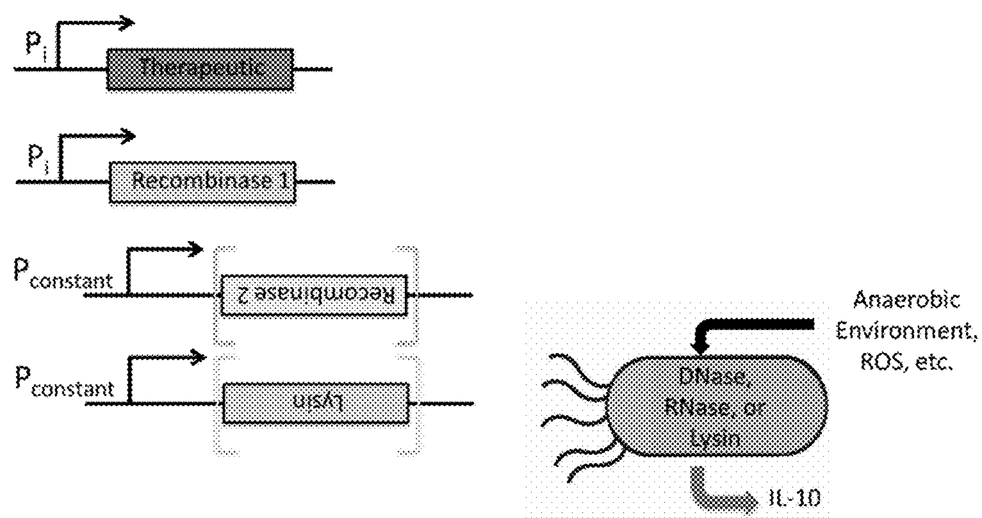
FIG. 59 depicts one non-limiting embodiment of the disclosure, where an exogenous environmental condition or one or more environmental signals activates expression of a heterologous gene and a first recombinase from an inducible promoter or inducible promoters. The recombinase then flips a second recombinase from an inverted orientation to an active conformation. The activated second recombinase flips the toxin gene into an activated conformation, and the natural kinetics of the recombinase create a time delay in expression of the toxin, allowing the heterologous gene to be fully expressed. Once the toxin is expressed, it kills the cell.
Figure 60:
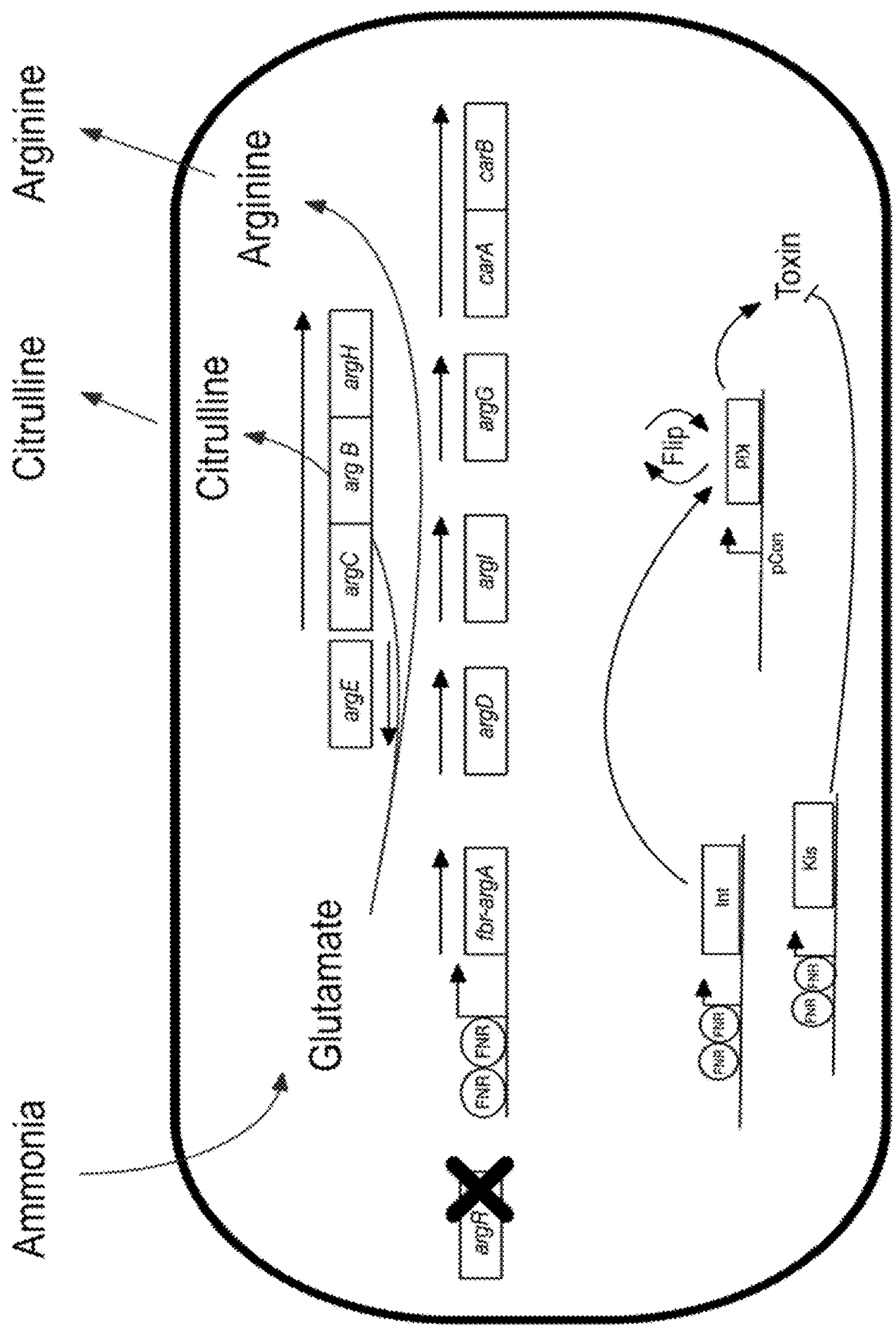
FIG. 60 depicts a synthetic biotic engineered to target urea cycle disorder (UCD) having the kill-switch embodiment described in FIG. 59. In this example, the Int recombinanse and the Kid-Kis toxin-antitoxin system are used in a recombinant bacterial cell for treating UCD. The recombinant bacterial cell is engineered to consume excess ammonia to produce beneficial byproducts to improve patient outcomes. The recombinant bacterial cell also comprises a highly controllable kill switch to ensure safety. In response to a low oxygen environment (e.g., such as that found in the gut), the FNR promoter induces expression of the Int recombinase and also induces expression of the Kis anti-toxin. The Int recombinase causes the Kid toxin gene to flip into an activated conformation, but the presence of the accumulated Kis anti-toxin suppresses the activity of the expressed Kid toxin. In the presence of oxygen (e.g., outside the gut), expression of the anti-toxin is turned off. Since the toxin is constitutively expressed, it continues to accumulate and kills the bacterial cell.
Figure 61:
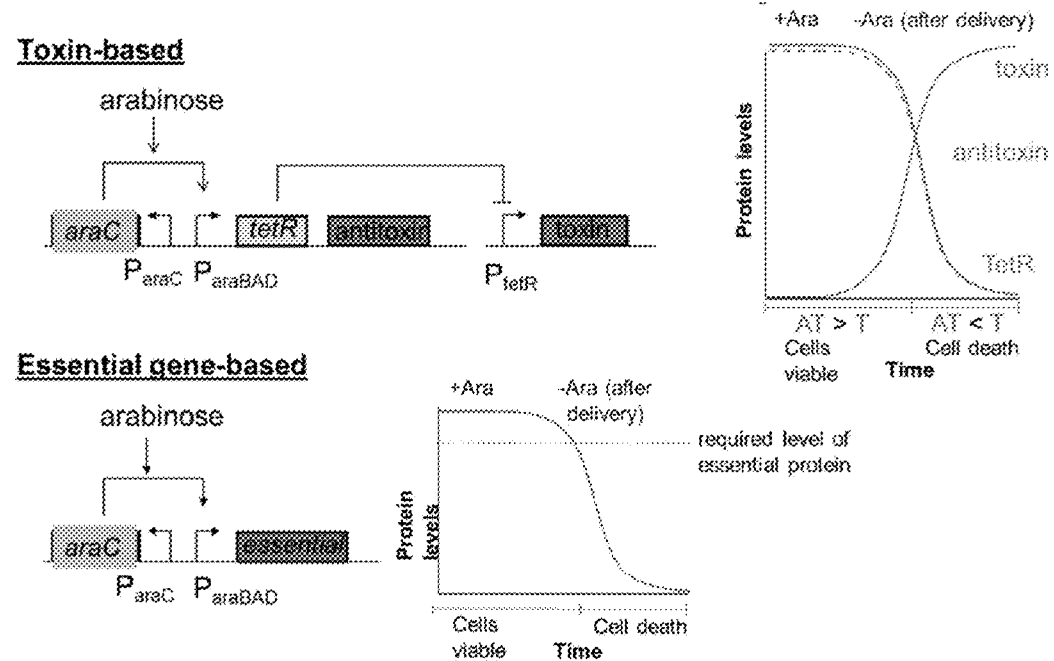
FIG. 61 depicts another non-limiting embodiment of the disclosure, wherein the expression of a heterologous gene is activated by an exogenous environmental signal. In the absence of arabinose, the AraC transcription factor adopts a conformation that represses transcription. In the presence of arabinose, the AraC transcription factor undergoes a conformational change that allows it to bind to and activate the AraBAD promoter, which induces expression of TetR (tet repressor) and an antitoxin. The antitoxin builds up in the recombinant bacterial cell, while TetR prevents expression of a toxin (which is under the control of a promoter having a TetR binding site). However, when arabinose is not present, both the antitoxin and TetR are not expressed. Since TetR is not present to repress expression of the toxin, the toxin is expressed and kills the cell.
Figure 62:
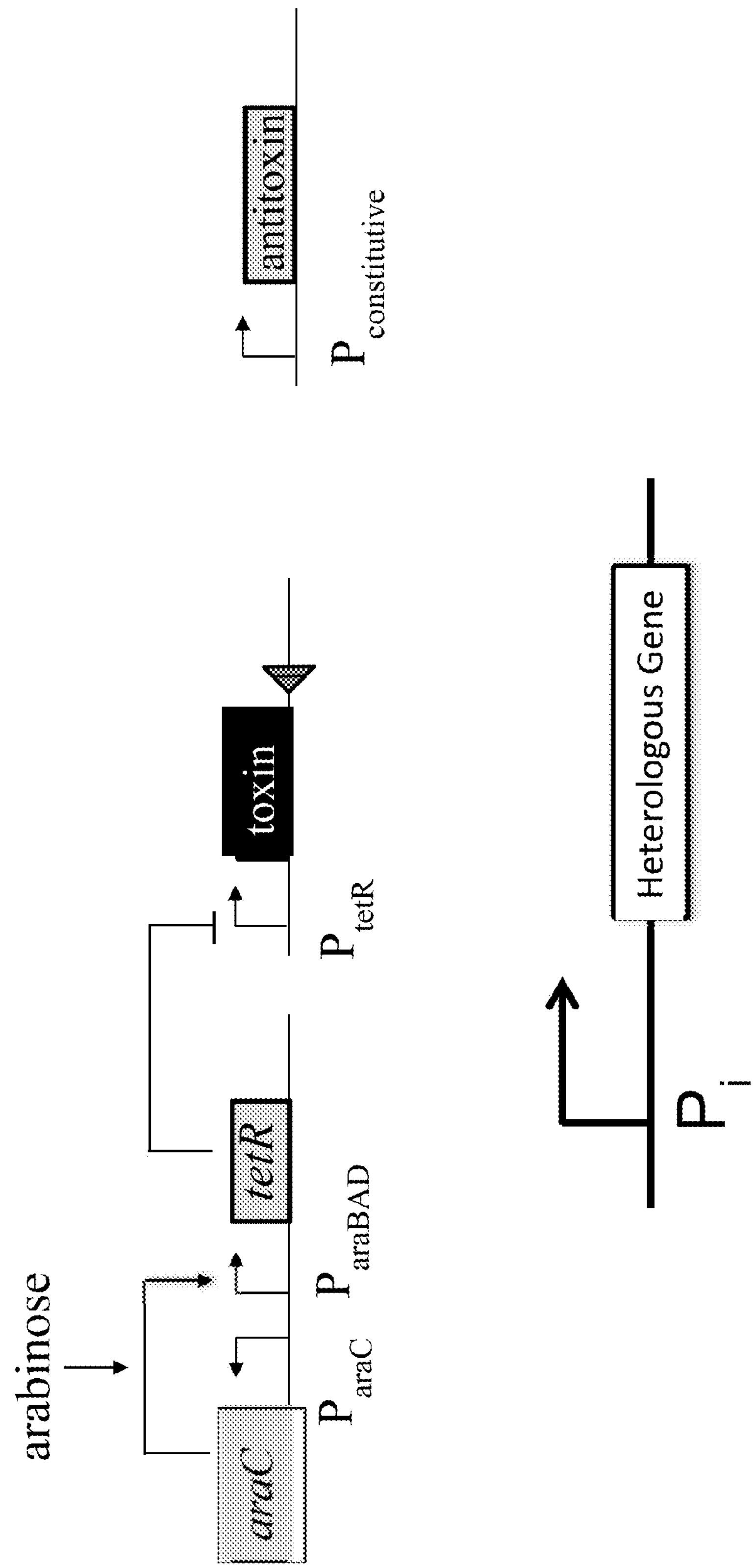
FIG. 62 depicts a non-limiting embodiment of the disclosure, where an anti-toxin is expressed from a constitutive promoter, and expression of a heterologous gene is activated by an exogenous environmental signal. In the absence of arabinose, the AraC transcription factor adopts a conformation that represses transcription. In the presence of arabinose, the AraC transcription factor undergoes a conformational change that allows it to bind to and activate the AraBAD promoter, which induces expression of TetR, thus preventing expression of a toxin. However, when arabinose is not present, TetR is not expressed, and the toxin is expressed, eventually overcoming the antitoxin and killing the cell. The constitutive promoter regulating expression of the anti-toxin should be a weaker promoter than the promoter driving expression of the toxin.

FIG. 51 depicts a bar graph of in vitro arginine levels produced by unmodified Nissle, SYN-UCD201, SYN-UCD202 and SYN-UCD203 under inducing (+ATC) and non-inducing (−ATC) conditions. Both SYN-UCD202 and SYN-UCD203 were capable of producing arginine in vitro as compared to the unmodified Nissle and SYN-UCD201. SYN-UCD203 exhibited lower levels of arginine production under non-inducing conditions as compared to SYN-UCD202.

Figure 24:
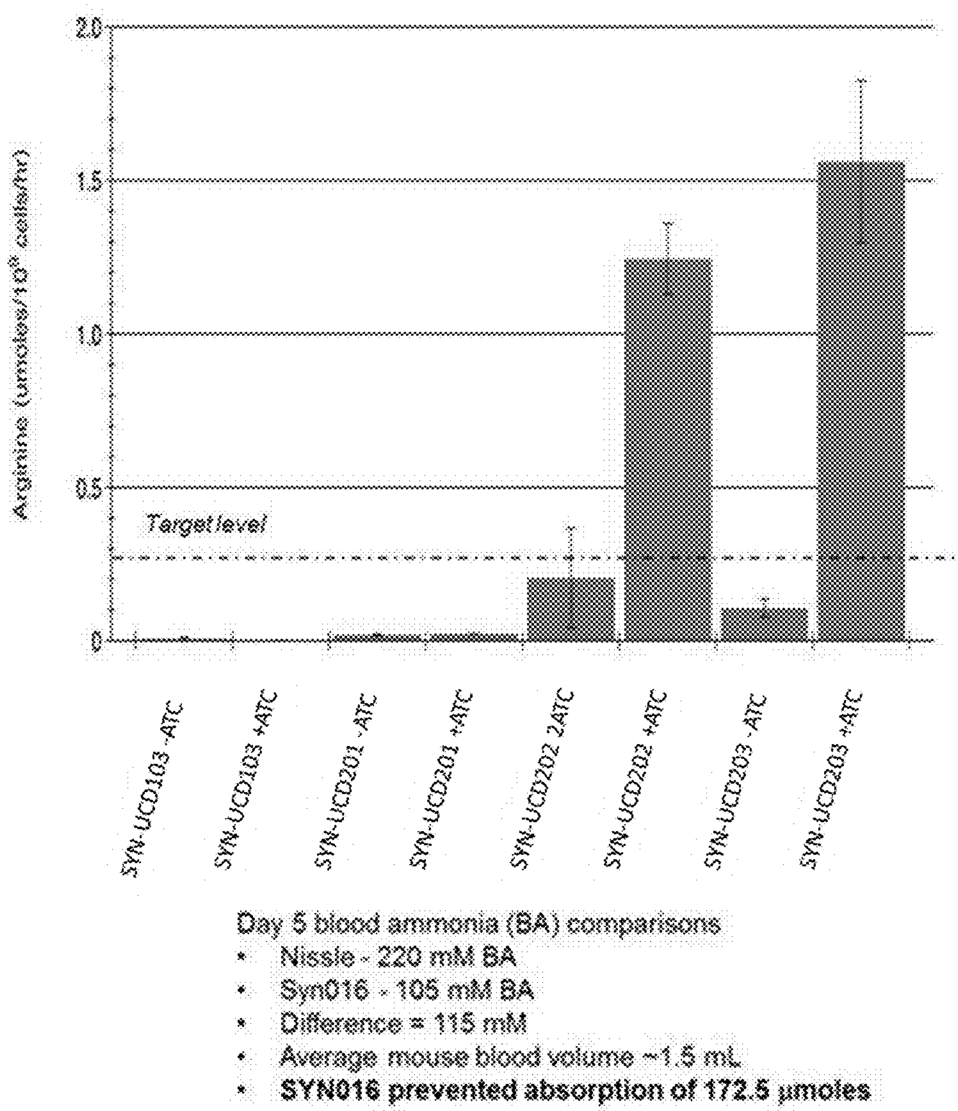
FIG. 24 depicts a bar graph of in vitro arginine levels produced by streptomycin-resistant control Nissle (SYN-UCD103), SYN-UCD201, SYN-UCD202, and SYN-UCD203 under inducing (+ATC) and non-inducing (−ATC) conditions. SYN-UCD201 comprises ΔArgR and no argA$^{fbr}$. SYN-UCD202 comprises ΔArgR and tetracycline-inducible argA$^{fbr}$ on a high-copy plasmid. SYN-UCD203 comprises ΔArgR and tetracycline-driven argA$^{fbr}$ on a low-copy plasmid.

FIG. 24 depicts a bar graph of in vitro arginine levels produced by SYN-UCD103, SYN-UCD201, SYN-UCD202, and SYN-UCD203 under inducing (+ATC) and non-inducing (−ATC) conditions. SYN-UCD201 comprises ΔArgR and no arg$A^{fbr}$. SYN-UCD202 comprises ΔArgR and tetracycline-inducible arg$A^{fbr}$ on a high-copy plasmid. SYN-UCD203 comprises ΔArgR and tetracycline-driven arg$A^{fbr}$ on a low-copy plasmid.

FIG. 25 depicts a bar graph of in vitro levels of arginine and citrulline produced by SYN-UCD103, SYN-UCD104, SYN-UCD204, and SYN-UCD 105 under inducing conditions.

Figure 26:
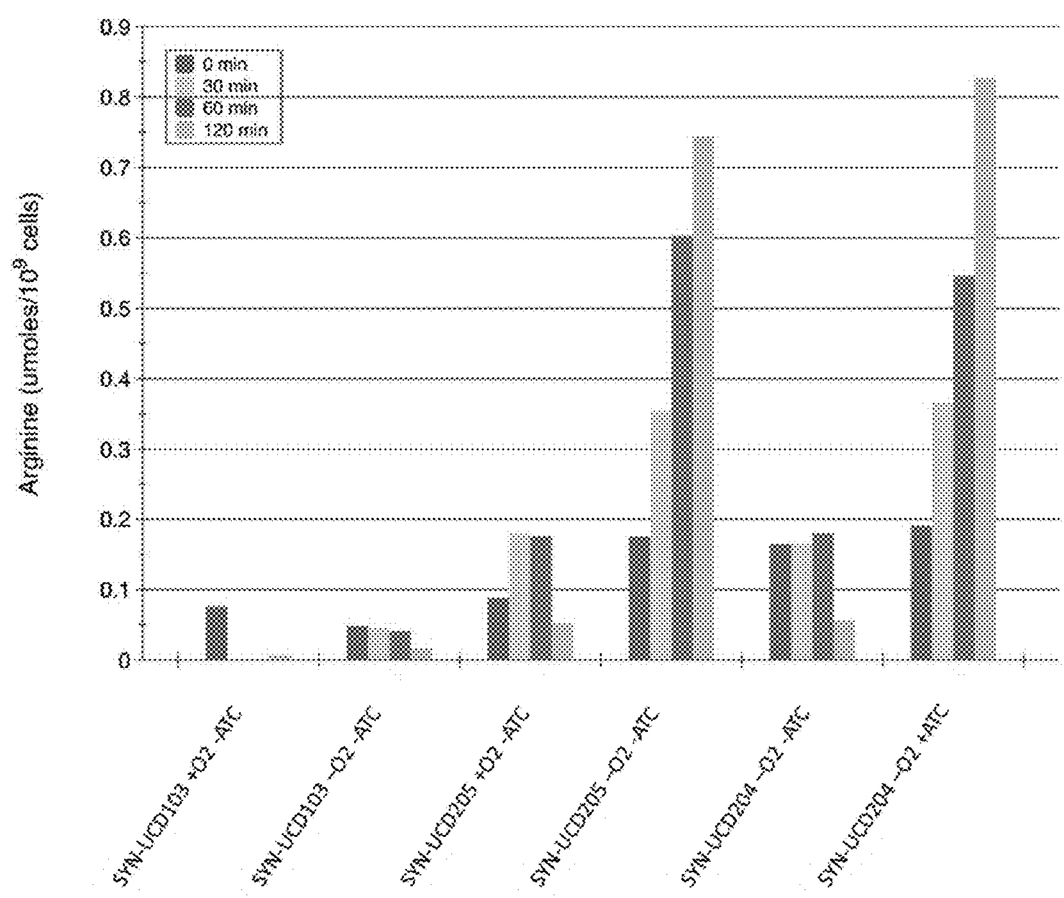
FIG. 26 depicts a bar graph of in vitro arginine levels produced by streptomycin-resistant Nissle (SYN-UCD103), SYN-UCD205, and SYN-UCD204 under inducing (+ATC) and non-inducing (−ATC) conditions, in the presence (+$O_2$) or absence (−$O_2$) of oxygen. SYN-UCD103 is a control Nissle construct. SYN-UCD205 comprises ΔArgR and argA$^{fbr}$ expressed under the control of a FNR-inducible promoter (fnrS2) on a low-copy plasmid. SYN204 comprises ΔArgR and argA$^{fbr}$ expressed under the control of a tetracycline-inducible promoter on a low-copy plasmid.

FIG. 26 depicts a bar graph of in vitro arginine levels produced by SYN-UCD103, SYN-UCD205, and SYN-UCD204 under inducing (+ATC) and non-inducing (−ATC) conditions, in the presence (+$O_2$) or absence (−$O_2$) of oxygen.

FIG. 27 depicts a graph of Nissle residence in vivo. Streptomycin-resistant Nissle was administered to mice via oral gavage without antibiotic pre-treatment. Fecal pellets from six total mice were monitored post-administration to determine the amount of administered Nissle still residing within the mouse gastrointestinal tract. The bars represent the number of bacteria administered to the mice. The line represents the number of Nissle recovered from the fecal samples each day for 10 consecutive days.

FIG. 28A depicts a bar graph of ammonia levels in hyperammonemic mice treated with unmodified control Nissle or SYN-UCD202, a genetically engineered strain in which the Arg repressor gene is deleted and the arg$A^{fbr}$ gene is under the control of a tetracycline-inducible promoter on a high-copy plasmid. FIG. 28B depicts a bar graph showing in vivo efficacy (ammonia consumption) of SYN-UCD204 in the TAA mouse model of hepatic encephalopathy, relative to streptomycin-resistant control Nissle (SYN-UCD103) and vehicle-only controls. FIG. 28C depicts a bar graph of the percent change in blood ammonia concentration between 24-48 hours post-TAA treatment.

Figure 29:
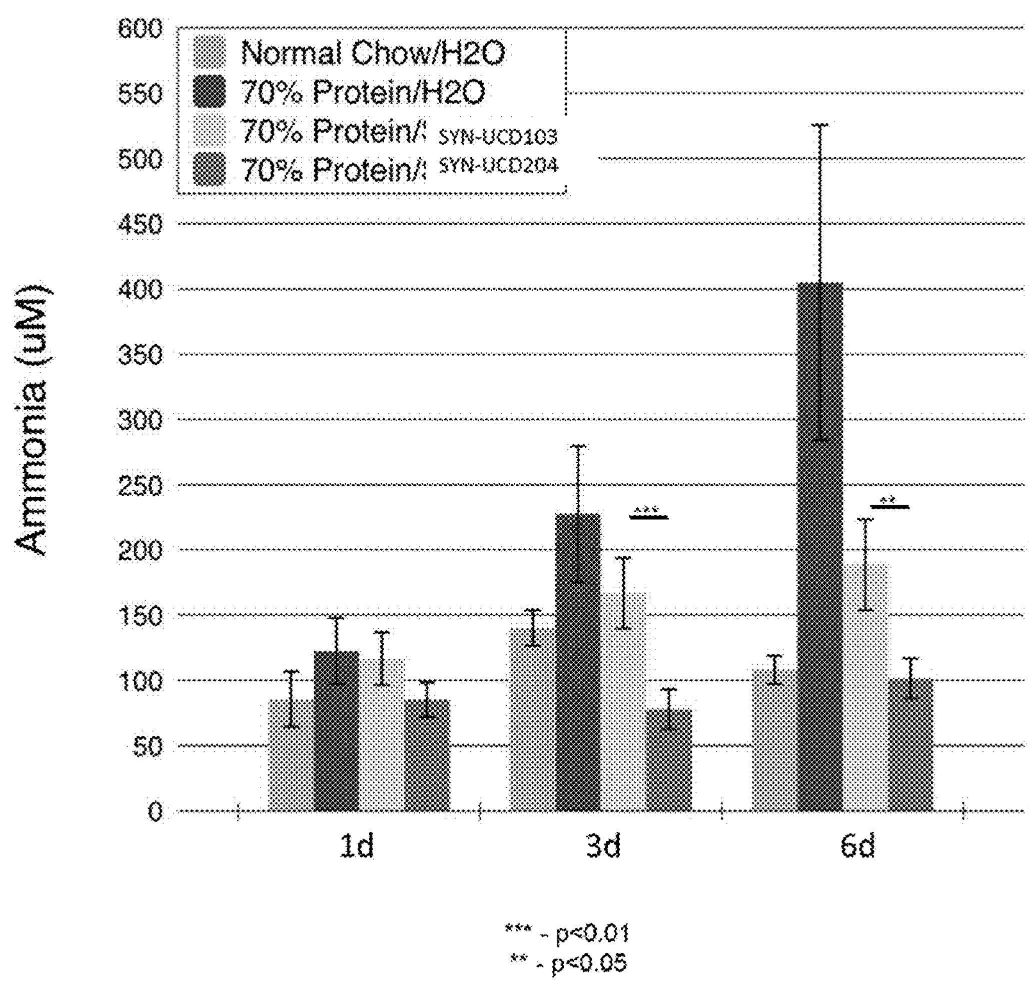
FIG. 29 depicts a bar graph of ammonia levels in hyperammonemic spf$^{ash}$ mice. Fifty-six spf$^{ash}$ mice were separated into four groups. Group 1 was fed normal chow, and groups 2-4 were fed 70% protein chow following an initial blood draw. Groups were gavaged twice daily, with water, streptomycin-resistant Nissle control (SYN-UCD103), or SYN-UCD204, and blood was drawn 4 hours following the first gavage. SYN-UCD204, comprising ΔArgR and $argA^{fbr}$ expressed under the control of a tetracycline-inducible promoter on a low-copy plasmid, significantly reduced blood ammonia to levels below the hyperammonemia threshold.

FIG. 29 depicts a bar graph of ammonia levels in hyperammonemic $spf^{ash}$ micetreated with streptomycin-resistant Nissle control (SYN-UCD103) or SYN-UCD204.

Intracellular arginine and secreted (supernatant) arginine production in the genetically engineered bacteria in the presence or absence an ATC or anaerobic inducer is measured and compared to control bacteria of the same strain under the same conditions.

Total arginine production over six hours in the genetically engineered bacteria in the genetically engineered bacteria in the presence or absence an ATC or anaerobic inducer is measured and compared to control bacteria of the same strain under the same conditions Example 17

Efficacy of Genetically Engineered Bacteria in a Mouse Model of Hyperammonemia and Acute Liver Failure Wild-type C57BL6/J mice are treated with thiol acetamide (TAA), which causes acute liver failure and hyperammonemia (Nicaise et al., 2008). Mice are treated with unmodified control Nissle bacteria or Nissle bacteria engineered to produce high levels of arginine or citrulline as described above.

On day 1, 50 mL of the bacterial cultures are grown overnight and pelleted. The pellets are resuspended in 5 mL of PBS at a final concentration of approximately $10^{11}$ CFU/mL. Blood ammonia levels in mice are measured by mandibular bleed, and ammonia levels are determined by the PocketChem Ammonia Analyzer (Arkray). Mice are gavaged with 100 μL of bacteria (approximately $10^{10}$ CFU). Drinking water for the mice is changed to contain 0.1 mg/mL anhydrotetracycline (ATC) and 5% sucrose for palatability.

On day 2, the bacterial gavage solution is prepared as described above, and mice are gavaged with 100 μL of bacteria. The mice continue to receive drinking water containing 0.1 mg/mL ATC and 5% sucrose.

On day 3, the bacterial gavage solution is prepared as described above, and mice are gavaged with 100 μL of bacteria. The mice continue to receive drinking water containing 0.1 mg/mL ATC and 5% sucrose. Mice receive an intraperitoneal (IP) injection of 100 μL of TAA (250 mg/kg body weight in 0.5% NaCl).

On day 4, the bacterial gavage solution is prepared as described above, and mice are gavaged with 100 μL of bacteria. The mice continue to receive drinking water containing 0.1 mg/mL ATC and 5% sucrose. Mice receive another IP injection of 100 μL of TAA (250 mg/kg body weight in 0.5% NaCl). Blood ammonia levels in the mice are measured by mandibular bleed, and ammonia levels are determined by the PocketChem Ammonia Analyzer (Arkray).

On day 5, blood ammonia levels in mice are measured by mandibular bleed, and ammonia levels are determined by the PocketChem Ammonia Analyzer (Arkray). Fecal pellets are collected from mice to determine arginine content by liquid chromatography-mass spectrometry (LC-MS). Ammonia levels in mice treated with genetically engineered Nissle and unmodified control Nissle are compared.

Example 18

Efficacy of Genetically Engineered Bacteria in a Mouse Model of Hyperammonemia and UCD Ornithine transcarbamylase is urea cycle enzyme, and mice comprising an spf-ash mutation exhibit partial ornithine transcarbamylase deficiency, which serves as a model for human UCD. Mice are treated with unmodified control Nissle bacteria or Nissle bacteria engineered to produce high levels of arginine or citrulline as described above.

60 spf-ash mice were treated with the genetically engineered bacteria of the invention (SYN-UCD103, SYN-UCD204) or H2O control at 100 ul PO QD: H2O control, normal chow (n=15); H2O control, high protein chow (n=15); SYN-UCD103, high protein chow (n=15); SYN-UCD204, high protein chow (n=15). On Day 1, mice were weighed and sorted into groups to minimize variance in mouse weight per cage. Mice were gavaged and water with 20 mg/L ATC was added to the cages. On day 2, mice were gavaged in the morning and afternoon. On day 3, mice were gavaged in the morning and weighed, and blood was drawn 4 h post-dosing to obtain baseline ammonia levels. Mice were gavaged in the afternoon and chow changed to 70% protein chow. On day 4, mice were gavaged in the morning and afternoon. On day 5, mice were gavaged in the morning and weighed, and blood was drawn 4 h post-dosing to obtain ammonia levels. On days 6 and 7, mice were gavaged in the morning. On day 8, mice were gavaged in the morning and weighed, and blood was drawn 4 h post-dosing to obtain ammonia levels. On day 9, mice were gavaged in the morning and afternoon. On day 10, mice were gavaged in the morning and weighed, and blood was drawn 4 h post-dosing to obtain ammonia levels. On day 12, mice were gavaged in the morning and afternoon. On day 13, mice were gavaged in the morning and weighed, and blood was drawn 4 h post-dosing to obtain ammonia levels. Blood ammonia levels, body weight, and survival rates are analyzed (FIG. 29).

Example 19

Nissle Residence

Unmodified *E. coli* Nissle and the genetically engineered bacteria of the invention may be destroyed, e.g., by defense factors in the gut or blood serum. The residence time of bacteria in vivo may be calculated. A non-limiting example using a streptomycin-resistant strain of *E. coli* Nissle is described below. In alternate embodiments, residence time is calculated for the genetically engineered bacteria of the invention.

C57BL/6 mice were acclimated in the animal facility for 1 week. After one week of acclimation (i.e., day 0), streptomycin-resistant Nissle (SYN-UCD103) was administered to the mice via oral gavage on days 1-3. Mice were not pre-treated with antibiotic. The amount of bacteria administered, i.e., the inoculant, is shown in Table 4. In order to determine the CFU of the inoculant, the inoculant was serially diluted, and plated onto LB plates containing streptomycin (300 pg/ml). The plates were incubated at 37° C. overnight, and colonies were counted.

TABLE 4

| CFU administered via oral gavage<br>CFU administered via oral gavage | | | |
|---|---|---|---|
| Strain | Day 1 | Day 2 | Day 3 |
| SYN-UCD103 | 1.30E+08 | 8.50E+08 | 1.90E+09 |

On days 2-10, fecal pellets were collected from up to 6 mice (ID NOs. 1-6; Table 5). The pellets were weighed in tubes containing PBS and homogenized. In order to determine the CFU of Nissle in the fecal pellet, the homogenized fecal pellet was serially diluted, and plated onto LB plates containing streptomycin (300 pg/ml). The plates were incubated at 37° C. overnight, and colonies were counted.

Fecal pellets from day 1 were also collected and plated on LB plates containing streptomycin (300 μg/ml) to determine if there were any strains native to the mouse gastrointestinal tract that were streptomycin resistant. The time course and amount of administered Nissle still residing within the mouse gastrointestinal tract is shown in Table 5.

FIG. 27 depicts a graph of Nissle residence in vivo. Streptomycin-resistant Nissle was administered to mice via oral gavage without antibiotic pre-treatment. Fecal pellets from six total mice were monitored post-administration to determine the amount of administered Nissle still residing within the mouse gastrointestinal tract. The bars represent the number of bacteria administered to the mice. The line represents the number of Nissle recovered from the fecal samples each day for 10 consecutive days.

TABLE 5

| Nissle residence in vivo | | | | | | | | | |
|---|---|---|---|---|---|---|---|---|---|
| ID | Day 2 | Day 3 | Day 4 | Day 5 | Day 6 | Day 7 | Day 8 | Day 9 | Day 10 |
| 1 | 2.40E+05 | 6.50E+03 | 6.00E+04 | 2.00E+03 | 9.10E+03 | 1.70E+03 | 4.30E+03 | 6.40E+03 | 2.77E+03 |
| 2 | 1.00E+05 | 1.00E+04 | 3.30E+04 | 3.00E+03 | 6.00E+03 | 7.00E+02 | 6.00E+02 | 0.00E+00 | 0.00E+00 |
| 3 | 6.00E+04 | 1.70E+04 | 6.30E+04 | 2.00E+02 | 1.00E+02 | 2.00E+02 | 0.00E+00 | 0.00E+00 | 0.00E+00 |
| 4 | 3.00E+04 | 1.50E+04 | 1.10E+05 | 3.00E+02 | 1.50E+03 | 1.00E+02 | | 0.00E+00 | 0.00E+00 |
| 5 | | 1.00E+04 | 3.00E+05 | 1.50E+04 | 3.10E+04 | 3.60E+03 | | 0.00E+00 | 0.00E+00 |
| 6 | | 1.00E+06 | 4.00E+05 | 2.30E+04 | 1.50E+03 | 1.40E+03 | 4.20E+03 | 1.00E+02 | 0.00E+00 |
| Avg | 1.08E+05 | 1.76E+05 | 1.61E+05 | 7.25E+03 | 8.20E+03 | 1.28E+03 | 2.28E+03 | 1.08E+03 | 4.62E+02 |

The invention claimed is:

1. A genetically engineered bacterium comprising an arginine regulon, wherein the bacterium comprises a gene encoding an arginine feedback resistant N-acetylglutamate synthetase ($ArgA^{fbr}$), wherein the $ArgA^{fbr}$ has reduced arginine feedback inhibition as compared to a wild-type N-acetylglutamate synthetase from the same bacterial subtype under the same conditions and wherein expression of the gene encoding $ArgA^{fbr}$ is controlled by a promoter that is induced by low-oxygen or anaerobic conditions; and wherein the bacterium has been genetically engineered to lack a functional ArgR.

2. The bacterium of claim 1, wherein each copy of a functional argR gene normally present in a corresponding wild-type bacterium has been deleted.

3. The bacterium of claim 1, wherein each copy of a functional argG gene normally present in a corresponding wild-type bacterium has been independently deleted or rendered inactive by one or more nucleotide deletions, insertions or substitutions.

4. The bacterium of claim 3, wherein each copy of the functional argG gene normally present in a corresponding wild-type bacterium has been deleted.

5. The bacterium of claim 1, wherein under low-oxygen or anaerobic conditions, the transcription of each gene that is present in an operon comprising a functional ARG box and which encodes an arginine biosynthesis enzyme is increased as compared to a corresponding gene in a wild-type bacterium under the same conditions.

6. The bacterium of claim 1, wherein the promoter that is induced under low-oxygen or anaerobic conditions is an FNR promoter.

7. The bacterium of claim 1, wherein the arginine feedback resistant N-acetylglutamate synthetase gene has a DNA sequence selected from:

a) SEQ ID NO:28, and b) a DNA sequence that, but for the redundancy of the genetic code, encodes the same polypeptide as encoded by SEQ ID NO:28.

8. The bacterium of claim 1, wherein the bacterium is a non-pathogenic bacterium.

9. The bacterium of claim 1, wherein the bacterium is a probiotic bacterium.

10. The bacterium of claim 1, wherein the bacterium is selected from the group consisting of *Bacteroides, Bifidobacterium, Clostridium, Escherichia, Lactobacillus*, and *Lactococcus*.

11. The bacterium of claim 1, wherein the bacterium is *Escherichia coli* strain Nissle.

12. The bacterium of claim 1, wherein the gene encoding the arginine feedback resistant N-acetylglutamate synthetase ($ArgA^{fbr}$) is present on a plasmid in the bacterium and operably linked on the plasmid to the promoter that is induced under low-oxygen or anaerobic conditions.

13. The bacterium of claim 1, wherein the gene encoding the arginine feedback resistant N-acetylglutamate synthetase ($ArgA^{fbr}$) is present in the bacterial chromosome and is operably linked in the chromosome to the promoter that is induced under low-oxygen or anaerobic conditions.

14. The bacterium of claim 1, wherein the bacterium is an auxotroph in a gene that is complemented when the bacterium is present in a mammalian gut.

15. The bacterium of claim 14, wherein the mammalian gut is a human gut.

16. A pharmaceutically acceptable composition comprising a genetically engineered bacterium comprising an arginine regulon, wherein the bacterium comprises a gene encoding an arginine feedback resistant N-acetylglutamate synthetase ($ArgA^{fbr}$), wherein the $ArgA^{fbr}$ has reduced arginine feedback inhibition as compared to a wild-type N-acetylglutamate synthetase from the same bacterial subtype under the same conditions, wherein expression of the gene encoding $ArgA^{fbr}$ is controlled by a promoter that is induced by low-oxygen or anaerobic conditions; and wherein the bacterium has been genetically engineered to lack a functional ArgR; and a pharmaceutically acceptable carrier.

17. The bacterium of claim 14, wherein the bacterium is a thyA or dapB auxotroph.

18. The bacterium of claim 1, wherein the bacterium comprises an antibiotic resistance gene.

* * * * *

UNITED STATES PATENT AND TRADEMARK OFFICE
CERTIFICATE OF CORRECTION

PATENT NO. : 9,487,764 B2
APPLICATION NO. : 14/960333
DATED : November 8, 2016
INVENTOR(S) : Dean Falb et al.

It is certified that error appears in the above-identified patent and that said Letters Patent is hereby corrected as shown below:

On the Title Page

Item (71) Applicant, please replace "Synlogic, Inc., Cambridge MA (US)" with --Synlogic Operating Company, Inc., Cambridge, MA (US)--

Signed and Sealed this
Second Day of April, 2019

Andrei Iancu
*Director of the United States Patent and Trademark Office*

SEQUENCE LISTING

<160> NUMBER OF SEQ ID NOS: 40

<210> SEQ ID NO 1
<211> LENGTH: 60
<212> TYPE: DNA
<213> ORGANISM: Escherichia coli

<400> SEQUENCE: 1
gcaaaaaaac agaataaaaa tacaataatt tcgaataatc atgcaaagag gtgtaccgtg 60

<210> SEQ ID NO 2
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2
gcaaaaaaac actttaaaaa cttaataatt tcctttaatc acttaaagag gtgtaccgtg 60

<210> SEQ ID NO 3
<211> LENGTH: 76
<212> TYPE: DNA
<213> ORGANISM: Escherichia coli

<400> SEQUENCE: 3
agacttgcaa atgaataatc atccatatag attgaatttt aattcattaa ggcgttagcc 60
acaggaggga tctatg 76

```
<210> SEQ ID NO 4
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

agacttgcaa acttatactt atccatatag attttgtttt aatttgttaa ggcgttagcc     60

acaggaggga tctatg                                                     76


<210> SEQ ID NO 5
<211> LENGTH: 160
<212> TYPE: DNA
<213> ORGANISM: Escherichia coli

<400> SEQUENCE: 5

tcattgttga cacacctctg gtcatgatag tatcaatatt catgcagtat ttatgaataa     60

aaatacacta acgttgagcg taataaaacc caccagccgt aaggtgaatg ttttacgttt    120

aacctggcaa ccagacataa gaaggtgaat agccccgatg                          160


<210> SEQ ID NO 6
<211> LENGTH: 160
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

tcattgttga cacacctctg gtcatgatag tatcaaactt catgggatat ttatctttaa     60

aaatacttga acgttgagcg taataaaacc caccagccgt aaggtgaatg ttttacgttt    120

aacctggcaa ccagacataa gaaggtgaat agccccgatg                          160


<210> SEQ ID NO 7
<211> LENGTH: 160
<212> TYPE: DNA
<213> ORGANISM: Escherichia coli

<400> SEQUENCE: 7

catcggggct attcaccttc ttatgtctgg ttgccaggtt aaacgtaaaa cattcacctt     60

acggctggtg ggttttatta cgctcaacgt tagtgtattt ttattcataa atactgcatg    120

aatattgata ctatcatgac cagaggtgtg tcaacaatga                          160


<210> SEQ ID NO 8
<211> LENGTH: 160
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

catcggggct attcaccttc ttatgtctgg ttgccaggtt aaacgtaaaa cattcacctt     60

acggctggtg ggttttatta cgctcaacgt tcaagtattt ttaaagataa atatcccatg    120

aagtttgata ctatcatgac cagaggtgtg tcaacaatga                          160


<210> SEQ ID NO 9
<211> LENGTH: 81
```

<212> TYPE: DNA
<213> ORGANISM: Escherichia coli

<400> SEQUENCE: 9
agcagatttg cattgattta cgtcatcatt gtgaattaat atgcaaataa agtgagtgaa 60
tattctctgg agggtgtttt g 81

<210> SEQ ID NO 10
<211> LENGTH: 81
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 10
agcagatttg cattgattta cgtcatcatt gtcttttaat atcttaataa ctggagtgac 60
gtttctctgg agggtgtttt g 81

<210> SEQ ID NO 11
<211> LENGTH: 88
<212> TYPE: DNA
<213> ORGANISM: Escherichia coli

<400> SEQUENCE: 11
tttctgattg ccattcagtg attttttatg catattttgt gattataatt tcatatttat 60
ttatgcgtaa cagggtgatc atgagatg 88

<210> SEQ ID NO 12
<211> LENGTH: 88
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 12
tttctgattg ccattcagtc ttttttact tatattttgt ctttataatc ttatatttat 60
ttatgcgtaa cagggtgatc atgagatg 88

<210> SEQ ID NO 13
<211> LENGTH: 219
<212> TYPE: DNA
<213> ORGANISM: Escherichia coli

<400> SEQUENCE: 13
ctaatcacgt gaatgaatat ccagttcact ttcatttgtt gaatactttt accttctcct 60
gctttccctt aagcgcatta ttttacaaaa aacacactaa actcttcctg tctccgataa 120
aagatgatta aatgaaaact catttatttt gcataaaaat tcagtgaaag cagaaatcca 180
ggctcatcat cagttaatta agcagggtgt tattttatg 219

<210> SEQ ID NO 14
<211> LENGTH: 219
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14
ctaatcacct taatgaatct tcagttcact ttcatttgtt gaatactttt accttctcct 60
gctttccctt aagcgcatta ttttacaaaa aacacactaa actcttcctg tctccgataa 120
aagatgatct tatgaaaacc tttttatttc ttataaaaat cttgtgaaag cagaaatcca 180
ggctcatcat cagttaatta agcagggtgt tattttatg 219

<210> SEQ ID NO 15
<211> LENGTH: 233
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15
cctgaaacgt ggcaaattct actcgttttg ggtaaaaaat gcaaatactg ctgggatttg 60
gtgtaccgag acgggacgta aaatctgcag gcattatagt gatccacgcc acattttgtc 120
aacgtttatt gctaatcatt gacggctagc tcagtcctag gtacagtgct agcacccgtt 180
tttttgggct agaaataatt ttgtttaact ttaagaagga gatatacata ccc 233

<210> SEQ ID NO 16
<211> LENGTH: 117
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16
atccccatca ctcttgatgg agatcaattc cccaagctgc tagagcgtta ccttgccctt 60
aaacattagc aatgtcgatt tatcagaggg ccgacaggct cccacaggag aaaaccg 117

<210> SEQ ID NO 17
<211> LENGTH: 108
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17
ctcttgatcg ttatcaattc ccacgctgtt tcagagcgtt accttgccct taaacattag 60
caatgtcgat ttatcagagg gccgacaggc tcccacagga gaaaaccg 108

<210> SEQ ID NO 18
<211> LENGTH: 290
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18
gtcagcataa caccctgacc tctcattaat tgttcatgcc gggcggcact atcgtcgtcc 60
ggccttttcc tctcttactc tgctacgtac atctatttct ataaatccgt tcaatttgtc 120 tgtttttgc acaaacatga aatatcagac aattccgtga cttaagaaaa tttatacaaa 180
tcagcaatat accccttaag gagtatataa aggtgaattt gatttacatc aataagcggg 240
gttgctgaat cgttaaggta ggcggtaata gaaaagaaat cgaggcaaaa 290

<210> SEQ ID NO 19

<211> LENGTH: 433
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19

```
cggcccgatc gttgaacata gcggtccgca ggcggcactg cttacagcaa acggtctgta     60

cgctgtcgtc tttgtgatgt gcttcctgtt aggtttcgtc agccgtcacc gtcagcataa    120

caccctgacc tctcattaat tgctcatgcc ggacggcact atcgtcgtcc ggccttttcc    180

tctcttcccc cgctacgtgc atctatttct ataaacccgc tcattttgtc tattttttgc    240

acaaacatga aatatcagac aattccgtga cttaagaaaa tttatacaaa tcagcaatat    300

acccattaag gagtatataa aggtgaattt gatttacatc aataagcggg gttgctgaat    360

cgttaaggta ggcggtaata gaaaagaaat cgaggcaaaa atgtttgttt aactttaaga    420

aggagatata cat                                                       433
```

<210> SEQ ID NO 20
<211> LENGTH: 290
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20

```
gtcagcataa caccctgacc tctcattaat tgctcatgcc ggacggcact atcgtcgtcc     60

ggccttttcc tctcttcccc cgctacgtgc atctatttct ataaacccgc tcattttgtc    120

tattttttgc acaaacatga aatatcagac aattccgtga cttaagaaaa tttatacaaa    180

tcagcaatat acccattaag gagtatataa aggtgaattt gatttacatc aataagcggg    240

gttgctgaat cgttaaggta ggcggtaata gaaaagaaat cgaggcaaaa               290
```

<210> SEQ ID NO 21
<211> LENGTH: 173
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21

```
atttcctctc atcccatccg ggtgagagt  cttttccccc gacttatggc tcatgcatgc     60

atcaaaaaag atgtgagctt gatcaaaaac aaaaaatatt tcactcgaca ggagtattta    120

tattgcgccc gttacgtggg cttcgactgt aaatcagaaa ggagaaaaca cct           173
```

<210> SEQ ID NO 22
<211> LENGTH: 305
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

```
gtcagcataa caccctgacc tctcattaat tgttcatgcc gggcggcact atcgtcgtcc     60

ggccttttcc tctcttactc tgctacgtac atctatttct ataaatccgt tcaatttgtc    120

tgtttttttgc acaaacatga aatatcagac aattccgtga cttaagaaaa tttatacaaa    180
```

```
tcagcaatat accccttaag gagtatataa aggtgaattt gatttacatc aataagcggg    240

gttgctgaat cgttaaggat ccctctagaa ataattttgt ttaactttaa gaaggagata    300

tacat                                                                305


<210> SEQ ID NO 23
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

catttcctct catcccatcc ggggtgagag tcttttcccc cgacttatgg ctcatgcatg     60

catcaaaaaa gatgtgagct tgatcaaaaa caaaaaatat ttcactcgac aggagtattt    120

atattgcgcc cggatccctc tagaaataat tttgtttaac tttaagaagg agatatacat    180


<210> SEQ ID NO 24
<211> LENGTH: 199
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

agttgttctt attggtggtg ttgctttatg gttgcatcgt agtaaatggt tgtaacaaaa     60

gcaatttttc cggctgtctg tatacaaaaa cgccgtaaag tttgagcgaa gtcaataaac    120

tctctaccca ttcagggcaa tatctctctt ggatccctct agaaataatt ttgtttaact    180

ttaagaagga gatatacat                                                 199


<210> SEQ ID NO 25
<211> LENGTH: 207
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

agttgttctt attggtggtg ttgctttatg gttgcatcgt agtaaatggt tgtaacaaaa     60

gcaatttttc cggctgtctg tatacaaaaa cgccgcaaag tttgagcgaa gtcaataaac    120

tctctaccca ttcagggcaa tatctctctt ggatccaaag tgaactctag aaataatttt    180

gtttaacttt aagaaggaga tatacat                                        207


<210> SEQ ID NO 26
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

tcgtctttgt gatgtgcttc ctgttaggtt tcgtcagccg tcaccgtcag cataacaccc     60

tgacctctca ttaattgctc atgccggacg gcactatcgt cgtccggcct tttcctctct    120

tcccccgcta cgtgcatcta tttctataaa cccgctcatt ttgtctattt tttgcacaaa    180
```

```
catgaaatat cagacaattc cgtgacttaa gaaaatttat acaaatcagc aatataccca    240

ttaaggagta tataaaggtg aatttgattt acatcaataa gcggggttgc tgaatcgtta    300

aggtagaaat gtgatctagt tcacatttgc ggtaatagaa aagaaatcga ggcaaaaatg    360

tttgtttaac tttaagaagg agatatacat                                     390


<210> SEQ ID NO 27
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

agttgttctt attggtggtg ttgctttatg gttgcatcgt agtaaatggt tgtaacaaaa     60

gcaatttttc cggctgtctg tatacaaaaa cgccgcaaag tttgagcgaa gtcaataaac    120

tctctaccca ttcagggcaa tatctctcaa atgtgatcta gttcacattt tttgtttaac    180

tttaagaagg agatatacat                                                200


<210> SEQ ID NO 28
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

atggtaaagg aacgtaaaac cgagttggtc gagggattcc gccattcggt tccctgtatc     60

aatacccacc ggggaaaaac gtttgtcatc atgctcggcg gtgaagccat tgagcatgag    120

aatttctcca gtatcgttaa tgatatcggg ttgttgcaca gcctcggcat ccgtctggtg    180

gtggtctatg gcgcacgtcc gcagatcgac gcaaatctgg ctgcgcatca ccacgaaccg    240

ctgtatcaca agaatatacg tgtgaccgac gccaaaacac tggaactggt gaagcaggct    300

gcgggaacat tgcaactgga tattactgct cgcctgtcga tgagtctcaa taacacgccg    360

ctgcagggcg cgcatatcaa cgtcgtcagt ggcaatttta ttattgccca gccgctgggc    420

gtcgatgacg gcgtggatta ctgccatagc gggcgtatcc ggcggattga tgaagacgcg    480

atccatcgtc aactggacag cggtgcaata gtgctaatgg ggccggtcgc tgtttcagtc    540

actggcgaga gctttaacct gacctcggaa gagattgcca ctcaactggc catcaaactg    600

aaagctgaaa agatgattgg tttttgctct tcccagggcg tcactaatga cgacggtgat    660

attgtctccg aacttttccc taacgaagcg caagcgcggg tagaagccca ggaagagaaa    720

ggcgattaca actccggtac ggtgcgcttt ttgcgtggcg cagtgaaagc ctgccgcagc    780

ggcgtgcgtc gctgtcattt aatcagttat caggaagatg gcgcgctgtt gcaagagttg    840

ttctcacgcg acggtatcgg tacgcagatt gtgatggaaa gcgccgagca gattcgtcgc    900

gcaacaatca acgatattgg cggtattctg gagttgattc gcccactgga gcagcaaggt    960

attctggtac gccgttctcg cgagcagctg gagatggaaa tcgacaaatt caccattatt   1020

cagcgcgata acacgactat tgcctgcgcc gcgctctatc cgttcccgga agagaagatt   1080

ggggaaatgg cctgtgtggc agttcacccg gattaccgca gttcatcaag ggtgaagtt    1140

ctgctggaac gcattgccgc tcaggctaag cagagcggct taagcaaatt gtttgtgctg   1200

accacgcgca gtattcactg gttccaggaa cgtggattta ccccagtgga tattgattta   1260
```

ctgcccgaga gcaaaaagca gttgtacaac taccagcgta aatccaaagt gttgatggcg 1320
gatttagggt aa 1332

<210> SEQ ID NO 29
<211> LENGTH: 5417
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29
gtaaaacgac ggccagtgaa ttcgagctcg gtaccatccc catcactctt gatggagatc 60
aattccccaa gctgctagag cgttaccttg cccttaaaca ttagcaatgt cgatttatca 120
gagggccgac aggctcccac aggagaaaac cgatggtaaa ggaacgtaaa accgagttgg 180
tcgagggatt ccgccattcg gttccctgta tcaataccca ccggggaaaa acgtttgtca 240
tcatgctcgg cggtgaagcc attgagcatg agaatttctc cagtatcgtt aatgatatcg 300
ggttgttgca cagcctcggc atccgtctgg tggtggtcta tggcgcacgt ccgcagatcg 360
acgcaaatct ggctgcgcat caccacgaac cgctgtatca caagaatata cgtgtgaccg 420
acgccaaaac actggaactg gtgaagcagg ctgcgggaac attgcaactg gatattactg 480
ctcgcctgtc gatgagtctc aataacacgc cgctgcaggg cgcgcatatc aacgtcgtca 540
gtggcaattt tattattgcc cagccgctgg gcgtcgatga cggcgtggat tactgccata 600
gcgggcgtat ccggcggatt gatgaagacg cgatccatcg tcaactggac agcggtgcaa 660
tagtgctaat ggggccggtc gctgtttcag tcactggcga gagctttaac ctgacctcgg 720
aagagattgc cactcaactg gccatcaaac tgaaagctga aaagatgatt ggtttttgct 780
cttcccaggg cgtcactaat gacgacggtg atattgtctc cgaacttttc cctaacgaag 840
cgcaagcgcg ggtagaagcc caggaagaga aaggcgatta caactccggt acggtgcgct 900
ttttgcgtgg cgcagtgaaa gcctgccgca gcggcgtgcg tcgctgtcat ttaatcagtt 960
atcaggaaga tggcgcgctg ttgcaagagt tgttctcacg cgacggtatc ggtacgcaga 1020
ttgtgatgga aagcgccgag cagattcgtc gcgcaacaat caacgatatt ggcggtattc 1080
tggagttgat tcgcccactg gagcagcaag gtattctggt acgccgttct cgcgagcagc 1140
tggagatgga aatcgacaaa ttcaccatta ttcagcgcga taacacgact attgcctgcg 1200
ccgcgctcta tccgttcccg gaagagaaga ttggggaaat ggcctgtgtg gcagttcacc 1260
cggattaccg cagttcatca aggggtgaag ttctgctgga acgcattgcc gctcaggcta 1320
agcagagcgg cttaagcaaa ttgtttgtgc tgaccacgcg cagtattcac tggttccagg 1380
aacgtggatt taccccagtg gatattgatt tactgcccga gagcaaaaag cagttgtaca 1440
actaccagcg taaatccaaa gtgttgatgg cggatttagg gtaaacagaa taaaaataca 1500
ataatttcga ataatcatgc aaagcttggc gtaatcatgg tcatagctgt ttcctgtgtg 1560
aaattgttat ccgctcacaa ttccacacaa catacgagcc ggaagcatgt acgggttttg 1620
ctgcccgcaa acgggctgtt ctggtgttgc tagtttgtta tcagaatcgc agatccggct 1680
tcaggtttgc cggctgaaag cgctatttct tccagaattg ccatgatttt ttccccacgg 1740
gaggcgtcac tggctcccgt gttgtcggca gctttgattc gataagcagc atcgcctgtt 1800
tcaggctgtc tatgtgtgac tgttgagctg taacaagttg tctcaggtgt tcaatttcat 1860
gttctagttg ctttgtttta ctggtttcac ctgttctatt aggtgttaca tgctgttcat 1920

```
ctgttacatt gtcgatctgt tcatggtgaa cagctttaaa tgcaccaaaa actcgtaaaa   1980
gctctgatgt atctatcttt tttacaccgt tttcatctgt gcatatggac agttttccct   2040
ttgatatcta acggtgaaca gttgttctac ttttgtttgt tagtcttgat gcttcactga   2100
tagatacaag agccataaga acctcagatc cttccgtatt tagccagtat gttctctagt   2160
gtggttcgtt gtttttgcgt gagccatgag aacgaaccat tgagatcatg cttactttgc   2220
atgtcactca aaaattttgc ctcaaaactg gtgagctgaa tttttgcagt taaagcatcg   2280
tgtagtgttt ttcttagtcc gttacgtagg taggaatctg atgtaatggt tgttggtatt   2340
ttgtcaccat tcatttttat ctggttgttc tcaagttcgg ttacgagatc catttgtcta   2400
tctagttcaa cttggaaaat caacgtatca gtcgggcggc ctcgcttatc aaccaccaat   2460
ttcatattgc tgtaagtgtt taaatcttta cttattggtt tcaaaaccca ttggttaagc   2520
cttttaaact catggtagtt attttcaagc attaacatga acttaaattc atcaaggcta   2580
atctctatat ttgccttgtg agttttcttt tgtgttagtt cttttaataa ccactcataa   2640
atcctcatag agtatttgtt ttcaaaagac ttaacatgtt ccagattata ttttatgaat   2700
ttttttaact ggaaaagata aggcaatatc tcttcactaa aaactaattc taatttttcg   2760
cttgagaact tggcatagtt tgtccactgg aaaatctcaa agcctttaac caaaggattc   2820
ctgatttcca cagttctcgt catcagctct ctggttgctt tagctaatac accataagca   2880
ttttccctac tgatgttcat catctgagcg tattggttat aagtgaacga taccgtccgt   2940
tctttccttg tagggttttc aatcgtgggg ttgagtagtg ccacacagca taaaattagc   3000
ttggtttcat gctccgttaa gtcatagcga ctaatcgcta gttcatttgc tttgaaaaca   3060
actaattcag acatacatct caattggtct aggtgatttt aatcactata ccaattgaga   3120
tgggctagtc aatgataatt actagtcctt ttcctttgag ttgtgggtat ctgtaaattc   3180
tgctagacct ttgctggaaa acttgtaaat tctgctagac cctctgtaaa ttccgctaga   3240
cctttgtgtg ttttttttgt ttatattcaa gtggttataa tttatagaat aaagaaagaa   3300
taaaaaaaga taaaaagaat agatcccagc cctgtgtata actcactact ttagtcagtt   3360
ccgcagtatt acaaaaggat gtcgcaaacg ctgtttgctc ctctacaaaa cagaccttaa   3420
aaccctaaag gcttaagtag caccctcgca agctcgggca aatcgctgaa tattcctttt   3480
gtctccgacc atcaggcacc tgagtcgctg tctttttcgt gacattcagt tcgctgcgct   3540
cacggctctg gcagtgaatg ggggtaaatg gcactacagg cgccttttat ggattcatgc   3600
aaggaaacta cccataatac aagaaaagcc cgtcacgggc ttctcagggc gttttatggc   3660
gggtctgcta tgtggtgcta tctgactttt tgctgttcag cagttcctgc cctctgattt   3720
tccagtctga ccacttcgga ttatcccgtg acaggtcatt cagactggct aatgcaccca   3780
gtaaggcagc ggtatcatca acaggcttac ccgtcttact gtcttttcta cggggtctga   3840
cgctcagtgg aacgaaaact cacgttaagg gattttggtc atgagattat caaaaaggat   3900
cttcacctag atccttttaa attaaaaatg aagttttaaa tcaatctaaa gtatatatga   3960
gtaaacttgg tctgacagtt accaatgctt aatcagtgag gcacctatct cagcgatctg   4020
tctatttcgt tcatccatag ttgcctgact ccccgtcgtg tagataacta cgatacggga   4080
gggcttacca tctggcccca gtgctgcaat gataccgcga gacccacgct caccggctcc   4140
agatttatca gcaataaacc agccagccgg aagggccgag cgcagaagtg gtcctgcaac   4200
tttatccgcc tccatccagt ctattaattg ttgccgggaa gctagagtaa gtagttcgcc   4260
```

```
agttaatagt ttgcgcaacg ttgttgccat tgctacaggc atcgtggtgt cacgctcgtc   4320

gtttggtatg gcttcattca gctccggttc ccaacgatca aggcgagtta catgatcccc   4380

catgttgtgc aaaaaagcgg ttagctcctt cggtcctccg atcgttgtca gaagtaagtt   4440

ggccgcagtg ttatcactca tggttatggc agcactgcat aattctctta ctgtcatgcc   4500

atccgtaaga tgcttttctg tgactggtga gtactcaacc aagtcattct gagaatagtg   4560

tatgcggcga ccgagttgct cttgcccggc gtcaatacgg gataataccg cgccacatag   4620

cagaacttta aaagtgctca tcattggaaa acgttcttcg gggcgaaaac tctcaaggat   4680

cttaccgctg ttgagatcca gttcgatgta acccactcgt gcacccaact gatcttcagc   4740

atcttttact ttcaccagcg tttctgggtg agcaaaaaca ggaaggcaaa atgccgcaaa   4800

aaagggaata agggcgacac ggaaatgttg aatactcata ctcttccttt ttcaatatta   4860

ttgaagcatt tatcagggtt attgtctcat gagcggatac atatttgaat gtatttagaa   4920

aaataaacaa ataggggttc cgcgcacatt tccccgaaaa gtgccacctg acgtctaaga   4980

aaccattatt atcatgacat taacctataa aaataggcgt atcacgaggc cctttcgtct   5040

cgcgcgtttc ggtgatgacg gtgaaaacct ctgacacatg cagctcccgg agacggtcac   5100

agcttgtctg taagcggatg ccgggagcag acaagcccgt cagggcgcgt cagcgggtgt   5160

tggcgggtgt cggggctggc ttaactatgc ggcatcagag cagattgtac tgagagtgca   5220

ccatatgcgg tgtgaaatac cgcacagatg cgtaaggaga aaataccgca tcaggcgcca   5280

ttcgccattc aggctgcgca actgttggga agggcgatcg gtgcgggcct cttcgctatt   5340

acgccagctg gcgaaagggg gatgtgctgc aaggcgatta agttgggtaa cgccagggtt   5400

ttcccagtca cgacgtt                                                  5417
```

```
<210> SEQ ID NO 30
<211> LENGTH: 1539
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

agttgttctt attggtggtg ttgctttatg gttgcatcgt agtaaatggt tgtaacaaaa     60

gcaatttttc cggctgtctg tatacaaaaa cgccgcaaag tttgagcgaa gtcaataaac    120

tctctaccca ttcagggcaa tatctctctt ggatccaaag tgaactctag aaataatttt    180

gtttaacttt aagaaggaga tatacatatg gtaaaggaac gtaaaaccga gttggtcgag    240

ggattccgcc attcggttcc ctgtatcaat acccaccggg gaaaaacgtt tgtcatcatg    300

ctcggcggtg aagccattga gcatgagaat ttctccagta tcgttaatga tatcgggttg    360

ttgcacagcc tcggcatccg tctggtggtg gtctatggcg cacgtccgca gatcgacgca    420

aatctggctg cgcatcacca cgaaccgctg tatcacaaga atatacgtgt gaccgacgcc    480

aaaacactgg aactggtgaa gcaggctgcg ggaacattgc aactggatat tactgctcgc    540

ctgtcgatga gtctcaataa cacgccgctg cagggcgcgc atatcaacgt cgtcagtggc    600

aattttatta ttgcccagcc gctgggcgtc gatgacggcg tggattactg ccatagcggg    660

cgtatccggc ggattgatga agacgcgatc catcgtcaac tggacagcgg tgcaatagtg    720

ctaatggggc cggtcgctgt ttcagtcact ggcgagagct ttaacctgac ctcggaagag    780

attgccactc aactggccat caaactgaaa gctgaaaaga tgattggttt ttgctcttcc    840
```

```
cagggcgtca ctaatgacga cggtgatatt gtctccgaac ttttccctaa cgaagcgcaa    900

gcgcgggtag aagcccagga agagaaaggc gattacaact ccggtacggt gcgctttttg    960

cgtggcgcag tgaaagcctg ccgcagcggc gtgcgtcgct gtcatttaat cagttatcag   1020

gaagatggcg cgctgttgca agagttgttc tcacgcgacg gtatcggtac gcagattgtg   1080

atggaaagcg ccgagcagat tcgtcgcgca acaatcaacg atattggcgg tattctggag   1140

ttgattcgcc cactggagca gcaaggtatt ctggtacgcc gttctcgcga gcagctggag   1200

atggaaatcg acaaattcac cattattcag cgcgataaca cgactattgc ctgcgccgcg   1260

ctctatccgt tcccggaaga gaagattggg gaaatggcct gtgtggcagt tcacccggat   1320

taccgcagtt catcaagggg tgaagttctg ctggaacgca ttgccgctca ggctaagcag   1380

agcggcttaa gcaaattgtt tgtgctgacc acgcgcagta ttcactggtt ccaggaacgt   1440

ggatttaccc cagtggatat tgatttactg cccgagagca aaaagcagtt gtacaactac   1500

cagcgtaaat ccaaagtgtt gatggcggat ttagggtaa                          1539
```

<210> SEQ ID NO 31
<211> LENGTH: 1053
<212> TYPE: DNA
<213> ORGANISM: Escherichia coli

<400> SEQUENCE: 31

```
gtgatccacg ccacattttg tcaacgttta ttgctaatca cgtgaatgaa tatccagttc     60

actttcattt gttgaatact tttaccttct cctgctttcc cttaagcgca ttattttaca    120

aaaaacacac taaactcttc ctgtctccga taaaagatga ttaaatgaaa actcatttat    180

tttgcataaa aattcagtga aagcagaaat ccaggctcat catcagttaa ttaagcaggg    240

tgttatttta tgacgacgat tctcaagcat ctcccggtag gtcaacgtat tggtatcgct    300

ttttccggcg gtctggacac cagtgccgca ctgctgtgga tgcgacaaaa gggagcggtt    360

ccttatgcat atactgcaaa cctgggccag ccagacgaag aggattatga tgcgatccct    420

cgtcgtgcca tggaatacgg cgcggagaac gcacgtctga tcgactgccg caaacaactg    480

gtggccgaag gtattgccgc tattcagtgt ggcgcatttc ataacaccac tggtggactg    540

acctatttca acacgacgcc gctgggccgc gccgtgaccg gcaccatgct ggttgctgct    600

atgaaagaag atggcgtgaa tatctggggt gacggcagca cctataaagg aaacgatatc    660

gaacgtttct accgttacgg tctgctgacc aatgctgaac tgcagattta caaaccgtgg    720

cttgatactg actttattga tgaactgggt ggccgtcatg agatgtctga atttatgatt    780

gcctgcggtt tcgactacaa aatgtctgtc gaaaaagctt actccacgga ctccaacatg    840

cttggtgcaa cgcatgaagc gaaggatctg gaatacctca actccagcgt caaaatcgtc    900

aacccaatta tgggcgtgaa gttttgggat gagagcgtga aaatcccggc agaagaagtc    960

acagtacgct ttgagcaagg tcatccggtg gcgctgaacg gtaaaacctt tagcgacgac   1020

gtagaaatga tgctggaagc taaccgcatc ggc                                1053
```

<210> SEQ ID NO 32
<211> LENGTH: 734
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32
ttgacggcta gctcagtcct aggtacagtg ctagcacccg ttttttttggg ctagaaataa 60 ttttgtttaa ctttaagaag gagatataca tacccatgac gacgattctc aagcatctcc 120
cggtaggtca acgtattggt atcgcttttt ccggcggtct ggacaccagt gccgcactgc 180
tgtggatgcg acaaaaggga gcggttcctt atgcatatac tgcaaacctg ggccagccag 240
acgaagagga ttatgatgcg atccctcgtc gtgccatgga atacggcgcg gagaacgcac 300
gtctgatcga ctgccgcaaa caactggtgg ccgaaggtat tgccgctatt cagtgtggcg 360
catttcataa caccactggt ggactgacct atttcaacac gacgccgctg ggccgcgccg 420
tgaccggcac catgctggtt gctgctatga aagaagatgg cgtgaatatc tggggtgacg 480
gcagcaccta taaaggaaac gatatcgaac gtttctaccg ttacggtctg ctgaccaatg 540
ctgaactgca gatttacaaa ccgtggcttg atactgactt tattgatgaa ctgggtggcc 600
gtcatgagat gtctgaattt atgattgcct gcggtttcga ctacaaaatg tctgtcgaaa 660
aagcttactc cacggactcc aacatgcttg gtgcaacgca tgaagcgaag gatctggaat 720
acctcaactc cagc 734

<210> SEQ ID NO 33
<211> LENGTH: 3518
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 33
cgacggtggc gataggcatc cgggtggtgc tcaaaagcag cttcgcctga ctgatgcgct 60
ggtcctcgcg ccagcttaat acgctaatcc ctaactgctg gcggaacaaa tgcgacagac 120
gcgacggcga caggcagaca tgctgtgcga cgctggcgat atcaaaatta ctgtctgcca 180
ggtgatcgct gatgtactga caagcctcgc gtacccgatt atccatcggt ggatggagcg 240
actcgttaat cgcttccatg cgccgcagta acaattgctc aagcagattt atcgccagca 300
attccgaata gcgcccttcc ccttgtccgg cattaatgat ttgcccaaac aggtcgctga 360
aatgcggctg gtgcgcttca tccgggcgaa agaaaccggt attggcaaat atcgacggcc 420
agttaagcca ttcatgccag taggcgcgcg gacgaaagta aacccactgg tgataccatt 480
cgtgagcctc cggatgacga ccgtagtgat gaatctctcc aggcgggaac agcaaaatat 540
cacccggtcg gcagacaaat tctcgtccct gatttttcac cacccccctga ccgcgaatgg 600 tgagattgag aatataacct ttcattccca gcggtcggtc gataaaaaaa tcgagataac 660
cgttggcctc aatcggcgtt aaacccgcca ccagatgggc gttaaacgag tatcccggca 720
gcaggggatc attttgcgct tcagccatac ttttcatact cccgccattc agagaagaaa 780
ccaattgtcc atattgcatc agacattgcc gtcactgcgt cttttactgg ctcttctcgc 840
taacccaacc ggtaaccccg cttattaaaa gcattctgta acaaagcggg accaaagcca 900
tgacaaaaac gcgtaacaaa agtgtctata atcacggcag aaaagtccac attgattatt 960
tgcacggcgt cacactttgc tatgccatag catttttatc cataagatta gcggatccag 1020
cctgacgctt tttttcgcaa ctctctactg tttctccata cccgtttttt tggatggagt 1080
gaaacgatgg taaaggaacg taaaaccgag ttggtcgagg gattccgcca ttcggttccc 1140
tgtatcaata cccaccgggg aaaaacgttt gtcatcatgc tcggcggtga agccattgag 1200
catgagaatt tctccagtat cgttaatgat atcgggttgt tgcacagcct cggcatccgt 1260

```
ctggtggtgg tctatggcgc acgtccgcag atcgacgcaa atctggctgc gcatcaccac   1320
gaaccgctgt atcacaagaa tatacgtgtg accgacgcca aaacactgga actggtgaag   1380
caggctgcgg gaacattgca actggatatt actgctcgcc tgtcgatgag tctcaataac   1440
acgccgctgc agggcgcgca tatcaacgtc gtcagtggca attttattat tgcccagccg   1500
ctgggcgtcg atgacggcgt ggattactgc catagcgggc gtatccggcg gattgatgaa   1560
gacgcgatcc atcgtcaact ggacagcggt gcaatagtgc taatggggcc ggtcgctgtt   1620
tcagtcactg gcgagagctt taacctgacc tcggaagaga ttgccactca actggccatc   1680
aaactgaaag ctgaaaagat gattggtttt tgctcttccc agggcgtcac taatgacgac   1740
ggtgatattg tctccgaact tttccctaac gaagcgcaag cgcgggtaga agcccaggaa   1800
gagaaaggcg attacaactc cggtacggtg cgctttttgc gtggcgcagt gaaagcctgc   1860
cgcagcggcg tgcgtcgctg tcatttaatc agttatcagg aagatggcgc gctgttgcaa   1920
gagttgttct cacgcgacgg tatcggtacg cagattgtga tggaaagcgc cgagcagatt   1980
cgtcgcgcaa caatcaacga tattggcggt attctggagt tgattcgccc actggagcag   2040
caaggtattc tggtacgccg ttctcgcgag cagctggaga tggaaatcga caaattcacc   2100
attattcagc gcgataacac gactattgcc tgcgccgcgc tctatccgtt cccggaagag   2160
aagattgggg aaatggcctg tgtggcagtt cacccggatt accgcagttc atcaaggggt   2220
gaagttctgc tggaacgcat tgccgctcag gctaagcaga gcggcttaag caaattgttt   2280
gtgctgacca cgcgcagtat tcactggttc caggaacgtg gatttacccc agtggatatt   2340
gatttactgc ccgagagcaa aaagcagttg tacaactacc agcgtaaatc caaagtgttg   2400
atggcggatt tagggtaatg ggaattagcc atggtccata tgaatatcct ccttagttcc   2460
tattccgaag ttcctattcc gaagttccta ttctctagaa agtataggaa cttcgaagca   2520
gctccagcct acacaatcgc tcaagacgtg taatgctgca atctgcatgc aagcttggca   2580
ctggccacgc aaaaaggcca tccgtcagga tggccttctg cttaatttga tgcctggcag   2640
tttatggcgg gcgtcctgcc cgccaccctc cgggccgttg cttcgcaacg ttcaaatccg   2700
ctcccggcgg atttgtccta ctcaggagag cgttcaccga caaacaacag ataaaacgaa   2760
aggcccagtc tttcgactga gcctttcgtt ttatttgatg cctggcagtt ccctactctc   2820
gcatgctcga gccatgggac gtccaggtat tagaagccaa cctggcgctg ccaaaacaca   2880
acctggtcac gctcacctgg ggcaatgtca gcgccgttga tcgcgggcgc ggcgtcctgg   2940
tgatcaaacc ttccggcgtc gactacagca tcatgaccgc tgacgatatg gtcgtggtca   3000
gcatcgaaac cggtgaagtg gttgaaggta cgaaaaagcc ctcctccgac acgccaactc   3060
accggctgct ctatcaggca ttcccgtcta ttggcggcat tgtgcacaca cactcgcgcc   3120
acgccaccat ctgggcgcag gcgggccagt cgattccagc agccggcacc acccacgccg   3180
actatttcta cggcaccatt ccctgcaccc gcaaaatgac cgacgcagaa atcaacggtg   3240
aatatgagtg ggaaaccggt aacgtcatcg tagaaacctt cgaaaaacag ggtatcaatg   3300
cagcgcaaat gcccggcgtg ctggtccatt ctcacggccc atttgcatgg ggaaaaaacg   3360
ccgaagatgc ggtgcataac gccatcgtgc tggaagaagt cgcttatatg ggatattct   3420
gccgtcagtt agcgccgcag ttaccggata tgcagcaaac gctgctggat aaacactatc   3480
tgcgtaagca tggcgcgaag gcatattacg ggcagtaa                           3518
```

<210> SEQ ID NO 34
<211> LENGTH: 3995

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34

```
attaagttgg gtaacgccag ggttttccca gtcacgacgt tattgcgttg cgctcactgc     60
ccgctttcca gtcgggaaac ctgtcgtgcc agctgcatta atgaatcggc caacgcgcgg    120
ggagaggcgg tttgcgtatt gggcgctctt ccgcttcctc gctcactgac tcgctgcgct    180
cggtcgttcg gctgcggcga gcggtatcag ctcactcaaa ggcggtagta cgggttttgc    240
tgcccgcaaa cgggctgttc tggtgttgct agtttgttat cagaatcgca gatccggctt    300
caggtttgcc ggctgaaagc gctatttctt ccagaattgc catgattttt tccccacggg    360
aggcgtcact ggctcccgtg ttgtcggcag ctttgattcg ataagcagca tcgcctgttt    420
caggctgtct atgtgtgact gttgagctgt aacaagttgt ctcaggtgtt caatttcatg    480
ttctagttgc tttgttttac tggtttcacc tgttctatta ggtgttacat gctgttcatc    540
tgttacattg tcgatctgtt catggtgaac agctttaaat gcaccaaaaa ctcgtaaaag    600
ctctgatgta tctatctttt ttacaccgtt ttcatctgtg catatggaca gttttccctt    660
tgatatctaa cggtgaacag ttgttctact tttgtttgtt agtcttgatg cttcactgat    720
agatacaaga gccataagaa cctcagatcc ttccgtattt agccagtatg ttctctagtg    780
tggttcgttg tttttgcgtg agccatgaga acgaaccatt gagatcatgc ttactttgca    840
tgtcactcaa aaattttgcc tcaaaactgg tgagctgaat ttttgcagtt aaagcatcgt    900
gtagtgtttt tcttagtccg ttacgtaggt aggaatctga tgtaatggtt gttggtattt    960
tgtcaccatt catttttatc tggttgttct caagttcggt tacgagatcc atttgtctat   1020
ctagttcaac ttggaaaatc aacgtatcag tcgggcggcc tcgcttatca accaccaatt   1080
tcatattgct gtaagtgttt aaatctttac ttattggttt caaaacccat tggttaagcc   1140
ttttaaactc atggtagtta ttttcaagca ttaacatgaa cttaaattca tcaaggctaa   1200
tctctatatt tgccttgtga gttttctttt gtgttagttc ttttaataac cactcataaa   1260
tcctcataga gtatttgttt tcaaaagact taacatgttc cagattatat tttatgaatt   1320
tttttaactg gaaaagataa ggcaatatct cttcactaaa aactaattct aatttttcgc   1380
ttgagaactt ggcatagttt gtccactgga aaatctcaaa gcctttaacc aaaggattcc   1440
tgatttccac agttctcgtc atcagctctc tggttgcttt agctaataca ccataagcat   1500
tttccctact gatgttcatc atctgagcgt attggttata agtgaacgat accgtccgtt   1560
ctttccttgt agggttttca atcgtggggt tgagtagtgc cacacagcat aaaattagct   1620
tggtttcatg ctccgttaag tcatagcgac taatcgctag ttcatttgct ttgaaaacaa   1680
ctaattcaga catacatctc aattggtcta ggtgatttta atcactatac caattgagat   1740
gggctagtca atgataatta ctagtccttt tcctttgagt tgtgggtatc tgtaaattct   1800
gctagacctt tgctggaaaa cttgtaaatt ctgctagacc ctctgtaaat tccgctagac   1860
ctttgtgtgt tttttttgtt tatattcaag tggttataat ttatagaata aagaaagaat   1920
aaaaaaagat aaaaagaata gatcccagcc ctgtgtataa ctcactactt tagtcagttc   1980
cgcagtatta caaaaggatg tcgcaaacgc tgtttgctcc tctacaaaac agaccttaaa   2040
accctaaagg cttaagtagc accctcgcaa gctcgggcaa atcgctgaat attccttttg   2100
tctccgacca tcaggcacct gagtcgctgt ctttttcgtg acattcagtt cgctgcgctc   2160
```

```
acggctctgg cagtgaatgg gggtaaatgg cactacaggc gccttttatg gattcatgca   2220

aggaaactac ccataataca agaaaagccc gtcacgggct tctcagggcg ttttatggcg   2280

ggtctgctat gtggtgctat ctgacttttt gctgttcagc agttcctgcc ctctgatttt   2340

ccagtctgac cacttcggat tatcccgtga caggtcattc agactggcta atgcacccag   2400

taaggcagcg gtatcatcaa caggcttacc cgtcttactg tcttttctac ggggtctgac   2460

gctcagtgga acgaaaactc acgttaaggg attttggtca tgagattatc aaaaaggatc   2520

ttcacctaga tccttttaaa ttaaaaatga agttttaaat caatctaaag tatatatgag   2580

taaacttggt ctgacagtta ccaatgctta atcagtgagg cacctatctc agcgatctgt   2640

ctatttcgtt catccatagt tgcctgactc cccgtcgtgt agataactac gatacgggag   2700

ggcttaccat ctggccccag tgctgcaatg ataccgcgag acccacgctc accggctcca   2760

gatttatcag caataaacca gccagccgga agggccgagc gcagaagtgg tcctgcaact   2820

ttatccgcct ccatccagtc tattaattgt tgccgggaag ctagagtaag tagttcgcca   2880

gttaatagtt tgcgcaacgt tgttgccatt gctacaggca tcgtggtgtc acgctcgtcg   2940

tttggtatgg cttcattcag ctccggttcc caacgatcaa ggcgagttac atgatccccc   3000

atgttgtgca aaaaagcggt tagctccttc ggtcctccga tcgttgtcag aagtaagttg   3060

gccgcagtgt tatcactcat ggttatggca gcactgcata attctcttac tgtcatgcca   3120

tccgtaagat gcttttctgt gactggtgag tactcaacca agtcattctg agaatagtgt   3180

atgcggcgac cgagttgctc ttgcccggcg tcaatacggg ataataccgc gccacatagc   3240

agaactttaa aagtgctcat cattggaaaa cgttcttcgg ggcgaaaact ctcaaggatc   3300

ttaccgctgt tgagatccag ttcgatgtaa cccactcgtg cacccaactg atcttcagca   3360

tcttttactt tcaccagcgt ttctgggtga gcaaaaacag gaaggcaaaa tgccgcaaaa   3420

aagggaataa gggcgacacg gaaatgttga atactcatac tcttcctttt tcaatattat   3480

tgaagcattt atcagggtta ttgtctcatg agcggataca tatttgaatg tatttagaaa   3540

aataaacaaa taggggttcc gcgcacattt ccccgaaaag tgccacctga cgtctaagaa   3600

accattatta tcatgacatt aacctataaa aataggcgta tcacgaggcc ctttcgtctc   3660

gcgcgtttcg gtgatgacgg tgaaaacctc tgacacatgc agctcccgga gacggtcaca   3720

gcttgtctgt aagcggatgc cgggagcaga caagcccgtc agggcgcgtc agcgggtgtt   3780

ggcgggtgtc ggggctggct taactatgcg gcatcagagc agattgtact gagagtgcac   3840

catatgcggt gtgaaatacc gcacagatgc gtaaggagaa aataccgcat caggcgccat   3900

tcgccattca ggctgcgcaa ctgttgggaa gggcgatcgg tgcgggcctc ttcgctatta   3960

cgccagctgg cgaaaggggg atgtgctgca aggcg                              3995
```

```
<210> SEQ ID NO 35
<211> LENGTH: 5660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
```

```
ggtaccagtt gttcttattg gtggtgttgc tttatggttg catcgtagta aatggttgta     60

acaaaagcaa tttttccggc tgtctgtata caaaaacgcc gcaaagtttg agcgaagtca    120

ataaactctc tacccattca gggcaatatc tctcttggat ccaaagtgaa ctctagaaat    180
```

```
aattttgttt aactttaaga aggagatata catatggtaa aggaacgtaa aaccgagttg    240
gtcgagggat tccgccattc ggttccctgt atcaataccc accggggaaa aacgtttgtc    300
atcatgctcg gcggtgaagc cattgagcat gagaatttct ccagtatcgt taatgatatc    360
gggttgttgc acagcctcgg catccgtctg gtggtggtct atggcgcacg tccgcagatc    420
gacgcaaatc tggctgcgca tcaccacgaa ccgctgtatc acaagaatat acgtgtgacc    480
gacgccaaaa cactggaact ggtgaagcag gctgcgggaa cattgcaact ggatattact    540
gctcgcctgt cgatgagtct caataacacg ccgctgcagg gcgcgcatat caacgtcgtc    600
agtggcaatt ttattattgc ccagccgctg ggcgtcgatg acggcgtgga ttactgccat    660
agcgggcgta tccggcggat tgatgaagac gcgatccatc gtcaactgga cagcggtgca    720
atagtgctaa tggggccggt cgctgtttca gtcactggcg agagctttaa cctgacctcg    780
gaagagattg ccactcaact ggccatcaaa ctgaaagctg aaaagatgat tggtttttgc    840
tcttcccagg gcgtcactaa tgacgacggt gatattgtct ccgaactttt ccctaacgaa    900
gcgcaagcgc gggtagaagc ccaggaagag aaaggcgatt acaactccgg tacggtgcgc    960
tttttgcgtg gcgcagtgaa agcctgccgc agcggcgtgc gtcgctgtca tttaatcagt   1020
tatcaggaag atggcgcgct gttgcaagag ttgttctcac gcgacggtat cggtacgcag   1080
attgtgatgg aaagcgccga gcagattcgt cgcgcaacaa tcaacgatat tggcggtatt   1140
ctggagttga ttcgcccact ggagcagcaa ggtattctgg tacgccgttc tcgcgagcag   1200
ctggagatgg aaatcgacaa attcaccatt attcagcgcg ataacacgac tattgcctgc   1260
gccgcgctct atccgttccc ggaagagaag attggggaaa tggcctgtgt ggcagttcac   1320
ccggattacc gcagttcatc aaggggtgaa gttctgctgg aacgcattgc cgctcaggct   1380
aagcagagcg gcttaagcaa attgtttgtg ctgaccacgc gcagtattca ctggttccag   1440
gaacgtggat ttaccccagt ggatattgat ttactgcccg agagcaaaaa gcagttgtac   1500
aactaccagc gtaaatccaa agtgttgatg gcggatttag ggtaaggaag tttgtctaga   1560
tctcaggcgt ggatggcttg gcgtaatcat ggtcatagct gtttcctgtg tgaaattgtt   1620
atccgctcac aattccacac aacatacgag ccggaagcat aaagtgtaaa gcctggggtg   1680
cctaatgagt gagctaactc acattaattg cgttgcgctc actgcccgct ttccagtcgg   1740
gaaacctgtc gtgccagctg cattaatgaa tcggccaacg cgcggggaga ggcggtttgc   1800
gtattgggcg ctcttccgct tcctcgctca ctgactcgct gcgctcggtc gttcggctgc   1860
ggcgagcggt atcagctcac tcaaaggcgg tagtacgggt tttgctgccc gcaaacgggc   1920
tgttctggtg ttgctagttt gttatcagaa tcgcagatcc ggcttcaggt ttgccggctg   1980
aaagcgctat ttcttccaga attgccatga tttttcccc acgggaggcg tcactggctc   2040
ccgtgttgtc ggcagctttg attcgataag cagcatcgcc tgtttcaggc tgtctatgtg   2100
tgactgttga gctgtaacaa gttgtctcag gtgttcaatt tcatgttcta gttgctttgt   2160
tttactggtt tcacctgttc tattaggtgt tacatgctgt tcatctgtta cattgtcgat   2220
ctgttcatgg tgaacagctt taaatgcacc aaaaactcgt aaaagctctg atgtatctat   2280
ctttttaca ccgttttcat ctgtgcatat ggacagtttt ccctttgata tctaacggtg   2340
aacagttgtt ctacttttgt ttgttagtct tgatgcttca ctgatagata caagagccat   2400
aagaacctca gatccttccg tatttagcca gtatgttctc tagtgtggtt cgttgttttt   2460
gcgtgagcca tgagaacgaa ccattgagat catgcttact ttgcatgtca ctcaaaaatt   2520
```

```
ttgcctcaaa actggtgagc tgaatttttg cagttaaagc atcgtgtagt gtttttctta   2580
gtccgttacg taggtaggaa tctgatgtaa tggttgttgg tattttgtca ccattcattt   2640
ttatctggtt gttctcaagt tcggttacga gatccatttg tctatctagt tcaacttgga   2700
aaatcaacgt atcagtcggg cggcctcgct tatcaaccac caatttcata ttgctgtaag   2760
tgtttaaatc tttacttatt ggtttcaaaa cccattggtt aagcctttta aactcatggt   2820
agttattttc aagcattaac atgaacttaa attcatcaag gctaatctct atatttgcct   2880
tgtgagtttt cttttgtgtt agttctttta ataaccactc ataaatcctc atagagtatt   2940
tgttttcaaa agacttaaca tgttccagat tatattttat gaattttttt aactggaaaa   3000
gataaggcaa tatctcttca ctaaaaacta attctaattt ttcgcttgag aacttggcat   3060
agtttgtcca ctggaaaatc tcaaagcctt taaccaaagg attcctgatt tccacagttc   3120
tcgtcatcag ctctctggtt gctttagcta atacaccata agcattttcc ctactgatgt   3180
tcatcatctg agcgtattgg ttataagtga acgataccgt ccgttctttc cttgtagggt   3240
tttcaatcgt ggggttgagt agtgccacac agcataaaat tagcttggtt tcatgctccg   3300
ttaagtcata gcgactaatc gctagttcat ttgctttgaa aacaactaat tcagacatac   3360
atctcaattg gtctaggtga ttttaatcac tataccaatt gagatgggct agtcaatgat   3420
aattactagt ccttttcctt tgagttgtgg gtatctgtaa attctgctag acctttgctg   3480
gaaaacttgt aaattctgct agaccctctg taaattccgc tagacctttg tgtgtttttt   3540
ttgtttatat tcaagtggtt ataatttata gaataaagaa agaataaaaa aagataaaaa   3600
gaatagatcc cagccctgtg tataactcac tactttagtc agttccgcag tattacaaaa   3660
ggatgtcgca aacgctgttt gctcctctac aaaacagacc ttaaaaccct aaaggcttaa   3720
gtagcaccct cgcaagctcg ggcaaatcgc tgaatattcc ttttgtctcc gaccatcagg   3780
cacctgagtc gctgtctttt tcgtgacatt cagttcgctg cgctcacggc tctggcagtg   3840
aatgggggta aatggcacta caggcgcctt ttatggattc atgcaaggaa actacccata   3900
atacaagaaa agcccgtcac gggcttctca gggcgtttta tggcgggtct gctatgtggt   3960
gctatctgac tttttgctgt tcagcagttc ctgccctctg attttccagt ctgaccactt   4020
cggattatcc cgtgacaggt cattcagact ggctaatgca cccagtaagg cagcggtatc   4080
atcaacaggc ttacccgtct tactgtcttt tctacggggt ctgacgctca gtggaacgaa   4140
aactcacgtt aagggatttt ggtcatgaga ttatcaaaaa ggatcttcac ctagatcctt   4200
ttaaattaaa aatgaagttt taaatcaatc taaagtatat atgagtaaac ttggtctgac   4260
agttaccaat gcttaatcag tgaggcacct atctcagcga tctgtctatt tcgttcatcc   4320
atagttgcct gactccccgt cgtgtagata actacgatac gggagggctt accatctggc   4380
cccagtgctg caatgatacc gcgagaccca cgctcaccgg ctccagattt atcagcaata   4440
aaccagccag ccggaagggc cgagcgcaga agtggtcctg caactttatc cgcctccatc   4500
cagtctatta attgttgccg ggaagctaga gtaagtagtt cgccagttaa tagtttgcgc   4560
aacgttgttg ccattgctac aggcatcgtg gtgtcacgct cgtcgtttgg tatggcttca   4620
ttcagctccg gttcccaacg atcaaggcga gttacatgat cccccatgtt gtgcaaaaaa   4680
gcggttagct ccttcggtcc tccgatcgtt gtcagaagta agttggccgc agtgttatca   4740
ctcatggtta tggcagcact gcataattct cttactgtca tgccatccgt aagatgcttt   4800
tctgtgactg gtgagtactc aaccaagtca ttctgagaat agtgtatgcg gcgaccgagt   4860
tgctcttgcc cggcgtcaat acgggataat accgcgccac atagcagaac tttaaaagtg   4920
```

```
ctcatcattg gaaaacgttc ttcggggcga aaactctcaa ggatcttacc gctgttgaga   4980

tccagttcga tgtaacccac tcgtgcaccc aactgatctt cagcatcttt tactttcacc   5040

agcgtttctg ggtgagcaaa aacaggaagg caaaatgccg caaaaaaggg aataagggcg   5100

acacggaaat gttgaatact catactcttc ctttttcaat attattgaag catttatcag   5160

ggttattgtc tcatgagcgg atacatattt gaatgtattt agaaaaataa acaaataggg   5220

gttccgcgca catttccccg aaaagtgcca cctgacgtct aagaaaccat tattatcatg   5280

acattaacct ataaaaatag gcgtatcacg aggccctttc gtctcgcgcg tttcggtgat   5340

gacggtgaaa acctctgaca catgcagctc ccggagacgg tcacagcttg tctgtaagcg   5400

gatgccggga gcagacaagc ccgtcagggc gcgtcagcgg gtgttggcgg gtgtcggggc   5460

tggcttaact atgcggcatc agagcagatt gtactgagag tgcaccatat gcggtgtgaa   5520

ataccgcaca gatgcgtaag gagaaaatac cgcatcaggc gccattcgcc attcaggctg   5580

cgcaactgtt gggaagggcg atcggtgcgg gcctcttcgc tattacgcca gctggcgaaa   5640

gggggatgtg ctgcaaggcg                                                 5660
```

<210> SEQ ID NO 36
<211> LENGTH: 967
<212> TYPE: DNA
<213> ORGANISM: Escherichia coli

<400> SEQUENCE: 36

```
caaatatcac ataatcttaa catatcaata aacacagtaa agtttcatgt gaaaaacatc     60

aaacataaaa tacaagctcg gaatacgaat cacgctatac acattgctaa caggaatgag    120

attatctaaa tgaggattga tatattaatt ggacatacta gtttttttca tcaaaccagt    180

agagataact tccttcacta tctcaatgag gaagaaataa aacgctatga tcagtttcat    240

tttgtgagtg ataaagaact ctatatttta agccgtatcc tgctcaaaac agcactaaaa    300

agatatcaac ctgatgtctc attacaatca tggcaattta gtacgtgcaa atatggcaaa    360

ccatttatag tttttcctca gttggcaaaa aagatttttt ttaacctttc ccatactata    420

gatacagtag ccgttgctat tagttctcac tgcgagcttg gtgtcgatat tgaacaaata    480

agagatttag acaactctta tctgaatatc agtcagcatt tttttactcc acaggaagct    540

actaacatag tttcacttcc tcgttatgaa ggtcaattac ttttttggaa aatgtggacg    600

ctcaaagaag cttacatcaa atatcgaggt aaaggcctat ctttaggact ggattgtatt    660

gaatttcatt taacaaataa aaaactaact tcaaaatata gaggttcacc tgtttatttc    720

tctcaatgga aaatatgtaa ctcatttctc gcattagcct ctccactcat cacccctaaa    780

ataactattg agctatttcc tatgcagtcc caactttatc accacgacta tcagctaatt    840

cattcgtcaa atgggcagaa ttgaatcgcc acggataatc tagacacttc tgagccgtcg    900

ataatattga ttttcatatt ccgtcggtgg tgtaagtatc ccgcataatc gtgccattca    960

catttag                                                              967
```

<210> SEQ ID NO 37
<211> LENGTH: 424
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 37
ggatgggggg aaacatggat aagttcaaag aaaaaaaccc gttatctctg cgtgaaagac 60
aagtattgcg catgctggca caaggtgatg agtactctca aatatcacat aatcttaaca 120
tatcaataaa cacagtaaag tttcatgtga aaaacatcaa acataaaata caagctcgga 180
atacgaatca cgctatacac attgctaaca ggaatgagat tatctaaatg aggattgatg 240
tgtaggctgg agctgcttcg aagttcctat actttctaga gaataggaac ttcggaatag 300
gaacttcgga ataggaacta aggaggatat tcatatgtcg tcaaatgggc agaattgaat 360
cgccacggat aatctagaca cttctgagcc gtcgataata ttgattttca tattccgtcg 420
gtgg 424

<210> SEQ ID NO 38
<211> LENGTH: 471
<212> TYPE: DNA
<213> ORGANISM: Escherichia coli

<400> SEQUENCE: 38
atgcgaagct cggctaagca agaagaacta gttaaagcat ttaaagcatt acttaaagaa 60
gagaaattta gctcccaggg cgaaatcgtc gccgcgttgc aggagcaagg ctttgacaat 120
attaatcagt ctaaagtctc gcggatgttg accaagtttg gtgctgtacg tacacgcaat 180
gccaaaatgg aaatggttta ctgcctgcca gctgaactgg gtgtaccaac cacctccagt 240
ccattgaaga atctggtact ggatatcgac tacaacgatg cagttgtcgt gattcatacc 300
agccctggtg cggcgcagtt aattgctcgc ctgctggact cactgggcaa agcagaaggt 360
attctgggca ccatcgctgg cgatgacacc atctttacta cccctgctaa cggtttcacc 420
gtcaaagagc tgtacgaagc gattttagag ctgttcgacc aggagcttta a 471

<210> SEQ ID NO 39
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 39
atgcgaagct cggctaagca agaagagagc tgttcgacca ggagctttaa 50

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other

<400> SEQUENCE: 40
wntgaatwww wattcanw 18